US012692264B2

(12) United States Patent
Feng et al.

(10) Patent No.: US 12,692,264 B2
(45) Date of Patent: Jul. 28, 2026

(54) PYRIMIDINE OR PYRIDINE DERIVATIVE, PREPARATION METHOD THEREFOR, AND APPLICATION THEREOF IN PHARMACY

(71) Applicant: ABBISKO THERAPEUTICS CO., LTD., Pudong New Area (CN)

(72) Inventors: Tao Feng, Pudong New Area (CN); Baowei Zhao, Pudong New Area (CN); Mingming Zhang, Pudong New Area (CN); Shuqun Yang, Pudong New Area (CN); Hongping Yu, Pudong New Area (CN); Zhui Chen, Pudong New Area (CN); Yaochang Xu, Pudong New Area (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 353 days.

(21) Appl. No.: 18/576,252

(22) PCT Filed: Aug. 3, 2022

(86) PCT No.: PCT/CN2022/109819

§ 371 (c)(1),
(2) Date: Jan. 3, 2024

(87) PCT Pub. No.: WO2023/011505

PCT Pub. Date: Feb. 9, 2023

(65) Prior Publication Data

US 2024/0327402 A1 Oct. 3, 2024

(30) Foreign Application Priority Data

Aug. 6, 2021 (CN) ......................... 202110899844.4
Jan. 25, 2022 (CN) ......................... 202210087511.6

(51) Int. Cl.

| | |
|---|---|
| ***C07D 471/04*** | (2006.01) |
| ***A61K 31/506*** | (2006.01) |
| ***A61P 35/00*** | (2006.01) |
| ***C07D 403/04*** | (2006.01) |
| ***C07D 403/14*** | (2006.01) |
| ***C07D 519/00*** | (2006.01) |

(52) U.S. Cl.

CPC .......... *C07D 471/04* (2013.01); *A61K 31/506* (2013.01); *A61P 35/00* (2018.01); *C07D 403/04* (2013.01); *C07D 403/14* (2013.01); *C07D 519/00* (2013.01)

(58) Field of Classification Search

CPC .................................................... C07D 471/04
See application file for complete search history.

(56) References Cited

U.S. PATENT DOCUMENTS 10,179,784 B2 * 1/2019 Jiang .................... C07D 413/04
11,498,921 B1 * 11/2022 Jiang .................... C07D 403/04

FOREIGN PATENT DOCUMENTS

| | | | |
|---|---|---|---|
| CN | 103702990 | A | 4/2014 |
| CN | 106928150 | A | 7/2017 |
| CN | 109328059 | A | 2/2019 |
| WO | WO 2016/029839 | A1 | 3/2016 |
| WO | WO 2016/070816 | A1 | 5/2016 |

OTHER PUBLICATIONS

International Search Report with English Translation, dated Nov. 1, 2022, pp. 1-10, issued in International Application No. PCT/CN2022/109819, China National Intellectual Property Administration, Beijing, China.
Written Opinion with Chinese Translation only, dated Nov. 1, 2022, pp. 5, issued in International Application No. PCT/CN2022/109819, China National Intellectual Property Administration, Beijing China.

* cited by examiner

*Primary Examiner* — Golam M Shameem
(74) *Attorney, Agent, or Firm* — Crowell & Moring LLP; Yuezhong Feng

(57) ABSTRACT

A pyrimidine or pyridine derivative having a structure represented by formula (I), a preparation method therefor, a pharmaceutical composition containing same, a use thereof as an EGFR inhibitor, and a use thereof in the preparation of a drug for treating and/or preventing cancer, tumors, or metastatic diseases associated at least in part with EGFR exon 20 insertions, deletions, or other mutations, especially a use thereof in the preparation of a drug for treating and/or preventing hyperproliferative diseases and the induction of cell death disorders.

(I)

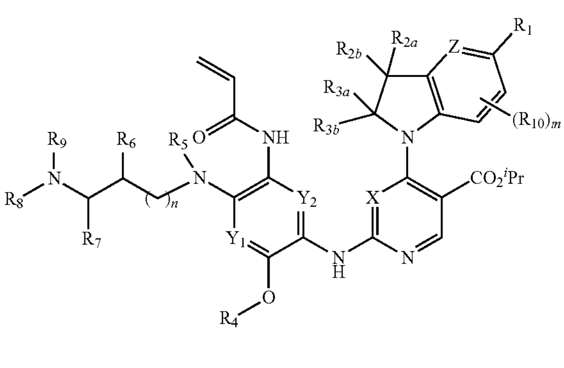

13 Claims, No Drawings

PYRIMIDINE OR PYRIDINE DERIVATIVE, PREPARATION METHOD THEREFOR, AND APPLICATION THEREOF IN PHARMACY

RELATED APPLICATIONS

This application is a U.S. National Phase entry under 35 U.S.C. § 371 of International Application No. PCT/CN2022/109819, filed 3 Aug. 2022, which claims the benefit of Chinese Patent Application No. 202110899844.4, filed 6 Aug. 2021, and Chinese Patent Application No. 202210087511.6, filed 25 Jan. 2022, the contents of each of which are incorporated herein by reference in their entireties.

TECHNICAL FIELD

The present invention belongs to the field of pharmaceutical synthesis, and particularly relates to a pyrimidine or pyridine derivative, preparation method therefor, and pharmaceutical application thereof.

BACKGROUND

Lung cancer is the leading cause of cancer death worldwide, with non-small cell lung cancer (NSCLC) accounting for 85%. Multi-target therapies against epidermal growth factor receptor (EGFR) mutations, anaplastic lymphoma kinase (ALK) translocations, ROS1 proto-oncogene receptor tyrosine kinase (ROS1) rearrangements and B-raf proto-oncogenes, serine/threonine kinases (BRAF) have been successfully developed and clinically validated. Inhibitors against EGFR can significantly improve progression-free survival of adenocarcinoma in NSCLC, while acquired resistance mutations of these inhibitors can be targeted by the third-generation EGFR inhibitors.

Although classical EGFR activating mutations (Exons 19 and 21) and drug resistance mutation (T790M) can be inhibited by existing medicaments, insertion mutation of Exon 20 also results in structural activation of EGFR signaling and is insensitive to all of existing EGFR inhibitors. The mutation of Exon 20 is heterogeneous and includes insertions or repeats of 1-7 amino acids between amino acids at positions 762-774 of the EGFR protein. In NSCLC, the mutation frequency of Exon 20 in EGFR is 4-10% of all mutations in EGFR. These mutations are mutually exclusive with other known oncogene-driven mutations and are enriched in adenocarcinomas of women, non-smokers, Asian populations, and non-small cell lung cancer patients. In addition to NSCLC, the insertion mutation of EGFR Exon 20 is also seen in a rare head and neck cancer, namely sinonasal squamous cell carcinoma (SNSCC). In addition, a structurally-similar insertion mutation of Exon 20 is also found in HER2, another member of the EGFR family.

Several retrospective analytical studies have shown that currently-available first-, second- and third-generation EGFR inhibitors have limited the therapeutic effect against the insertion mutation of Exon 20, with the exception of the mutation of A763-Y764insFQEA. An irreversible inhibitor Poziotinib and an EGFR/MET bispecific antibody Anivantamab are in clinical trials. Several small-molecule inhibitors, including TAK-788 and TAS-6417, have shown clinically-significant efficacy in non-small cell lung cancer patients with EGFR Exon 20. However, due to their limited selectivity for EGFR wild type, adverse effects in clinical use are unavoidable and may lead to dose limiting toxicity. Meanwhile, the existing compounds may show clinically the problem of insufficient exposure. Thus, there is an urgent need for small-molecule inhibitors with higher exposure and/or high selectivity against the insertion mutation of EGFR Exon 20 for these patients.

SUMMARY

The object of the present invention is to provide a pyrimidine or pyridine derivative, preparation method therefor and pharmaceutical application thereof. A series of compounds of the present invention have strong inhibitory effects on the cytological activity of an insertion, deletion or other mutation of EGFR Exon 20, have a high selectivity for EGFR wild type, and can be widely applied to the preparation of medicaments for treating and/or preventing cancer, tumor or metastatic disease at least partially related to the insertion, deletion or other mutation of EGFR Exon 20, particularly medicaments for treating hyperproliferative disease and disease of dysfunction in cell death induction, so that a new generation of EGFR inhibitors is expected to be developed.

The first aspect of the present invention provides a compound of formula (I), a stereoisomer or pharmaceutically acceptable salt thereof:

(I)

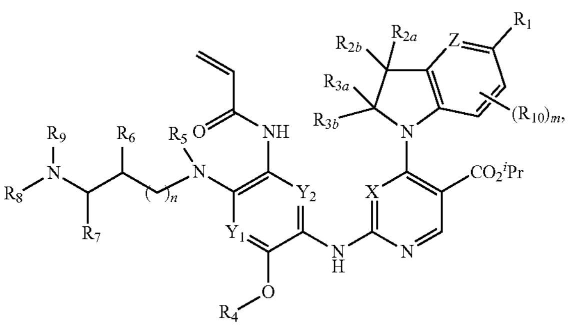

wherein, X is CH or N; $Y_1$ and $Y_2$ are each independently CH or N; Z is $CR_{11}$ or N;

$R_1$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-S(O)$_r$$R_{12}$, —$C_{0-8}$ alkyl-O—$R_{13}$, —$C_{0-8}$ alkyl-C(O)O$R_{13}$, —$C_{0-8}$ alkyl-C(O)$R_{14}$, —$C_{0-8}$ alkyl-O—C(O)$R_{14}$, —$C_{0-8}$ alkyl-N$R_{15}R_{16}$, —$C_{0-8}$ alkyl-C(═N$R_{15}$)$R_{14}$, —$C_{0-8}$ alkyl-N($R_{15}$)—C(═N$R_{16}$)$R_{14}$, —$C_{0-8}$ alkyl-C(O)N$R_{15}R_{16}$ and —$C_{0-8}$ alkyl-N($R_{15}$)—C(O)$R_{14}$, or $R_1$ and adjacent $R_{10}$, together with the moiety to which they are directly attached, form a $C_{3-12}$ cycloalkyl or 3-12 membered heterocyclyl, the above groups are optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, ═O, —$C_{0-8}$ alkyl-$SF_5$, —$C_{0-8}$ alkyl-S(O)$_r$$R_{12}$, —$C_{0-8}$ alkyl-O—$R_{13}$, —$C_{0-8}$ alkyl-C(O)O$R_{13}$, —$C_{0-8}$ alkyl-C(O)$R_{14}$, —$C_{0-8}$ alkyl-O—C(O)$R_{14}$, —$C_{0-8}$ alkyl-N$R_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$;

$R_{2a}$ and $R_{2b}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl and 5-10 membered heteroaryl, or $R_{2a}$ and $R_{2b}$, together with the carbon atom to which they are directly attached, form a $C_{3-6}$ cycloalkyl or 3-6 membered heterocyclyl, the above groups are optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_{12}$, $—C_{0-8}$ alkyl-O—$R_{13}$, $—C_{0-8}$ alkyl-$C(O)OR_{13}$, $—C_{0-8}$ alkyl-$C(O)R_{14}$, $—C_{0-8}$ alkyl-O—$C(O)R_{14}$, $—C_{0-8}$ alkyl-$NR_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$;

$R_{3a}$ and $R_{3b}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl and 5-10 membered heteroaryl;

$R_4$ is selected from the group consisting of hydrogen, deuterium, $C_{1-10}$ alkyl, $C_{2-10}$ alkenyl, $C_{3-12}$ cycloalkyl, 3-12 membered heterocyclyl, $C_{6-10}$ aryl and 5-10 membered heteroaryl, the above groups are optionally further substituted with one or more substituents selected from the group consisting of deuterium, halogen, hydroxy, =O, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and $—C_{0-8}$ alkyl-$NR_{15}R_{16}$—;

$R_5$ is selected from the group consisting of hydrogen, deuterium, hydroxy, $C_{1-10}$ alkyl, $C_{1-10}$ haloalkyl, $C_{1-10}$ deuterioalkyl, $C_{2-4}$ alkenyl, $C_{3-6}$ cycloalkyl and 3-6 membered heterocyclyl;

$R_6$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, $—C_{0-8}$ alkyl-$SF_5$, $—C_{0-8}$ alkyl-$S(O)_rR_{12}$, $—C_{0-8}$ alkyl-O—$R_{13}$, $—C_{0-8}$ alkyl-$C(O)OR_{13}$, $—C_{0-8}$ alkyl-$C(O)R_{14}$, $—C_{0-8}$ alkyl-O—$C(O)R_{14}$, $—C_{0-8}$ alkyl-$NR_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$;

$R_7$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, $—C_{0-8}$ alkyl-$SF_5$, $—C_{0-8}$ alkyl-$S(O)_rR_{12}$, $—C_{0-8}$ alkyl-O—$R_{13}$, $—C_{0-8}$ alkyl-$C(O)OR_{13}$, $—C_{0-8}$ alkyl-$C(O)R_{14}$, $—C_{0-8}$ alkyl-O—$C(O)R_{14}$, $—C_{0-8}$ alkyl-$NR_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$;

$R_8$ and $R_9$ are each independently selected from the group consisting of hydrogen, deuterium, hydroxy, $C_{1-10}$ alkyl, $C_{2-4}$ alkenyl, $C_{3-4}$ cycloalkyl and 3-6 membered heterocyclyl, or $R_8$ and $R_9$, together with the nitrogen atom to which they are directly attached, form a 3-12 membered heterocyclyl, the above group is optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy. $C_{6-10}$ aryl, $C_{6-10}$ aryloxy, 5-10 membered heteroaryl, 5-10 membered heteroaryloxy, and $—C_{0-8}$ alkyl-$NR_{15}R_{16}$;

or, $R_5$ and one of $R_6$, $R_7$ and $R_9$, together with the moiety to which they are directly attached, form a 4-6 membered heterocyclyl, the other two of $R_6$, $R_7$ and $R_9$ are as previously defined, the 4-6 membered heterocyclyl is optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_{12}$, $—C_{0-8}$ alkyl-O—$R_{13}$, $—C_{0-8}$ alkyl-$C(O)OR_{13}$, $—C_{0-8}$ alkyl-$C(O)R_{14}$, $—C_{0-8}$ alkyl-O—$C(O)R_4$, $—C_{0-8}$ alkyl-$NR_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$, or $R_7$ and $R_8$, together with the moiety to which they are directly attached, form a 4-6 membered heterocyclyl, the 4-6 membered heterocyclyl is optionally further substituted with one or more substituents selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, $—C_{0-8}$ alkyl-$SF_5$, $—C_{0-8}$ alkyl-$S(O)_rR_{12}$, $—C_{0-8}$ alkyl-O—$R_{13}$, $—C_{0-8}$ alkyl-$C(O)OR_{13}$, $—C_{0-8}$ alkyl-$C(O)R_{14}$, $—C_{0-8}$ alkyl-O—$C(O)R_4$, $—C_{0-8}$ alkyl-$NR_{15}R_{16}$, $—C_{0-8}$ alkyl-$C(=NR_{15})R_{14}$, $—C_{0-8}$ alkyl-$N(R_{15})—C(=NR_{16})R_{14}$, $—C_{0-8}$ alkyl-$C(O)NR_{15}R_{16}$ and $—C_{0-8}$ alkyl-$N(R_{15})—C(O)R_{14}$, or

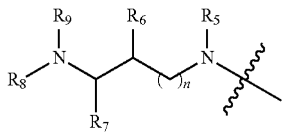

is a structure shown as follows:

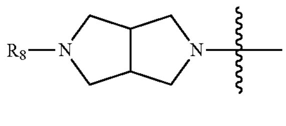

wherein $R_8$ is as previously defined;

each $R_{10}$ is independently selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-S(O)$_r$$R_{12}$, —$C_{0-8}$ alkyl-O—$R_{13}$, —$C_{0-8}$ alkyl-C(O)O$R_{13}$, —$C_{0-8}$ alkyl-C(O)$R_{14}$, —$C_{0-8}$ alkyl-O—C(O)$R_{14}$, —$C_{0-8}$ alkyl-N$R_{15}$$R_{16}$, —$C_{0-8}$ alkyl-C(═N$R_{15}$)$R_{14}$, —$C_{0-8}$ alkyl-N($R_{15}$)—C(═N$R_{16}$)$R_{14}$, —$C_{0-8}$ alkyl-C(O)N$R_{15}$$R_{16}$ and —$C_{0-8}$ alkyl-N($R_{15}$)—C(O)$R_{14}$, or when m=2, two $R_{10}$, together with the moiety to which they are directly attached, form a $C_{3-12}$ cycloalkyl or 3-12 membered heterocyclyl;

$R_{11}$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-S(O)$_r$$R_{12}$, —$C_{0-8}$ alkyl-O—$R_{13}$, —$C_{0-8}$ alkyl-C(O)O$R_{13}$, —$C_{0-8}$ alkyl-C(O)$R_{14}$, —$C_{0-8}$ alkyl-O—C(O)$R_{14}$, —$C_{0-8}$ alkyl-N$R_{15}$$R_{16}$, —$C_{0-8}$ alkyl-C(═N$R_{15}$)$R_{14}$, —$C_{0-8}$ alkyl-N($R_{15}$)—C(═N$R_{16}$)$R_{14}$, —$C_{0-8}$ alkyl-C(O)N$R_{15}$$R_{16}$ and —$C_{0-8}$ alkyl-N($R_{15}$)—C(O)$R_{14}$;

each $R_{12}$ is independently selected from the group consisting of hydrogen, deuterium, hydroxy, $C_{1-10}$ alkyl, $C_{2-10}$ alkenyl, $C_{3-12}$ cycloalkyl, 3-12 membered heterocyclyl, $C_{6-10}$ aryl, 5-10 membered heteroaryl and —$C_{0-8}$ alkyl-N$R_{15}$$R_{16}$, the above groups are optionally further substituted with one or more substituents selected from the group consisting of deuterium, halogen, hydroxy, oxo, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$C_{0-8}$ alkyl-N$R_{15}$$R_{16}$;

each $R_{13}$ is independently selected from the group consisting of hydrogen, deuterium, $C_{1-10}$ alkyl, $C_{2-10}$ alkenyl, $C_{3-12}$ cycloalkyl, 3-12 membered heterocyclyl, $C_{6-10}$ aryl and 5-10 membered heteroaryl, the above groups are optionally further substituted with one or more substituents selected from the group consisting of deuterium, halogen, hydroxy, oxo, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$C_{0-8}$ alkyl-N$R_{15}$$R_{16}$;

each $R_{14}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$C_{0-8}$ alkyl-N$R_{15}$$R_{16}$, the above groups are optionally further substituted with one or more substituents selected from the group consisting of deuterium, halogen, hydroxy, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$C_{0-8}$ alkyl-N$R_{15}$$R_{16}$;

each of $R_{15}$ and $R_{16}$ is independently selected from the group consisting of hydrogen, deuterium, hydroxy, $C_{1-10}$ alkoxy, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-10}$ alkylamino, di$C_{1-10}$alkylamino and $C_{1-10}$ alkanoyl, the above groups are optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino and $C_{1-10}$ alkanoyl, or, $R_{15}$ and $R_{16}$, together with the nitrogen atom to which they are directly attached, form a 5-10 membered heterocyclyl or 5-10 membered heteroaryl, the above groups are optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy. $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino and $C_{1-10}$ alkanoyl;

m is 0, 1 or 2;

n is 0, 1, or 2; and each r is independently 0, 1 or 2.

As a preferred embodiment, in the compound of formula (I), the stereoisomer or pharmaceutically acceptable salt thereof, Z is C$R_{11}$ or N;

$R_1$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-S(O)$_r$$R_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}$$R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}$$R_{16}$ and —$C_{0-4}$ alkyl-N($R_{15}$)—C(O)$R_{14}$, or $R_1$ and adjacent $R_{10}$, together with the moiety to which they are directly attached, form a $C_{3-6}$ cycloalkyl or 3-6 membered heterocyclyl, the above groups are optionally further substituted with one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, ═O, —$C_{0-4}$ alkyl-$SF_5$, —$C_{0-4}$ alkyl-S(O)$_r$$R_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}$$R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}$$R_{16}$ and —$C_{0-4}$ alkyl-N($R_{15}$)—C(O)$R_{14}$;

$R_{2a}$ and $R_{2b}$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl and 5-8 membered heteroaryl, or $R_{2a}$ and $R_{2b}$, together with the carbon atom to which they are directly attached, form a $C_{3-6}$ cycloalkyl or 3-6 membered heterocyclyl, the above groups are optionally further substituted with one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C(=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$;

$R_{3a}$ and $R_{3b}$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl and 5-8 membered heteroaryl;

$R_4$ is selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl and 5-8 membered heteroaryl, the above groups are optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-8}$ alkyl-$NR_{15}R_{16}$;

$R_5$ is selected from the group consisting of hydrogen, deuterium, hydroxy, $C_{1-4}$ alkyl, $C_{1-4}$ haloalkyl, $C_{1-4}$ deuterioalkyl, $C_{2-4}$ alkenyl, $C_{3-6}$ cycloalkyl and 3-6 membered heterocyclyl;

$R_6$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-8}$ alkyl-O—C(O)$R_{14}$, —$C_{0-4}$ alkyl-$NR_{15}R_{16}$, —Cod alkyl-C(=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$;

$R_7$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C(=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$;

$R_8$ and $R_9$ are each independently selected from the group consisting of hydrogen, deuterium, hydroxy, $C_{1-4}$ alkyl, $C_{2-4}$ alkenyl, $C_{3-6}$ cycloalkyl and 3-6 membered heterocyclyl, or $R_8$ and $R_9$, together with the nitrogen atom to which they are directly attached, form a 3-6 membered heterocyclyl, the above group is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-4}$ alkyl-$NR_{15}R_{16}$;

or, $R_5$ and one of $R_6$, $R_7$ and $R_9$, together with the moiety to which they are directly attached, form a 4-6 membered heterocyclyl, the other two of $R_6$, $R_7$ and $R_9$ are as previously defined, the 4-6 membered heterocyclyl is optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C(=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$, or $R_7$ and $R_8$, together with the moiety to which they are directly attached, form a 4-6 membered heterocyclyl, the 4-6 membered heterocyclyl is optionally further substituted with one or more substituents selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C(=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$, or

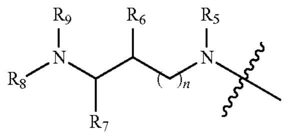

is a structure shown as follows:

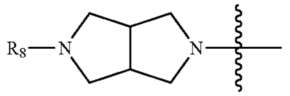

wherein $R_8$ is as previously defined;

each $R_{10}$ is independently selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C(=$NR_{15}$)$R_{14}$, —$C_{0-8}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$, or when m=2, two $R_{10}$, together with the moiety to which they are directly attached, form a $C_{3-6}$ cycloalkyl or 3-6 membered heterocyclyl;

$R_{11}$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)$OR_{13}$, —$C_{0-4}$ alkyl-C(O)$R_{14}$, —$C_{0-4}$ alkyl-O—C(O)$R_{14}$, —$C_{0-4}$ alkyl-$NR_{15}R_{16}$, —$C_{0-4}$ alkyl-C (=$NR_{15}$)$R_{14}$, —$C_{0-4}$ alkyl-N($R_{15}$)—C(=$NR_{16}$)$R_{14}$, —$C_{0-4}$ alkyl-C(O)$NR_{15}R_{16}$ and —$C_{0-4}$ alkyl-N($R_{15}$)—C(O)$R_{14}$; and wherein, $R_{12}$, $R_{13}$, $R_{14}$, $R_{15}$, $R_{16}$, m, n and r are defined as those in the compound of formula (I).

As a preferred embodiment, in the compound of formula (I), the stereoisomer or pharmaceutically acceptable salt thereof, each $R_{12}$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{6-8}$ aryl, 5-8 membered heteroaryl and —$C_{0-4}$ alkyl-$NR_{15}R_{16}$, the above groups are optionally further substituted with one or more substituents selected from the group consisting of deuterium, halogen, hydroxy, oxo, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-4}$ alkyl-$NR_{15}R_{16}$;

each $R_{13}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl and 5-8 membered heteroaryl, the above groups are optionally further substituted with one or more substituents selected from the group consisting of deuterium, halogen, hydroxy, oxo, cyano. $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-4}$ alkyl-$NR_{15}R_{16}$;

each $R_{14}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-4}$ alkyl-$NR_{15}R_{16}$, the above groups are optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$C_{0-4}$ alkyl-$NR_{15}R_{16}$;

each of $R_{15}$ and $R_{16}$ is independently selected from the group consisting of hydrogen, deuterium, hydroxy, $C_{1-4}$ alkoxy, $C_{1-4}$ alkyl, $C_{2-4}$ alkenyl, $C_{2-4}$ alkynl, $C_{3-6}$ cycloalkyl, 3-6 membered heterocyclyl, $C_{6-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-4}$ alkylamino, di$C_{1-4}$ alkylamino and $C_{1-4}$ alkanoyl, the above groups are optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{1-4}$ alkanoyl, or, $R_{15}$ and $R_{16}$, together with the nitrogen atom to which they are directly attached, form a 5-8 membered heterocyclyl or 5-8 membered heteroaryl, the above groups are optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{1-4}$ alkanoyl.

As a preferred embodiment, in the compound of formula (I), the stereoisomer or pharmaceutically acceptable salt thereof, the compound of formula (I) is a compound of the following formula (II):

(II)

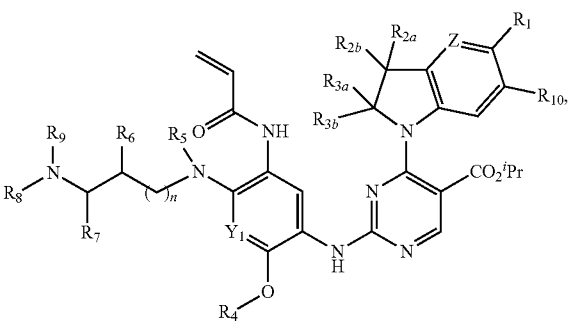

wherein, $Y_1$ is CH or N; Z is CH or N;

$R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —$S(O)_rR_{12}$, —O—$R_{13}$, —C(O)$OR_{13}$, —C(O)$R_{14}$, —O—C(O)$R_{14}$, —$NR_{15}R_{16}$, —C(=$NR_{15}$)$R_{14}$, —N($R_{15}$)—C(=$NR_{16}$)$R_{14}$, —C(O)$NR_{15}R_{16}$ and —N($R_{15}$)—C(O)$R_{14}$, or $R_1$ and $R_{10}$, together with the moiety to which they are directly attached, form a $C_{3-6}$ cycloalkyl or 3-6 membered heterocyclyl, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —C(O)$OR_{13}$, —C(O)$R_{14}$, —O—C(O)$R_{14}$, —$NR_{15}R_{16}$, —C(=$NR_{15}$)$R_{14}$, —N($R_{15}$)—C(=$NR_{16}$)$R_{14}$, —C(O)$NR_{15}R_{16}$ and —N($R_{15}$)—C(O)$R_{14}$;

$R_{2a}$ and $R_{2b}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl and 3-6 membered heterocyclyl, or $R_{2a}$ and $R_{2b}$, together with the carbon atom to which they are directly attached, form a $C_{3-6}$ cycloalkyl or 3-6 membered heterocyclyl, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —C(O)$OR_{13}$, —C(O)$R_{14}$, —O—C(O)$R_{14}$, —$NR_{13}R_{16}$, —C(=$NR_{15}$)$R_{14}$, —N($R_{15}$)—C(=$NR_{16}$)$R_{14}$, —C(O)$NR_{15}R_{16}$ and —N($R_{15}$)—C(O)$R_{14}$;

$R_{3a}$ and $R_{3b}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl and 3-6 membered heterocyclyl;

$R_4$ is selected from hydrogen, deuterium, $C_{1-4}$ alkyl, $C_{2-4}$ alkenyl, $C_{3-6}$ cycloalkyl and 3-6 membered heterocyclyl, the above groups are optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and $—NR_{15}R_{16}$;

$R_5$ is selected from the group consisting of hydrogen, deuterium, hydroxy, $C_{1-4}$ alkyl, $C_{1-4}$ haloalkyl, $C_{1-4}$ deuterioalkyl and $C_{3-6}$ cycloalkyl;

$R_6$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_{12}$, $—O—R_{13}$, $—C(O)OR_{13}$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$;

$R_7$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl. $C_{3-6}$ cycloalkyl, 3-6 membered heterocyclyl, $C_{6-8}$ aryl, 5-8 membered heteroaryl, $—SF_5$, $—S(O)_rR_{12}$, $—O—R_{13}$, $—C(O)OR_{13}$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$;

$R_8$ and $R_9$ are each independently selected from the group consisting of hydrogen, deuterium, hydroxy, $C_{1-4}$ alkyl, $C_{2-4}$ alkenyl, $C_{3-6}$ cycloalkyl and 3-6 membered heterocyclyl, or $R_8$ and $R_9$, together with the nitrogen atom to which they are directly attached, form a 3-6 membered heterocyclyl, the above group is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and $—C_{0-4}$ alkyl-$NR_{15}R_{16}$;

or, $R_5$ and one of $R_6$, $R_7$ and $R_9$, together with the moiety to which they are directly attached, form a 4-6 membered heterocyclyl, the other two of $R_6$, $R_7$ and $R_9$ are as previously defined, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $—SF_5$, $—S(O)_rR_{12}$, $—O—R_{13}$, $—C(O)OR_3$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$, or, $R_7$ and $R_8$ together with the moiety to which they are directly attached, form a 4-6 membered heterocyclyl, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-4}$ aryl, 5-8 membered heteroaryl, =O, $—SF_5$, $—S(O)_rR_2$, $—O—R_{13}$, $—C(O)OR_{13}$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$, or

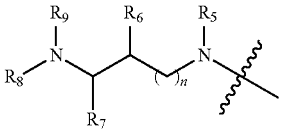

is a structure shown as follows:

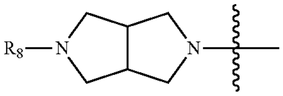

wherein $R_8$ is as previously defined;

$R_{10}$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—S(O)_rR_{12}$, $—O—R_{13}$, $—C(O)OR_{13}$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$;

wherein, $R_{12}$, $R_{13}$, $R_{14}$, $R_{15}$, $R_{16}$, n and r are defined as those in the compound of formula (I).

As a more further preferred embodiment, in the compound of formula (I), the stereoisomer or pharmaceutically acceptable salt thereof. $R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $—SF_5$, $—O—R_{13}$, $—O—C(O)R_{14}$ and $—NR_{15}R_{16}$, or $R_1$ and $R_{10}$, together with the moiety to which they are directly attached, form a $C_{3-6}$ cycloalkyl or 4-6 membered heterocyclyl, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, $—SF_5$, $—S(O)_rR_{12}$, $—O—R_{13}$, $—C(O)OR_{13}$, $—C(O)R_{14}$, $—O—C(O)R_{14}$, $—NR_{15}R_{16}$, $—C(=NR_{15})R_{14}$, $—N(R_{15})—C(=NR_{16})R_{14}$, $—C(O)NR_{15}R_{16}$ and $—N(R_{15})—C(O)R_{14}$;

$R_{2a}$ and $R_{2b}$ are each independently hydrogen, deuterium. $C_{1-4}$ alkyl or $C_{3-6}$ cycloalkyl, or $R_{2a}$ and $R_{2b}$, together with the carbon atom to which they are directly attached, form a $C_{3-6}$ cycloalkyl or 3-6 membered heterocyclyl, the above groups are optionally further substituted with one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl and $C_{3-6}$ cycloalkyl;

$R_{3a}$ and $R_{3b}$ are each independently selected from the group consisting of hydrogen, deuterium, halogen, $C_{1-4}$ alkyl and $C_{3-6}$ cycloalkyl;

$R_4$ is hydrogen, deuterium, $C_{1-4}$ alkyl or $C_{3-6}$ cycloalkyl, the above groups are optionally further substituted with one or more substituents selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{15}R_{16}$;

$R_5$ is selected from the group consisting of hydrogen, deuterium, hydroxy. $C_{1-4}$ alkyl, $C_{1-4}$ haloalkyl, $C_{1-4}$ deuterioalkyl and $C_{3-6}$ cycloalkyl;

$R_6$ is selected from the group consisting of hydrogen, deuterium, halogen, cyano, $C_{1-4}$ alkyl, $C_{1-4}$ haloalkyl, $C_{1-4}$ deuterioalkyl and $C_{3-6}$ cycloalkyl;

$R_7$ is selected from the group consisting of hydrogen, deuterium, halogen, cyano, $C_{1-4}$ alkyl, $C_{1-4}$ haloalkyl, $C_{1-4}$ deuterioalkyl and $C_{3-6}$ cycloalkyl;

$R_8$ and $R_9$ are each independently selected from the group consisting of hydrogen, deuterium, hydroxy, $C_{1-4}$ alkyl and $C_{3-6}$ cycloalkyl, or $R_8$ and $R_9$, together with the nitrogen atom to which they are directly attached, form a 3-6 membered heterocyclyl, the above group is optionally further substituted with one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl and —$NR_{15}R_{16}$;

or, $R_5$ and one of $R_6$, $R_7$ and $R_9$, together with the moiety to which they are directly attached, form a 4-6 membered heterocyclyl, the other two of $R_6$, $R_7$ and $R_9$ are as previously defined, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl and $C_{3-6}$ cycloalkyl, or, $R_7$ and $R_8$, together with the moiety to which they are directly attached, form a 4-6 membered heterocyclyl, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynl and $C_{3-6}$ cycloalkyl, or

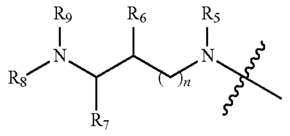

is a structure shown as follows:

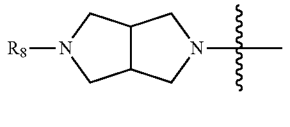

wherein $R_8$ is as previously defined:

$R_{10}$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl and $C_{3-6}$ cycloalkyl;

wherein, $R_{12}$, $R_{13}$, $R_{14}$, $R_{15}$, $R_{16}$, n and r are defined as those in the compound of formula (II).

As a more further preferred embodiment, in the compound of formula (I), the stereoisomer or pharmaceutically acceptable salt thereof, each $R_1$ is independently selected from the group consisting of hydrogen, deuterium, fluoro, chloro, bromo, cyano, methyl, ethyl, isopropyl, vinyl, ethynyl, cyclopropyl, cyclobutyl, oxacyclobutyl, azacyclobutyl, pyrazolyl, imidazolyl, oxazolyl, triazolyl, methoxy, amino, dimethylamino and methylamino, or $R_1$ and $R_{10}$, together with the moiety to which they are directly attached, form a cyclopentyl, the above group is optionally further substituted with one or more substituents selected from the group consisting of deuterium, fluoro, chloro, bromo, cyano, methyl, ethyl, isopropyl, vinyl, ethynyl, trifluoromethyl, difluoromethyl, trideuteriomethyl, dideuteriomethyl, cyclopropyl and cyclobutyl;

$R_{10}$ is selected from the group consisting of hydrogen, deuterium, fluoro, chloro, bromo, cyano, methyl, ethyl, isopropyl, trifluoromethyl, difluoromethyl, trideuteriomethyl, dideuteriomethyl, vinyl, ethynyl, cyclopropyl and cyclobutyl.

As a more further preferred embodiment, in the compound of formula (I), the stereoisomer or pharmaceutically acceptable salt thereof, $R_4$ is selected from the group consisting of hydrogen, deuterium, methyl, ethyl, isopropyl, cyclopropyl and cyclobutyl, the above groups are optionally further substituted with one or more substituents selected from deuterium, fluoro, $C_{1-4}$ alkyl and $C_{3-6}$ cycloalkyl.

As a more further preferred embodiment, in the compound of formula (I), the stereoisomer or pharmaceutically acceptable salt thereof, $R_{2a}$ and $R_{2b}$ are each independently selected from the group consisting of hydrogen, deuterium, methyl, ethyl, isopropyl, cyclopropyl and cyclobutyl, or $R_{2a}$ and $R_{2b}$, together with the carbon atom to which they are directly attached, form a cyclopropyl, cyclobutyl or cyclopentyl, the above groups are optionally further substituted with one or more substituents selected from the group consisting of deuterium, fluoro, chloro, bromo, cyano, methyl, ethyl, isopropyl, trifluoromethyl, difluoromethyl, trideuteriomethyl, dideuteriomethyl, cyclopropyl and cyclobutyl.

As a more further preferred embodiment, in the compound of formula (I), the stereoisomer or pharmaceutically acceptable salt thereof, $R_{3a}$ and $R_{3b}$ are each independently selected from the group consisting of hydrogen, deuterium, methyl, ethyl, isopropyl, cyclopropyl and cyclobutyl.

As a more further preferred embodiment, in the compound of formula (I), the stereoisomer or pharmaceutically acceptable salt thereof, $R_5$ is selected from the group consisting of hydrogen, deuterium, methyl, ethyl, isopropyl, trifluoromethyl, difluoromethyl, trideuteriomethyl, dideuteriomethyl, cyclopropyl and cyclobutyl;

$R_6$ is selected from the group consisting of hydrogen, deuterium, methyl, ethyl, isopropyl, trifluoromethyl, difluoromethyl, trideuteriomethyl, dideuteriomethyl, cyclopropyl and cyclobutyl;

$R_7$ is selected from the group consisting of hydrogen, deuterium, methyl, ethyl, isopropyl, trifluoromethyl, difluoromethyl, trideuteriomethyl, dideuteriomethyl, cyclopropyl and cyclobutyl;

$R_8$ and $R_9$ are each independently selected from the group consisting of hydrogen, deuterium, methyl, ethyl, isopropyl, trifluoromethyl, difluoromethyl, trideuteriomethyl, dideuteriomethyl, cyclopropyl and cyclobutyl, or $R_8$ and $R_9$, together with the nitrogen atom to which they are directly attached, form a 4-6 membered heterocyclyl;

or, $R_5$ and one of $R_6$, $R_7$ and $R_9$, together with the moiety to which they are directly attached, form a 4-6 membered heterocyclyl, the other two of $R_6$, $R_7$ and $R_9$ are as previously defined, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl and $C_{3-6}$ cycloalkyl, or, $R_7$ and $R_8$, together with the moiety to which they are directly attached, form a 4-6 membered heterocyclyl, the 4-6 membered heterocyclyl is optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl and $C_{3-6}$ cycloalkyl, or

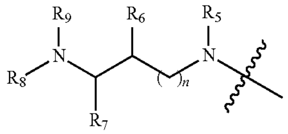

is a structure shown as follows:

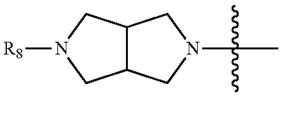

wherein $R_8$ is as previously defined.

As a still more further preferred embodiment, in the compound of formula (I), the stereoisomer or pharmaceutically acceptable salt thereof,

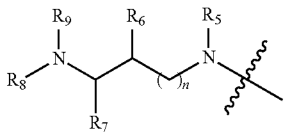

is selected from the group consisting of the structures shown as follows:

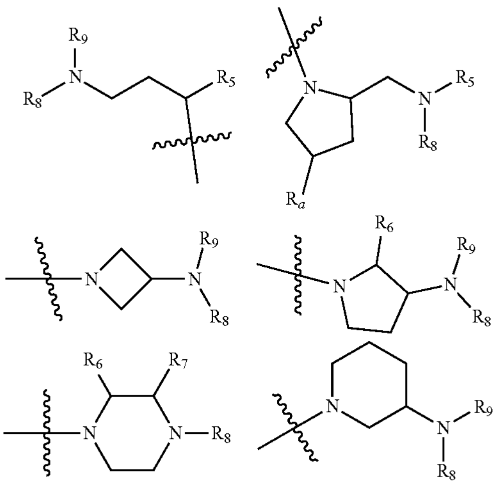

-continued

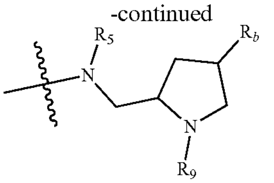

and

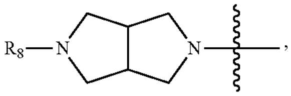

, wherein, each $R_5$ is independently selected from the group consisting of hydrogen, deuterium, methyl, ethyl, trideuteriomethyl and dideuteriomethyl;

each $R_6$ is independently selected from the group consisting of hydrogen, deuterium, methyl, ethyl, isopropyl, trifluoromethyl, difluoromethyl, trideuteriomethyl, dideuteriomethyl, cyclopropyl and cyclobutyl;

$R_7$ is selected from the group consisting of hydrogen, deuterium, halogen, cyano, $C_{1-4}$ alkyl, $C_{1-4}$ haloalkyl, $C_{1-4}$ deuterioalkyl and $C_{3-6}$ cycloalkyl, each of $R_8$ and $R_9$ is independently selected from the group consisting of hydrogen, deuterium, methyl, ethyl, isopropyl, trifluoromethyl, difluoromethyl, trideuteriomethyl, dideuteriomethyl, cyclopropyl and cyclobutyl, or $R_8$ and $R_9$, together with the nitrogen atom to which they are directly attached, form a 4-6 membered heterocyclyl;

$R_a$ is selected from the group consisting of hydrogen, deuterium, halogen, cyano, $C_{1-4}$ alkyl, $C_{1-4}$ haloalkyl, $C_{1-4}$ deuterioalkyl and $C_{3-6}$ cycloalkyl;

$R_b$ is selected from the group consisting of hydrogen, deuterium, halogen, cyano, $C_{1-4}$ alkyl, $C_{1-4}$ haloalkyl, $C_{1-4}$ deuterioalkyl and $C_{3-6}$ cycloalkyl.

As the most preferred embodiment, the compound of formula (I), the stereoisomer or pharmaceutically acceptable salt thereof include, but are not limited to, the following compounds:

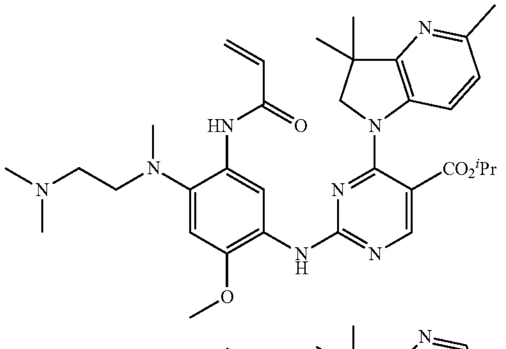

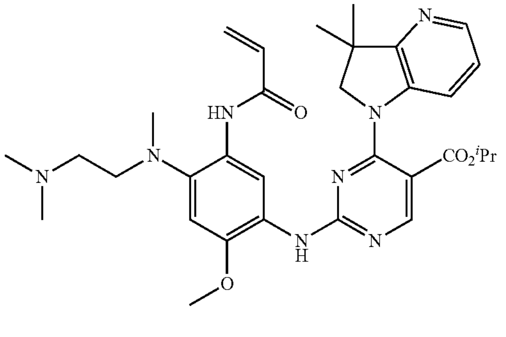

-continued
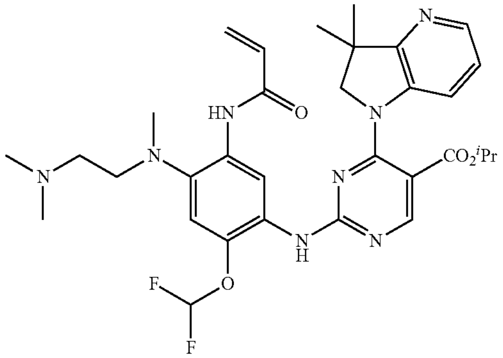
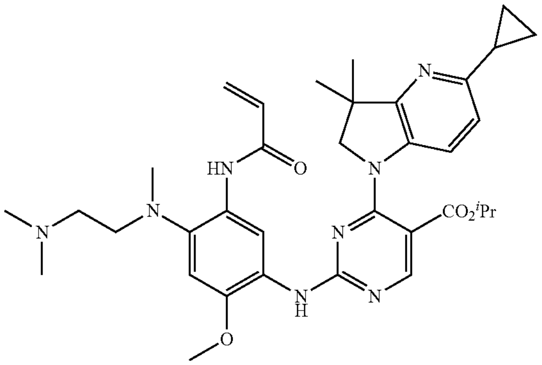
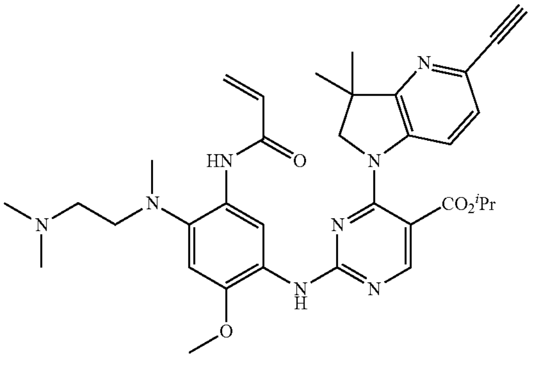
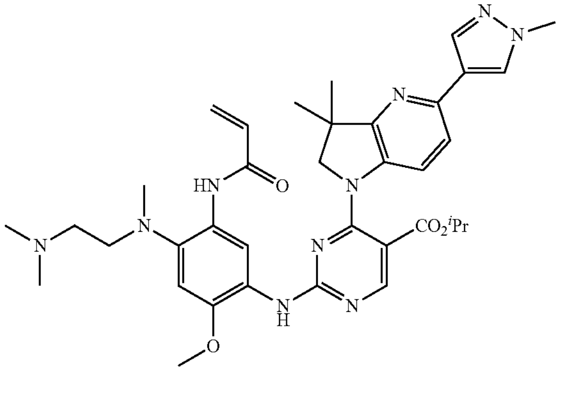
-continued
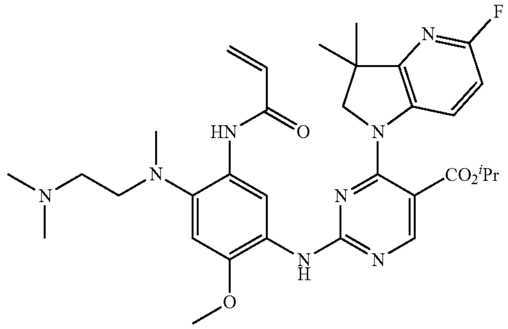
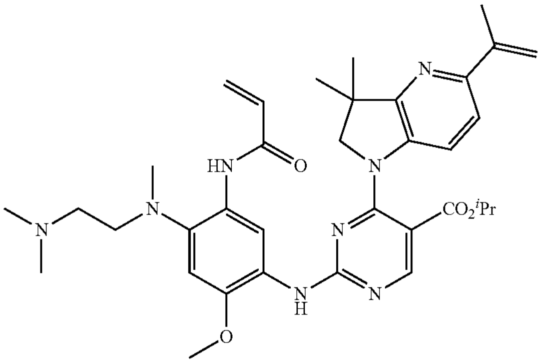
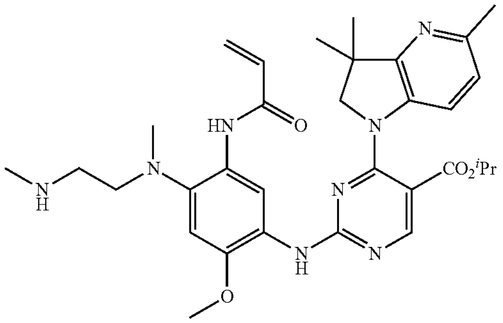
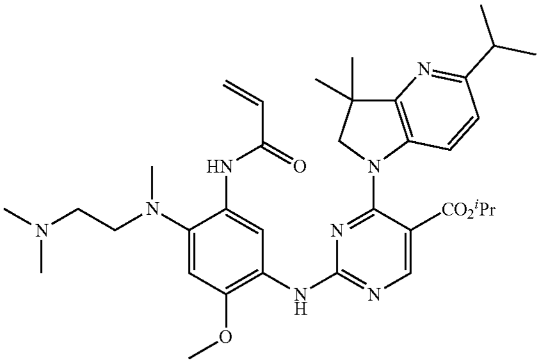
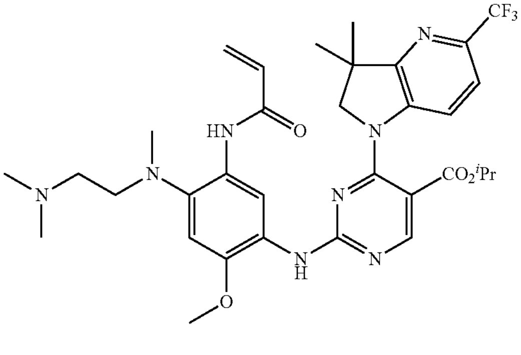

-continued
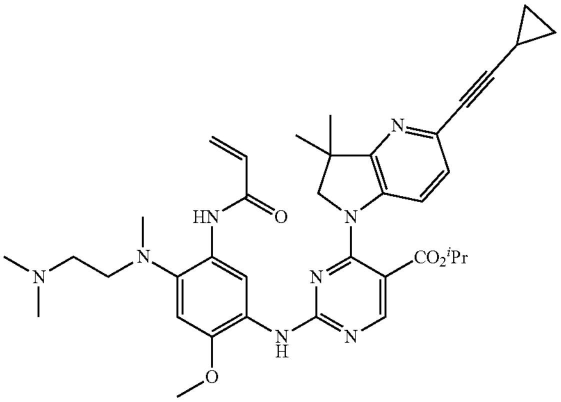
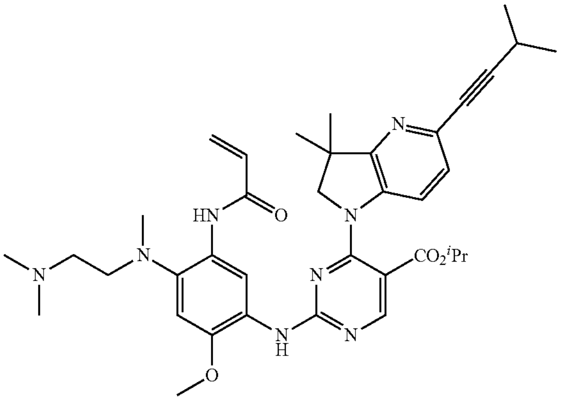
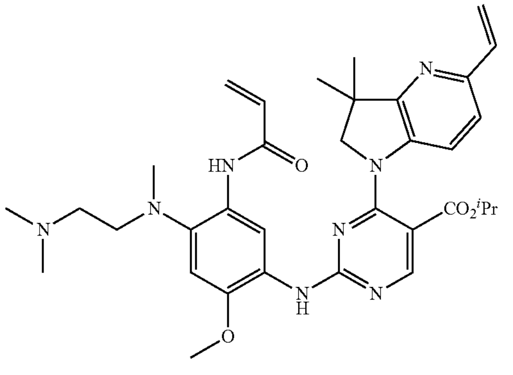
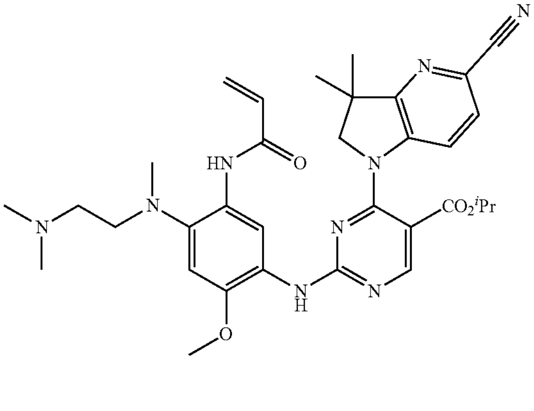
-continued
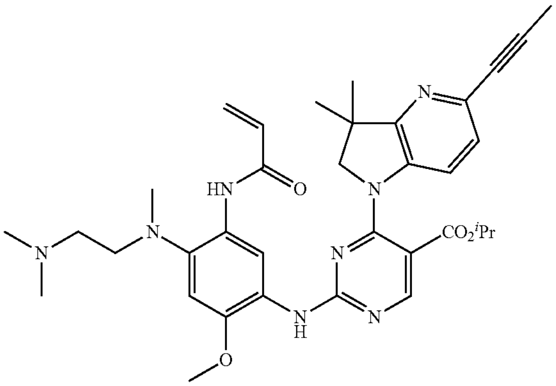
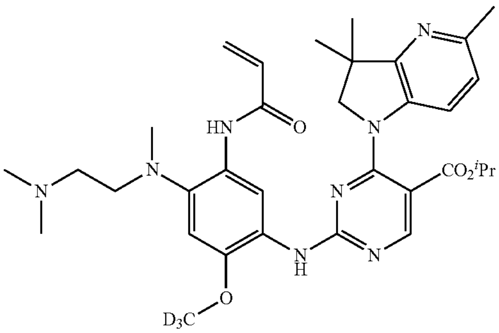
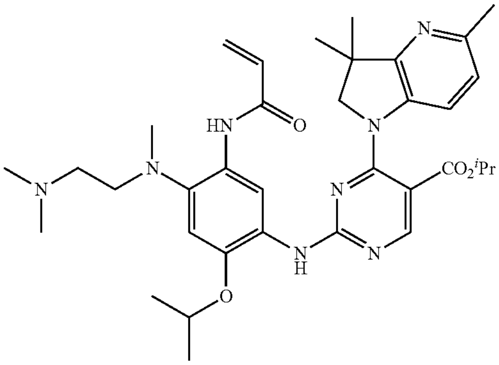
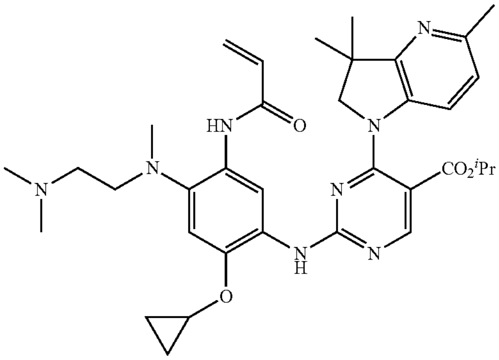

-continued
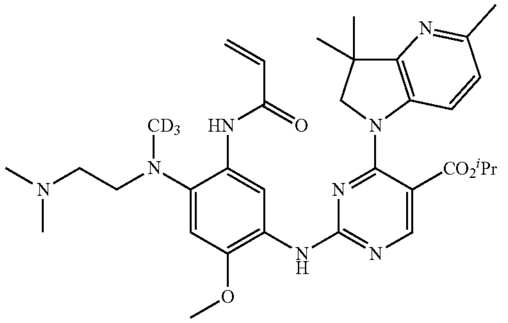
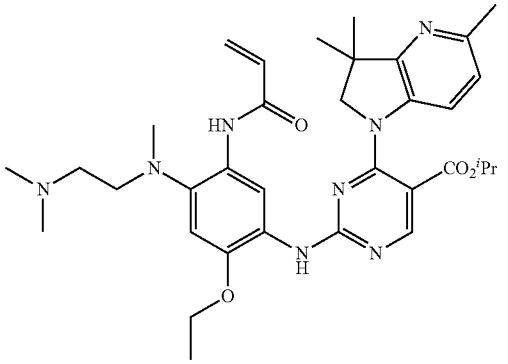
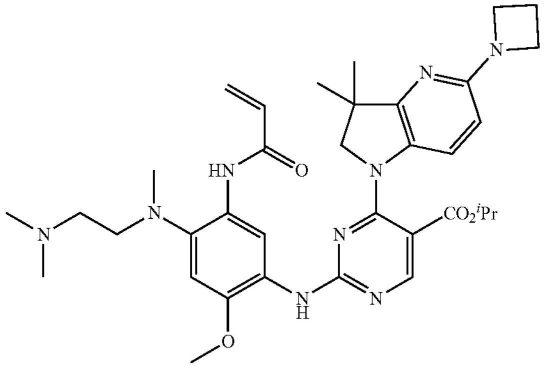
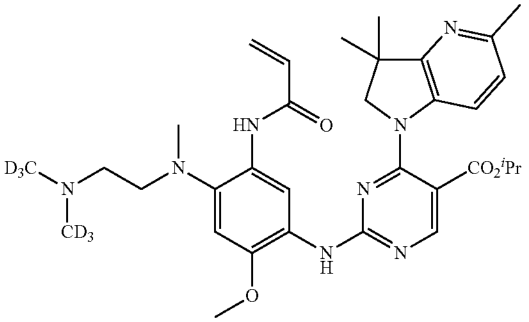
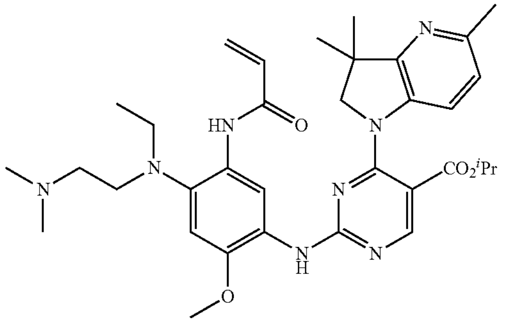
-continued
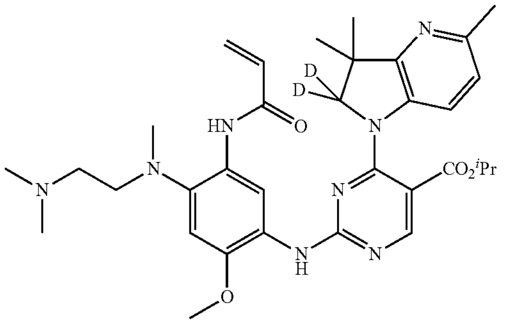
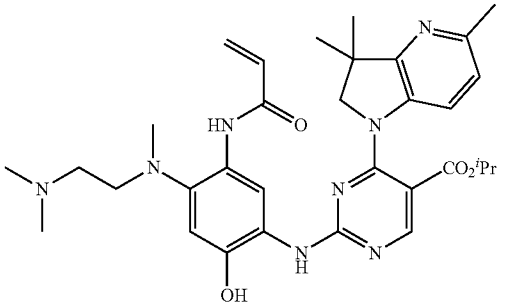
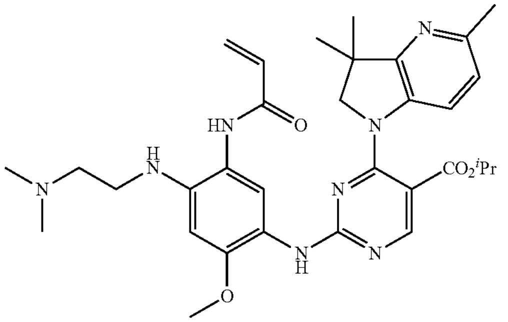
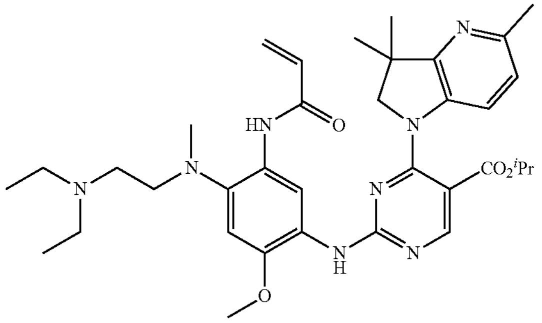
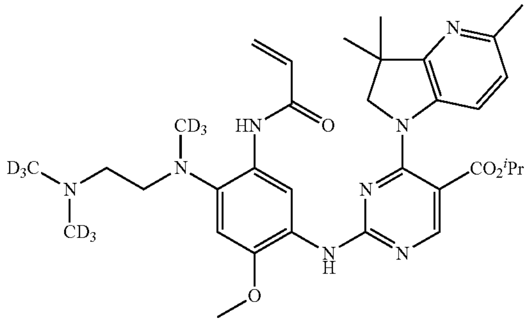

-continued
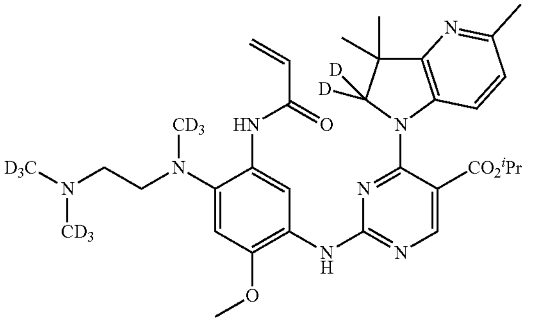
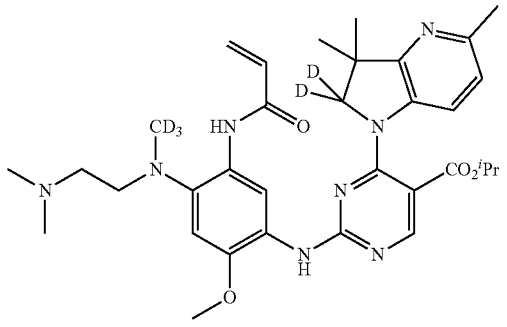
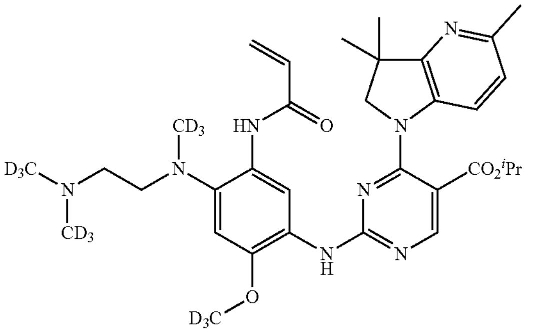
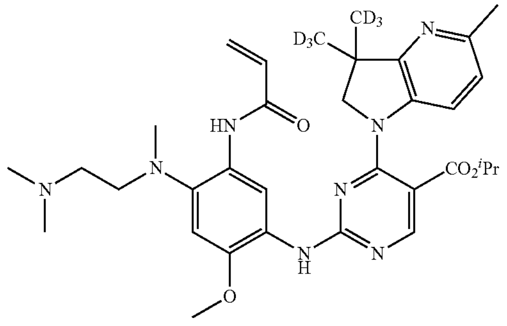
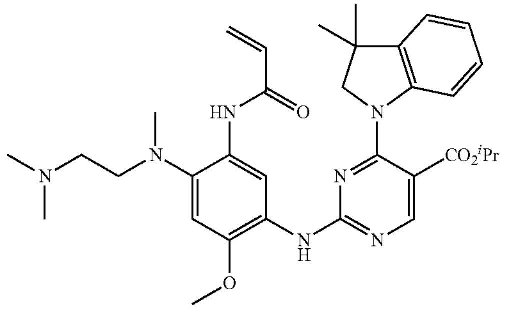
-continued
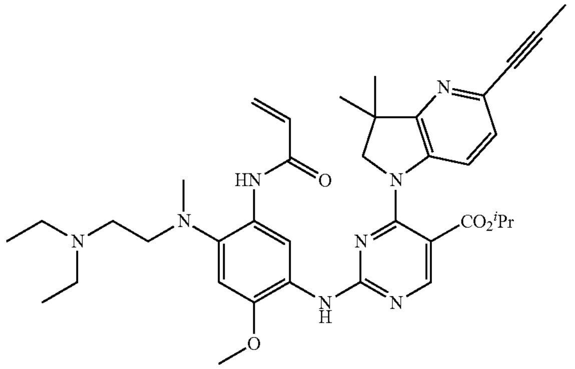
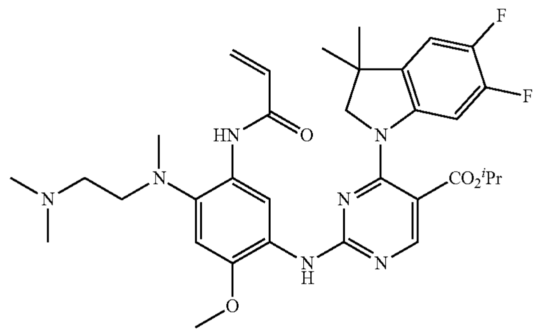
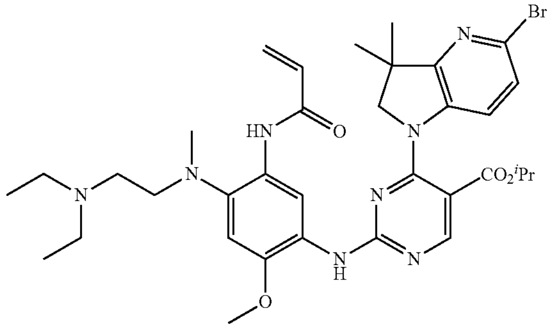
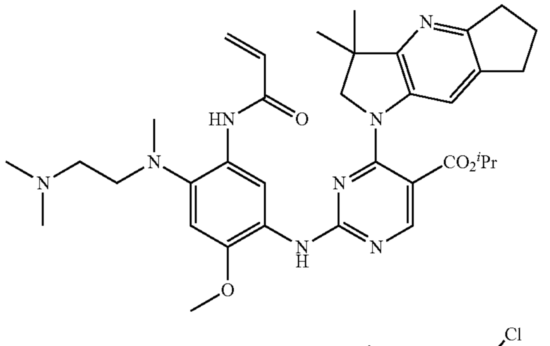
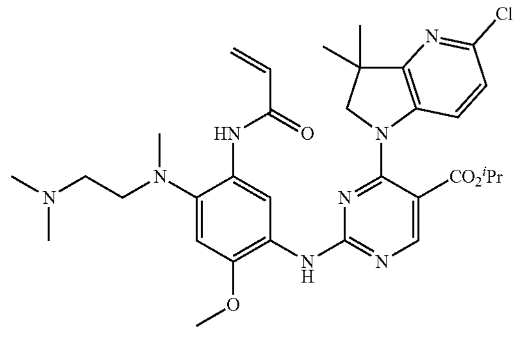

-continued
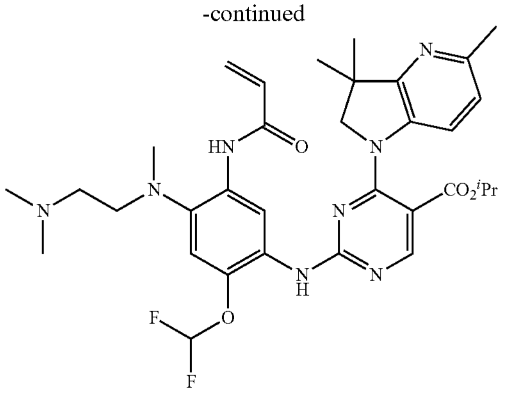
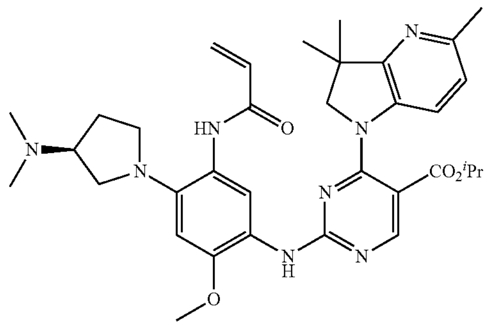
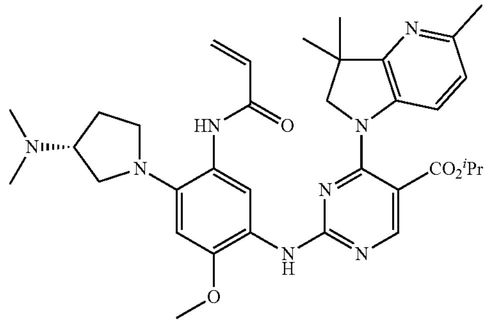
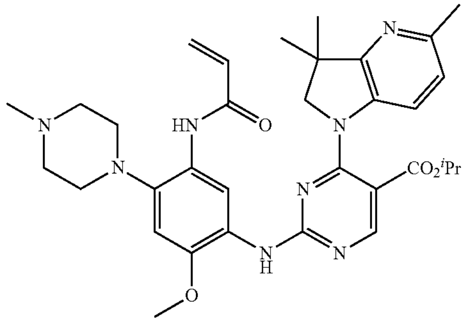
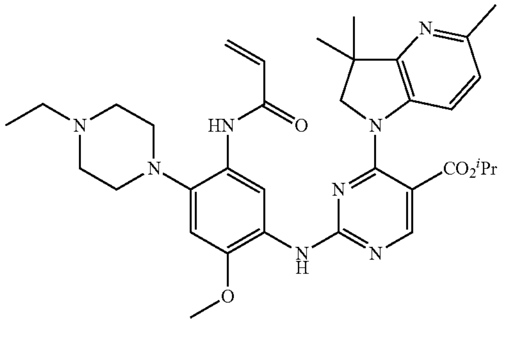
-continued
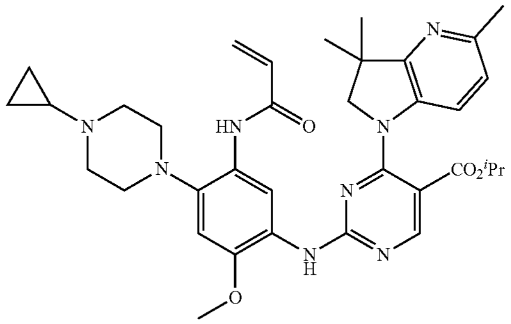
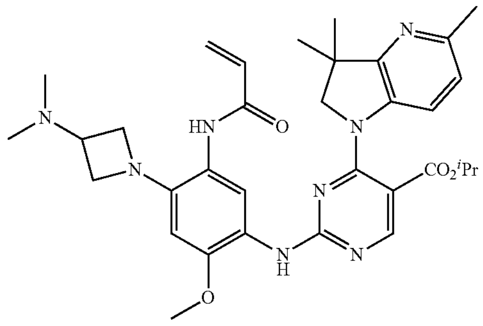
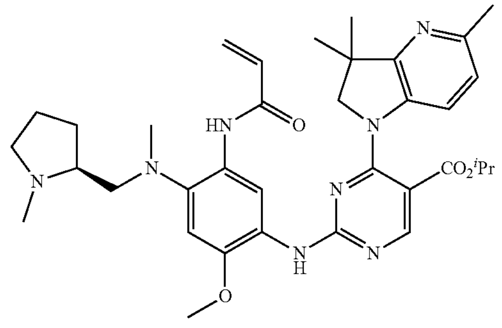
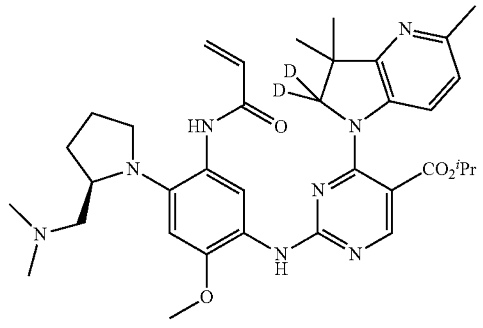
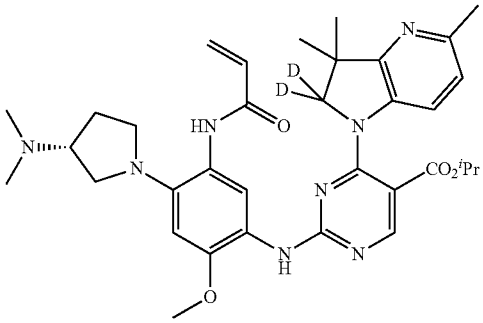

-continued
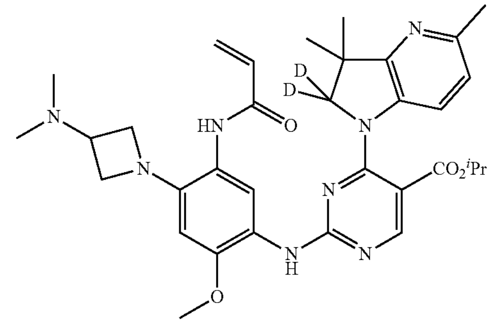
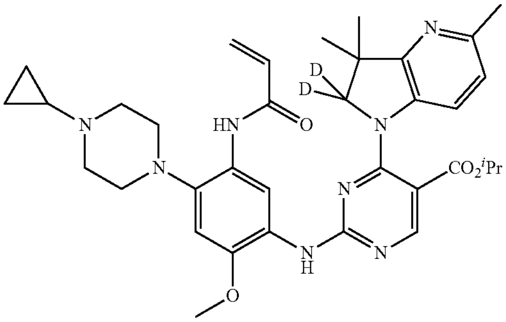
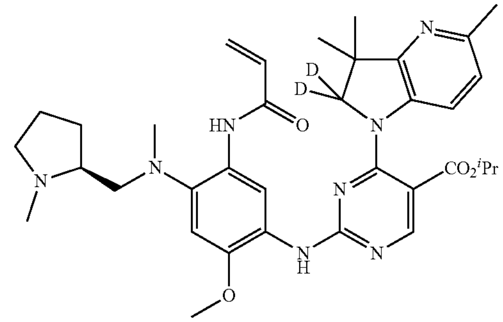
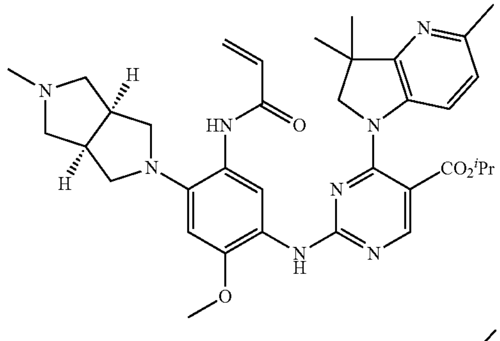
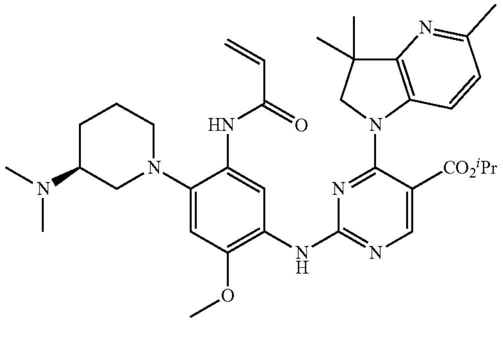
-continued
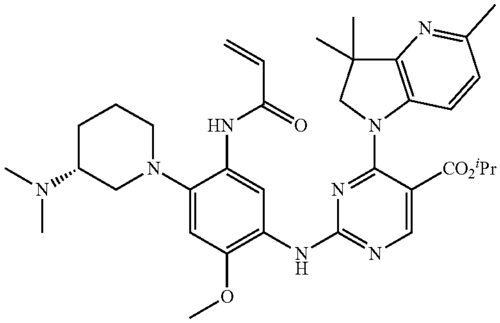
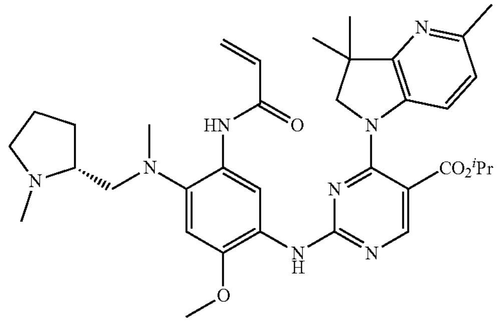
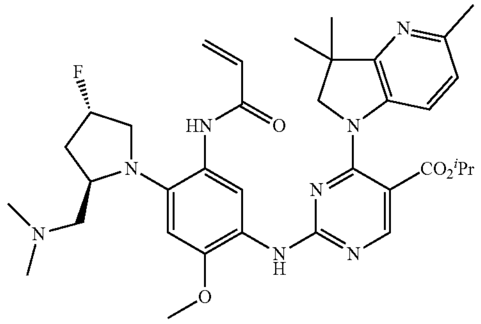
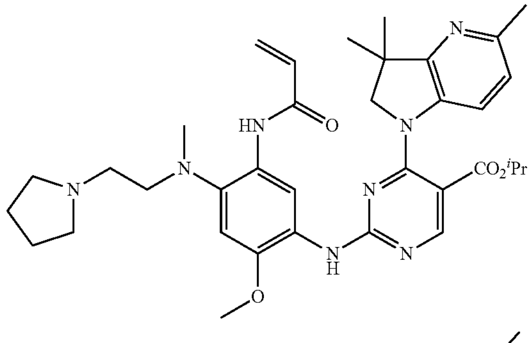
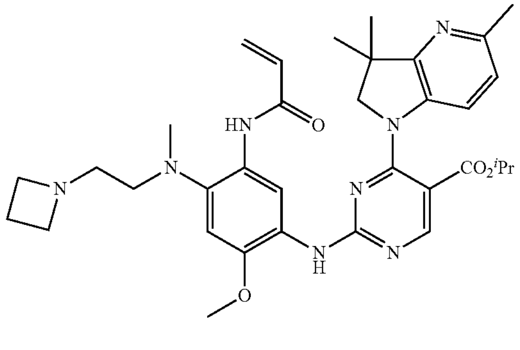

-continued
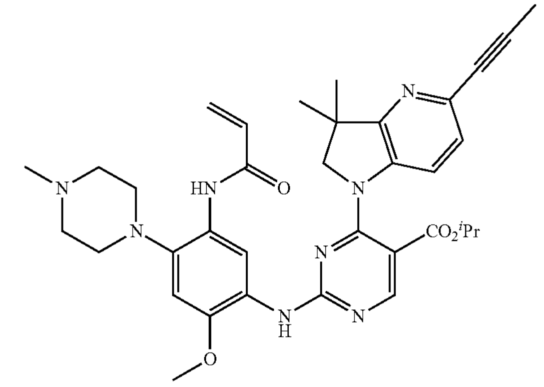
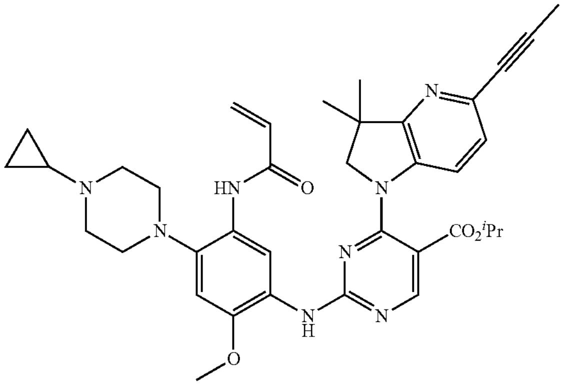
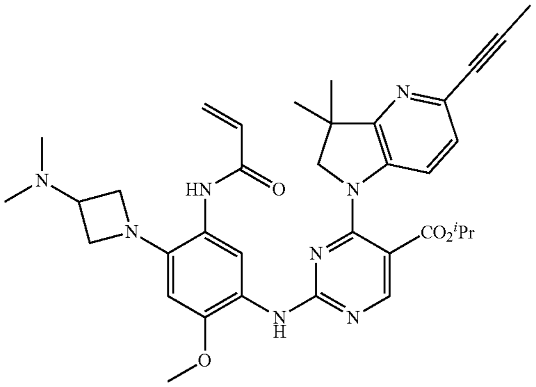
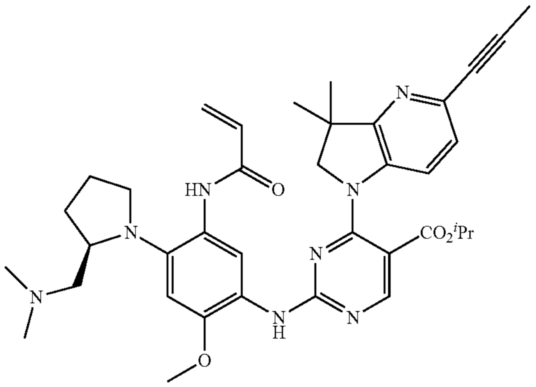
-continued
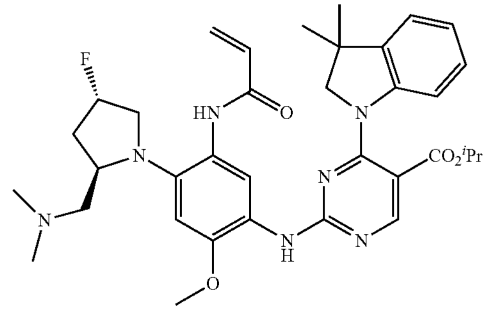
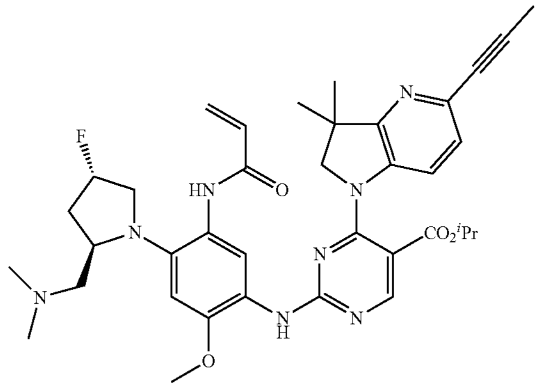
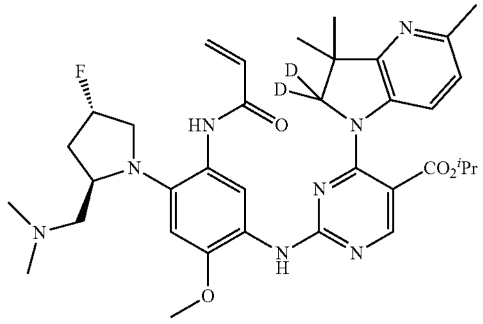
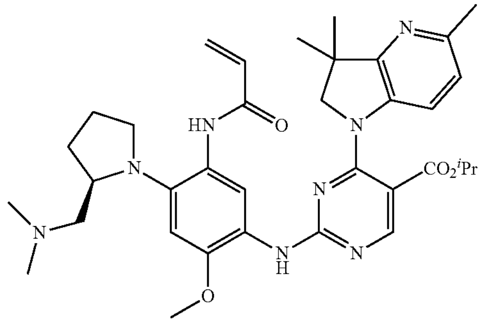
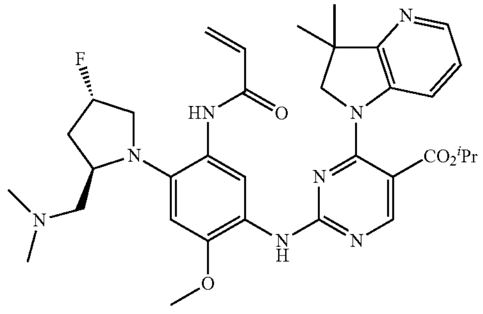

-continued
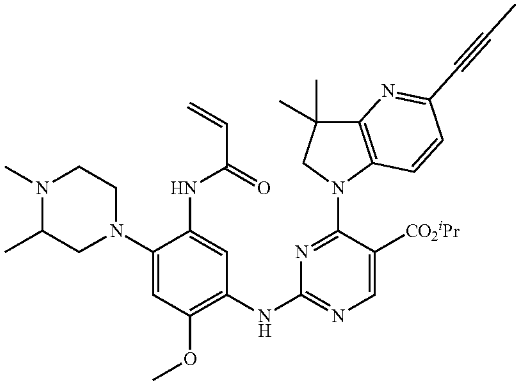
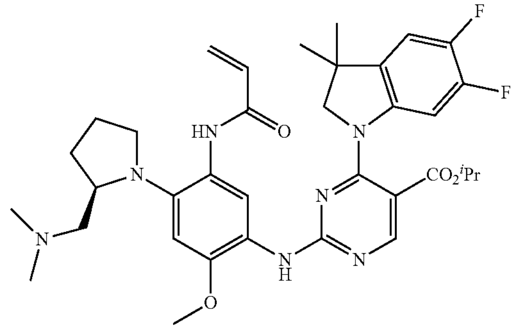
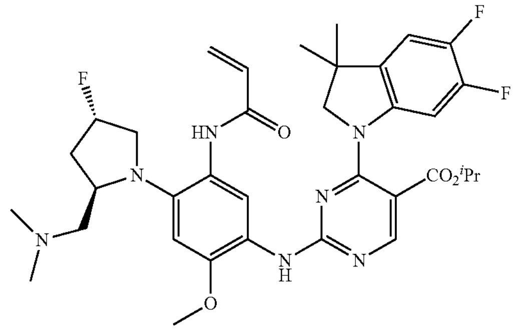
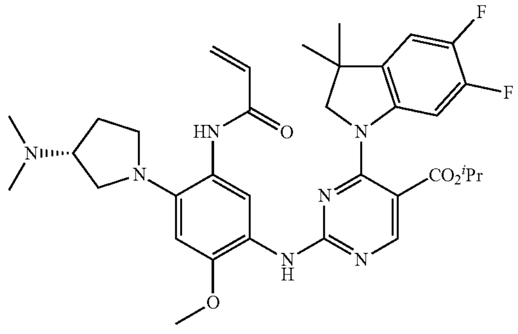
-continued
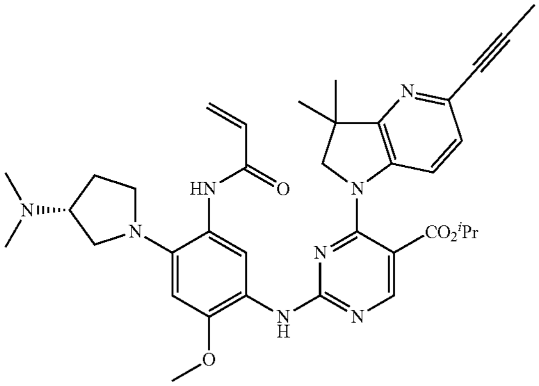
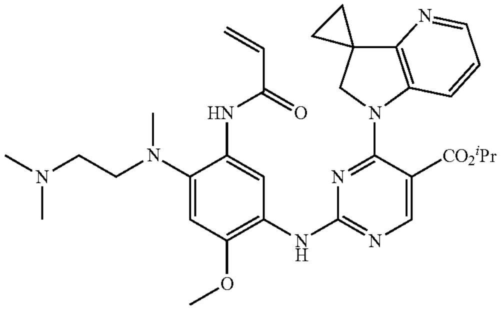
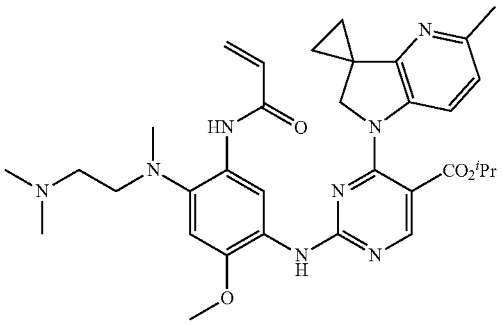
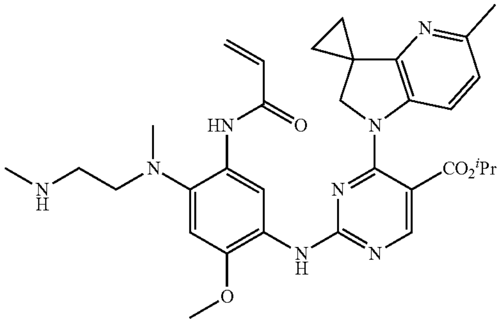
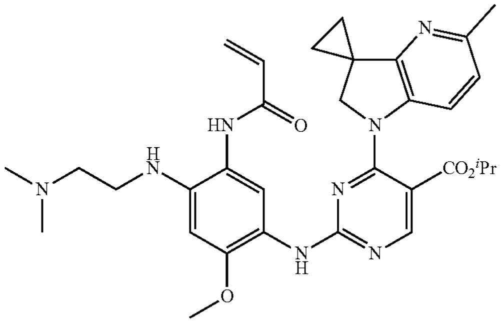

-continued
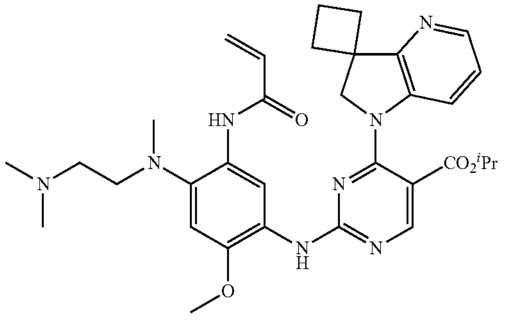
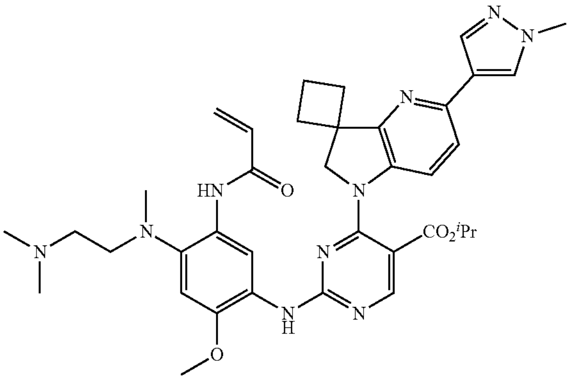
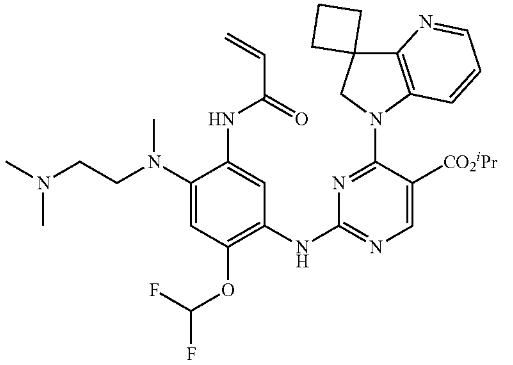
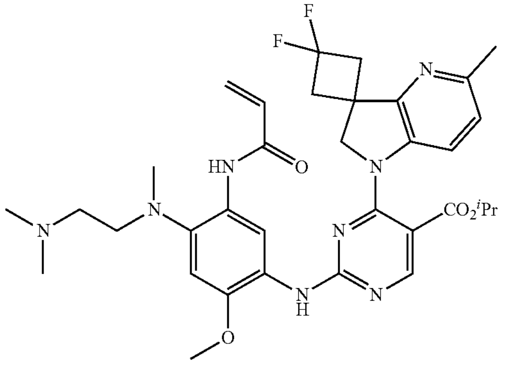
-continued
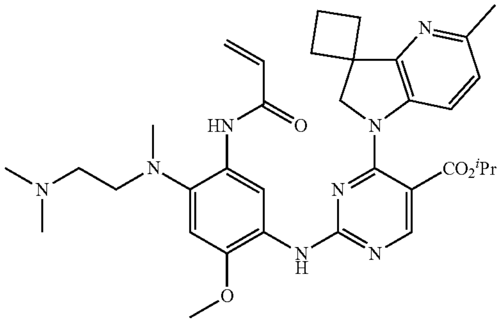
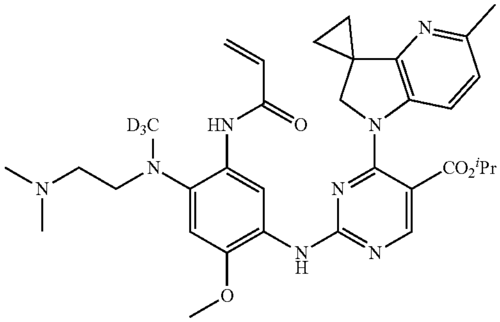
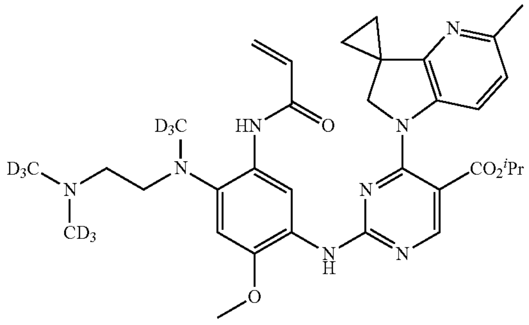
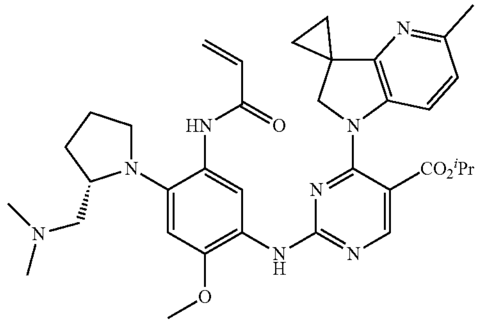
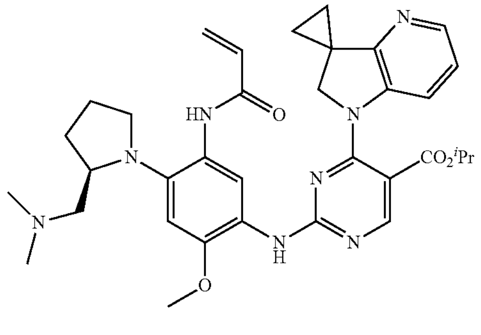

-continued
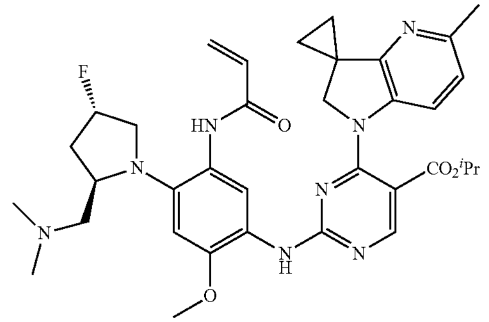
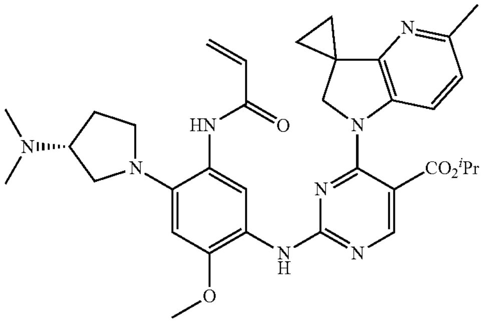
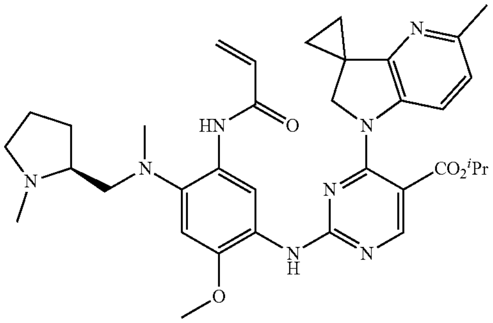
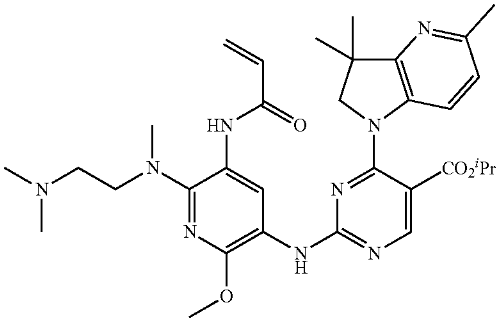
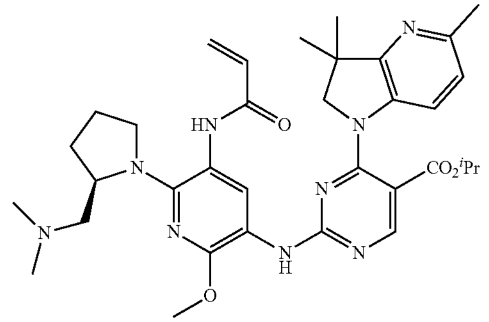
-continued
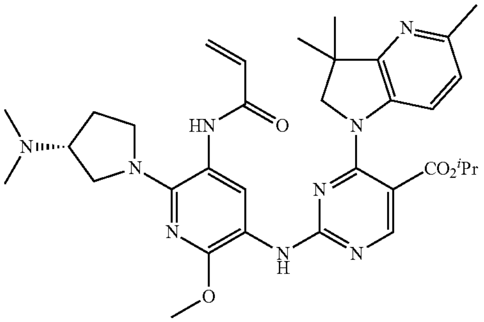
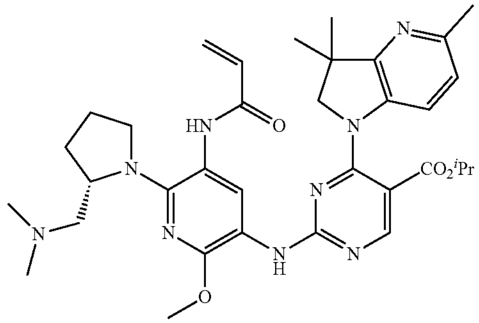
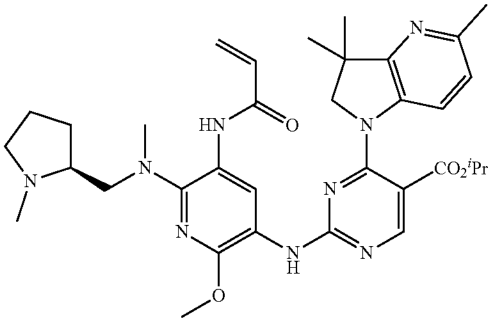
and
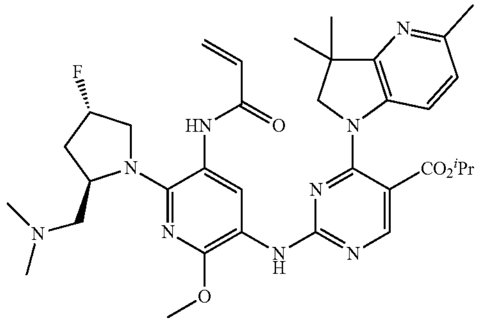
.
The second aspect of the present invention provides a preparation method for the compound of formula (I), the stereoisomer or pharmaceutically acceptable salt thereof, comprising the following step:

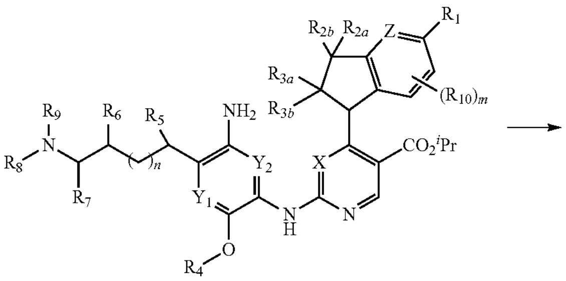

(Ia)

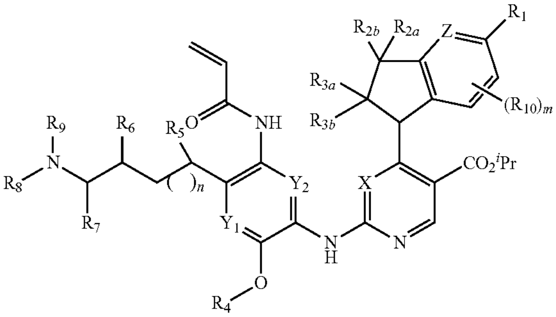

(I)

wherein, X, $Y_1$, $Y_2$, Z, $R_1$, $R_{2a}$, $R_{2b}$, $R_{3a}$, $R_{3b}$, $R_4$, $R_5$, $R_6$, $R_7$, $R_8$, $R_9$, $R_{10}$, m and n are defined as those in the compound of formula (I).

The third aspect of the present invention provides a pharmaceutical composition, which comprises the compound of formula (I), the stereoisomer or pharmaceutically acceptable salt thereof, and a pharmaceutically acceptable carrier.

The present invention also relates to use of the compound of formula (I), the stereoisomer or pharmaceutically acceptable salt thereof in preparation of a medicament for treating and/or preventing cancer, tumor or metastatic disease at least partially related to an insertion, deletion or other mutation of EGFR Exon 20.

The present invention also relates to use of the compound of formula (I), the stereoisomer or pharmaceutically acceptable salt thereof in preparation of a medicament for preventing and/or treating tumor, cancer and/or metastatic disease caused by hyperproliferation and dysfunction in cell death induction.

The present invention also relates to use of the compound of formula (I), the stereoisomer or pharmaceutically acceptable salt thereof described above in preparation of a medicament for preventing and/or treating lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma, which are at least partially related to an insertion, deletion or other mutation of EGFR Exon 20.

The present invention also relates to the compound of formula (I), the stereoisomer or pharmaceutically acceptable salt thereof for use as a medicament.

The present invention also relates to the compound of formula (I), the stereoisomer or pharmaceutically acceptable salt thereof for use in the treatment and/or prevention of cancer, tumor or metastatic disease at least partially related to an insertion, deletion or other mutation of EGFR Exon 20.

The present invention also relates to the compound of formula (I), the stereoisomer or pharmaceutically acceptable salt thereof for use in the prevention and/or treatment of tumor, cancer and/or metastatic disease caused by hyperproliferation and dysfunction in cell death induction.

The present invention also relates to the compound of formula (I), the stereoisomer or pharmaceutically acceptable salt thereof for use in the treatment and/or prevention of lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma, which are at least partially related to an insertion, deletion or other mutation of EGFR Exon 20.

The present invention also relates to a method for treating and/or preventing cancer, tumor or metastatic disease at least partially related to an insertion, deletion or other mutation of EGFR Exon 20, which comprises administering to a patient in need thereof a therapeutically effective amount of the compound of formula (I), the stereoisomer or pharmaceutically acceptable salt thereof.

The present invention also relates to a method for preventing and/or treating tumor, cancer and/or metastatic disease caused by hyperproliferation and dysfunction in cell death induction, which comprises administering to a patient in need thereof a therapeutically effective amount of the compound of formula (I), the stereoisomer or pharmaceutically acceptable salt thereof.

The present invention also relates to a method for treating and/or preventing lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma, which are at least partially related to an insertion, deletion or other mutation of EGFR Exon 20, which comprises administering to a patient in need thereof a therapeutically effective amount of the compound of formula (I), the stereoisomer or pharmaceutically acceptable salt thereof.

DETAILED DESCRIPTION OF THE INVENTION

After an extensive and intensive research, the inventors of the present application have developed, for the first time, a pyrimidine or pyridine derivative with a structure shown as formula (I) below. A series of compounds of the present invention can be widely applied to the preparation of medicaments for treating and/or preventing cancer, tumor or metastatic disease at least partially related to an insertion, deletion or other mutation of EGFR Exon 20, particularly medicaments for treating hyperproliferative disease and disease of dysfunction in cell death induction, so that a new generation of EGFR inhibitors is expected to be developed. The present invention is achieved on this basis.

Detailed description: unless otherwise stated or specified, the following terms used in the specification and claims have the following meanings.

"Alkyl" refers to linear or branched saturated aliphatic alkyl groups, preferably linear alkyl or branched alkyl containing 1 to 10, 1 to 6 or 1 to 4 carbon atoms, including but not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, and the like. "$C_{1-10}$ alkyl" refers to linear alkyl and branched alkyl containing 1 to 10 carbon atoms, "$C_{1-4}$ alkyl" refers to linear alkyl and branched alkyl containing 1 to 4 carbon atoms, "$C_{0-8}$ alkyl" refers to linear alkyl and branched alkyl containing 0 to 8 carbon atoms, and "$C_{0-4}$ alkyl" refers to linear alkyl and branched alkyl containing 0 to 4 carbon atoms.

Alkyl may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{6-10}$ haloalkyl, $C_{6-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Cycloalkyl" or "carbocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; cycloalkyl is classified into monocyclic cycloalkyl and polycyclic cycloalkyl, and is preferably cycloalkyl containing 3 to 12, 3 to 8, or 3 to 6 carbon atoms. For example. "$C_{3-12}$ cycloalkyl" refers to cycloalkyl containing 3 to 12 carbon atoms, and "$C_{3-6}$ cycloalkyl" refers to cycloalkyl containing 3 to 6 carbon atoms, wherein monocyclic cycloalkyl includes, but is not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl and the like;

polycyclic cycloalkyl includes spirocycloalkyl, fused cycloalkyl and bridged cycloalkyl. "Spirocycloalkyl" refers to a polycyclic group in which a carbon atom (called a spiro-atom) is shared among monocyclic rings, wherein those rings may contain one or more (preferably, 1, 2 or 3) double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

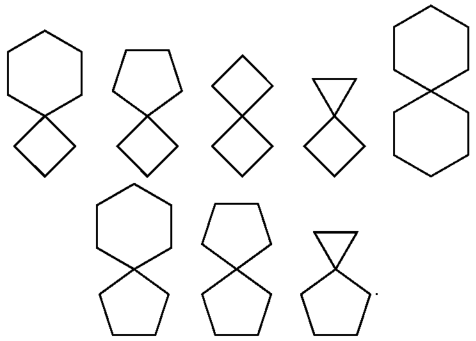

"Fused cycloalkyl" refers to an all-carbon polycyclic group in which each ring shares a pair of adjacent carbon atoms with the other rings in the system, wherein one or more of the rings may contain one or more (preferably, 1, 2 or 3) double bonds, but none of them has a fully conjugated π-electron system. According to the number of formed rings, the fused cycloalkyl may be bicyclic, tricyclic, tetracyclic or polycyclic, including but not limited to:

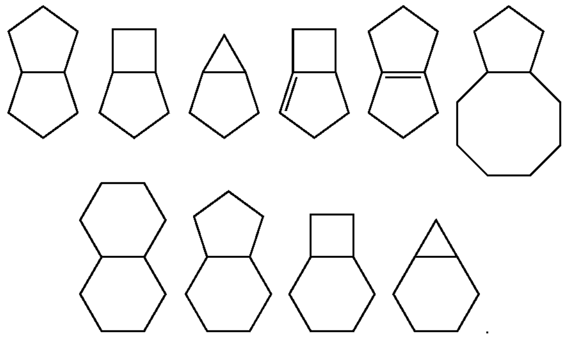

"Bridged cycloalkyl" refers to an all-carbon polycyclic group in which any two rings share two carbon atoms that are not directly connected to each other, wherein these rings may contain one or more (preferably, 1, 2 or 3) double bonds, but none of them has a fully conjugated π-electron system. According to the number of formed rings, the bridged cycloalkyl may be bicyclic, tricyclic, tetracyclic or polycyclic, including but not limited to:

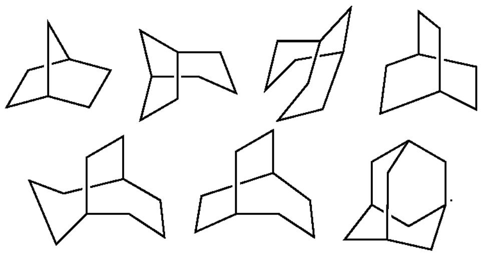

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl and the like.

Cycloalkyl may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r$-$R_{12}$, —$C_{0-8}$ alkyl-O—$R_{13}$, —$C_{0-8}$ alkyl-C(O)O$R_{13}$, —$C_{0-8}$ alkyl-C(O)$R_{14}$, —$C_{0-8}$ alkyl-O—C(O)$R_{14}$, —$C_{0-8}$ alkyl-N$R_{15}R_{16}$, —$C_{0-8}$ alkyl-C(=N$R_{15}$)$R_{14}$, —$C_{0-8}$ alkyl-N($R_{15}$)—C(=N$R_{16}$)$R_{14}$, —$C_{0-8}$ alkyl-C(O)N$R_{15}R_{16}$ and —$C_{0-8}$ alkyl-N($R_{15}$)—C(O)$R_{14}$.

"Heterocyclyl" or "heterocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; in heterocyclyl, one or more (preferably 1, 2, 3 or 4) ring atoms are heteroatoms selected from nitrogen, oxygen, S(O)(=NH) and S(O) (where r is an integer of 0, 1 or 2), excluding ring moiety of —O—O—, —O—S— or —S—S—, and the remaining ring atoms are carbon atoms. Preferably, heterocyclyl is one containing 3 to 12, 3 to 8, 3 to 6, or 5 to 6 ring atoms; for example, "3-6 membered heterocyclyl" refers to a cyclic group containing 3 to 6 ring atoms, "3-12 membered heterocyclyl" refers to a cyclic group containing 3 to 12 ring atoms, "5 membered heterocyclyl" refers to a cyclic group containing 5 ring atoms, "5-8 membered heterocyclyl" refers to a cyclic group containing 5 to 8 ring atoms, and "5-10 membered heterocyclyl" refers to a cyclic group containing 5 to 10 ring atoms.

Monocyclic heterocyclyl includes, but is not limited to, pyrrolidinyl, piperidinyl, piperazinyl, morpholinyl, thiomorpholinyl, homopiperazinyl and the like.

Polycyclic heterocyclyl includes spiroheterocyclyl, fused heterocyclyl, and bridged heterocyclyl. "Spiroheterocyclyl" refers to a polycyclic heterocyclyl group in which an atom (called a spiro-atom) is shared among monocyclic rings, wherein one or more (preferably 1, 2, 3 or 4) ring atoms are heteroatoms selected from nitrogen, oxygen, S(O)(=NH) and S(O) (wherein r is an integer of 0, 1 or 2), and the remaining ring atoms are carbon atoms. These rings may contain one or more (preferably, 1, 2 or 3) double bonds, but none of them has a fully conjugated π-electron system. According to the number of spiro-atoms shared among the rings, the spiroheterocyclyl may be monospiroheterocyclyl, bispiroheterocyclyl or polyspiroheterocyclyl. Spiroheterocyclyl includes, but is not limited to:

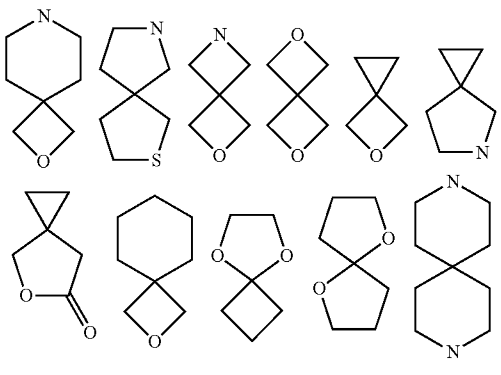

-continued

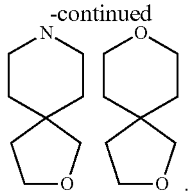

"Fused heterocyclyl" refers to a polycyclic heterocyclyl group in which each ring shares a pair of adjacent atoms with the other rings in the system, wherein one or more (preferably, 1, 2, 3 or 4) of the rings may contain one or more (preferably, 1, 2 or 3) double bonds, but none of them has a fully conjugated π-electron system, wherein one or more (preferably, 1, 2, 3 or 4) ring atoms are heteroatoms selected from nitrogen, oxygen, S(O)(=NH) and $S(O)_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including, but not limited to:

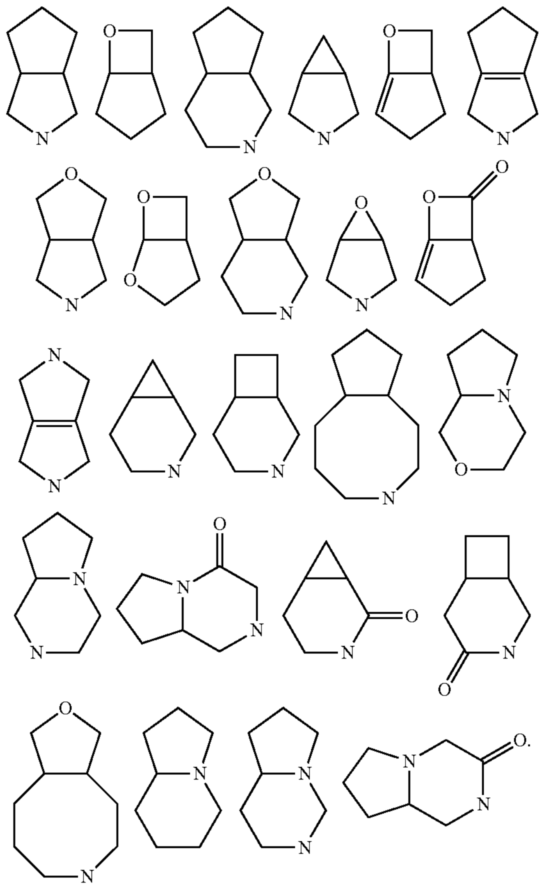

"Bridged heterocyclyl" refers to a polycyclic heterocyclyl group in which any two rings share two carbon atoms that are not directly connected to each other, wherein these rings may contain one or more (preferably, 1, 2 or 3) double bonds, but none of them has a fully conjugated π-electron system, wherein one or more (preferably, 1, 2, 3 or 4) ring atoms are heteroatoms selected from the group consisting of nitrogen, oxygen, S(O)(=NH) and $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

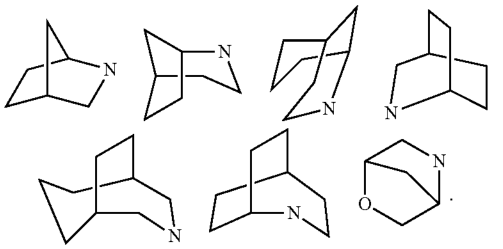

The heterocyclyl ring may be fused to an aryl heteroaryl or cycloalkyl ring, wherein the ring attached to the parent structure is heterocyclyl, including but not limited to:

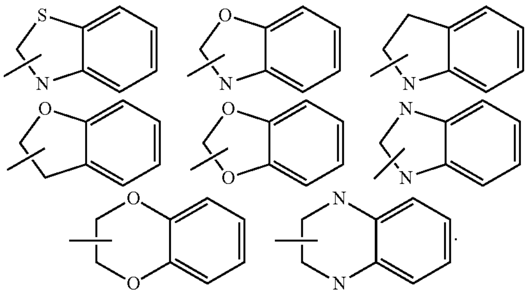

Heterocyclyl may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r R_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Aryl" or "aromatic ring" refers to an all-carbon monocyclic or fused-polycyclic group (i.e., rings that share a pair of adjacent carbon atoms) and a polycyclic group having a conjugated π-electron system (i.e., rings with adjacent pairs of carbon atoms), and is preferably all-carbon aryl containing 6 to 10, 6 to 8, or 6 carbon atoms. For example, "$C_{6-10}$ aryl" refers to all-carbon aryl containing 6 to 10 carbon atoms, and "$C_{6-8}$ aryl" refers to all-carbon aryl containing 6 to 8 carbon atoms. The aryl or aromatic ring includes, but is not limited to, phenyl and naphthyl. The aryl ring can be fused to a heteroaryl, heterocyclyl or cycloalkyl ring, wherein the ring attached to the parent structure is the aryl ring, including but not limited to:

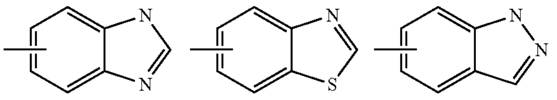

-continued

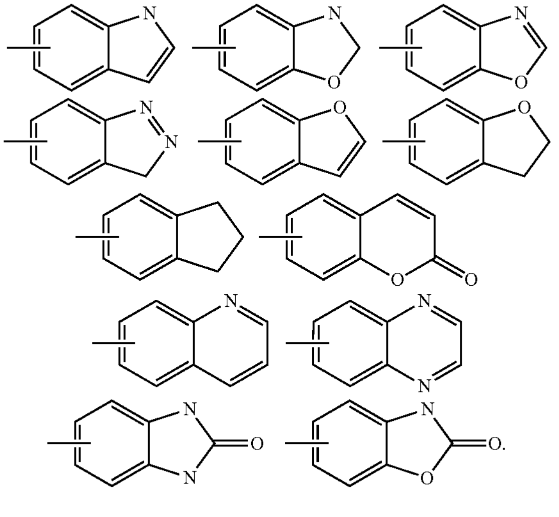

"Aryl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{6-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_r R_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-4}$ alkyl-N($R_{15}$)—C(O)$R_{14}$.

"Heteroaryl" refers to a heteroaromatic system containing one or more (preferably 1, 2, 3 or 4) heteroatoms including nitrogen, oxygen and S(O) (wherein r is an integer of 0, 1 or 2), and is preferably a heteroaromatic system containing 5 to 10, 5 to 8, or 5 to 6 ring atoms. For example, "5-8 membered heteroaryl" refers to a heteroaromatic system containing 5 to 8 ring atoms, and "5-10 membered heteroaryl" refers to a heteroaromatic system containing 5 to 10 ring atoms. The heteroaryl includes, but is not limited to, furyl, thiophenyl, pyridyl, pyrrolyl, N-alkylpyrrolyl, pyrimidinyl, pyrazinyl, imidazolyl, tetrazolyl and the like. The heteroaryl ring can be fused to an aryl, heterocyclyl or cycloalkyl ring, wherein the ring attached to the parent structure is the heteroaryl ring, including but not limited to:

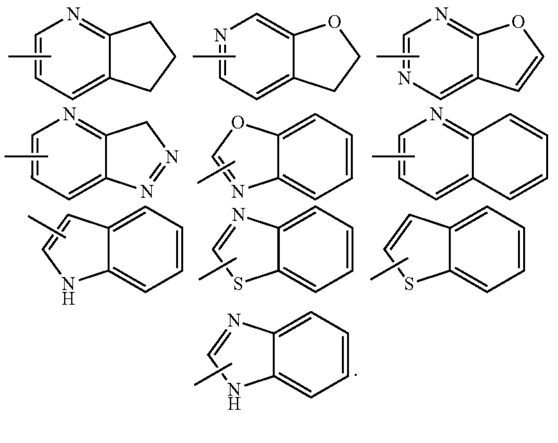

"Heteroaryl" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —CO—$_8$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Alkenyl" refers to alkyl defined as above consisting of at least two carbon atoms and at least one carbon-carbon double bond, and is preferably linear or branched alkenyl containing 2 to 10 or 2 to 4 carbon atoms. For example, "$C_{2-10}$ alkenyl" refers to linear or branched alkenyl containing 2 to 10 carbon atoms, and "$C_{2-4}$ alkenyl" refers to linear or branched alkenyl containing 2 to 4 carbon atoms. The alkenyl includes, but is not limited to, vinyl, 1-propenyl, 2-propenyl, 1-, 2- or 3-butenyl, and the like.

"Alkenyl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_3$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Alkynyl" refers to alkyl defined as above consisting of at least two carbon atoms and at least one carbon-carbon triple bond, and is preferably linear or branched alkynyl containing 2 to 10 or 2 to 4 carbon atoms. For example, "$C_{2-10}$ alkynyl" refers to linear or branched alkynyl containing 2 to 10 carbon atoms, and "$C_{2-4}$ alkynyl" refers to linear or branched alkynyl containing 2 to 4 carbon atoms. The alkynyl includes, but is not limited to, ethynyl, 1-propynyl, 2-propynyl, 1-, 2- or 3-butynyl, and the like.

"Alkynyl" may be substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)R_2$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-4}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Alkoxy" refers to —O-alkyl, wherein the alkyl is defined as above. For example, "$C_{1-10}$ alkoxy" refers to alkoxy containing 1 to 10 carbon atoms, and "$C_{1-4}$ alkoxy" refers to alkoxy containing 1 to 4 carbon atoms. The alkoxy includes, but is not limited to, methoxy, ethoxy, propoxy, butoxy and the like.

"Alkoxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Cycloalkyloxy" refers to —O-cycloalkyl, wherein the cycloalkyl is defined as above. For example, "$C_{3-12}$ cycloalkyloxy" refers to cycloalkyloxy containing 3 to 12 carbon atoms, and "$C_{3-8}$ cycloalkyloxy" refers to cycloalkyloxy containing 3 to 8 carbon atoms. The cycloalkyloxy includes, but is not limited to, cyclopropyloxy, cyclobutyloxy, cyclopentyloxy, cyclohexyloxy and the like.

"Cycloalkyloxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"Heterocyclyloxy" refers to —O-heterocyclyl, wherein the heterocyclyl is defined as above, and the heterocyclyloxy includes, but is not limited to, azacyclobutyloxy, oxacyclobutyloxy, azacyclopentyloxy, nitrogen, oxacyclohexyloxy and the like.

"Heterocyclyloxy" may be optionally substituted or unsubstituted, and when it is substituted, the substituent is preferably one or more (preferably 1, 2, 3 or 4) of the groups independently selected from the group consisting of deuterium, halogen, cyano, nitro, azido, $C_{1-10}$ alkyl, $C_{2-10}$ alkenyl, $C_{2-10}$ alkynl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$ and —$C_{0-8}$ alkyl-N($R_{15}$)—C(O)$R_{14}$.

"$C_{1-10}$ alkanoyl" refers to a monovalent atomic group which is obtained after hydroxy is removed from $C_{1-10}$ alkyl acid, and is also generally referred to as "$C_{0-9}$ alkyl-C(O)—". For example, "$C_1$ alkyl-C(O)—" refers to acetyl; "$C_2$ alkyl-C(O)—" refers to propionyl; and "$C_3$ alkyl-C(O)—" refers to butyryl or isobutyryl.

"$C_{1-4}$" refers to "$C_{1-4}$ alkyl", "$C_{0-4}$" refers to "$C_{0-4}$ alkyl", "$C_{1-8}$" refers to $C_{1-8}$ alkyl, "$C_{0-8}$" refers to $C_{0-8}$ alkyl, and these groups are defined as above.

"—$C_{0-8}$ alkyl-$S(O)_rR_{12}$" means that the sulfur atom in —$S(O)_rR_{12}$ is connected to $C_{0-8}$ alkyl, wherein $C_{0-8}$ alkyl is defined as above.

"—$C_{0-8}$ alkyl-O—$R_{13}$" means that the oxygen atom in —O—$R_{13}$ is connected to $C_{0-8}$ alkyl, wherein $C_{0-8}$ alkyl is defined as above.

"—$C_{0-8}$ alkyl-C(O)$OR_{13}$" means that the carbonyl in —C(O)$OR_{13}$ is connected to $C_{0-8}$ alkyl, wherein $C_{0-8}$ alkyl is defined as above.

"—$C_{0-8}$ alkyl-C(O)$R_{14}$" means that the carbonyl in —C(O)$R_{14}$ is connected to $C_{0-8}$ alkyl, wherein $C_{0-8}$ alkyl is defined as above.

"—$C_{0-8}$ alkyl-O—C(O)$R_{14}$" means that the oxygen atom in —O—C(O)$R_{14}$ is connected to $C_{0-4}$ alkyl, wherein $C_{0-8}$ alkyl is defined as above.

"—$C_{0-8}$ alkyl-$NR_{15}R_{16}$" means that the nitrogen atom in —$NR_{15}R_{16}$ is connected to $C_{0-8}$ alkyl, wherein $C_{0-8}$ alkyl is defined as above.

"—$C_{0-8}$ alkyl-C(=$NR_{15}$)$R_{14}$" means that the carbon atom in —C(=$NR_{15}$)$R_{14}$ is connected to $C_{0-8}$ alkyl, wherein $C_{0-8}$ alkyl is defined as above.

"—$C_{0-8}$ alkyl-N($R_{15}$)—C(=$NR_{16}$)$R_{14}$" means that the nitrogen atom in —N($R_{15}$)—C(=$NR_{16}$)$R_4$ is connected to $C_{0-4}$ alkyl, wherein $C_{0-8}$ alkyl is defined as above.

"—$C_{0-8}$ alkyl-C(O)$NR_{15}R_{16}$" means that the carbonyl in —C(O)$NR_{15}R_{16}$ is connected to $C_{0-4}$ alkyl, wherein $C_{0-8}$ alkyl is defined as above.

"—$C_{0-8}$ alkyl-N($R_{15}$)—C(O)$R_{14}$" means that the nitrogen atom in —N($R_{15}$)—C(O)$R_{14}$ is connected to $C_{0-8}$ alkyl, wherein $C_{0-8}$ alkyl is defined as above.

"$C_{1-10}$ haloalkyl" refers to an alkyl group having 1 to 10 carbon atoms in which hydrogens on the alkyl are optionally substituted with a fluorine, chlorine, bromine or iodine atom, including but not limited to, difluoromethyl (—$CHF_2$), dichloromethyl (—$CHCl_2$), dibromomethyl (—$CHBr_2$), trifluoromethyl (—$CF_3$), trichloromethyl (—$CCl_3$), tribromomethyl (—$CBr_3$) and the like.

"$C_{1-10}$ haloalkoxy" refers to an alkoxy group having 1 to 10 carbon atoms in which hydrogens on the alkyl are optionally substituted with a fluorine, chlorine, bromine or iodine atom, including but not limited to, difluoromethoxy, dichloromethoxy, dibromomethoxy, trifluoromethoxy, trichloromethoxy, tribromomethoxy and the like.

"$C_{1-10}$ deuterioalkyl" refers to an alkyl group having 1 to 10 carbon atoms in which hydrogens on the alkyl are optionally substituted with a deuterium atom, including but not limited to, monodeuteriomethyl (—$CH_2D$), dideuteriomethyl (—$CHD_2$), trideuteriomethyl (—$CD_3$) and the like.

"$C_{1-10}$ deuterioalkoxy" refers to an alkyl group having 1 to 10 carbon atoms in which hydrogens on the alkyl are optionally substituted with a deuterium atom, including but not limited to, monodeuteriomethoxy, dideuteriomethoxy, trideuteriomethoxy and the like.

"Halogen" refers to fluorine, chlorine, bromine or iodine. "EtOAc" refers to ethyl acetate. "PE" refers to petroleum ether. "DMF" refers to dimethylformamide.

The term "optional" or "optionally" means that the event or circumstance subsequently described may, but not necessarily, occur, and that the description includes instances where the event or circumstance occurs or does not occur, that is, instances where substitution occurs or does not occur. For example, "heterocyclyl group optionally substituted with alkyl" means that alkyl may be, but not necessarily, present, and that the description includes instances where the heterocyclyl group is or is not substituted with alkyl.

The term "substituted" means that one or more "hydrogen atoms" in the group are each independently substituted by a corresponding number of substituents. It goes without saying that a substituent is only in its possible chemical position and consistent with chemical valence bond theory, and those skilled in the art will be able to determine (by studies or theories) possible or impossible substitution without undue efforts. For example, it may be unstable when amino or hydroxy having free hydrogen is bound to a carbon atom having an unsaturated bond (such as olefin).

"Stereoisomers" refer to isomers produced by different spatial arrangements of atoms in molecules, and can be classified into cis-trans isomers and enantiomers, and also into enantiomers and diastereomers. Stereoisomers resulting from rotation of single bonds are referred to as conformational stereo-isomers and sometimes also as rotamers. Stereoisomers resulting from bond lengths, bond angles, intramolecular double bonds, rings and the like are referred to as configuration stereo-isomers, and the configuration stereo-isomers are classified into two categories. Among them, isomers resulting from the fact that a double bond or a single bond of a ring-forming carbon atom cannot rotate freely are referred to as geometric isomers and also as cis-trans isomers, and the isomers are classified into Z, E configurations. For example, cis-2-butene and trans-2-butene are a pair of geometric isomers, and the compounds of the present invention may be understood to comprise the E and/or Z forms if they contain a double bond, as not specifically indicated. Stereoisomers having different optical rotation properties due to the absence of anti-axisymmetry in the molecule are referred to as optical isomers, and are classified into R and S configurations. In the present invention, the term "stereoisomer" is understood to include one or more of the above enantiomers, configuration isomers and conformational isomers, unless otherwise specified.

"Pharmaceutically acceptable salt" as used herein refers to pharmaceutically acceptable acid addition salts or base addition salts, including inorganic and organic acid salts, which may be prepared by methods known in the art.

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to examples, which are not intended to limit the present invention, and the present invention is not merely limited to the contents of the examples.

The compound structure of the present invention is determined by nuclear magnetic resonance (NMR) and/or liquid chromatography-mass spectrometry (LC-MS). The NMR chemical shift (S) is given in parts per million (ppm). The NMR determination is conducted by using a Bruker AVANCE-400/500 nuclear magnetic resonance apparatus, with hexadeuterodimethyl sulfoxide (DMSO-$d_6$), tetradeuteromethanol (MeOH-$d_4$), and deuterated chloroform ($CDCl_3$) as determination solvents, and tetramethylsilane (TMS) as an internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

A Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for product separation and purification is 0.4-0.5 mm. The Yantai Yellow Sea silica gel of 200-300 mesh is generally utilized as a carrier in column chromatography.

Starting materials in the examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

I. PREPARATION OF INTERMEDIATES

Preparation of Intermediate A1: $N^1$,$N^1$-dimethyl-$N^2$-(methyl-$d_3$)ethane-1,2-diamine

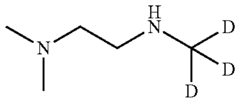

Methyl-$d_3$-amine hydrochloride (4.9 g, 69.43 mmol) and water (5 mL) were added to a round-bottom flask and the solution was cooled to −12° C. Sodium hydroxide (2.78 g, 0.07 mmol) was dissolved in water (4 mL) and the resulting solution was added dropwise to the round-bottom flask. The mixture was stirred at −12° C. for 15 min, and then an aqueous solution (4 mL) of 2-chloro-N,N-dimethylethane-1-amine hydrochloride (1 g, 6.94 mmol) was added dropwise thereto. The reaction mixture was stirred at room temperature for 4 hrs and then cooled to 0° C. Sodium hydroxide (2.9 g, 0.07 mmol) was dissolved in water (10 mL) and the resulting solution was added dropwise to the round-bottom flask. The mixture was extracted with dichloromethane (3*7 mL), and the organic phase was dried over anhydrous sodium sulfate and distilled at low temperature under reduced pressure to obtain $N^1$,$N^1$-dimethyl-$N^2$-(methyl-$d_3$)ethane-1,2-diamine, which was directly used in the next step.

Preparation of Intermediate A2: 2-((methyl-$d_3$)amino)ethan-1-ol hydrochloride

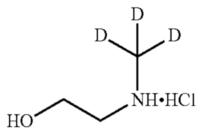

Step 1: Synthesis of tert-butyl (2-((tert-butyldimethylsilyl)oxy)ethyl) carbamate

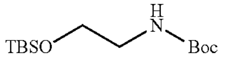

To a solution of tert-butyl N-(2-hydroxyethyl)carbamate (5.3 g, 32.87 mmol) in dichloromethane (80 mL), imidazole (3.36 g, 49.31 mmol) and 4-(dimethylamino)pyridine (0.6 g, 4.91 mmol) was added at room temperature. The mixture was stirred at room temperature for 5 min, and then a solution of chlorodimethyl(2-methylpropan-2-yl)silane (5.45 g, 36.16 mmol) in dichloromethane (20 mL) was slowly added dropwise to the mixture. The reaction mixture was stirred at room temperature overnight. After the reaction was completed, the reaction mixture was extracted with water and dichloromethane, and the organic layer was dried over anhydrous sodium sulfate and distilled under reduced pressure. The residue was separated by rapid silica gel column chromatography [eluent: ethyl acetate/petroleum ether: 0-25%] to obtain tert-butyl (2-((tert-butyldimethylsilyl)oxy)ethyl)carbamate (7.5 g, yield: 82%).

$^1$H NMR ($CDCl_3$) δ 4.78 (s, 1H), 3.60 (t, J=5.2 Hz, 2H), 3.16 (q, J=5.4 Hz, 2H), 1.39 (s, 9H), 0.84 (s, 9H), 0.00 (s, 6H).

Step 2: Synthesis of tert-butyl (2-((tert-butyldimethylsilyl)oxy)ethyl)(methyl-$d_3$) carbamate

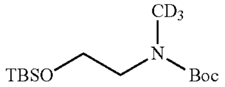

Sodium hydride (1.57 g, 39.20 mmol) was added slowly to a solution of tert-butyl (2-((tert-butyldimethylsilyl)oxy)ethyl)carbamate (7.2 g, 26.13 mmol) in N,N-dimethylformamide (100 mL) at 0° C. After the mixture was stirred for 30 min, deuterated iodomethane (1.8 mL, 28.75 mmol) was added dropwise. The resulting mixture was stirred at 0° C. for 30 min and then extracted with water and dichloromethane. The organic layer was dried over anhydrous sodium sulfate and distilled under reduced pressure, and then the residue was separated by rapid silica gel column chromatography [eluent: ethyl acetate/petroleum ether: 0-25%] to obtain tert-butyl (2-((tert-butyldimethylsilyl)oxy)ethyl)(methyl-$d_3$)carbamate (5.5 g, yield: 71%).

$^1$H NMR ($CDCl_3$) δ 3.65 (d, J=10.3 Hz, 2H), 3.24 (d, J=7.4 Hz, 2H), 1.40 (s, 9H), 0.84 (s, 9H), 0.00 (s, 6H).

Step 3: Synthesis of 2-((methyl-$d_3$)amino)ethan-1-ol hydrochloride

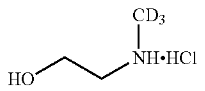

To a solution of tert-butyl (2-((tert-butyldimethylsilyl)oxy)ethyl)(methyl-$d_3$)carbamate (5.5 g, 18.80 mmol) in tetrahydrofuran (15 mL), a 4 N solution of hydrochloric acid/dioxane (14 mL) was added at room temperature. The mixture was stirred at room temperature for 3 hrs, and then the reaction mixture was distilled under reduced pressure to obtain 2-((methyl-$d_3$)amino)ethan-1-ol hydrochloride (1.5 g).

Preparation of Intermediate A3: $N^1$-(4-methoxybenzyl)-$N^2$,$N^2$-dimethylethane-1,2-diamine

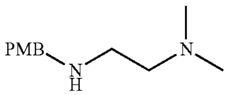

$N^1$,$N^1$-dimethylethane-1,2-diamine (10 g, 113.4 mmol) and 4-methoxybenzaldehyde (18.5 g, 136.1 mmol) were dissolved in dichloromethane (10 mL). To the above solution, acetic acid (0.65 mL, 11.6 mmol) and sodium acetylborohydride (35 g, 170.1 mmol) were added. The reaction mixture was stirred at room temperature for 18 hrs. Ethyl acetate and water were added, and then the mixture solution was separated. The organic phase was successively washed with water and saturated brine, then dried over anhydrous sodium sulfate, filtered, and concentrated, and then the residue was separated by silica gel column chromatography [petroleum ether:ethyl acetate=4:1] to obtain $N^1$-(4-methoxybenzyl)-$N^2$,$N^2$-dimethylethane-1,2-diamine (16 g, yield: 67%). ESI-MS: 209.0 $[M+1]^+$.

Preparation of Intermediate A4: 1-((2R,4S)-4-fluoropyrrolidin-2-yl)-N,N-dimethylmethanamine

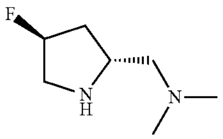

Step 1: Synthesis of 1-(tert-butyl) 2-methyl (2R,4S)-4-fluoropyrrolidine-1,2-dicarboxylate

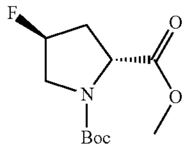

To a solution of 1-(tert-butyl) 2-methyl (2R,4R)-4-hydroxypyrrolidine-1,2-dicarboxylate (15.0 g, 61.1 mmol) in dichloromethane (100 mL), N,N-diethyl-1,1,1-trifluoro-l4-sulfanamine (19.7 g, 122.3 mmol) was added under an ice bath. The mixture was stirred under an ice bath for 30 min and then stirred for 2 hrs at 30° C. After the reaction was completed, the reaction mixture was slowly poured into a saturated sodium bicarbonate solution. After the reaction was quenched, dichloromethane was added for extraction, and then the mixture solution was separated. The organic phase was concentrated, and then the residue was separated by rapid silica gel column chromatography [eluent: ethyl acetate/petroleum ether: 0-30%] to obtain 1-tert-butyl) 2-methyl (2R,4S)-4-fluoropyrrolidine-1,2-dicarboxylate (8.20 g, yield: 54.23%).

$^1H$ NMR (DMSO-$d_6$) δ 5.31 (dt, J=52.6, 3.5 Hz, 1H), 4.34-4.21 (m, 1H), 3.72-3.61 (m, 4H), 3.58-3.42 (m, 1H), 2.61-2.52 (m, 1H), 2.22-2.00 (m, 1H), 1.37 (d, J=24.0 Hz, 9H).

Step 2: Synthesis of (2R,4S)-1-(tert-butoxycarbonyl)-4-fluoropyrrolidine-2-carboxylic acid

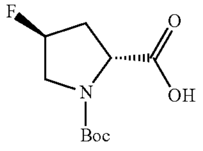

To a solution of 1-(tert-butyl) 2-methyl (2R,4S)-4-fluoropyrrolidine-1,2-dicarboxylate (8.2 g, 33.1 mmol) in methanol/tetrahydrofuran/water (20 mL/20 mL/20 mL), lithium hydroxide (6.9 g, 165.8 mmol) was added at room temperature. The mixture was stirred at room temperature for 2 hrs. After the reaction was completed, water was added. The resulting mixture was adjusted to pH=4-5 with concentrated hydrochloric acid, then dichloromethane was added for extraction, and then the mixture solution was separated. The organic phase was concentrated to obtain (2R,4S)-1-(tert-butoxycarbonyl)-4-fluoropyrrolidine-2-carboxylic acid (8.0 g, yield: 103.4%). ESI-MS: 232.0 $[M-1]^+$.

Step 3: Synthesis of tert-butyl (2R,4S)-4-fluoro-2-(hydroxymethyl)pyrrolidine-1-carboxylate

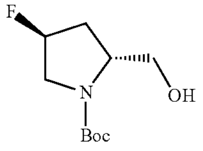

To a solution of (2R,4S)-1-(tert-butoxycarbonyl)-4-fluoropyrrolidine-2-carboxylic acid (6.5 g, 27.8 mmol) in tetrahydrofuran (80 mL), a borane-tetrahydrofuran solution (55.7 g, 55.7 mmol, 1 M) was added under an ice bath. The mixture was stirred under an ice bath for 30 min and then stirred for 1 hr at 75° C. After the reaction was completed, the reaction mixture was slowly poured into saturated ice water. After the reaction was quenched, dichloromethane was added for extraction, and then the mixture solution was separated. The organic phase was concentrated, and then the residue was separated by rapid silica gel column chromatography [eluent: ethyl acetate/petroleum ether: 0-70%] to obtain tert-butyl (2R,4S)-4-fluoro-2-(hydroxymethyl)pyrrolidine-1-carboxylate (5.1 g, yield: 83.4%). ESI-MS: 164.2 [M+1-56].

Step 4: Synthesis of tert-butyl (2R,4S)-2-(((ethylsulfonyl)oxy)methyl)-4-fluoropyrrolidine-1-carboxylate

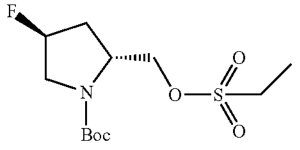 [SMILES: CCS(=O)(=O)OC[C@H]1C[C@H](F)CN1C(=O)OC(C)(C)C]

To a solution of tert-butyl (2R,4S)-4-fluoro-2-(hydroxymethyl)pyrrolidine-1-carboxylate (4.6 g, 20.9 mmol) in dichloromethane (50 mL), N,N-diisopropylethylamine (8.1 g, 62.9 mmol) and ethylsulfonyl chloride (4.0 g, 31.5 mmol) were added under an ice bath. The mixture was stirred for 30 min under an ice bath. After the reaction was completed, dichloromethane and water were added for extraction, and then the mixture solution was separated. The organic phase was concentrated, and then the residue was separated by rapid silica gel column chromatography [eluent: ethyl acetate/petroleum ether: 0-50%] to obtain tert-butyl (2R, 4S)-2-(((ethylsulfonyl)oxy)methyl)-4-fluoropyrrolidine-1-carboxylate (5.2 g, yield: 79.6%). ESI-MS: 212.2 $[M+1-100]^+$.

Step 5: Synthesis of tert-butyl (2R,4S)-2-((dimethylamino)methyl)-4-fluoropyrrolidine-1-carboxylate

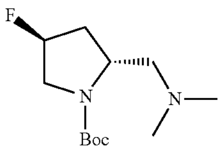 [SMILES: CN(C)C[C@H]1C[C@H](F)CN1C(=O)OC(C)(C)C]

In a sealed tube, tert-butyl (2R,4S)-2-(((ethylsulfonyl)oxy)methyl)-4-fluoropyrrolidine-1-carboxylate (5.2 g, 16.7 mmol) and a solution of dimethylamine in tetrahydrofuran (50 mL, 100.0 mmol, 2 M) were stirred at 80° C. for 3 hrs. After the reaction was completed, the reaction mixture was concentrated, and then the residue was separated by rapid silica gel column chromatography [eluent: dichloromethanol/methanol: 0-10%] to obtain tert-butyl (2R,4S)-2-((dimethylamino)methyl)-4-fluoropyrrolidine-1-carboxylate (3.0 g, yield: 72.9%). ESI-MS: 247.3 $[M+1]^+$.

$^1$H NMR (DMSO-$d_6$) δ 5.20 (dt, J=53.4, 3.7 Hz, 1H), 3.91 (s, 1H), 3.76-3.67 (m, 1H), 3.32-3.21 (s, 1H), 2.49-2.39 (m, 1H), 2.33-2.19 (m, 2H), 2.15 (s, 6H), 2.10-1.97 (m, 1H), 1.41 (s, 9H).

Step 6: Synthesis of 1-((2R,4S)-4-fluoropyrrolidin-2-yl)-N,N-dimethylmethanamine

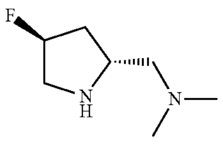

Tert-butyl (2R,4S)-2-((dimethylamino)methyl)-4-fluoropyrrolidine-1-carboxylate (3.0 g, 12.2 mmol) and a solution of hydrochloric acid/1,4-dioxane (50 mL, 200.0 mmol, 4 M) were stirred at room temperature for 3 hrs. After the reaction was completed, the reaction mixture was concentrated to obtain a hydrochloride of 1-((2R,4S)-4-fluoropyrrolidin-2-yl)-N,N-dimethylmethanamine (3.0 g, yield: 77.3%). ESI-MS: 147.3 $[M+1]^+$.

Preparation of Intermediate B1: $N^1$-(2-(dimethylamino)ethyl)-5-methoxy-$N^1$-methyl-2-nitrobenzene-1,4-diamine

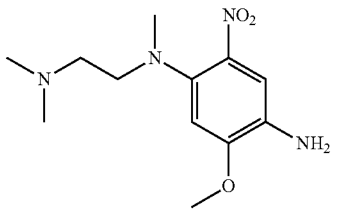 [SMILES: COc1cc(N(C)CCN(C)C)c([N+](=O)[O-])cc1N]

4-fluoro-2-methoxy-5-nitroaniline (1.86 g, 10.0 mmol) was dissolved in 10 mL of N,N-dimethylformamide. To the resulting solution, $N^1$,$N^1$,$N^2$-trimethylethane-1,2-diamine (1.53 g, 15.0 mmol) and potassium carbonate (2.76 g, 20.0 mmol) were added at room temperature. The reaction mixture was stirred at 85° C. for 3 hrs. Water was added to the solution, and the resulting mixture was extracted three times with dichloromethane. The organic phases were combined, then washed with saturated brine, and dried over anhydrous sodium sulfate. After the solvent was removed, the residue was separated by silica gel column chromatography [dichloromethane:methanol=10:1] to obtain $N^1$-(2-(dimethylamino)ethyl)-5-methoxy-$N^1$-methyl-2-nitrobenzene-1,4-diamine (2.5 g, yield: 93%). ESI-MS: 269.0 $[M+1]^+$.

Preparation of Intermediate B2: N-(4-((2-(dimethylamino)ethyl)(methyl) amino)-2-methoxy-5-nitrophenyl)formamide

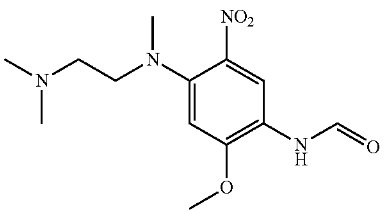 [SMILES: COc1cc(N(C)CCN(C)C)c([N+](=O)[O-])cc1NC=O]

$N^1$-(2-(dimethylamino)ethyl)-5-methoxy-$N^1$-methyl-2-nitrobenzene-1,4-diamine (2.68 g, 10 mmol) and formic acid (20 mL) were added to a reaction flask, and the reaction mixture was stirred at 100° C. for 2 hrs. The formic acid was removed by distillation under reduced pressure, and then the residue was separated by silica gel column chromatography [dichloromethane:methanol=10:1] to obtain N-(4-((2-(dimethylamino)ethyl)(methyl)amino)-2-methoxy-5-nitrophenyl)formamide (2.89 g, yield: 93%). ESI-MS: 296.0 [M+11].

Preparation of Intermediate B3: 5-(difluoromethoxy)-$N^1$-(2-(dimethylamino) ethyl)-$N^1$-methyl-2-nitrobenzene-1,4-diamine

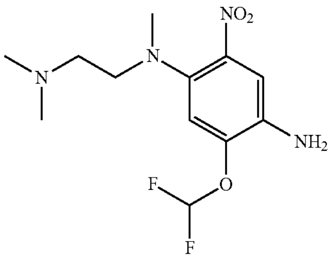 [SMILES: CN(C)CCN(C)c1cc(OC(F)F)c(N)cc1[N+](=O)[O-]]

Step 1: Synthesis of 2-(difluoromethoxy)-4-fluoro-1-nitrobenzene

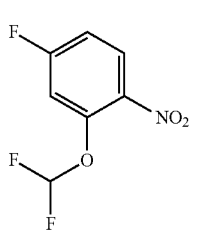 [SMILES: O=[N+]([O-])c1ccc(F)cc1OC(F)F]

To a solution of 5-fluoro-2-nitrophenol (10 g, 63.6 mmol) in N,N-dimethylformamide (100 mL), sodium carbonate (20.2 g, 190.9 mmol) was added. The reaction mixture was heated to 90° C., and sodium 2-chloro-2,2-difluoroacetate (34.0 g, 222.8 mmol) was added in batches, followed by stirring for another 3 hrs. The reaction mixture was then poured into ice water, and ethyl acetate was added for extraction. The organic phases were combined, washed with saturated brine, and concentrated, and then the residue was separated by column chromatography [eluent: petroleum ether/ethyl acetate: 0-10%] to obtain 2-(difluoromethoxy)-4-fluoro-1-nitrobenzene (10.3 g, yield: 78%).

$^1$H NMR ($CDCl_3$) δ 7.96 (dd, J=9.1, 5.6 Hz, 1H), 7.11-6.97 (m, 2H), 6.57 (t, J=72.4 Hz, 1H).

Step 2: Synthesis of 2-(difluoromethoxy)-4-fluoroaniline

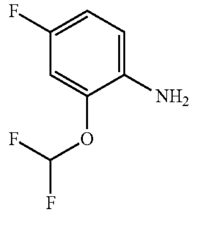 [SMILES: Nc1ccc(F)cc1OC(F)F]

To a solution of 2-(difluoromethoxy)-4-fluoro-1-nitrobenzene (10.3 g, 49.7 mmol) in ethanol, 10% palladium on carbon (1.0 g) was added. The mixture was stirred under hydrogen at room temperature overnight, and after the reaction was completed, the mixture was filtered and distilled under reduced pressure to obtain 2-(difluoromethoxy)-4-fluoroaniline (8.1 g, yield: 86%). ESI-MS: 178.1 $[M+1]^+$.

Step 3: Synthesis of 2-(difluoromethoxy)-4-fluoro-5-nitroaniline

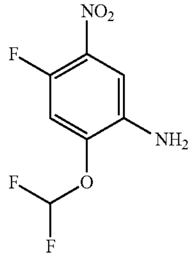 [SMILES: Nc1cc([N+](=O)[O-])c(F)cc1OC(F)F]

To a solution of 2-(difluoromethoxy)-4-fluoroaniline (8.1 g, 45.7 mmol) in sulfuric acid (40 mL), potassium nitrate (5.1 g, 50.3 mmol) was added in batches under an ice bath. The reaction mixture was stirred under an ice bath for 0.5 hrs and then stirred at room temperature for 2 hrs. The reaction mixture was then slowly poured into ice water (500 mL) and extracted with ethyl acetate. The organic layer was dried over anhydrous sodium sulfate and distilled under reduced pressure, and then the residue was separated by rapid silica gel column chromatography [eluent: petroleum ether/ethyl acetate: 0-15%] to obtain 2-(difluoromethoxy)-4-fluoro-5-nitroaniline (8.0 g, yield: 77%).

$^1$H NMR ($CDCl_3$) δ 7.49 (d, J=7.1 Hz, 1H), 7.03 (d, J=10.9 Hz, 1H), 6.61 (t, J=72.1 Hz, 1H), 4.06 (s, 2H).

Step 4: Synthesis of 5-(difluoromethoxy)-$N^1$-(2-(dimethylamino)ethyl)-M-methyl-2-nitrobenzene-1,4-diamine

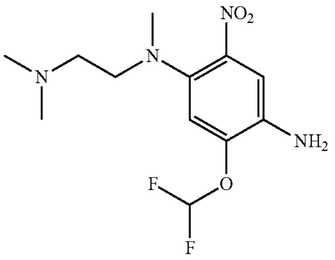 [SMILES: CN(C)CCN(C)c1cc(OC(F)F)c(N)cc1[N+](=O)[O-]]

To a solution of 2-(difluoromethoxy)-4-fluoro-5-nitroaniline (1.0 g, 4.5 mmol) in acetonitrile (30 mL), $N^1$,$N^1$,$N^2$-trimethylethane-1,2-diamine (690 mg, 6.7 mmol) and potassium carbonate (1.2 g, 9.0 mmol) were added. The reaction mixture was stirred at 80° C. for 3 hrs. After the solvent was removed, the residue was separated by silica gel column chromatography [dichloromethane:methanol=10:1] to obtain 5-(difluoromethoxy)-$N^1$-(2-(dimethylamino)ethyl)-$N^1$-methyl-2-nitrobenzene-1,4-diamine (0.25 g, yield: 83%). ESI-MS: 305.2 $[M+1]^+$.

Intermediates B4 to B5 were prepared according to the preparation method for intermediate B3: the procedures were consistent, except that in step 1, sodium 2-chloro-2,2-difluoroacetate was replaced by deuterated iodomethane, iodoethane or isopropyl iodide, and the reaction conditions were changed to stirring at 37° C. for 18 hrs. B6 was prepared according to steps 1-3 of the preparation method for intermediate B3.

| Intermediate No. | Structure | Chemical name | ESI-MS: $[M + 1]^+$ |
|---|---|---|---|
| B4 | 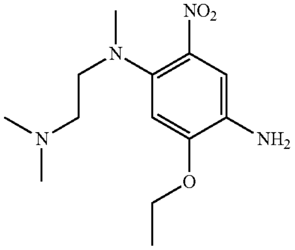 [SMILES: CCOc1cc(N(C)CCN(C)C)c([N+](=O)[O-])cc1N] | $N^1$-(2-(dimethylamino)ethyl)-5-ethoxy-$N^1$-methyl-2-nitrobenzene-1,4-diamine | 283.1 |
| B5 | 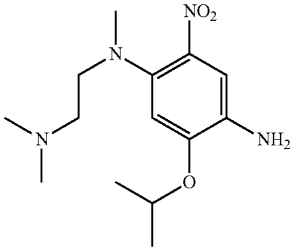 [SMILES: CC(C)Oc1cc(N(C)CCN(C)C)c([N+](=O)[O-])cc1N] | $N^1$-(2-(dimethylamino)ethyl)-5-isopropoxy-$N^1$-methyl-2-nitrobenzene-1,4-diamine | 297.2 |
| B6 | 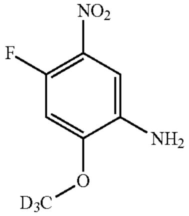 | 4-fluoro-2-(methoxy-$d_3$)-5-nitroaniline | 207.0 |

Preparation of Intermediate B7: $N^1$-(2-(bis(methyl-$d_3$)amino)ethyl)-5-methoxy-$N^1$-methyl-2-nitrobenzene-1,4-diamine

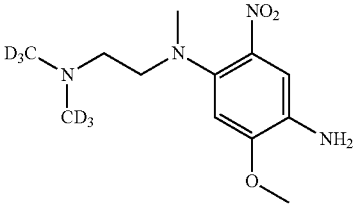 [SMILES: [2H]C([2H])([2H])N(CCN(C)c1cc(OC)c(N)cc1[N+](=O)[O-])C([2H])([2H])[2H]]

Step 1: Synthesis of tert-butyl (4-fluoro-2-methoxy-5-nitrophenyl)carbamate

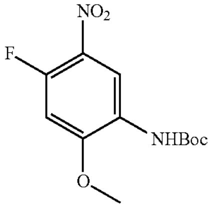 [SMILES: COc1cc(F)c([N+](=O)[O-])cc1NC(=O)OC(C)(C)C]

4-fluoro-2-methoxy-5-nitroaniline (1 g, 5.4 mmol) was dissolved in 1,4-dioxane (30 mL), and di-tert-butyl dicarbonate (2.2 g, 10.8 mmol) was added. The mixture was stirred at 120° C. overnight, the solvent was removed, and then the residue was separated by column chromatography to obtain tert-butyl (4-fluoro-2-methoxy-5-nitrophenyl)carbamate (1.3 g, yield: 84.4%). ESI-MS: 287.2 $[M+1]^+$.

Step 2: Synthesis of tert-butyl (4-((2-hydroxyethyl)(methyl)amino)-2-methoxy-5-nitrophenyl)carbamate

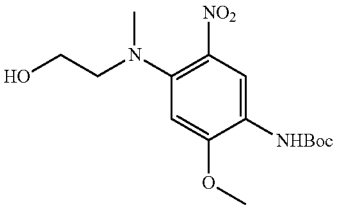 [SMILES: COc1cc(N(C)CCO)c([N+](=O)[O-])cc1NC(=O)OC(C)(C)C]

To a solution of tert-butyl (4-fluoro-2-methoxy-5-nitrophenyl)carbamate (328 mg, 1.15 mmol) in 1,4-dioxane (10 mL), 2-(methylamino)ethan-1-ol (129 mg, 1.72 mmol) and N,N-diisopropylethylamine (296 mg, 2.3 mmol) were added. The reaction mixture was stirred at 120° C. for 1 hr. After the solvent was removed, the residue was separated by silica gel column chromatography [dichloromethane:methanol=10:1] to obtain tert-butyl (4-((2-hydroxyethyl)(methyl)amino)-2-methoxy-5-nitrophenyl)carbamate (390 mg, yield: 90.7%). ESI-MS: 342.0 $[M+1]^+$.

Step 3: Synthesis of 2-((4-((tert-butoxycarbonyl) amino)-5-methoxy-2-nitrophenyl)(methyl)amino) ethyl methanesulfonate

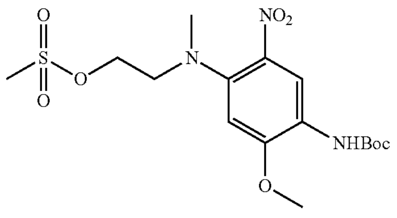 [SMILES: COc1cc(N(C)CCOS(C)(=O)=O)c([N+](=O)[O-])cc1NC(=O)OC(C)(C)C]

A solution of tert-butyl (4-((2-hydroxyethyl)(methyl) amino)-2-methoxy-5-nitrophenyl)carbamate (390 mg, 1.14 mmol) in dichloromethane (10 mL) was cooled to 0° C., and then N,N-diisopropylethylamine (443 mg, 3.4 mmol) and methanesulfonyl chloride (157 mg, 1.37 mmol) were added. The reaction mixture was stirred at 0° C. for 0.5 hrs. After the solvent was removed, the residue was separated by silica gel column chromatography [dichloromethane:methanol=10:1] to obtain 2-((4-((tert-butoxycarbonyl)amino)-5-methoxy-2-nitrophenyl)(methyl)amino)ethyl methanesulfonate (480 mg, yield: 100%). ESI-MS: 420.0 $[M+1]^+$.

Step 4: Synthesis of tert-butyl (4-((2-(bis(methyl-$d_3$)amino)ethyl)(methyl) amino)-2-methoxy-5-nitrophenyl)carbamate

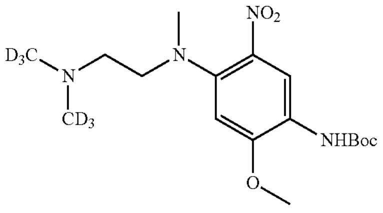 [SMILES: [2H]C([2H])([2H])N(CCN(C)c1cc(OC)c(NC(=O)OC(C)(C)C)cc1[N+](=O)[O-])C([2H])([2H])[2H]]

To a sealed tube, 2-((4-((tert-butoxycarbonyl)amino)-5-methoxy-2-nitrophenyl) (methyl)amino)ethyl methanesulfonate (480 mg, 1.14 mmol), acetonitrile (8 mL), potassium carbonate (474.5 mg, 3.4 mmol) and bis(methyl-$d_3$) amine hydrochloride (501 mg, 5.72 mmol) were added. The reaction mixture was stirred at 60° C. for 5 hrs. After the solvent was removed, the residue was separated by silica gel column chromatography [dichloromethane:methanol=10:1] to obtain tert-butyl (4-((2-(bis(methyl-$d_3$)amino)ethyl) (methyl)amino)-2-methoxy-5-nitrophenyl)carbamate (293 mg, yield: 68.1%). ESI-MS: 375.2 $[M+1]^+$.

Step 5: Synthesis of $N^1$-(2-(bis(methyl-$d_3$)amino) ethyl)-5-methoxy-$N^1$-methyl-2-nitrobenzene-1,4-diamine

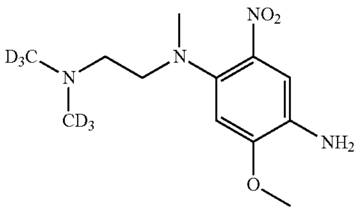 [SMILES: [2H]C([2H])([2H])N(CCN(C)c1cc(OC)c(N)cc1[N+](=O)[O-])C([2H])([2H])[2H]]

To a solution of tert-butyl (4-((2-(bis(methyl-$d_3$)amino) ethyl)(methyl)amino)-2-methoxy-5-nitrophenyl)carbamate (293 mg, 0.78 mmol) in dichloromethane (4 m L), trifluoroacetic acid (1 mL) was added. The reaction mixture was stirred at room temperature for 1 hr. The solvent was removed to obtain $N^1$-(2-(bis(methyl-$d_3$)amino)ethyl)-5-methoxy-$N^1$-methyl-2-nitrobenzene-1,4-diamine (180 mg, yield: 83, 8%). ESI-MS: 275.1 $[M+1]^+$.

Preparation of Intermediate B8: $N^1$-(2-(dimethylamino)ethyl)-5-((4-methoxybenzyl)oxy)-2-nitrobenzene-1,4-diamine

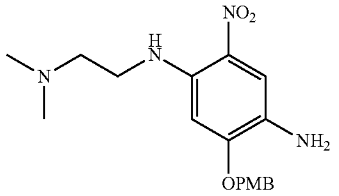

Step 1: Synthesis of 2-amino-5-fluoro-4-nitrophenol

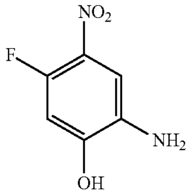 [SMILES: Nc1cc([N+](=O)[O-])c(F)cc1O]

2-amino-5-fluorophenol (5.08 g, 39.96 mmol) was dissolved in dichloromethane, and the resulting solution was cooled to −10° C. A mixed solution of 63% (by mass) concentrated nitric acid (4.44 g, 47.96 mmol) and 98% (by mass) concentrated sulfuric acid (10 mL, 179.85 mmol) was added dropwise to the solution. After the dropwise addition was completed, the reaction mixture was stirred at −10° C. for 2 hrs. A saturated sodium sulfate solution was added to quench reaction, and the resulting mixture was diluted with ethyl acetate and then separated. The organic phase was successively washed twice with water and once with saturated brine, then dried, and distilled under reduced pressure to remove the solvent. The residue was separated by column chromatography to obtain 2-amino-5-fluoro-4-nitrophenol (1.4 g, yield: 18.93%). ESI-MS: 190.0 $[M+NH_4]^+$.

Step 2: Synthesis of N-(4-fluoro-2-hydroxy-5-nitrophenyl)acetamide

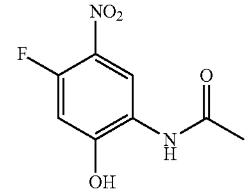

To a round-bottom flask, 2-amino-5-fluoro-4-nitrophenol (500 mg, 2.91 mmol) and acetic anhydride (20 mL) were added, and the reaction mixture was stirred at room temperature for 1 hr. After the reaction was completed, water was added to quench the reaction, and the resulting mixture was filtered. The solid was collected and dried to obtain N-(4-fluoro-2-hydroxy-5-nitrophenyl)acetamide (580 mg, yield: 88.57%). ESI-MS: 232.0 $[M+NH_4]^+$.

Step 3: Synthesis of N-(4-fluoro-2-((4-methoxybenzyl)oxy)-5-nitrophenyl) acetamide

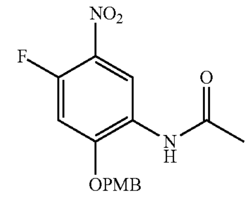

N-(4-fluoro-2-hydroxy-5-nitrophenyl)acetamide (580 mg, 2.71 mmol) was dissolved in acetonitrile (20 mL), and then potassium carbonate (748.6 mg, 5.42 mmol) and p-methoxybenzyl chloride (0.55 mL, 4.06 mmol) were added to the resulting solution. The reaction mixture was stirred at 50° C. for 2 hrs, and the reaction was completed. The reaction mixture was washed with saturated brine and extracted with ethyl acetate, and then the organic layer was dried over anhydrous sodium sulfate, distilled under reduced pressure to remove the solvent to obtain N-(4-fluoro-2-((4-methoxybenzyl)oxy)-5-nitrophenyl)acetamide (720 mg, yield: 43.74%). ESI-MS: 352.0 $[M+NH_4]^+$.

Step 4: Synthesis of N-(4-((2-(dimethylamino)ethyl)(methyl)amino)-2-((4-methoxybenzyl)oxy)-5-nitrophenyl)acetamide

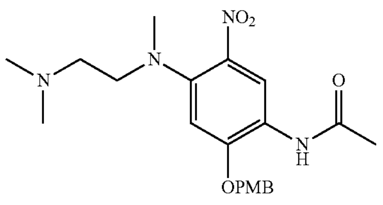

To a solution of N-(4-fluoro-2-((4-methoxybenzyl)oxy)-5-nitrophenyl)acetamide (720 mg, 2.15 mmol) in 1,4-dioxane (30 mL), $N^1,N^1,N^2$-trimethylethane-1,2-diamine (0.65 mL, 4.31 mmol) and diisopropylethylamine (0.65 mL, 4.31 mmol) were added. The reaction mixture was stirred at 50° C. for 2 hrs. After the solvent was removed, the residue was separated by silica gel column chromatography [dichloromethane methanol=10:1] to obtain N-(4-((2-(dimethylamino)ethyl)(methyl)amino)-2-((4-methoxybenzyl)oxy)-5-nitrophenyl)acetamide (620 mg, yield: 53%). ESI-MS: 417.2 $[M+1]^+$.

Step 5: Synthesis of $N^1$-(2-(dimethylamino)ethyl)-5-((4-methoxybenzyl)oxy)-2-nitrobenzene-1,4-diamine

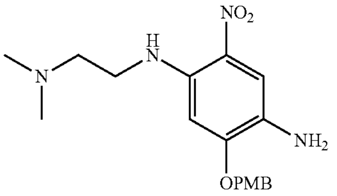

N-(4-((2-(dimethylamino)ethyl)(methyl)amino)-2-((4-methoxybenzyl)oxy)-5-nitro phenyl)acetamide (620 mg, 1.49 mmol) was dissolved in ethanol (20 mL) and water (5 mL), then sodium hydroxide (297.73 mg, 7.44 mmol) was added, and the reaction mixture was stirred at 50° C. for 2 hrs. After the reaction was completed, the reaction mixture was washed with saturated brine, extracted with ethyl acetate, dried over anhydrous sodium sulfate, and concentrated, and then the residue was separated by column chromatography to obtain $N^1$-(2-(dimethylamino)ethyl)-5-((4-methoxybenzyl)oxy)-2-nitrobenzene-1,4-diamine (150 mg, yield: 24.9%). ESI-MS: 361.2 $[M+1]^+$.

Preparation of Intermediate B9: $N^2$-(2-(dimethylamino)ethyl)-6-methoxy-$N^2$-methyl-3-nitropyridine-2,5-diamine

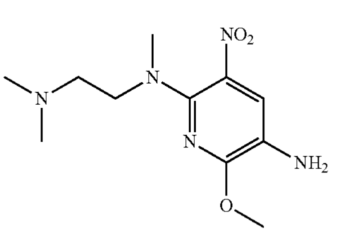 [SMILES: COc1nc(N(C)CCN(C)C)c([N+](=O)[O-])cc1N]

Step 1: Synthesis of 6-bromo-2-methoxy-3-nitropyridine

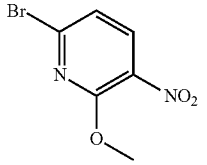

To a solution of 2,6-dibromo-3-nitropyridine (20 g, 70.9 mmol) in tetrahydrofuran (300 mL), sodium methoxide (5.3 g, 78.0 mmol) was added under an ice bath. The reaction mixture was stirred at room temperature for 3 hrs. The reaction mixture was then poured into ice water, and ethyl acetate was added for extraction. The organic phases were combined, washed with saturated brine, and concentrated, and then the residue was separated by column chromatography [petroleum ether:ethyl acetate=5:1] to obtain 6-bromo-2-methoxy-3-nitropyridine (13.9 g, yield: 85%). ESI-MS: 217.1 $[M-15]^+$.

Step 2: Synthesis of 6-bromo-2-methoxypyridin-3-amine

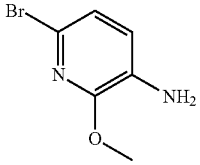

To a solution of 6-bromo-2-methoxy-3-nitropyridine (13.9 g, 60.1 mmol) in [ethanol/water=2:1], iron powder (26.9 g, 480.8 mmol) and ammonium chloride (25.9 g, 480.8 mmol) were added. The reaction mixture was stirred at about 90° C. for 3 hrs. Dichloromethane and water were added, and then the mixture solution was separated. The organic phase was concentrated, and then the residue was separated by column chromatography [petroleum ether:ethyl acetate=3:1] to obtain 6-bromo-2-methoxypyridin-3-amine (9.1 g, yield: 75%). ESI-MS: 203.1 $[M+1]^+$.

$^1$H NMR (DMSO-$d_6$) δ 6.89 (d, J=7.9 Hz, 1H), 6.83 (d, J=7.9 Hz, 1H), 5.10 (s, 2H), 3.84 (s, 3H).

Step 3: Synthesis of N-(6-bromo-2-methoxypyridin-3-yl)acetamide

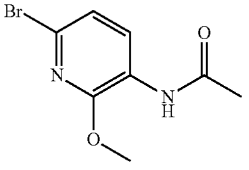

To a solution of 6-bromo-2-methoxypyridin-3-amine (9.1 g, 44.8 mmol) in dichloromethane (200 mL), triethylamine (6.7 g, 67.2 mmol) and acetyl chloride (3.8 g, 49.2 mmol) were added under an ice bath. The reaction mixture was stirred under an ice bath for 1 hr. Dichloromethane and water were added, and then the mixture solution was separated. The organic phase was concentrated, and then the residue was separated by column chromatography [petroleum ether: ethyl acetate=5:1] to obtain N-(6-bromo-2-methoxypyridin-3-yl)acetamide (9.5 g, yield: 86%), which was directly used in the next step.

Step 4: Synthesis of N-(6-bromo-2-methoxy-5-nitropyridin-3-yl)acetamide

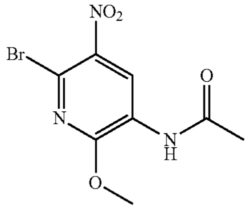 [SMILES: COc1nc(Br)c([N+](=O)[O-])cc1NC(C)=O]

To a solution of N-(6-bromo-2-methoxypyridin-3-yl)acetamide (9.5 g, 38.9 mmol) in trifluoroacetic anhydride (80 mL), concentrated nitric acid (65%, 46.6 mmol) was added under an ice bath. The reaction mixture was stirred under an ice bath for 1 hr. The reaction mixture was slowly poured into ice water, and the resulting mixture was stirred for 1 hr. A solid was precipitated, then the mixture was filtered under vacuum, and the filter cake was dried to obtain N-(6-bromo-2-methoxy-5-nitropyridin-3-yl)acetamide (11.5 g, yield: 100%). ESI-MS: 290.1 $[M+1]^+$.

$^1$H NMR (DMSO-$d_6$) δ 9.90 (s, 1H), 9.12 (s, 1H), 4.06 (s, 3H), 2.16 (s, 3H).

Step 5 (intermediate B9-1): Synthesis of N-(6-((2-(dimethylamino)ethyl) (methyl)amino)-2-methoxy-5-nitropyridin-3-yl)acetamide

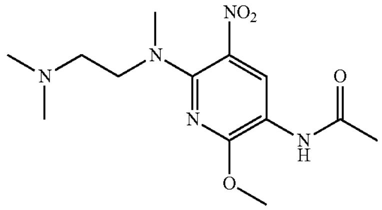 [SMILES: COc1nc(N(C)CCN(C)C)c([N+](=O)[O-])cc1NC(C)=O]

To a solution of N-(6-bromo-2-methoxy-5-nitropyridin-3-yl)acetamide (1.0 g, 3.4 mmol) in acetonitrile (20 mL), $N^1,N^1,N^2$-trimethylethane-1,2-diamine (520 mg, 5.1 mmol) was added. The reaction mixture was stirred at 80° C. for 1 hr. After the solvent was removed, the residue was separated by silica gel column chromatography [dichloromethane methanol=10:1] to obtain N-(6-((2-(dimethylamino)ethyl) (methyl)amino)-2-methoxy-5-nitropyridin-3-yl)acetamide (756 mg, yield: 71%). ESI-MS: 312.3 $[M+1]^+$.

Step 6: Synthesis of N2-(2-(dimethylamino)ethyl)-6-methoxy-$N^2$-methyl-3-nitropyridine-2,5-diamine

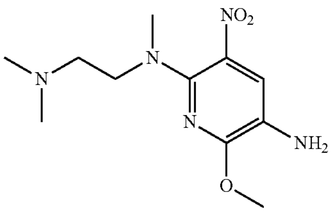 [SMILES: COc1nc(N(C)CCN(C)C)c([N+](=O)[O-])cc1N]

To a solution of N-(6-((2-(dimethylamino)ethyl)(methyl)amino)-2-methoxy-5-nitropyridin-3-yl)acetamide (756 mg, 2.4 mmol) in methanol (10 mL), concentrated hydrochloric acid (37%, 1.5 mL, 18 mmol) was added. The reaction mixture was stirred at 60° C. for 5 hrs. A saturated sodium bicarbonate solution and dichloromethane were added, and then the mixture solution was separated. The organic phase was concentrated to obtain $N^2$-(2-(dimethylamino)ethyl)-6-methoxy-$N^2$-methyl-3-nitropyridine-2,5-diamine (645 mg, yield: 100%). ESI-MS: 270.3 $[M+1]^+$.

Intermediates B10-1 to B14-1 were Prepared According to the Preparation Method for Intermediate B9-1:

| Intermediate No. | Structure | Chemical name | ESI-MS: $[M + 1]^+$ |
|---|---|---|---|
| B10-1 | 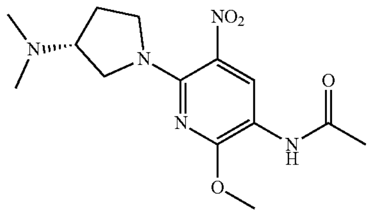 [SMILES: COc1nc(N2CC[C@@H](N(C)C)C2)c([N+](=O)[O-])cc1NC(C)=O] | (R)-N-(6-(3-(dimethylamino)pyrrolidin-1-yl)-2-methoxy-5-nitropyridin-3-yl)acetamide | 324.3 |
| B11-1 | 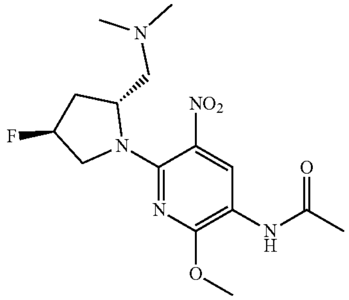 [SMILES: COc1nc(N2C[C@@H](F)C[C@@H]2CN(C)C)c([N+](=O)[O-])cc1NC(C)=O] | N-(6-((2R,4S)-2-((dimethylamino)methyl)-4-fluoropyrrolidin-1-yl)-2-methoxy-5-nitropyridin-3-yl)acetamide | 356.0 |
| B12-1 | 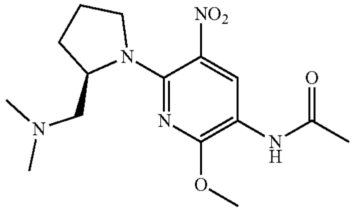 [SMILES: COc1nc(N2CCC[C@@H]2CN(C)C)c([N+](=O)[O-])cc1NC(C)=O] | (R)-N-(6-(2-((dimethylamino)methyl)pyrrolidin-1-yl)-2-methoxy-5-nitropyridin-3-yl)acetamide | 338.2 |
| B13-1 | 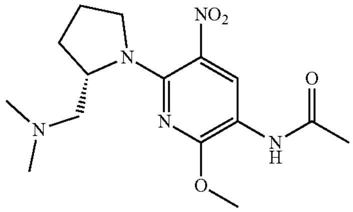 [SMILES: COc1nc(N2CCC[C@H]2CN(C)C)c([N+](=O)[O-])cc1NC(C)=O] | (S)-N-(6-(2-((dimethylamino)methyl)pyrrolidin-1-yl)-2-methoxy-5-nitropyridin-3-yl)acetamide | 338.2 |
| B14-1 | 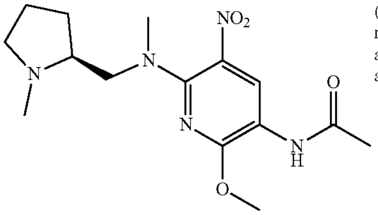 | (S)-N-(2-methoxy-6-(methyl((1-methylpyrrolidin-2-yl)methyl)amino)-5-nitropyridin-3-yl)acetamide | 338.2 |

Intermediates B10 to B14 were Prepared According to the Preparation Method for Intermediate 139:

| Intermediate No. | Structure | Chemical name | ESI-MS; [M + 1]+ |
|---|---|---|---|
| B10 | 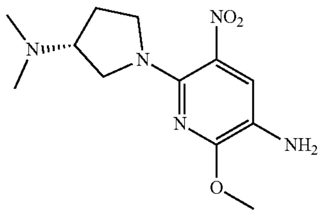 [SMILES: COc1nc(N2CC[C@@H](N(C)C)C2)c([N+](=O)[O-])cc1N] | (R)-6-(3-(dimethylamino) pyrrolidin-1-yl)-2-methoxy-5-nitropyridin-3-amine | 282.3 |
| B11 | 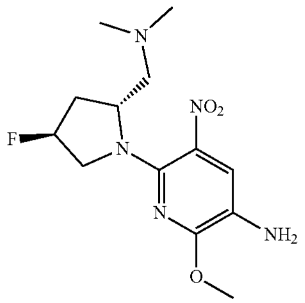 [SMILES: COc1nc(N2C[C@@H](F)C[C@@H]2CN(C)C)c([N+](=O)[O-])cc1N] | 6-((2R,4S)-2-((dimethylamino) methyl)-4-fluoropyrrolidin-1-yl)-2-methoxy-5-nitropyridin-3-amine | 314.2 |
| B12 | 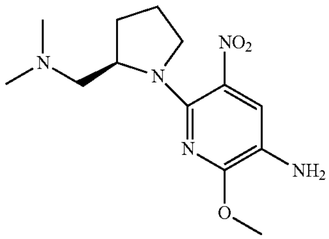 [SMILES: COc1nc(N2CCC[C@@H]2CN(C)C)c([N+](=O)[O-])cc1N] | (R)-6-(2-((dimethylamino) methyl)pyrrolidin-1-yl)-2-methoxy-5-nitropyridin-3-amine | 296.0 |
| B13 | 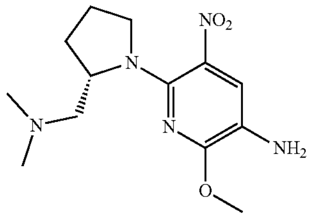 [SMILES: COc1nc(N2CCC[C@H]2CN(C)C)c([N+](=O)[O-])cc1N] | (S)-6-(2-((dimethylamino) methyl)pyrrolidin-1-yl)-2-methoxy-S-nitropyridin-3-amine | 296.0 |
| B14 | 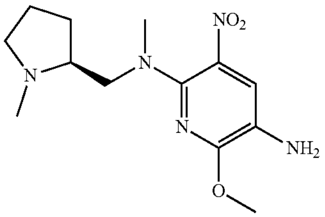 [SMILES: COc1nc(N(C)C[C@@H]2CCCN2C)c([N+](=O)[O-])cc1N] | (S)-6-methoxy-$N^2$-methyl-$N^2$-((1-methylpyrrolidin-2-yl) methyl)-3-nitropyridine-2,5-diamine | 296.0 |

Preparation of Intermediate B15: 2-cyclopropoxy-4-fluoro-5-nitroaniline

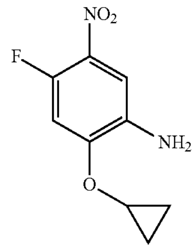 [SMILES: Nc1cc([N+](=O)[O-])c(F)cc1OC1CC1]

Step 1: Synthesis of 2-cyclopropoxy-4-fluoroaniline

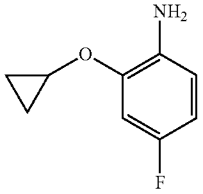 [SMILES: Nc1ccc(F)cc1OC1CC1]

To a solution of 2,4-difluoro-1-nitrobenzene (4.0 g, 25.14 mmol) in tetrahydrofuran (80 mL), cyclopropanol (1.46 g, 25.14 mmol) and cesium carbonate (8.19 g, 25.14 mmol) were added. The reaction mixture was stirred at 40° C. for 16 hrs. After the reaction was completed, the reaction mixture was diluted with water and extracted three times with ethyl acetate (100 mL). The organic phases were combined, washed with saturated brine, dried over anhydrous sodium sulfate, and filtered to obtain 2-cyclopropoxy-4-fluoro-1-nitrobenzene. The residue was dissolved in methanol (120 mL), and then water (30 mL), iron powder (7.0 g, 125.70 mmol) and ammonium chloride (10.86 g, 201.12 mmol) were added. The reaction mixture was stirred at 80° C. for 2 hrs. After the reaction was completed, the reaction mixture was filtered through diatomaceous earth. To the resulting solution, ethyl acetate and water were added, and then the mixture solution was separated. The organic phase was successively washed with water and saturated brine, then dried over anhydrous sodium sulfate, filtered, and concentrated to obtain 2-cyclopropoxy-4-fluoroaniline (2.68 g, yield: 64%). ESI-MS: 168.0 $[M+1]^+$.

Step 2: Synthesis of N-(2-cyclopropoxy-4-fluorophenyl)acetamide

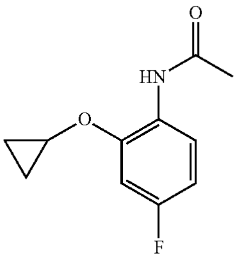

To a solution of 2-cyclopropoxy-4-fluoroaniline (1.3 g, 7.77 mmol) in dichloromethane (30 mL), N,N-diisopropylethylamine (1.93 mL, 11.66 mmol) and acetyl chloride (0.61 mL, 8.55 mmol) were added at 0° C. The reaction mixture was stirred at 0° C. for 30 min. After the reaction was completed, the reaction mixture was diluted with dichloromethane and a saturated aqueous sodium bicarbonate solution, and the organic phase obtained after separation was washed with saturated brine, dried over anhydrous sodium sulfate, and filtered to remove the solvent to obtain N-(2-cyclopropoxy-4-fluorophenyl)acetamide (1.55 g, yield: 95%). ESI-MS: 210.0 $[M+1]^+$.

Step 3: Synthesis of N-(2-cyclopropoxy-4-fluoro-5-nitrophenyl)acetamide

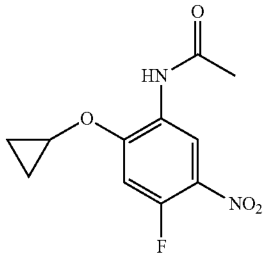 [SMILES: CC(=O)Nc1cc([N+](=O)[O-])c(F)cc1OC1CC1]

To a 250 mL single-necked flask, N-(2-cyclopropoxy-4-fluorophenyl)acetamide (1.55 g, 7.38 mmol) and trifluoroacetic anhydride (16 mL) were added, and then the resulting mixture was cooled to −10° C. under an ice-salt bath. Concentrated nitric acid (0.8 mL, 11.8 mmol) was then added dropwise, with the temperature being controlled to below −5° C., and after the dropwise addition was completed, the mixture was stirred at −10° C. for reaction for another 1.5 hrs. The reaction mixture was slowly poured into 90 mL of ice water, and a solid was precipitated. The mixture was filtered, and the filter cake was dried to obtain a crude product. The crude product was separated by column chromatography to obtain N-(2-cyclopropoxy-4-fluoro-5-nitrophenyl)acetamide (621 mg, yield: 33%). ESI-MS: 255.0 $[M+1]^+$.

Step 4: Synthesis of 2-cyclopropoxy-4-fluoro-5-nitroaniline

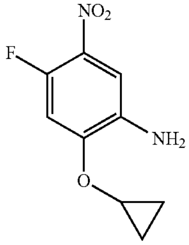

To a solution of N-(2-cyclopropoxy-4-fluoro-5-nitrophenyl)acetamide (138 mg, 0.54 mmol) in methanol (10 mL), concentrated hydrochloric acid (1 mL) was added. The reaction mixture was stirred at 60° C. for 3 hrs. After the reaction was completed, the solvent was removed, then dichloromethane (10 mL) was added, and the resulting mixture was neutralized to alkalinous with a saturated sodium bicarbonate solution. The resulting solution was extracted with dichloromethane and the organic phases were combined. The resulting organic phase was washed with saturated brine, dried over anhydrous sodium sulfate, and filtered to remove the solvent to obtain 2-cyclopropoxy-4-fluoro-5-nitroaniline (85 mg, yield: 73%). ESI-MS: 213.0 $[M+1]^+$.

Preparation of Intermediate C1: 3,3-dimethyl-2,3-dihydro-1H-pyrrolo [3,2-b]pyridine

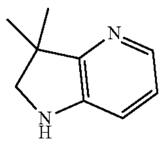

Step 1: Synthesis of 1-(tert-butyl) 3-ethyl 2-(3-nitropyridin-2-yl)malonate

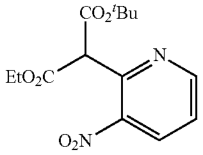 [SMILES: CCOC(=O)C(C(=O)OC(C)(C)C)c1ncccc1[N+](=O)[O-]]

tert-Butyl ethyl malonate (44.52 g, 236.5 mmol) was slowly added dropwise to a suspension of sodium hydride (9.46 g, 236.5 mmol) in tetrahydrofuran (200 mL) at 0° C. The mixture was stirred at room temperature for 0.5 hrs, and then 2-chloro-3-nitropyridine (25.0 g, 157.7 mmol) was added to the mixture. The reaction mixture was stirred at 60° C. for 1.5 hrs, and after the reaction was completed, the reaction mixture was cooled to 0° C., and a saturated ammonium chloride solution was slowly added to quench the reaction. The mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-50%] to obtain 1-(tert-butyl) 3-ethyl 2-(3-nitropyridin-2-yl)malonate (32.7 g, yield: 66.8%). ESI-MS: 255.0 $[M-55]^+$.

Step 2: Synthesis of ethyl 2-(3-nitropyridin-2-yl)acetate

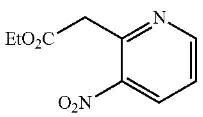 [SMILES: CCOC(=O)Cc1ncccc1[N+](=O)[O-]]

Trifluoroacetic acid (18.8 ml, 252.9 mmol) was added to 1-(tert-butyl) 3-ethyl 2-(3-nitropyridin-2-yl)malonate (32.7 g, 84.3 mmol). The mixture was stirred at 60° C. for 1 hr. The reaction mixture was cooled to room temperature and then distilled under reduced pressure to remove trifluoroacetic acid. A saturated sodium bicarbonate solution was added to the residue, and the resulting mixture was extracted with ethyl acetate. The organic layer was dried over anhydrous sodium sulfate and distilled under reduced pressure to obtain ethyl 2-(3-nitropyridin-2-yl)acetate (17.7 g, yield: 91.9%). ESI-MS: 211.0 $[M+1]^+$.

Step 3: Synthesis of ethyl 2-methyl-2-(3-nitropyridin-2-yl)propanoate

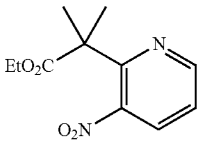 [SMILES: CCOC(=O)C(C)(C)c1ncccc1[N+](=O)[O-]]

To a solution of ethyl 2-(3-nitropyridin-2-yl)acetate (3.1 g, 14.7 mmol) in N,N-dimethylformamide (30 mL), methyl iodide (6.25 g, 44 mmol) and 18-crown-6 (0.39 g, 1.47 mmol) were added at 0° C. and then sodium hydride (1.2 g, 29.4 mmol) was slowly added. The mixture was stirred at 0° C. for 1 hr, and after the reaction was completed, ice water was added to quench the reaction, and the resulting mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-25%] to obtain ethyl 2-methyl-2-(3-nitropyridin-2-yl)propanoate (3.2 g, yield: 91%). ESI-MS: 239.0 $[M+1]^+$.

Step 4: Synthesis of 3,3-dimethyl-1,3-dihydro-2H-pyrrolo[3,2-b]pyridin-2-one

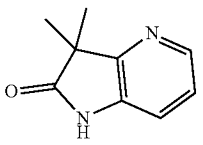

To a solution of ethyl 2-methyl-2-(3-nitropyridin-2-yl) propanoate (3.2 g, 13.4 mmol) in ethanol (20 mL), ammonium formate (3.4 g, 53.7 mmol) and 10% palladium on carbon (300 mg) were added, and the mixture was stirred at 90° C. for reaction for 2 hrs. After the reaction was completed, the reaction mixture was filtered, and the filtrate was concentrated. The residue was washed with water and extracted with ethyl acetate, and the organic layer was dried over anhydrous sodium sulfate and distilled under reduced pressure to obtain a crude product of 3,3-dimethyl-1,3-dihydro-2H-pyrrolo [3,2-b]pyridin-2-one (1.72 g, yield: 79%), which was directly used in the next step. ESI-MS: 163.0 $[M+1]^+$.

Step 5: Synthesis of 3,3-dimethyl-2,3-dihydro-1H-pyrrolo[3,2-b]pyridine

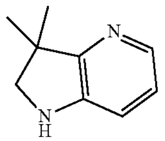

3,3-dimethyl-1,3-dihydro-2H-pyrrolo[3,2-b]pyridin-2-one (1.22 g, 7.53 mmol) was dissolved in tetrahydrofuran (20 mL), then the resulting solution was cooled to 0° C., and a solution of lithium aluminum hydride in tetrahydrofuran (4 mL, 2.5 M) was added dropwise to the solution. The mixture was stirred at 50° C. for 3 hrs. After the reaction was completed, sodium sulfate decahydrate was added to the reaction mixture to quench the reaction until no bubbles were generated. The mixture was filtered, and the filtrate was distilled under reduced pressure to obtain 3,3-dimethyl-2,3-dihydro-1H-pyrrolo [3,2-b]pyridine (1.2 g, yield: 100%). ESI-MS: 149.0 $[M+1]^+$.

Preparation of Intermediate C2: 1',2'-dihydrospiro (cyclopropane-1,3'-pyrrolo[3,2-b]pyridine)

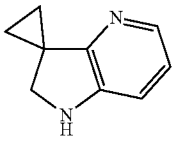 [SMILES: c1cnc2c(c1)NCC21CC1]

Step 1: Synthesis of ethyl 1-(3-nitropyridin-2-yl)cyclopropane-1-carboxylate

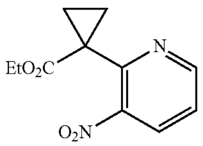

2-(3-nitropyridin-2-yl)acetate (2.18 g, 9.85 mmol) was dissolved in dimethyl sulfoxide (50 mL), and then diphenyl (vinyl)sulfonium trifluoromethanesulfonate (4.28 g, 11.82 mmol) was added to the resulting solution. The mixture was stirred at room temperature for 2 min, and 2,3,4,6,7,8,9,10-octahydropyrimido[1,2-a]azepine (4.42 mL, 29.56 mmol) was added dropwise. The reaction mixture was stirred at room temperature for 0.5 hrs, washed with water, extracted with ethyl acetate, and dried over anhydrous sodium sulfate to remove the solvent, and the residue was separated by column chromatography to obtain ethyl 1-(3-nitropyridin-2-yl)cyclopropane-1-carboxylate (2.05 g, yield: 82.79%). ESI-MS: 236.9$[M+1]^+$.

Step 2: Synthesis of ethyl 1-(3-aminopyridin-2-yl)cyclopropane-1-carboxylate

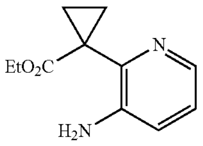 [SMILES: CCOC(=O)C1(c2ncccc2N)CC1]

To a solution of ethyl 1-(3-nitropyridin-2-yl)cyclopropane-1-carboxylate (2.05 g, 8.24 mmol) in ethanol (20 mL), 10% palladium on carbon (100 mg) was added, and the mixture was stirred at room temperature under a hydrogen atmosphere for reaction for 2 hrs. After the reaction was completed, the reaction mixture was filtered, and the filtrate was concentrated to obtain ethyl 1-(3-aminopyridin-2-yl) cyclopropane-1-carboxylate (1.70 g, yield: 100%), which was directly used in the next step. ESI-MS: 206.9 $[M+1]^+$.

Step 3: Synthesis of spiro(cyclopropane-1,3'-pyrrolo [3,2-b]pyridin)-2'(1'H)-one

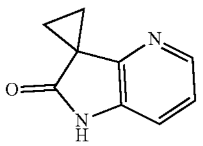 [SMILES: O=C1Nc2cccnc2C12CC2]

To a solution of ethyl 1-(3-aminopyridin-2-yl)cyclopropane-1-carboxylate (1.7 g, 8.24 mmol) in ethanol (20 mL), 36% (by mass) concentrated hydrochloric acid (0.5 mL) was added, and the mixture was stirred at 60° C. for reaction for 18 hrs. After the reaction was completed, the reaction mixture was neutralized with a sodium hydroxide solution, washed with water, extracted with dichloromethane, dried over anhydrous sodium sulfate, and filtered. The filtrate was concentrated, and then the residue was separated by column chromatography to obtain spiro(cyclopropane-1,3'-pyrrolo [3,2-b]pyridin)-2'(1'H)-one (0.4 g, yield: 28.8%). ESI-MS: 160.9 $[M+1]^+$.

Step 4: Synthesis of 1',2'-dihydrospiro(cyclopropane-1,3'-pyrrolo[3,2-b]pyridine)

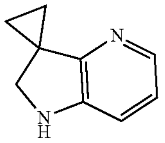 [SMILES: c1cnc2c(c1)NCC21CC1]

Spiro(cyclopropane-1,3'-pyrrolo[3,2-b]pyridine)-2'(1'H)-one (0.4 g, 2.48 mmol) was dissolved in tetrahydrofuran (10 mL), then the resulting solution was cooled to 0° C., and a solution of lithium aluminum hydride in tetrahydrofuran (3 mL, 2.5 M) was added dropwise to the solution. The mixture was stirred at 50° C. for 3 hrs. After the reaction was completed, sodium sulfate decahydrate was added to the reaction mixture to quench the reaction until no bubbles were generated. The mixture was filtered, and the filtrate was distilled under reduced pressure to obtain 1',2'-dihydrospiro (cyclopropane-1,3'-pyrrolo[3,2-b]pyridine) (327 mg, yield: 89.6%). ESI-MS: 147.0 [M+1]$^+$.

Preparation of Intermediate C3: 1',2'-dihydrospiro (cyclobutane-1,3'-pyrrolo [3,2-b]pyridine)

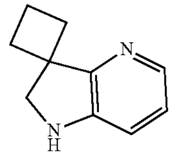 [SMILES: c1cnc2c(c1)NCC21CCC1]

Step 1: Synthesis of spiro(cyclobutane-1,3'-pyrrolo [3,2-b]pyridin)-2'(1'H)-one

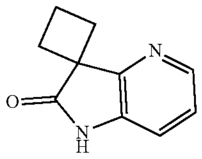 [SMILES: O=C1Nc2cccnc2C12CCC2]

Sodium hydride (3.0 g, 74.5 mmol) and hexamethylphosphoric triamide (12 mL) were dissolved in anhydrous N,N-dimethylformamide (60 mL), and 1,3-dihydro-2H-pyrrolo [3,2-b]pyridin-2-one (4.0 g, 29.8 mmol) and 1,3-diiodopropane (8.8 g, 29.8 mmol) were added to the reaction mixture. The reaction mixture was stirred at 0° C. under nitrogen protection for 1 hr, and after the reaction was completed, ethyl acetate (100 mL) and saturated brine (100 mL) were added to the reaction mixture, and then the mixture solution was separated. The organic phase was washed with saturated brine (50 mL). The resulting organic phase was concentrated, and then the residue was separated by rapid silica gel column chromatography [petroleum ether/ethyl acetate=3:1] to obtain spiro(cyclobutane-1,3'-pyrrolo [3,2-b]pyridin)-2'(1'H)-one (1.2 g, 23%). ESI-MS: 175.0 [M+1]$^+$.

Step 2: Synthesis of 1',2'-dihydrospiro(cyclobutane-1,3'-pyrrolo[3,2-b]pyridine)

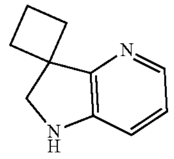 [SMILES: c1cnc2c(c1)NCC21CCC1]

Spiro(cyclobutane-1,3'-pyrrolo[3,2-b]pyridin)-2'(1'H)-one (240 mg, 1.38 mmol) was dissolved in tetrahydrofuran (10 mL), and then a borane dimethylsulfide solution (1.4 mL, 14 mmol) was added to the reaction mixture. The reaction mixture was stirred at 25° C. under nitrogen protection for 16 hrs, and after the reaction was completed, ethyl acetate (50 mL) and saturated brine (50 mL) were added to the reaction mixture, and then the mixture solution was separated. The organic phase was washed with saturated brine (50 mL). The resulting organic phase was concentrated, and then the residue was separated by rapid silica gel column chromatography [petroleum ether/ethyl acetate=2:1] to obtain 1',2'-dihydrospiro(cyclobutane-1,3'-pyrrolo[3,2-b]pyridine) (210 mg, 95%). ESI-MS: 161.0 [M+1]$^+$.

Preparation of Intermediate C4: 5'-(1-methyl-1H-pyrazol-4-yl)-1',2'-dihydrospiro(cyclobutane-1,3'-pyrrolo[3,2-b]pyridine)

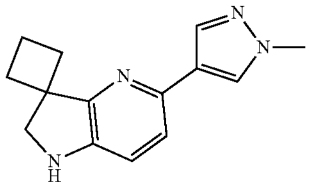 [SMILES: Cn1cc(-c2ccc3c(n2)C2(CCC2)CN3)cn1]

Step 1: Synthesis of 5'-bromo-1',2'-dihydrospiro (cyclobutane-1,3'-pyrrolo [3,2-b]pyridine)

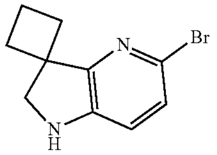 [SMILES: Brc1ccc2c(n1)C1(CCC1)CN2]

1',2'-dihydrospiro(cyclobutane-1,3'-pyrrolo[3,2-b]pyridine) (170 mg, 1.06 mmol) was dissolved in acetonitrile (10 mL), and then N-bromosuccinimide (188.8 mg, 1.06 mmol) was added to the reaction mixture. The reaction mixture was stirred at room temperature for 2 hrs. After the reaction was completed, the reaction mixture was distilled under reduced pressure to remove the solvent, and then the residue was separated by rapid silica gel column chromatography to obtain 5'-bromo-1',2'-dihydrospiro(cyclobutane-1,3'-pyrrolo [3,2-b]pyridine) (161 mg, 62.8%). ESI-MS: 239.1, 241.1 [M+1]$^+$.

Step 2: Synthesis of 5'-(1-methyl-1H-pyrazol-4-yl)-1',2'-dihydrospiro (cyclobutane-1,3'-pyrrolo[3,2-b] pyridine)

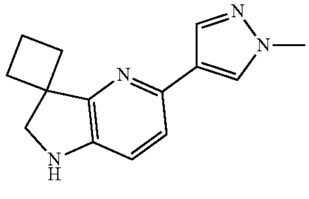 [SMILES: Cn1cc(-c2ccc3c(n2)C2(CCC2)CN3)cn1]

To a reaction flask, 5'-bromo-1',2'-dihydrospiro(cyclobutane-1,3'-pyrrolo[3,2-b]pyridine) (161 mg, 0.67 mmol), 1-methyl-4-(4,4,5,5-tetramethyl-1,3,2-dioxaborolan-2-yl)-1H-pyrazole (280.2 mg, 1.35 mmol), potassium phosphate (428.8 mg, 2.02 mmol), tricyclohexylphosphine (75.5 mg, 0.27 mmol), palladium acetate (30.2 mg, 0.14 mmol) and toluene (30 mL) were added. Nitrogen was charged to the mixture to replace three times, and under nitrogen protection, the mixture was heated to 110° C. and stirred for 16 hrs. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-50%] to obtain 5'-(1-methyl-1H-pyrazol-4-yl)-1',2'-dihydrospiro(cyclobutane-1, 3'-pyrrolo[3,2-b]pyridin e) (70 mg, yield: 40.2%). ESI-MS: 241.0 [M+1]*.

Preparation of Intermediate C5: 3,3,5-trimethyl-2,3-dihydro-1H-pyrrolo [3,2-b]pyridine

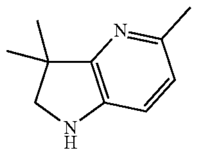

Step 1: Synthesis of 2-iodo-6-methyl-N-(2-methylallyl)pyridin-3-amine

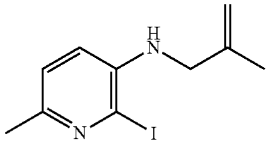

To a solution of 2-iodo-6-methylpyridin-3-amine (2 g, 8.5 mmol) in tetrahydrofuran (40 mL), potassium tert-butoxide (1.14 g, 10.2 mmol) was added at room temperature. The mixture was stirred at room temperature for 15 min, and then 3-bromo-2-methylprop-1-ene (1.27 g, 9.4 mmol) was slowly added dropwise to the mixture. The reaction mixture was stirred at room temperature for 2 hrs, and after the reaction was completed, the reaction mixture was concentrated under reduced pressure to remove the solvent, and then the residue was separated by rapid silica gel column chromatography [eluent: ethyl acetate/petroleum ether: 0-20%] to obtain 2-iodo-6-methyl-N-(2-methylallyl)pyridin-3-amine (1.46 g, yield: 59%). ESI-MS: 288.9 $[M+1]^+$.

Step 2: Synthesis of 3,3,5-trimethyl-2,3-dihydro-1H-pyrrolo[3,2-b]pyridine

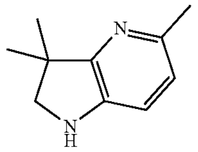

To a reaction flask, 2-iodo-6-methyl-N-(2-methylallyl) pyridin-3-amine (1.46 g, 5 mmol), sodium formate (413 mg, 6 mmol), tetrabutylammonium chloride (1.67 g, 6 mmol), triethylamine (1.5 g, 15 mmol), palladium acetate (224 mg, 1 mmol), dimethyl sulfoxide (40 mL) and water (1.5 mL) were added. Nitrogen was charged to the mixture to replace three times, and under nitrogen protection, the mixture was heated to 120° C. and stirred for 1 hr. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain 3,3,5-trimethyl-2,3-dihydro-1H-pyrrolo[3,2-b]pyridine (660 mg, yield: 81%). ESI-MS: 163.0 $[M+1]^+$.

Preparation of Intermediate C6: 5-cyclopropyl-3,3-dimethyl-2,3-dihydro-1H-pyrrolo[3,2-b]pyridine

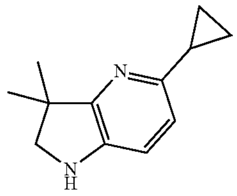

Step 1: Synthesis of 6-chloro-2-iodopyridin-3-amine

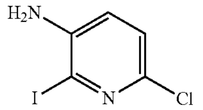

To a solution of 6-chloropyridin-3-amine (10 g, 77.8 mmol) in N,N-dimethylformamide (150 mL), N-iodosuccinimide (19.3 g, 85.6 mmol) was added at room temperature. The mixture was stirred at room temperature overnight. After the reaction was completed, the reaction mixture was washed with water and extracted with ethyl acetate. The organic layer was dried over anhydrous sodium sulfate and concentrated under reduced pressure to remove the solvent, and then the residue was separated by rapid silica gel column chromatography [eluent: ethyl acetate/petroleum ether: 0-20%] to obtain 6-chloro-2-iodopyridin-3-amine (15.5 g, yield: 78.3%). ESI-MS: 254.8 $[M+1]^+$.

Step 2: Synthesis of 6-chloro-2-iodo-N-(2-methylallyl)pyridin-3-amine

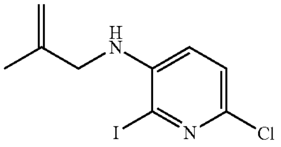

To a solution of 6-chloro-2-iodopyridin-3-amine (15.5 g, 60.9 mmol) in tetrahydrofuran (200 mL), potassium tert-butoxide (8.2 g, 73.1 mmol) was added at room temperature. The mixture was stirred at room temperature for 15 min, and then 3-bromo-2-methylprop-1-ene (9.9 g, 73.1 mmol) was slowly added dropwise to the mixture. The reaction mixture was stirred at room temperature for 2 hrs, and after the reaction was completed, the reaction mixture was concentrated under reduced pressure to remove the solvent, and then the residue was separated by rapid silica gel column chromatography [eluent: ethyl acetate/petroleum ether: 0-20%] to obtain 6-chloro-2-iodo-N-(2-methylallyl)pyridin-3-amine (15.5 g, yield: 82.5%). ESI-MS: 308.8 $[M+1]^+$.

Step 3: Synthesis of 5-chloro-3,3-dimethyl-2,3-dihydro-1H-pyrrolo[3,2-b]pyridine

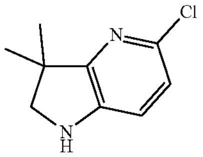

To a reaction flask, 6-chloro-2-iodo-N-(2-methylallyl) pyridin-3-amine (15.5 g, 50.2 mmol), sodium formate (4.2 g, 60.3 mmol), tetrabutylammonium chloride (16.8 g, 60.3 mmol), triethylamine (15.3 g, 150.7 mmol), palladium acetate (1.69 g, 7.5 mmol), dimethyl sulfoxide (200 mL) and water (6.7 mL) were added. Nitrogen was charged to the mixture to replace three times, and under nitrogen protection, the mixture was heated to 120° C. and stirred for 1 hr. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain 5-chloro-3,3-dimethyl-2,3-dihydro-1H-pyrrolo[3,2-b]pyridine (6.6 g, yield: 70.8%). ESI-MS: 183.1 $[M+1]^+$.

Step 4: Synthesis of 5-cyclopropyl-3,3-dimethyl-2,3-dihydro-1H-pyrrolo[3,2-b]pyridine

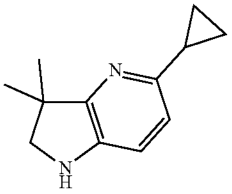

To a reaction flask, 5-chloro-3,3-dimethyl-2,3-dihydro-1H-pyrrolo[3,2-b]pyridine (450 mg, 2.5 mmol), cyclopropylboronic acid (1.1 g, 12.4 mmol), potassium phosphate (1.94 g, 9.1 mmol), tricyclohexylphosphine (138 mg, 0.5 mmol), palladium acetate (55 mg, 0.3 mmol) and toluene (30 mL) were added. Nitrogen was charged to the mixture to replace three times, and under nitrogen protection, the mixture was heated to 110° C. and stirred for 6 hrs. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain 5-cyclopropyl-3,3-dimethyl-2,3-dihydro-1H-pyrrolo[3,2-b]pyridine (152 mg, yield: 33.0%). ESI-MS: 189.0 $[M+1]^+$.

Preparation of Intermediate C7: 3,3-dimethyl-5-(1-methyl-1H-pyrazol-4-yl)-2,3-dihydro-1H-pyrrolo[3,2-b]pyridine

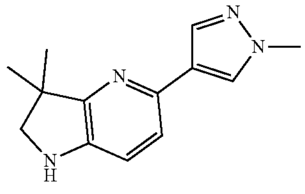

To a reaction flask, 5-chloro-3,3-dimethyl-2,3-dihydro-1H-pyrrolo[3,2-b]pyridine (274 mg, 1.5 mmol), 1-methyl-4-(4,4,5,5-tetramethyl-1,3,2-dioxaborolan-2-yl)-1H-pyrazole (623.3 mg, 3.0 mmol), potassium phosphate (955.3 mg, 4.5 mmol), tricyclohexylphosphine (168.3 mg, 0.6 mmol), palladium acetate (67 mg, 0.3 mmol) and toluene (50 mL) were added. Nitrogen was charged to the mixture to replace three times, and under nitrogen protection, the mixture was heated to 110° C. and stirred for 16 hrs. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-50%] to obtain 3,3-dimethyl-5-(1-methyl-1H-pyrazol-4-yl)-2,3-dihydro-1H-pyrrolo[3,2-b]pyridine (125 mg, yield: 35.8%). ESI-MS: 229.0 $[M+1]^+$.

Preparation of Intermediate C8: 5-bromo-3,3-dimethyl-2,3-dihydro-1H-pyrrolo[3,2-b]pyridine

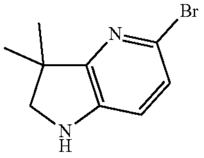

Step 1: Synthesis of 6-bromo-2-iodopyridin-3-amine

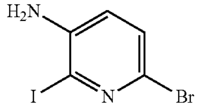

To a solution of 6-bromopyridin-3-amine 1.73 g, 10 mmol) in N,N-dimethylformamide (50 mL), N-iodosuccinimide (2.70 g, 12.0 mmol) was added at room temperature. The mixture was stirred at room temperature overnight. After the reaction was completed, the reaction mixture was washed with water and extracted with ethyl acetate. The organic layer was dried over anhydrous sodium sulfate and concentrated under reduced pressure to remove the solvent, and then the residue was separated by rapid silica gel column chromatography [eluent: ethyl acetate/petroleum ether: 0-20%] to obtain 6-bromo-2-iodopyridin-3-amine (2.1 g, yield: 66.4%). ESI-MS: 298.8, 300.8 $[M+1]^+$.

Step 2: Synthesis of 6-bromo-2-iodo-N-(2-methylallyl)pyridin-3-amine

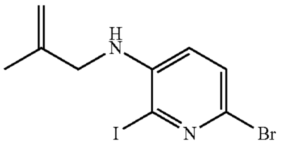

To a solution of 6-bromo-2-iodopyridin-3-amine (2.09 g, 7.0 mmol) in tetrahydrofuran (50 mL), potassium tert-butoxide (8.4 mL, 8.4 mmol, 1 M/mL) was added at room temperature. The mixture was stirred at room temperature for 15 min, and then 3-bromo-2-methylprop-1-ene (1.04 g, 7.7 mmol) was slowly added dropwise to the mixture. The reaction mixture was stirred at room temperature for 2 hrs, and after the reaction was completed, the reaction mixture was concentrated under reduced pressure to remove the solvent, and then the residue was separated by rapid silica gel column chromatography [eluent: ethyl acetate/petroleum ether: 0-20%] to obtain 6-bromo-2-iodo-N-(2-methylallyl) pyridin-3-amine (2.1 g, yield: 69.8%). ESI-MS: 352.8, 354.8 $[M+1]^+$.

Step 3: Synthesis of 5-bromo-3,3-dimethyl-2,3-dihydro-1H-pyrrolo[3,2-b]pyridine

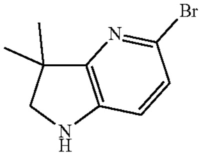

To a reaction flask, 6-bromo-2-iodo-N-(2-methylallyl) pyridin-3-amine (2.1 g, 5.9 mmol), sodium formate (0.49 g, 7.1 mmol), tetrabutylammonium chloride (1.98 g, 7.1 mmol), triethylamine (1.8 g, 17.8 mmol), palladium acetate (0.2 g, 0.9 mmol), dimethyl sulfoxide (20 mL) and water (2 mL) were added. Nitrogen was charged to the mixture to replace three times, and under nitrogen protection, the mixture was heated to 120° C. and stirred for 1 hr. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain 5-bromo-3,3-dimethyl-2,3-dihydro-1H-pyrrolo[3,2-b]pyridine (0.6 g, yield: 38.6%). ESI-MS: 226.9, 228.9 $[M+1]^+$.

Preparation of Intermediate C9: 3,3-dimethyl-5-(trifluoromethyl)-2,3-dihydro-1H-pyrrolo[3,2-b] pyridine

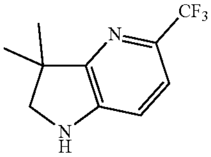

Step 1: Synthesis of 2-iodo-N-(2-methylallyl)-6-(trifluoromethyl)pyridin-3-amine

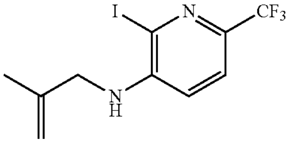 [SMILES: C=C(C)CNc1ccc(C(F)(F)F)nc1I]

To a solution of 2-iodo-6-(trifluoromethyl)pyridin-3-amine (2 g, 6.94 mmol) in tetrahydrofuran (30 mL), potassium tert-butoxide (933 mg, 8.33 mmol) was added at room temperature. The mixture was stirred at room temperature for 15 min, and then 3-bromo-2-methylprop-1-ene (1.17 g, 8.33 mmol) was slowly added dropwise to the mixture. The reaction mixture was stirred at room temperature for 2 hrs, and after the reaction was completed, the reaction mixture was concentrated under reduced pressure to remove the solvent, and then the residue was separated by rapid silica gel column chromatography [eluent: ethyl acetate/petroleum ether: 0-20%] to obtain 2-iodo-N-(2-methylallyl)-6-(trifluoromethyl)pyridin-3-amine (888 mg, yield; 37%). ESI-MS: 342.9 $[M+1]^+$.

Step 2: Synthesis of 3,3-dimethyl-5-(trifluoromethyl)-2,3-dihydro-1H-pyrrolo [3,2-b]pyridine

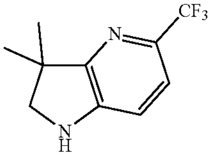

To a reaction flask, 2-iodo-N-(2-methylallyl)-6-(trifluoromethyl)pyridin-3-amine (888 mg, 2.6 mmol), sodium formate (212 mg, 3.1 mmol), tetrabutylammonium chloride (862 mg, 3.1 mmol), triethylamine (788 mg, 7.8 mmol), palladium acetate (116 mg, 0.52 mmol), dimethyl sulfoxide (10 mL) and water (1 mL) were added. Nitrogen was charged to the mixture to replace three times, and under nitrogen protection, the mixture was heated to 100° C. and stirred for 1 hr. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain 3,3-dimethyl-5-(trifluoromethyl)-2,3-dihydro-1H-pyrrolo[3,2-b]pyridine (430 mg, yield: 76%). ESI-MS: 217.0 $[M+1]^+$.

Preparation of Intermediate C10: 5-fluoro-3,3-dimethyl-2,3-dihydro-1H-pyrrolo[3,2-b]pyridine

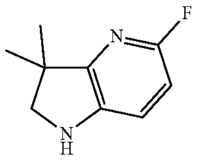

Step 1: Synthesis of 2-bromo-6-fluoro-N-(2-methylallyl)pyridin-3-amine

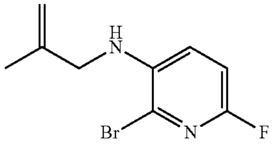

To a solution of 2-bromo-6-fluoropyridin-3-amine (1.91 g, 10.0 mmol) in tetrahydrofuran (50 mL), potassium tert-butoxide (12 mL, 12.0 mmol, 1 M/mL) was added at room temperature. The mixture was stirred at room temperature for 15 min, and then 3-bromo-2-methylprop-1-ene (1.48 g, 11.0 mmol) was slowly added dropwise to the mixture. The reaction mixture was stirred at room temperature for 1 hr, and after the reaction was completed, water and ethyl acetate were added for extraction. The organic layer was dried over anhydrous sodium sulfate and distilled under reduced pressure, and then the residue was separated by rapid silica gel column chromatography [eluent: ethyl acetate/petroleum ether: 0-10%] to obtain 2-bromo-6-fluoro-N-(2-methylallyl)pyridin-3-amine (1.7 g, yield: 69%). ESI-MS: 244.8 $[M+1]^+$.

Step 2: Synthesis of 5-fluoro-3,3-dimethyl-2,3-dihydro-1H-pyrrolo[3,2-b]pyridine

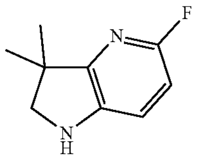

To a reaction flask, 2-bromo-6-fluoro-N-(2-methylallyl)pyridin-3-amine (1.55 g, 6.3 mmol), sodium formate (0.52 g, 7.6 mmol), tetrabutylammonium chloride (2.11 g, 7.6 mmol), triethylamine (1.92 g, 19.0 mmol), palladium acetate (0.14 g, 0.6 mmol) and dioxane (80 mL) were added. Nitrogen was charged to the mixture to replace three times, and under nitrogen protection, the mixture was heated to 100° C. and stirred for 5 hrs. The reaction mixture was filtered, and the filtrate was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-15%] to obtain 5-fluoro-3,3-dimethyl-2,3-dihydro-1H-pyrrolo[3,2-b]pyridine (0.54 g, yield: 51%). ESI-MS: 167.0 $[M+1]^+$.

Preparation of Intermediate C11: 3,3-dimethyl-1,2,3,5,6,7-hexahydrocyclopenta[b]pyrrolo[2,3-e]pyridine

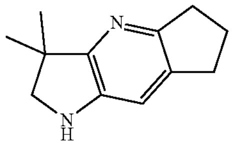

Step 1: Synthesis of 3-nitro-1,5,6,7-tetrahydro-2H-cyclopenta[b]pyridin-2-one

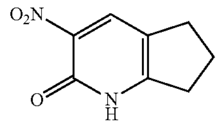 [SMILES: O=c1[nH]c2c(cc1[N+](=O)[O-])CCC2]

To a solution of 1,5,6,7-tetrahydro-2H-cyclopenta[b]pyridin-2-one (450 mg, 2.5 mmol) in concentrated sulfuric acid (98% by mass, 30 mL), nitric acid (65% by mass, 5.4 g, 55.6 mmol) was slowly added dropwise at 0° C., and the mixture was stirred at 0° C. for 1 hr, then slowly poured into ice water, stirred for another 1 hr, and filtered. The filter cake was dried to obtain 3-nitro-1,5,6,7-tetrahydro-2H-cyclopenta[b]pyridin-2-one (3.5 g, yield: 52.5%). ESI-MS: 181.0 $[M+1]^+$.

Step 2: Synthesis of 2-chloro-3-nitro-6,7-dihydro-5H-cyclopenta[b]pyridine

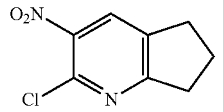 [SMILES: O=[N+]([O-])c1cc2c(nc1Cl)CCC2]

To a solution of 3-nitro-1,5,6,7-tetrahydro-2H-cyclopenta[b]pyridin-2-one (2.5 g, 13.9 mmol) in acetonitrile (50 mL), phosphorus oxychloride (6.4 g, 41.6 mmol) and triethylbenzylammonium chloride (1.9 g, 7.0 mmol) were added, and the mixture was stirred at 80° C. for 1 hr and concentrated under reduced pressure to remove the solvent. The residue was slowly poured into ice water, and the resulting mixture was stirred for 30 min and extracted with dichloromethane. The organic layer was dried over anhydrous sodium sulfate and distilled under reduced pressure, and then the residue was separated by rapid silica gel column chromatography [eluent: ethyl acetate/petroleum ether: 0-50%] to obtain 2-chloro-3-nitro-6,7-dihydro-5H-cyclopenta[b]pyridine (985 mg, yield: 36.0%). ESI-MS: 198.9 $[M+1]^+$.

Step 3: Synthesis of diethyl 2-(3-nitro-6,7-dihydro-5H-cyclopenta[b]pyridin-2-yl)malonate

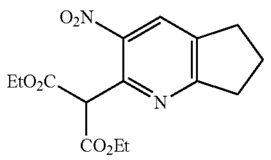 [SMILES: CCOC(=O)C(C(=O)OCC)c1nc2c(cc1[N+](=O)[O-])CCC2]

To a solution of 2-chloro-3-nitro-6,7-dihydro-5H-cyclopenta[b]pyridine (814 mg, 5.1 mmol) in dimethyl sulfoxide (10 mL), sodium hydride (220 mg, 5.5 mmol) was added at 0° C., and the mixture was stirred at 0° C. for 0.5 hrs. Diethyl malonate (840 mg, 4.2 mmol) was then added to the mixture, and the reactant was stirred at 100° C. for 1 hr and cooled to room temperature. A saturated ammonium chloride solution was added to quench the reaction, and the reaction mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-30%] to obtain diethyl 2-(3-nitro-6,7-dihydro-5H-cyclopenta[b]pyridin-2-yl)malonate (409 mg, yield: 30.0%). ESI-MS: 323.0 $[M+1]^+$.

Step 4: Synthesis of ethyl 2-(3-nitro-6,7-dihydro-5H-cyclopenta[b]pyridin-2-yl)acetate

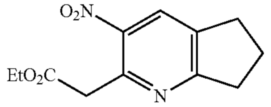 [SMILES: CCOC(=O)Cc1nc2c(cc1[N+](=O)[O-])CCC2]

To a solution of diethyl 2-(3-nitro-6,7-dihydro-5H-cyclopenta[b]pyridin-2-yl) malonate (409 mg, 1.3 mmol) in dimethyl sulfoxide (5 mL), water (0.91 mL, 5.1 mmol) and lithium chloride (267 mg, 6.4 mmol) were added. The mixture was stirred at 100° C. for 24 hrs. The reaction mixture was cooled to room temperature, washed with water, and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-50%] to obtain ethyl 2-(3-nitro-6,7-dihydro-5H-cyclopenta[b]pyridin-2-yl)acetate (240 mg, yield: 76.0%). ESI-MS: 251.0 $[M+1]^+$.

Step 5: Synthesis of ethyl 2-methyl-2-(3-nitro-6,7-dihydro-5H-cyclopenta[b]pyridin-2-yl)propanoate

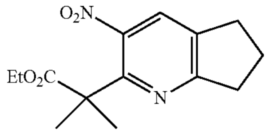 [SMILES: CCOC(=O)C(C)(C)c1nc2c(cc1[N+](=O)[O-])CCC2]

To a solution of ethyl 2-(3-nitro-6,7-dihydro-5H-cyclopenta[b]pyridin-2-yl)acetate (240 mg, 0.96 mmol) in N,N-dimethylformamide (5 mL), iodomethane (300 mg, 2.1 mmol) and 18-crown-6 (26 mg, 0.1 mmol) were added at 0° C., and then sodium hydride (88 mg, 2.2 mmol) was slowly added. The mixture was stirred at 0° C. for 1 hr, and after the reaction was completed, ice water was added to quench the reaction, and the resulting mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-25%] to obtain ethyl 2-methyl-2-(3-nitro-6,7-dihydro-5H-cyclopenta[b]pyridin-2-yl)propanoate (150 mg, yield: 56.0%). ESI-MS: 279.0 $[M+1]^+$.

Step 6: Synthesis of 3,3-dimethyl-3,5,6,7-tetrahydrocyclopenta[b]pyrrolo[2,3-e]pyridin-2(1H)-one

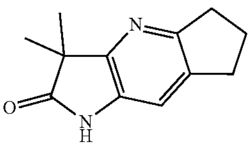

To a solution of ethyl 2-methyl-2-(3-nitro-6,7-dihydro-5H-cyclopenta[b]pyridin-2-yl) propanoate (150 mg, 0.54 mmol) in ethanol (5 mL), ammonium formate (272 mg, 4.3 mmol) and 10% palladium on carbon (50 mg) were added, and the mixture was stirred at 90° C. for reaction for 16 hrs. After the reaction was completed, the reaction mixture was filtered, and the filtrate was concentrated. The residue was washed with water and extracted with ethyl acetate, and the organic layer was dried over anhydrous sodium sulfate and distilled under reduced pressure to obtain a crude product of 3,3-dimethyl-3,5,6,7-tetrahydrocyclopenta[b]pyrrolo[2,3-e]pyridin-2(1H)-one, which was directly used in the next step. ESI-MS: 203.0 $[M+1]^+$.

Step 7: Synthesis of 3,3-dimethyl-1,2,3,5,6,7-hexahydrocyclopenta[b]pyrrolo [2,3-e]pyridine

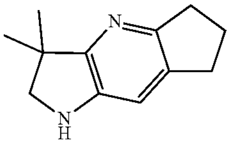

The crude product of 3,3-dimethyl-3,5,6,7-tetrahydrocyclopenta[b]pyrrolo[2,3-e]pyridin-2(1H)-one was dissolved in tetrahydrofuran (5 mL), then the resulting solution was cooled to 0° C., and a solution of lithium aluminum hydride in tetrahydrofuran (2 mL, 2.5 M) was added dropwise to the solution. The mixture was stirred at room temperature for 4 hrs. After the reaction was completed, sodium sulfate decahydrate was added to the reaction mixture to quench the reaction until no bubbles were generated. The mixture was filtered, and the filtrate was distilled under reduced pressure to obtain a crude product of 3,3-dimethyl-1,2,3,5,6,7-hexahydrocyclopenta[b]pyrrolo[2,3-e]pyridine. ESI-MS: 189.0 $[M+1]^+$.

Preparation of Intermediate C12: 5'-methyl-1',2'-dihydrospiro(cyclobutane-1,3'-pyrrolo[3,2-b]pyridine)

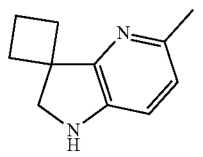

Step 1: Synthesis of 1-(tert-butyl) 3-ethyl 2-(6-methyl-3-nitropyridin-2-yl) malonate

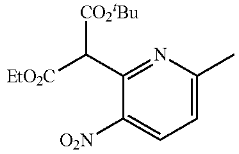 [SMILES: CCOC(=O)C(C(=O)OC(C)(C)C)c1nc(C)ccc1[N+](=O)[O-]]

1-tert-butyl 3-ethyl malonate (35.45 g, 188.3 mmol) was slowly added dropwise to a suspension of sodium hydride (6.95 g, 173.8 mmol) in tetrahydrofuran (200 mL) at 0° C. The mixture was stirred under an ice bath for 0.5 hrs, and then 2-chloro-6-methyl-3-nitropyridine (25 g, 144.8 mmol) was added to the mixture. The reaction mixture was stirred at 60° C. for 18 hrs, and after the reaction was completed, the reaction mixture was cooled to 0° C., and ice water was slowly added to quench the reaction. The mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-20%] to obtain 1-(tert-butyl) 3-ethyl 2-(6-methyl-3-nitropyridin-2-yl)malonate (41 g, yield: 73.3%). ESI-MS: 325.0 $[M+1]^+$.

Step 2: Synthesis of ethyl 2-(6-methyl-3-nitropyridin-2-yl)acetate

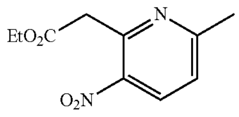

Trifluoroacetic acid (100 mL) was added to 1-(tert-butyl) 3-ethyl 2-(6-methyl-3-nitropyridin-2-yl)malonate (41 g, 106.2 mmol), and the mixture was stirred at 60° C. for 2 hrs. The reaction mixture was distilled under reduced pressure, and then the residue was diluted with dichloromethane and washed with saturated sodium bicarbonate. The organic layer was dried over anhydrous sodium sulfate and distilled under reduced pressure, and then the residue was separated by rapid silica gel column chromatography [eluent: ethyl acetate/petroleum ether: 0-15%] to obtain ethyl 2-(6-methyl-3-nitropyridin-2-yl)acetate (22 g, yield: 89%). ESI-MS: 225.0 $[M+1]^+$.

Step 3: Synthesis of ethyl 2-(3-amino-6-methylpyridin-2-yl)acetate

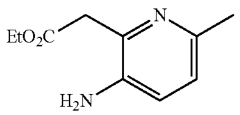 [SMILES: CCOC(=O)Cc1nc(C)ccc1[N+](=O)[O-]]

To a solution of ethyl 2-(6-methyl-3-nitropyridin-2-yl) acetate (22 g, 95.4 mmol) in methanol (150 mL), 10% palladium on carbon (3.0 g) was added. The mixture was stirred under hydrogen at room temperature overnight, and after the reaction was completed, the mixture was filtered and distilled under reduced pressure to obtain ethyl 2-(3-amino-6-methylpyridin-2-yl)acetate (17.5 g, yield: 82%). ESI-MS: 195.0 $[M+1]^+$.

Step 4: Synthesis of 5-methyl-1,3-dihydro-2H-pyrrolo[3,2-b]pyridin-2-one

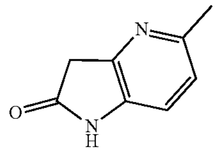

Ethyl 2-(3-amino-6-methylpyridin-2-yl)acetate (17.5 g, 78.4 mmol) was added to a solution of hydrochloric acid (1 M, 1(0) mL), and the mixture was stirred at 55° C. for reaction for 5 hrs. After the reaction was completed, the mixture was neutralized to alkalinous with saturated sodium bicarbonate and extracted several times with a solvent of dichloromethane:methanol (10:1). The organic layer was dried over anhydrous sodium sulfate and distilled under reduced pressure, and then the residue was separated by rapid silica gel column chromatography [eluent: dichloromethane/methanol: 0-10%] to obtain 5-methyl-1,3-dihydro-2H-pyrrolo[3,2-b]pyridin-2-one (7.8 g, yield: 67%). ESI-MS: 149.0 [M+1]1.

Step 5: Synthesis of 5'-methylspiro(cyclobutane-1,3'-pyrrolo[3,2-b]pyridin)-2'(1'H)-one

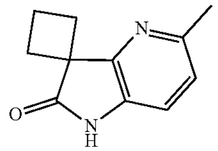

Sodium hydride (674.9 mg, 16.8 mmol) was dissolved in N,N-dimethylformamide (20 mL) and hexamethylphosphoric triamide (2 mL), then the resulting solution was cooled to 0° C., and a solution of 5-methyl-1,3-dihydro-2H-pyrrolo[3,2-b]pyridin-2-one (1.0 g, 6.7 mmol) and 1,3-diiodopropane (0.78 mL, 6.7 mmol) in N,N-dimethylformamide (20 mL) was added dropwise to the solution. The mixture was stirred at 0° C. for 1 hr. After the reaction was completed, the reaction mixture was poured into ice water, and the resulting mixture was extracted with ethyl acetate. The organic layer was dried over anhydrous sodium sulfate and distilled under reduced pressure, and then the residue was separated by rapid silica gel column chromatography [eluent: petroleum ether/ethyl acetate: 0-30%] to obtain 5'-methylspiro(cyclobutane-1,3'-pyrrolo[3,2-b]pyridin)-2'(1'H)-one (260 mg, yield: 20%). ESI-MS: 189.0 $[M+1]^+$.

Step 6: Synthesis of 5'-methyl-1',2'-dihydrospiro (cyclobutane-1,3'-pyrrolo [3,2-b]pyridine)

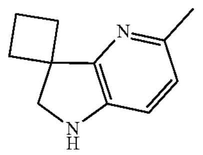

5'-methylspiro(cyclobutane-1,3'-pyrrolo[3,2-b]pyridin)-2'(1'H)-one (263 mg, 1.4 mmol) was dissolved in tetrahydrofuran (20 mL), then the resulting solution was cooled to 0° C., and a solution of lithium aluminum hydride in tetrahydrofuran (1.7 mL, 2.5 M) was added dropwise to the solution. The mixture was stirred at 50° C. for 2 hrs. After the reaction was completed, sodium sulfate decahydrate was added to the reaction mixture to quench the reaction until no bubbles were generated. The mixture was filtered, and the filtrate was distilled under reduced pressure to obtain 5'-methyl-1',2'-dihydrospiro (cyclobutane-1,3'-pyrrolo[3,2-b]pyridine) (260 mg, yield: 76%). ESI-MS: 175.0 $[M+1]^+$.

Preparation of Intermediate C13: 3,3,5-trimethyl-2,3-dihydro-1H-pyrrolo [3,2-b]pyridine-2,2-$d_2$

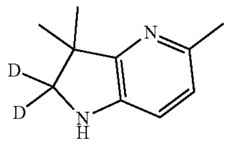

Step 1: Synthesis of ethyl 2-methyl-2-(6-methyl-3-nitropyridin-2-yl)propanoate

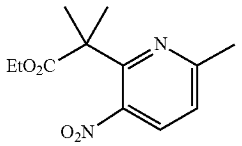 [SMILES: CCOC(=O)C(C)(C)c1nc(C)ccc1[N+](=O)[O-]]

To a solution of ethyl 2-(6-methyl-3-nitropyridin-2-yl) acetate (23 g, 102.58 mmol) in N,N-dimethylformamide (250 mL), methyl iodide (43.68 g, 307.7 mmol) and 18-crown-6 (0.39 g, 1.47 mmol) were added at 0° C., and then sodium hydride (10.3 g, 256.4 mmol) was slowly added. The mixture was stirred at 0° C. for 1 hr, and after the reaction was completed, ice water was added to quench the reaction, and the resulting mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-25%] to obtain ethyl 2-methyl-2-(6-methyl-3-nitropyridin-2-yl)propanoate (13 g, yield: 49.2%). ESI-MS: 253.0 $[M+1]^+$.

Step 2: Synthesis of 3,3,5-trimethyl-1,3-dihydro-2H-pyrrolo[3,2-b]pyridin-2-one

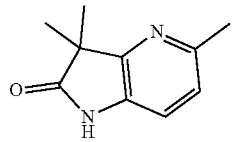

To a solution of ethyl 2-methyl-2-(6-methyl-3-nitropyridin-2-yl)propanoate (5.9 g, 23.4 mmol) in ethanol (100 mL), 10% palladium on carbon (300 mg) was added, and the mixture was stirred under a hydrogen atmosphere for reaction for 2 hrs. After the reaction was completed, the reaction mixture was filtered, the filtrate was concentrated, and the residue was dissolved in acetic acid (50 mL) and incubated at 90° C. for reaction overnight. After the reaction was completed, the reaction mixture was distilled under reduced pressure to obtain 3,3,5-trimethyl-1,3-dihydro-2H-pyrrolo[3,2-b]pyridin-2-one (4.0 g, yield: 97%), which was directly used in the next step. ESI-MS: 163.0 $[M+1]^+$.

Step 3: Synthesis of 3,3,5-trimethyl-2,3-dihydro-1H-pyrrolo[3,2-b]pyridine-2,2-$d_2$

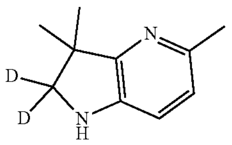

3,3,5-trimethyl-1,3-dihydro-2H-pyrrolo[3,2-b]pyridin-2-one (0.6 g, 3.4 mmol) was dissolved in tetrahydrofuran (25 mL), then the resulting solution was cooled to 0° C. and deuterated lithium aluminum hydride (0.43 g, 10.2 mmol) was added to the solution. The mixture was stirred at 50° C. for 2 hrs. After the reaction was completed, sodium sulfate decahydrate was added to the reaction mixture to quench the reaction until no bubbles were generated. The mixture was filtered, and the filtrate was distilled under reduced pressure to obtain a crude product, which was separated by rapid silica gel column chromatography [eluent: ethyl acetate/petroleum ether: 0-25%] to obtain 3,3,5-trimethyl-2,3-dihydro-1H-pyrrolo[3,2-b]pyridine-2,2-$d_2$ (0.49 g, yield: 87%). ESI-MS: 165.0 $[M+1]^+$.

Preparation of Intermediate C14: 5-methyl-3,3-bis (methyl-$d_3$)-2,3-dihydro-1H-pyrrolo[3,2-b]pyridine

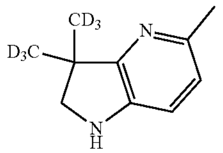 [SMILES: [2H]C([2H])([2H])C1(C([2H])([2H])[2H])CNc2ccc(C)nc21]

Step 1: Synthesis of ethyl 2-(methyl-$d_3$)-2-(6-methyl-3-nitropyridin-2-yl) propanoate-3,3,3-$d_3$

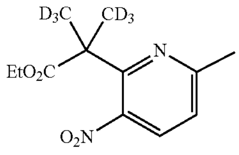 [SMILES: [2H]C([2H])([2H])C(C(=O)OCC)(c1nc(C)ccc1[N+](=O)[O-])C([2H])([2H])[2H]]

To a solution of ethyl 2-(6-methyl-3-nitropyridin-2-yl) acetate (4 g, 17.84 mmol) in N,N-dimethylformamide (30 mL), deuterated iodomethane (19.16 mL, 307.73 mmol) and 18-crown-6 (0.47 g, 1.78 mmol) were added at 0° C., and then sodium hydride (1.78 g, 44.60 mmol) was slowly added. The mixture was stirred at 0° C. for 1 hr, and after the reaction was completed, ice water was added to quench the reaction, and the resulting mixture was washed with water and extracted with ethyl acetate. The organic layer was dried over anhydrous sodium sulfate and distilled under reduced pressure, and then the residue was separated by rapid silica gel column chromatography [eluent: ethyl acetate/petroleum ether: 0-25%] to obtain ethyl 2-(methyl-$d_3$)-2-(6-methyl-3-nitropyridin-2-yl)propanoate-3,3,3-$d_3$ (3.2 g, yield: 91%). ESI-MS: 259.0 $[M+1]^+$.

Step 2: Synthesis of 5-methyl-3,3-bis(methyl-$d_3$)-1,3-dihydro-2H-pyrrolo[3,2-b]pyridin-2-one

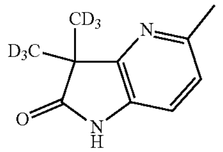 [SMILES: [2H]C([2H])([2H])C1(C([2H])([2H])[2H])C(=O)Nc2ccc(C)nc21]

To a solution of ethyl 2-(methyl-$d_3$)-2-(6-methyl-3-nitropyridin-2-yl)propanoate-3,3,3-$d_3$ (1.2 g, 4.64 mmol) in ethanol (20 mL), ammonium formate (3.4 g, 53.7 mmol) and 10% palladium on carbon (300 mg) were added, and the mixture was stirred at 90° C. for reaction for 2 hrs. After the reaction was completed, the reaction mixture was filtered, and the filtrate was concentrated. The residue was washed with water and extracted with ethyl acetate, and the organic layer was dried over anhydrous sodium sulfate and distilled under reduced pressure to obtain 5-methyl-3,3-bis(methyl-$d_3$)-1,3-dihydro-2H-pyrrolo[3,2-b]pyridin-2-one (0.75 g, yield: 88.6%), which was directly used in the next step. ESI-MS: 183.0 $[M+1]^+$.

Step 3: Synthesis of 5-methyl-3,3-bis(methyl-$d_3$)-2,3-dihydro-1H-pyrrolo[3,2-b]pyridine

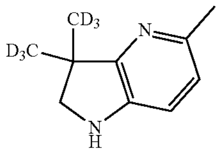 [SMILES: [2H]C([2H])([2H])C1(C([2H])([2H])[2H])CNc2ccc(C)nc21]

5-methyl-3,3-bis(methyl-$d_3$)-1,3-dihydro-2H-pyrrolo[3,2-b]pyridin-2-one (750 mg, 4.12 mmol) was dissolved in tetrahydrofuran (20 mL), then the resulting solution was cooled to 0° C., and a solution of lithium aluminum hydride in tetrahydrofuran (2 mL, 2.5 M) was added dropwise to the solution. The mixture was stirred at 50° C. for 3 hrs. After the reaction was completed, sodium sulfate decahydrate was added to the reaction mixture to quench the reaction until no bubbles were generated. The mixture was filtered, and the filtrate was distilled under reduced pressure to obtain 5-methyl-3,3-bis(methyl-$d_3$)-2,3-dihydro-1H-pyrrolo[3,2-b]pyridine (692 mg, yield: 89.9%). ESI-MS: 169.0 $[M+1]^+$.

Preparation of Intermediate C15: 5'-methyl-1',2'-dihydrospiro(cyclopropane-1,3'-pyrrolo[3,2-b]pyridine)

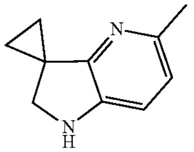

Step 1: Synthesis of ethyl 1-(6-methyl-3-nitropyridin-2-yl)cyclopropane-1-carboxylate

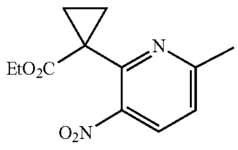

Ethyl 2-(6-methyl-3-nitropyridin-2-yl)acetate (4.9 g, 21.8 mmol) was dissolved in dimethyl sulfoxide (30 mL), and then diphenyl(vinyl)sulfonium trifluoromethanesulfonate (7.92 g, 21.8 mmol) was added. The mixture was stirred at room temperature for 10 min, and 2,3,4,6,7,8,9,10-octahydropyrimido[1,2-a]azapine (9.8 mL, 65.6 mmol) was added. The reaction mixture was stirred at room temperature for 1 hr. Ethyl acetate (100 mL) and saturated brine (100 mL) were added to the reaction mixture, and then the mixture solution was separated. The organic phase was concentrated, and then the residue was separated by rapid silica gel column chromatography [petroleum ether/ethyl acetate=3/1] to obtain ethyl 1-(6-methyl-3-nitropyridin-2-yl)cyclopropane-1-carboxylate (5.2 g, yield: 95%). ESI-MS: 251.0 $[M+1]^+$.

Step 2: Synthesis of 5'-methylspiro(cyclopropane-1, 3'-pyrrolo[3,2-b]pyridin)-2'(1'H)-one

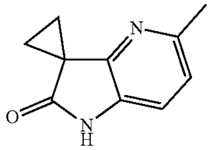

Ethyl 1-(6-methyl-3-nitropyridin-2-yl)cyclopropane-1-carboxylate (5.2 g, 20.8 mmol) was dissolved in ethanol (100 mL), and palladium/carbon (500 mg) was added. The reaction mixture was stirred under a hydrogen atmosphere at room temperature for 3 hrs, then concentrated hydrochloric acid (1 mL) was added for reaction, and the reaction mixture was heated and stirred for 18 hrs. After the reaction was completed, the reaction mixture was concentrated by filtration through diatomaceous earth, ethyl acetate (50 mL) and saturated brine (50 mL) were added to the residue, and then the mixture solution was separated. The organic phase was washed with saturated brine (50 mL). The resulting organic phase was concentrated, and then the residue was separated by rapid silica gel column chromatography [petroleum ether/ethyl acetate=1/1] to obtain 5'-methylspiro(cyclopropane-1, 3'-pyrrolo[3,2-b]pyridin)-2'(1'H)-one (3.5 g, yield: 96%). ESI-MS: 175.0 $[M+1]^+$.

Step 3: Synthesis of 5'-methyl-1',2'-dihydrospiro (cyclopropane-1,3'-pyrrolo [3,2-b]pyridine)

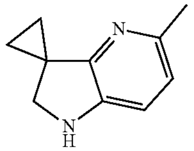

5'-methylspiro(cyclopropane-1,3'-pyrrolo[3,2-b]pyridin)-2'(1'H)-one (3.0 g, 17.2 mmol) was dissolved in tetrahydrofuran (100 mL), and then a solution of lithium aluminum hydride in tetrahydrofuran (17.0 mL, 42.5 mmol) was added to the reaction mixture. The reaction mixture was stirred at 60° C. under nitrogen protection for 2 hrs, and after the reaction was completed, sodium sulfate decahydrate was added to the reaction mixture to slowly quench the reaction. The mixture was then filtered, the filtrate was concentrated, and the residue was separated by rapid silica gel column chromatography [petroleum ether/ethyl acetate=3/1] to obtain 5'-methyl-1',2'-dihydrospiro(cyclopropane-1,3'-pyrrolo[3,2-b]pyridine) (1.0 g, yield: 36%). ESI-MS: 161.0 $[M+1]^+$.

Preparation of Intermediate C16: 3,3-difluoro-5'-methyl-1',2'-dihydrospiro (cyclobutane-1,3'-pyrrolo [3,2-b]pyridine)

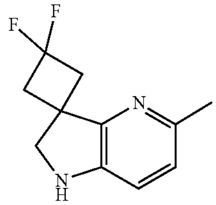

Step 1: Synthesis of N-(2-bromo-6-methylpyridin-3-yl)-3,3-difluorocyclobutane-1-carboxamide

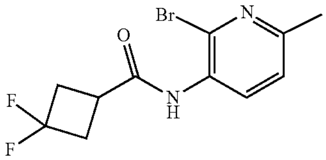 [SMILES: Cc1ccc(NC(=O)C2CC(F)(F)C2)c(Br)n1]

2-bromo-6-methylpyridin-3-amine (5.0 g, 26.73 mmol), 3,3-difluorocyclobutane-1-carboxylic acid (4.37 g, 32.08 mmol) and 1-methylimidazole (6.58 g, 80.2 mmol) were dissolved in acetonitrile (150 mL), then N,N,N',N'-tetramethylchloroformamidinium hexafluorophosphate (9.00 g, 32.08 mmol) was added, and the mixture was stirred at room temperature for 3 hrs. After the reaction was completed, the reaction mixture was poured into water and extracted with ethyl acetate. The organic layer was dried over anhydrous sodium sulfate and distilled under reduced pressure, and then the residue was separated by rapid silica gel column chromatography [eluent: petroleum ether/ethyl acetate: 0-30%] to obtain N-(2-bromo-6-methylpyridin-3-yl)-3,3-difluorocyclobutane-1-carboxamide (7.8 g, yield: 95%). ESI-MS: 304.8 $[M+1]^+$.

Step 2: Synthesis of N-(2-bromo-6-methylpyridin-3-yl)-3,3-difluoro-N-(4-methoxybenzyl)cyclobutane-1-carboxamide

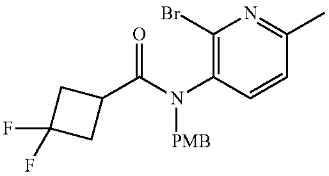

To a solution of N-(2-bromo-6-methylpyridin-3-yl)-3,3-difluorocyclobutane-1-carboxamide (3.0 g, 9.8 mmol) in acetonitrile (50 mL), 1-(chloromethyl)-4-methoxybenzene (2.01 mL, 14.75 mmol) and potassium carbonate (4.08 g, 29.5 mmol) were added. The mixture was stirred at 90° C. for reaction for 18 hrs, and after the reaction was completed, the reaction mixture was filtered and distilled under reduced pressure, and then the residue was separated by rapid silica gel column chromatography [eluent: petroleum ether/ethyl acetate: 0-25%] to obtain N-(2-bromo-6-methylpyridin-3-yl)-3,3-difluoro-N-(4-methoxybenzyl)cyclobutane-1-carboxamide (3.8 g, yield: 90%). ESI-MS: 425.0 [M+1]$^+$.

Step 3: Synthesis of 3,3-difluoro-1'-(4-methoxybenzyl)-5'-methylspiro (cyclobutane-1,3'-pyrrolo[3,2-b] pyridin)-2'(1'H)-one

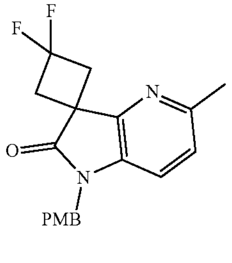

To a solution of N-(2-bromo-6-methylpyridin-3-yl)-3,3-difluoro-N-(4-methoxy benzyl) cyclobutane-1-carboxamide (3.2 g, 7.5 mmol) in dioxane (50 mL), [1,3-bis(2,6-diisopropylphenyl)imidazol-2-ylidene](3-chloropyridyl)palladium(II) dichloride (512 mg, 0.7 mmol) and sodium tert-butoxide (1.45 g, 15.0 mmol) were added, and the mixture was stirred at 100° C. under nitrogen protection for reaction for 5 hrs. After the reaction was completed, the reaction mixture was poured into water and extracted with ethyl acetate. The organic layer was dried over anhydrous sodium sulfate and distilled under reduced pressure, and then the residue was separated by rapid silica gel column chromatography [eluent: petroleum ether/ethyl acetate: 0-30%] to obtain 3,3-difluoro-1'-(4-methoxybenzyl)-5'-methylspiro (cyclobutane-1,3'-pyrrolo[3,2-b]pyridin)-2'(1'H)-one (2.0 g, yield: 77%). ESI-MS: 345.0 [M+1]$^+$.

Step 4: Synthesis of 3,3-difluoro-5'-methylspiro (cyclobutane-1,3'-pyrrolo[3,2-b]pyridin)-2'(1'H)-one

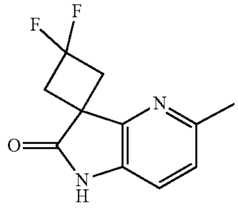 [SMILES: Cc1ccc2c(n1)C1(CC(F)(F)C1)C(=O)N2]

3,3-difluoro-1'-(4-methoxybenzyl)-5'-methylspiro(cyclobutane-1,3'-pyrrolo[3,2-b]pyridin)-2'(1'H)-one (1.8 g, 5.2 mmol) was dissolved in dichloromethane (3 mL), and trifluoromethanesulfonic acid (3.5 mL) was added to the solution. The mixture was stirred at room temperature overnight. After the reaction was completed, the residue was diluted with dichloromethane and washed with saturated sodium bicarbonate. The organic layer was dried over anhydrous sodium sulfate and distilled under reduced pressure, and then the residue was separated by rapid silica gel column chromatography [eluent: ethyl acetate/petroleum ether: 0-50%] to obtain 3,3-difluoro-5'-methylspiro(cyclobutane-1,3'-pyrrolo[3,2-b]pyridin)-2'(1'H)-one (1.1 g, yield: 93%). ESI-MS: 225.0 [M+1]$^+$.

Step 5: Synthesis of 3,3-difluoro-5'-methyl-1',2'-dihydrospiro(cyclobutane-1,3'-pyrrolo[3,2-b]pyridine)

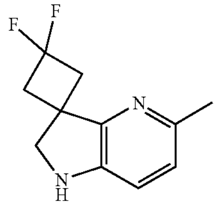

3,3-difluoro-5'-methylspiro(cyclobutane-1,3'-pyrrolo[3,2-b]pyridin)-2'(1'H)-one (250 mg, 1.1 mmol) was dissolved in tetrahydrofuran (20 mL), then the resulting solution was cooled to 0° C., and a solution of lithium aluminum hydride in tetrahydrofuran (1.3 mL, 2.5 M) was added dropwise to the solution. The mixture was stirred at 50° C. for 2 hrs. After the reaction was completed, sodium sulfate decahydrate was added to the reaction mixture to quench the reaction until no bubbles were generated. The mixture was filtered, and the filtrate was distilled under reduced pressure to obtain 3,3-difluoro-5'-methyl-1',2'-dihydrospiro(cyclobutane-1,3'-pyrrolo[3,2-b]pyridine) (250 mg, yield: 100%). ESI-MS: 211.0 [M+1]$^+$.

Preparation of Intermediate C17: 5,6-difluoro-3,3-dimethylindoline

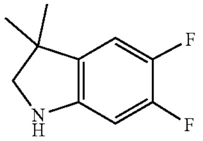

Step 1: Synthesis of 5,6-difluoro-3,3-dimethylindolin-2-one

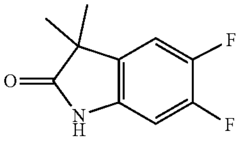

To a suspension of 5,6-difluoroindolin-2-one (5.0 g, 29.5 mmol) and lithium chloride (6.2 g, 148 mmol) in tetrahydrofuran (100 mL), a 2.5 M n-butyl lithium solution (59.2 mL, 148 mmol) was slowly added dropwise at −78° C. The reaction mixture was stirred at −78° C. for 30 min, and then methyl iodide (21.0 g, 148 mmol) was added. The reaction mixture was stirred at −78° C. for another 30 min and then stirred at room temperature for 2 hrs. Ethyl acetate and water were added, and then the mixture solution was separated. The organic phase was successively washed with water and saturated brine, then dried over anhydrous sodium sulfate, filtered, and concentrated, and then the residue was separated by column chromatography [petroleum ether/ethyl acetate=5:1] to obtain 5,6-difluoro-3,3-dimethylindolin-2-one (3.6 g, yield: 61%). ESI-MS: 198.0 [M+1]$^+$.

Step 2: Synthesis of 5,6-difluoro-3,3-dimethylindoline

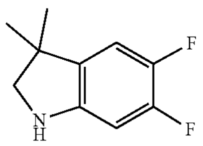

To a solution of 5,6-difluoro-3,3-dimethylindolin-2-one (3.6 g, 18 mmol) in tetrahydrofuran (80 mL), a 2.5 M solution of lithium aluminum hydride in tetrahydrofuran (28.8 mL, 72 mmol) was added. The reaction mixture was stirred at 50° C. for 3 hrs. Sodium sulfate decahydrate was added to quench the reaction, and the resulting mixture was filtered. The organic phase was concentrated, and then the residue was separated by column chromatography [petroleum ether/ethyl acetate=3:1] to obtain 5,6-difluoro-3,3-dimethylindoline (1.8 g, yield: 54%). ESI-MS: 184.0 [M+1]$^+$.

$^1$H NMR (DMSO-$d_6$) δ 7.03 (dd, J=10.4, 8.3 Hz, 1H), 6.40 (dd, J=11.8, 6.7 Hz, 1H), 5.58 (s, 1H), 3.19 (s, 2H), 1.20 (s, 6H).

Preparation of Intermediate D1: isopropyl 2-chloro-4-(3,3,5-trimethyl-2,3-dihydro-1H-pyrrolo[3,2-b]pyridin-1-yl)pyrimidine-5-carboxylate

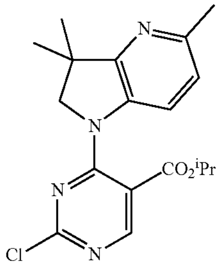

Isopropyl 2,4-dichloropyrimidine-5-carboxylate (147.8 mg, 0.63 mmol) was dissolved in isopropanol (5 mL) at room temperature, and 3,3,5-trimethyl-2,3-dihydro-1H-pyrrolo[3,2-b]pyridine (85.0 mg, 0.52 mmol) and N,N-diisopropylethylamine (101.6 mg, 0.77 mmol) were successively added. The reaction mixture was stirred under microwave at 100° C. for 16 hrs. After the reaction was completed, the solvent was removed, and then the residue was separated by silica gel column chromatography [petroleum ether:ethyl acetate=4:1] to obtain isopropyl 2-chloro-4-(3,3,5-trimethyl-2,3-dihydro-1H-pyrrolo[3,2-b]pyridin-1-yl)pyrimidine-5-carboxylate (100 mg, yield: 49.2%). ESI-MS: 361.0 [M+1]$^+$.

Intermediates D2 to D19 were prepared according to the preparation method for intermediate D1:

| Intermediate No. | Structure | Chemical name | ESI-MS: [M + 1]$^+$ |
|---|---|---|---|
| D2 | 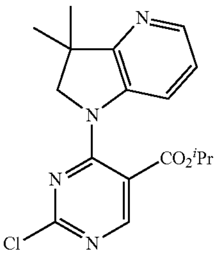 | isopropyl 2-chloro-4-(3,3-dimethyl-2,3-dihydro-1H-pyrrolo[3,2-b]pyridin-1-yl)pyrimidine-5-carboxylate | 347.0 |
| D3 | 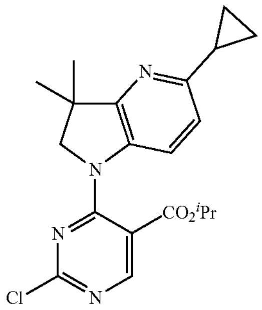 | isopropyl 2-chloro-4-(5-cyclopropyl-3,3-dimethyl-2,3-dihydro-1H-pyrrolo[3,2-b]pyridin-1-yl)pyrimidine-5-carboxylate | 387.0 |

-continued

| Intermediate No. | Structure | Chemical name | ESI-MS: [M + 1]+ |
|---|---|---|---|
| D4 | 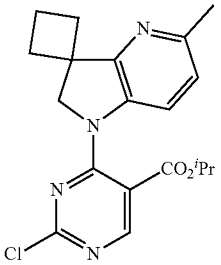 | isopropyl 2-chloro-4-(5'-methylspiro (cyclobutane-1,3'-pyrrolo [3,2-b]pyridin)-1'(2H)-yl) pyrimidine-S-carboxylate | 373.0 |
| D5 | 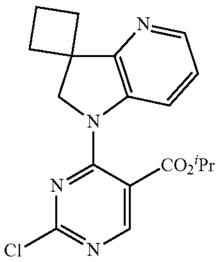 | isopropyl 2-chloro-4-(spiro(cyclobutane-1, 3'-pyrrolo[3,2-b]pyridin)-1'(2'H)-yl)pyrimidine-5-carboxylate | 359 |
| D6 | 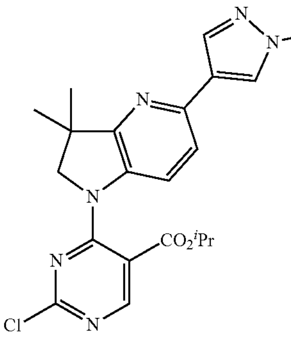 | isopropyl 2-chloro-4-(3,3-dimethyl-5-(1-methyl-1H-pyrazol-4-yl)-2,3-dihydro-1H-pyrrolo[3,2-b] pyridin-1-yl)pyrimidine-5-carboxylate | 427.0 |
| D7 | 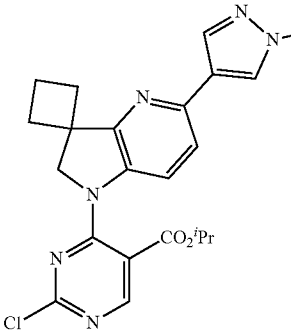 | isopropyl 2-chloro-4-(5'-(1-methyl-1H-pyrazol-4-yl)spiro (cyclobutane-1,3'-pyrrolo[3, 2-b]pyridin)-1'(2'H)-yl) pyrimidine-5-carboxylate | 439.0 |
| D8 | 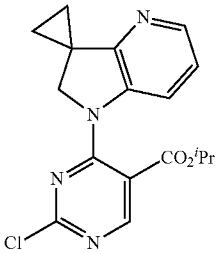 | isopropyl 2-chloro-4-(spiro(cyclopropane-1,3'-pyrrolo[3,2-6]pyridin)- 1'(2' H)-yl)pyrimidine-5-carboxylate isopropyl | 345.0 |

-continued

| Intermediate No. | Structure | Chemical name | ESI-MS: [M + 1]+ |
|---|---|---|---|
| D9 | 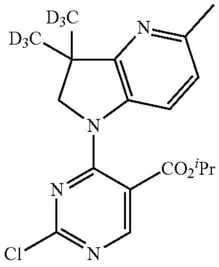 | isopropyl 2-chloro-4-(5-methyl-3,3-bis(methyl-d3)-2,3-dihydro-1H-pyrrolo[3,2-b]pyridin-1-yl)pyrimidine-5-carboxylate | 367.2 |
| D10 | 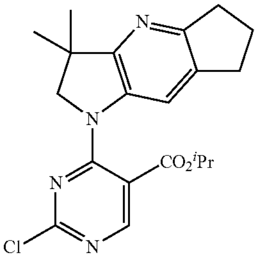 | isopropyl 2-chloro-4-(3,3-dimethyl-3,5,6,7-tetrahydrocyclopenta[b]pyrrolo[2,3-e]pyridin-1(2H)-yl)pyrimidine-5-carboxylate | 387.3 |
| D11 | 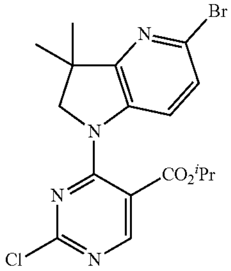 | isopropyl 4-(5-bromo-3,3-dimethyl-2,3-dihydro-1H-pyrrolo[3,2-b]pyridin-1-yl)-2-chloropyrimidine-5-carboxylate | 425.0 427.1 |
| D12 | 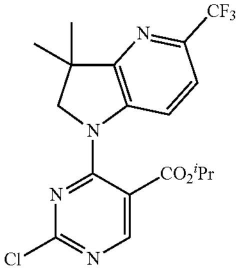 | isopropyl 2-chloro-4-(3,3-dimethyl-5-(trifluoromethyl)-2,3-dihydro-1H-pyrrolo[3,2-b]pyridin-1-yl)pyrimidine-S-carboxylate | 415.1 |
| D13 | 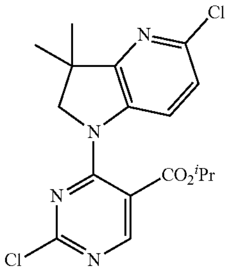 | isopropyl 4-(5-chloro-3,3-dimethyl-2,3-dihydro-1H-pyrrolo[3,2-b]pyridin-1-yl)-2-chloropyrimidine-5-carboxylate | 381.5 |

-continued

| Intermediate No. | Structure | Chemical name | ESI-MS: $[M + 1]^+$ |
|---|---|---|---|
| D14 | 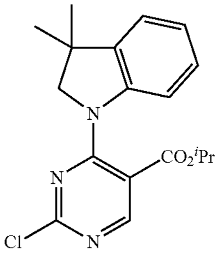 | isopropyl 2-chloro-4-(3,3-dimethylindolin-1-yl)pyrimidine-5-carboxylate | 346.1 |
| D15 | 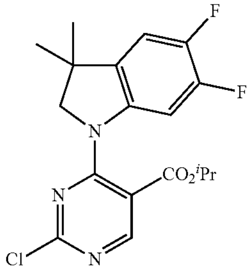 | isopropyl 2-chloro-4-(5,6-difluoro-3,3-dimethylindolin-1-yl)pyrimidine-5-carboxylate | 382.1 |
| D16 | 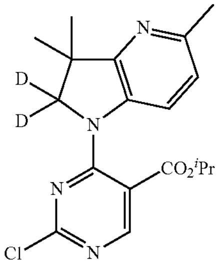 | isopropyl 2-chloro-4-(3,3,5-trimethyl-2,3-dihydro-1H-pyrrolo[3,2-b] pyridin-1-yl-2,2-d2)pyrimidine-5-carboxylate | 363.0 |
| D17 | 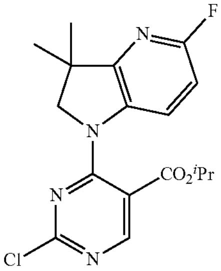 | isopropyl 2-chloro-4-(5-fluoro-3,3-dimethyl-2,3-dihydro-1H-pyrrolo[3,2-b]pyridin-1-yl) pyrimidine-5-carboxylate | 365.0 |
| D18 | 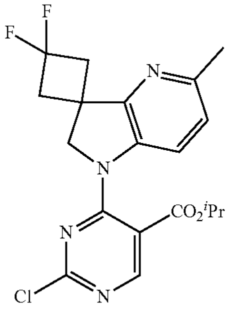 | isopropyl 2-chloro-4-(3,3-difluoro-5'-methylspiro(cyclobutane-1,3'-pyrrolo[3,2-b]pyridin)-1'(2'H)-yl)pyrimidine-5-carboxylate | 409.0 |

-continued

| Intermediate No. | Structure | Chemical name | ESI-MS: [M + 1]+ |
|---|---|---|---|
| D19 | 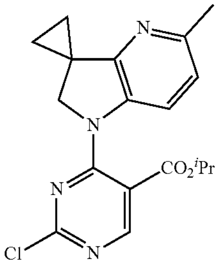 | isopropyl 2-chloro-4-(5'-methylspiro [cyclopropane-1,3'-pyrrolo [3,2-b]pyridin]-l'(2'H)-yl) pyrimidine-5-carboxylate | 359.0 |

Preparation of Intermediate E1: isopropyl 2-((4-((2-(dimethylamino)ethyl) (methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate

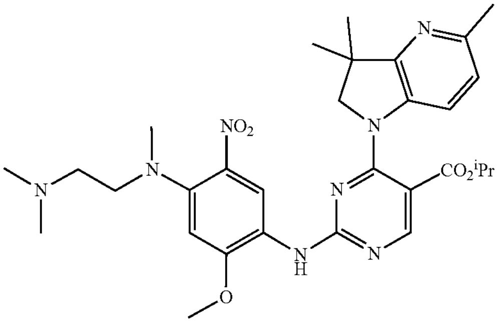

Isopropyl 2-chloro-4-(3,3,5-trimethyl-2,3-dihydro-1H-pyrrolo[3,2-b]pyridin-1-yl)pyrimidine-5-carboxylate (100 mg, 0.26 mmol), $N^1$-(2-(dimethylamino)ethyl)-5-methoxy-$N^1$-methyl-2-nitrobenzene-1,4-diamine (70 mg, 0.26 mmol), 1,1'-binaphthyl-2,2'-bis(diphenylphosphine) (51 mg, 0.08 mmol), palladium acetate (9.3 mg, 0.04 mmol) and cesium carbonate (135.3 mg, 0.4 mmol) were dissolved in dioxane (25 mL), and the reaction mixture was stirred at 120° C. under nitrogen protection for 2 hrs. After the reaction was completed, the reaction mixture was filtered through diatomaceous earth. The resulting filtrate was concentrated, and the residue was separated by rapid silica gel column chromatography [dichloromethane:methanol=10:1] to obtain isopropyl 2-((4-((2-(dimethylamino)ethyl) (methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate (72 mg, yield: 43%). ESI-MS: 593.4 $[M+1]^+$.

Intermediates E2 to E20 were Prepared According to the Preparation Method for Intermediate E1:

| Intermediate No. | Structure | Chemical name | ESI-MS: [M + 1]+ |
|---|---|---|---|
| E2 | 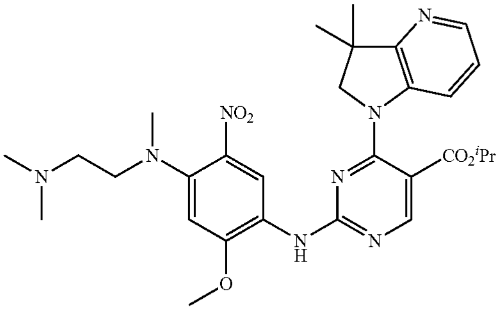 | isopropyl 4-(3,3-dimethyl-2,3-dihydro-1H-pyrrolo[3,2-b]pyridin-1-yl)-2-((4-((2-(dimethylamino)ethyl) (methyl)amino)-2-methoxy-5-nitrophenyl)amino)pyrimidine-5-carboxylate | 579.2 |
| E3 | 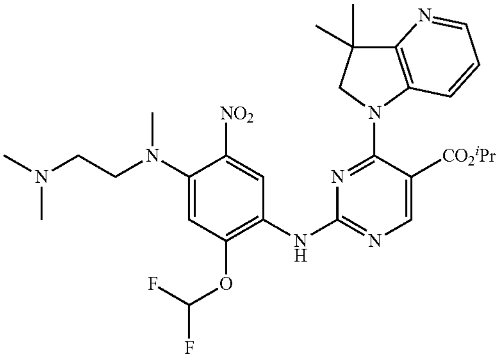 | isopropyl 2-((2-(difluoromethoxy )-4-((2-(dimethylamino)ethyl)(methyl) amino)-5-nitrophenyl)amino)-4-(3,3-dimethyl-2,3-dihydro-1H-pyrrolo[3,2-b]pyridin-1-yl) pyrimidine-5-carboxylate | 529.2 |

-continued

| Intermediate No. | Structure | Chemical name | ESI-MS: $[M + 1]^+$ |
|---|---|---|---|
| E4 | 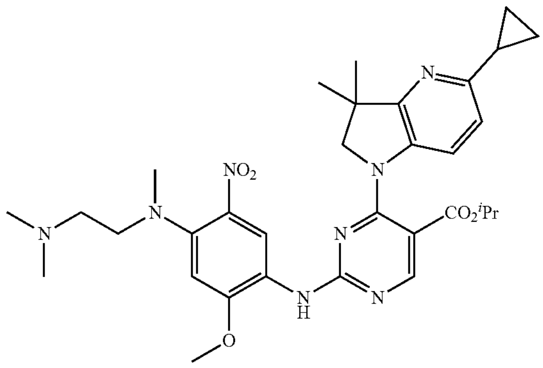 | isopropyl 4-(5-cyclopropyl-3,3-dimethyl-2,3-dihydro-1H-pyrrolo[3,2-6] pyridin-1-yl)-2-((4-((2-(dimethylamino)ethyl)(methyl) amino)-2-methoxy-S-nitrophenyl)amino) pyrimidine-5-carboxylate | 619.3 |
| E5 | 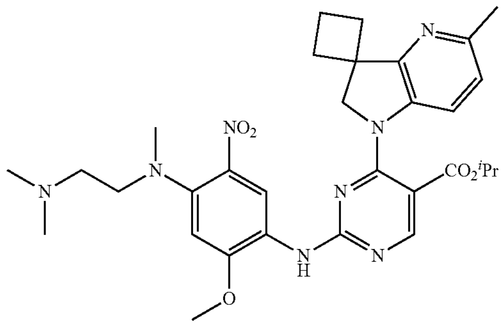 | isopropyl 2-((4-((2-(dimethylamino) ethyl)(methyl)amino)-2-methoxy-5-nitrophenyl) amino)-4-(5'-methylspiro (cyclobutane-1,3'-pyrrolo[3,2-b] pyridin)-1'(2'H)-yl)pyrimidine-5-carboxylate | 605.3 |
| E6 | 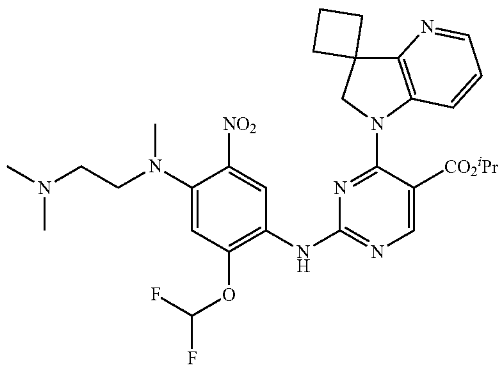 | isopropyl 2-((2-(difluoromethoxy)-4-((2-(dimethylamino)ethyl)(methyl) amino)-5-nitrophenyl)amino)-4-(spiro(cyclobutane-1,3'-pyrrolo[3,2-b]pyridin)-1'(2'H)-yl)pyrimidine-5-carboxylate | 627.2 |
| E7 | 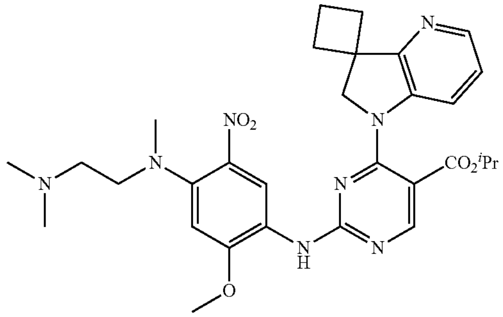 | isopropyl 2-((4-((2-(dimethylamino)ethyl) (methyl)amino)-2-methoxy-5-nitrophenyl)amino)-4-(spiro (cyclobutane-1,3'-pyrrolo[3,2-b] pyridin)-1'(2'H)-yl)pyrimidine-5-carboxylate | 591.2 |

-continued

| Intermediate No. | Structure | Chemical name | ESI-MS: [M + 1]+ |
|---|---|---|---|
| E8 | 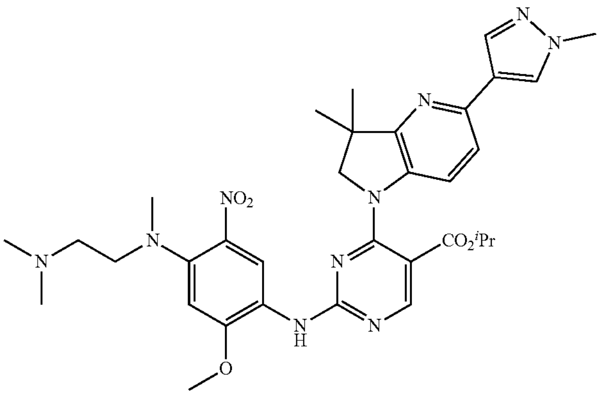 | isopropyl 4-(3,3-dimethyl-5-(1-methyl-1H-pyrazol-4-yl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate | 659.4 |
| E9 | 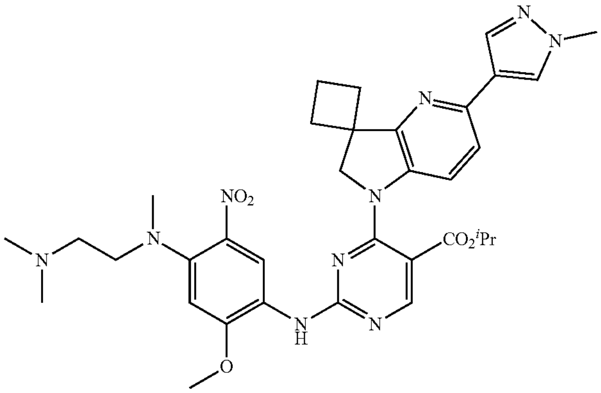 | isopropyl 2-((4-((2-(dimethylamino)ethyl)(methyl)amino)-2-methoxy-5-nitrophenyl)amino)-4-(5'-(1-methyl-1H-pyrazol-4-yl)spiro(cyclobutane-1,3'-pyrrolo[3,2-b]pyridin)-1'(2'H)-yl)pyrimidine-5-carboxylate | 671.3 |
| E10 | 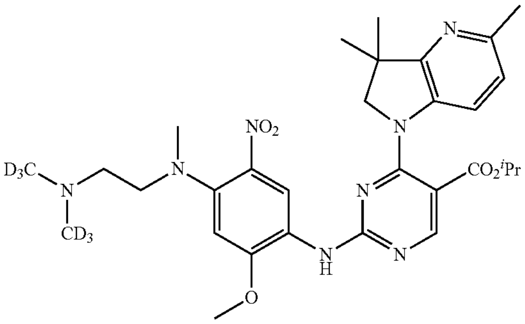 | isopropyl 2-((4-((2-(bis(methyl-$d_3$)amino)ethyl)(methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate | 599.3 |
| E11 | 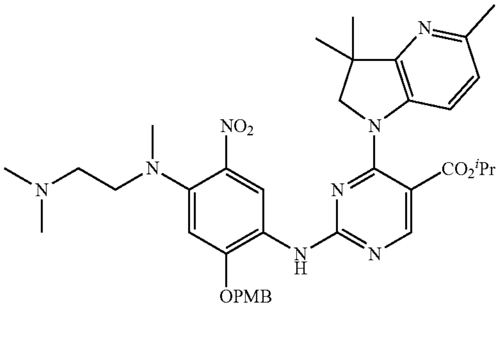 | isopropyl 2-((4-((2-(dimethy lamino)ethyl)(methyl)amino)-2-((4-methoxybenzyl)oxy)-5-nitrophenyl)amino)-4-(3,3,5-trimethyl-2,3-dihydro-1H-pyrrolo[3,2-b]pyridin-1-yl)pyrimidine-5-carboxylate | 699.4 |

-continued

| Intermediate No. | Structure | Chemical name | ESI-MS: [M + 1]+ |
|---|---|---|---|
| E12 | 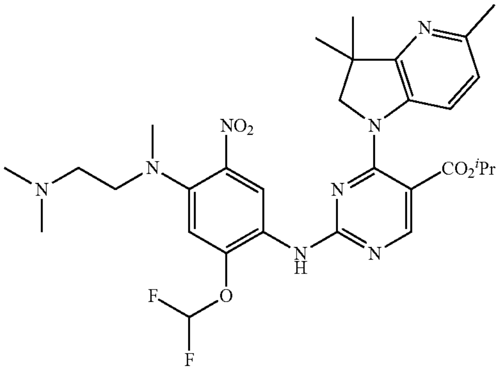 | isopropyl 2-((2-(difluoromethoxy)-4-((2-(dimethylamino)ethyl)(methyl) amino)-5-nitrophenyl )amino)-4-(3,3,5-trimethyl-2,3-dihydro-1H-pyrrolo[3,2-b]pyridin-1-yl)pyrimidine-5-carboxylate | 629.4 |
| E13 | 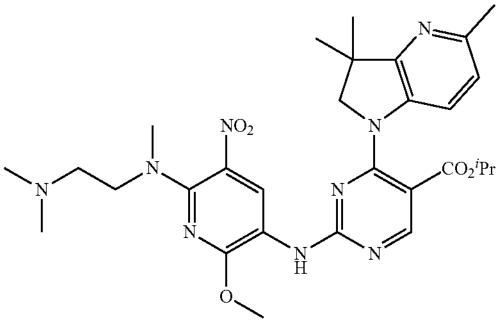 | isopropyl 2-((6-((2-(dimethylamino)ethyl) (methyl)amino)-2-methoxy-5-nitropyridin-3-yl)amino)-4-(3,3,5-trimethyl-2,3-dihydro-1H-pyrolo[3,2-b]pyridin-1-yl) pyrimidine-S-carboxylate | 594.3 |
| E14 | 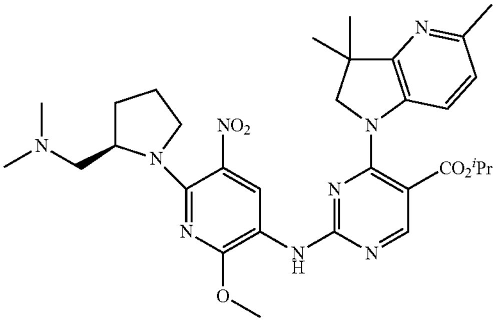 | isopropyl (R)-2-((6-(2-((dimethylamino) methyl)pyrrolidin-1-yl)-2-methoxy-5-nitropyridin-3-yl) amino)-4-(3,3,5-trimethyl-2,3-dibydro-1H-pyrrolo[3,2-b] pyridin-1-yl)pyrimidine-5-carboxylate | 620.3 |
| E15 | 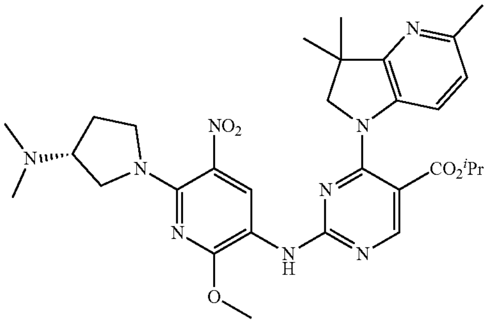 | isopropyl (R)-2-((6-(3-(dimethylamino) pyrrolidin- 1-yl)-2-methoxy-5-nitropyridin-3-yl)amino)-4-(3,3,5-trimethyl-2,3-dihydro-1H-pyrrolo[3,2-b]pyridin-1-yl) pyrimidine-5-carboxylate | 606.4 |

-continued

| Intermediate No. | Structure | Chemical name | ESI-MS: $[M + 1]^+$ |
|---|---|---|---|
| E16 | 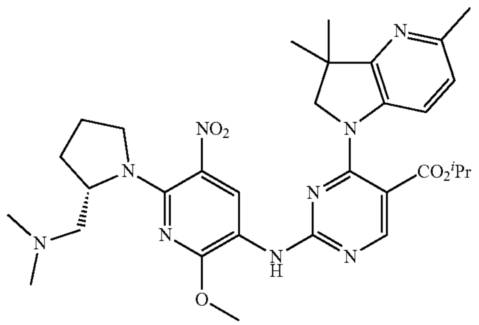 | isopropyl (S)-2-((6-(2-((dimethylamino) methyl)pyrrolidin-1-yl)-2-methoxy-5-nitropyridin-3-yl) amino)-4-(3,3,5-trimethyl-2,3-dihydro-1H-pyrrolo[3,2-b] pyridin-1-yl)pyrimidine-5-carboxylate | 621.4 |
| E17 | 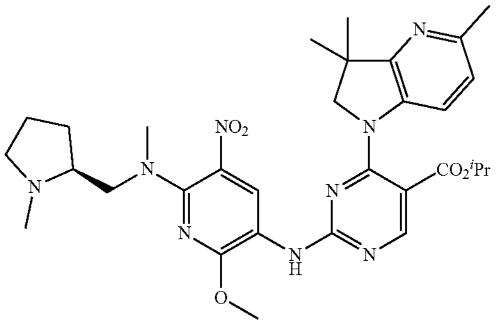 | isopropyl (S)-2-((2-methoxy-6-(methyl ((1-methylpyrrolidin-2-yl) methyl)amino)-5-nitropyridin-3-yl)amino)-4-(3,3,5-trimethyl-2,3-dibydro-1H-pyrrolo[3,2-b] pyridin-1-yl)pyrimidine-5-carboxylate | 620.3 |
| E18 | 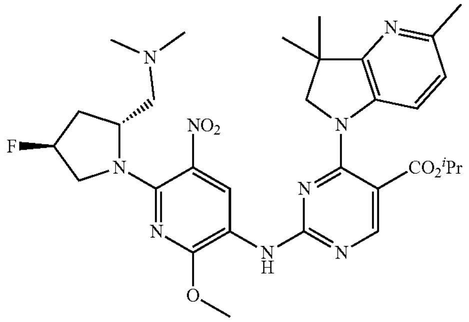 | isopropyl 2-((6-((2R,4S)-2-((dimethylamino)methyl)-4-fluoropyrrolidin-1-yl)-2-methoxy-5-nitropyridin-3-yl) amino)-4-(3,3,5-trimethyl-2,3-dihydro-1H-pyrrolo[3,2-b] pyridin-1-yl)pyrimidine-5-carboxylate | 638.3 |

-continued

| Intermediate No. | Structure | Chemical name | ESI-MS: $[M + 1]^+$ |
|---|---|---|---|
| E19 | 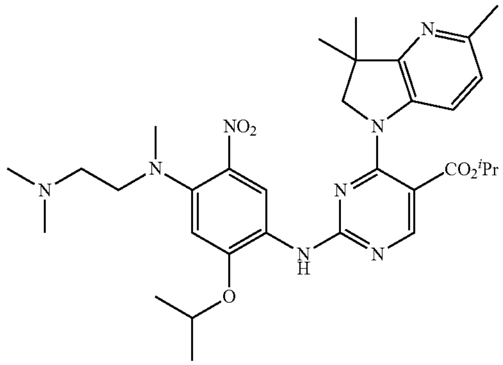 | isopropyl 2-((4-((2-(dimethylamino) ethyl)(methyl)amino)-2-isopropoxy-S-nitrophenyl) amino)-4-(3,3,5-trimethyl-2,3-dihydro-1H-pyrrolo[3,2-6] pyridin-1-yl)pyrimidine-5-carboxylate | 621.4 |
| E20 | 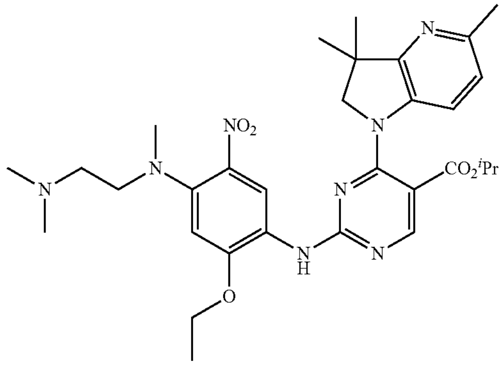 | isopropyl 2-((4-((2-(dimethylamino)ethyl) (methyl)amino)-2-ethoxy-5-nitrophenyl)amino)-4-(3,3,5-trimethyl-2,3-dihydro-1H-pyrrolo[3,2-b]pyridin-1-yl) pyrimidine-5-carboxylate | 607.3 |

Preparation of Intermediate E21-1: isopropyl 2-((4-fluoro-2-methoxy-5-nitrophenyl)amino)-4-(3,3,5-trimethyl-2,3-dihydro-1H-pyrrolo[3,2-b]pyridin-1-yl)pyrimidine-5-carboxylate

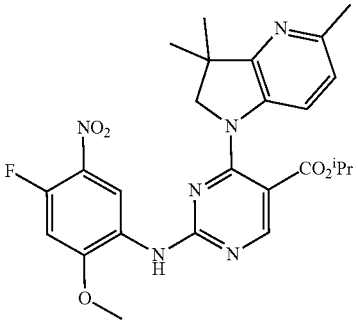

To a solution of 4-fluoro-2-methoxy-5-nitroaniline (103 mg, 0.55 mmol) in 1,4-dioxane (20 mL), isopropyl 2-chloro-4-(3,3,5-trimethyl-2,3-dihydro-1H-pyrrolo [3,2-b]pyridin-1-yl)pyrimidine-5-carboxylate (200 mg, 0.55 mmol) and p-toluenesulfonic acid monohydrate (95.4 mg, 0.55 mmol) were added. The reaction mixture was stirred at 120° C. for 5 hrs. Dichloromethane and water were added, and then the mixture solution was separated. The organic phase was successively washed with water and saturated brine, then dried over anhydrous sodium sulfate, filtered, and concentrated, and then the residue was separated by silica gel column chromatography to obtain isopropyl 2-((4-fluoro-2-methoxy-5-nitrophenyl)amino)-4-(3,3,5-trimethyl-2,3-dihydro-1H-pyrrolo[3,2-b]pyridin-1-yl)pyrimidine-5-carboxylate (212 mg, yield: 73.4%). ESI-MS: 511.2 $[M+1]^+$.

Intermediates E23-1 to E37-1 were Prepared According to the Preparation Method for Intermediate E21-1:

| Intermediate No. | Structure | Chemical name | ESI-MS: $[M + 1]^+$ |
| --- | --- | --- | --- |
| E23-1 | 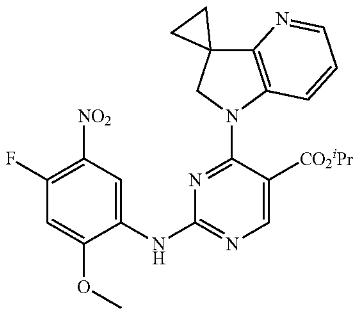 | isopropyl 2-((4-fluoro-2-methoxy-5-nitro phenyl)amino)-4-(spiro(cyclo-propane-1,3'-pyrrolo[3,2-b] pyridin)-1'(2'H)-yl)pyrimidine-5-carboxylate | 495.0 |
| E24-1 | 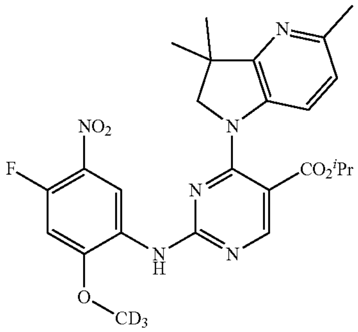 | isopropyl 2-((4-fluoro-2-(methoxy-$d_3$)-5-nitrophenyl)amino)-4-(3,3,5-trimethyl-2,3-dihydro-1H-pyrrolo[3,2-b]pyridin-1-yl) pyrimidine-5-carboxylate | 514.3 |
| E25-1 | 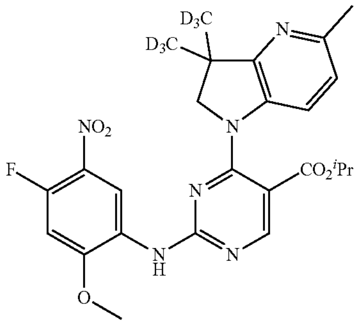 | isopropyl 2-((4-fluoro-2-methoxy-5-nitrophenyl)amino)-4-(5-methyl-3,3-bis(methyl-$d_3$)-2,3-dihydro-1H-pyrrolo[3,2-b]pyridin-1-yl) pyrimidine-5-carboxylate | 517.2 |
| E26-1 | 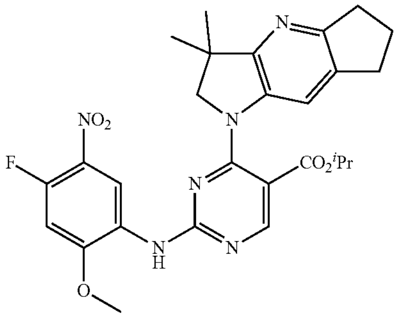 | isopropyl 4-(3,3-dimethyl-3,5,6,7-tetra-hydrocyclopenta[b]pyrrolo[2,3-e]pyridin-1(2H)-yl)-2-((4-fluoro-2-methoxy-5-nitrophenyl)amino) pyrimidine-5-carboxylate | 537.2 |

-continued

| Intermediate No. | Structure | Chemical name | ESI-MS: $[M + 1]^+$ |
|---|---|---|---|
| E27-1 | 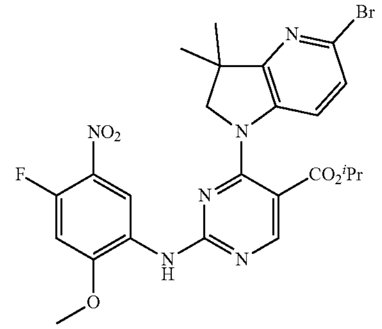 | isopropyl 4-(5-bromo-3,3-dimethyl-2,3-dihydro-1H-pyrrolo[3,2-b] pyridin-1-yl)-2-((4-fluoro-2-methoxy-5-nitrophenyl) amino)pyrimidine-5-carboxylate | 575.2<br>577.2 |
| E28-1 | 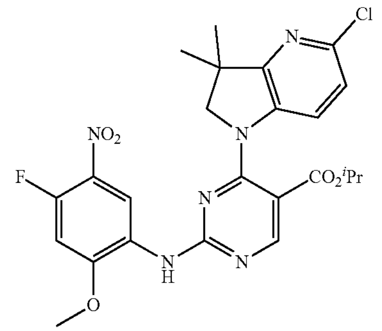 | isopropyl 4-(5-chloro-3,3-dimethyl-2,3-dihydro-1H-pyrrolo[3,2-b] pyridin-1-yl)-2-((4-fluoro-2-methoxy-5-nitrophenyl)amino) pyrimidine-5-carboxylate | 531.2 |
| E29-1 | 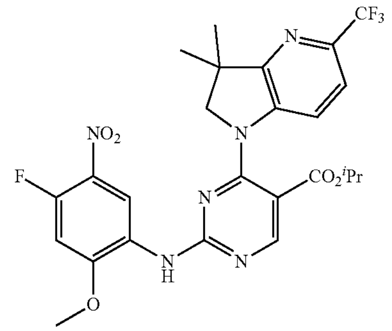 | isopropyl 4-(3,3-dimethyl-5-(trifluoro-methyl)-2,3-dihydro-1H-pyrrolo [3,2-b]pyridin-1-yl)-2-((4-fluoro-2-methoxy-5-nitrophenyl)amino) pyrimidine-5-carboxylate | 565.2 |
| E30-1 | 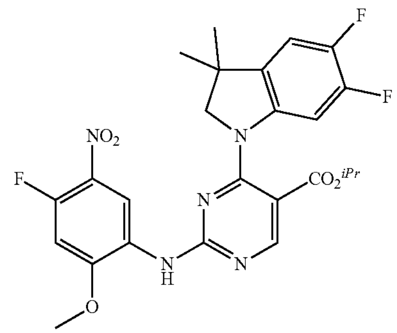 | isopropyl 4-(5,6-difluoro-3,3-dimethyl-indolin-1-yl)-2-((4-fluoro-2-methoxy-5-nitrophenyl)amino) pyrimidine-5-carboxylate | 532.2 |

-continued

| Intermediate No. | Structure | Chemical name | ESI-MS: $[M + 1]^+$ |
|---|---|---|---|
| E31-1 | 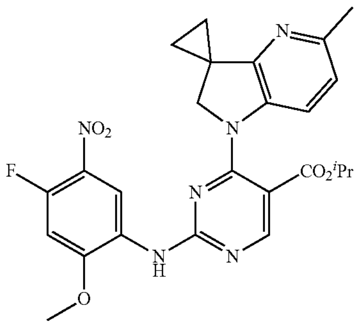 | isopropyl 2-((4-fluoro-2-methoxy-5-nitro phenyl)amino)-4-(5'-methyl-spiro(cyclopropane-1,3'-pyrrolo [3,2-b]pyridin)-1'(2'H)-yl) pyrimidine-5-carboxylate | 509.2 |
| E32-1 | 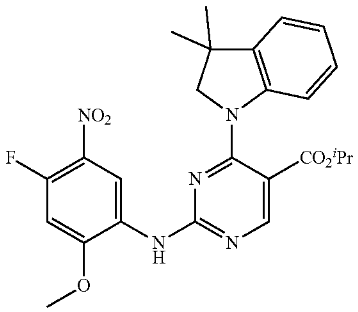 | isopropyl 4-(3,3-dimethylindolin-1-yl)-2-((4-fluoro-2-methoxy-5-nitrophenyl)amino)pyrimidine-5-carboxylate | 496.3 |
| E33-1 | 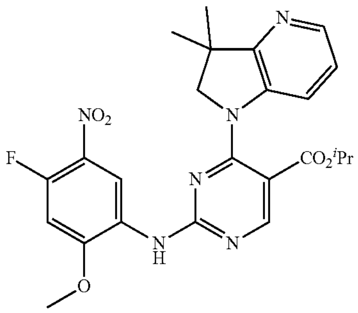 | isopropyl 4-(3,3-dimethyl-2,3-dihydro-1H-pyrrolo[3,2-b]pyridin-1-yl)-2-((4-fluoro-2-methoxy-5-nitrophenyl)amino)pyrimidine-5-carboxylate | 497.2 |
| E34-1 | 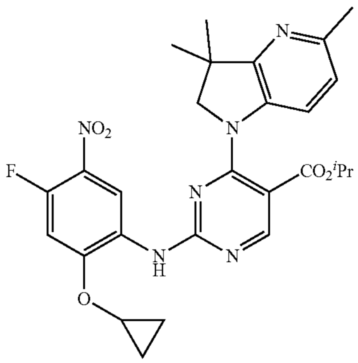 | isopropyl 2-((2-cyclopropoxy-4-fluoro-5-nitrophenyl)amino)-4-(3,3,5-trimethyl-2,3-dihydro-1H-pyrrolo[3,2-b]pyridin-1-yl) pyrimidine-5-carboxylate | 537.3 |

-continued

| Intermediate No. | Structure | Chemical name | ESI-MS: [M + 1]+ |
|---|---|---|---|
| E35-1 | 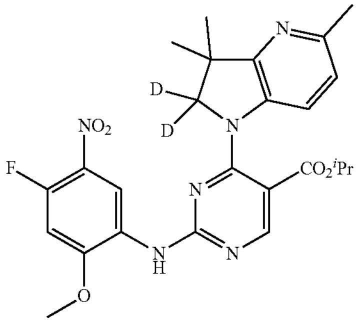 | isopropyl 2-((4-fluoro-2-methoxy-5-nitrophenyl)amino)-4-(3,3,5-trimethyl-2,3-dihydro-1H-pyrrolo[3,2-b]pyridin-1-yl)-2,2-$d_2$)pyrimidine-5-carboxylate | 513.2 |
| E36-1 | 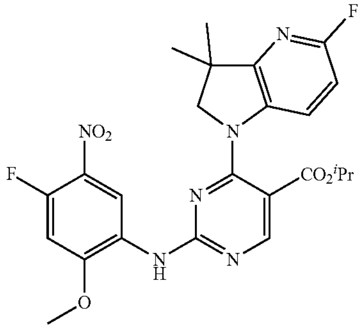 | isopropyl 2-((4-fluoro-2-methoxy-5-nitrophenyl)amino)-4-(5-fluoro-3,3-dimethyl-2,3-dihydro-1H-pyrrolo[3,2-b] pyridin-1-yl)pyrimidine-5-carboxylate | 515.0 |
| E37-1 | 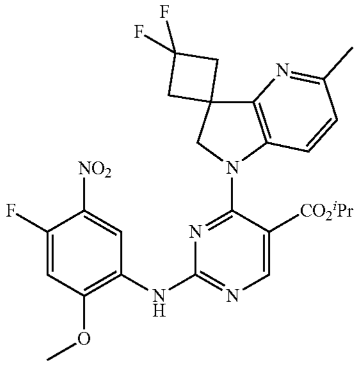 | isopropyl 4-(3,3-difluoro-5'-methylspiro (cyclobutane-1,3'-pyrrolo [3,2-b]pyridin)-1'(2'H)-yl)-2-((4-fluoro-2-methoxy-5-nitrophenyl)amino)pyrimidine-5-carboxylate | 473.0 |

Preparation of Intermediate E21: isopropyl (R)-2-((4-(3-(dimethylamino) pyrrolidin-1-yl)-2-methoxy-5-nitrophenyl)amino)-4-(3,3,5-trimethyl-2,3-dihydro-1H-pyrrolo[3,2-b]pyridin-1-yl)pyrimidine-5-carboxylate

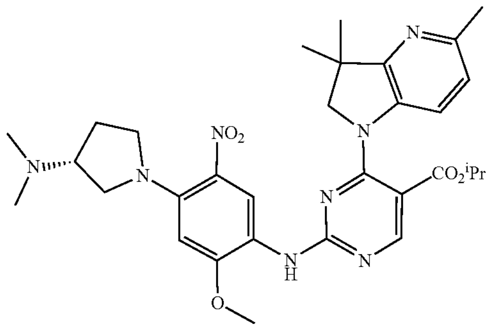

To a solution of isopropyl 2-((4-fluoro-2-methoxy-5-nitrophenyl)amino)-4-(3,3,5-trimethyl-2,3-dihydro-1H-pyrrolo[3,2-b]pyridin-1-yl)pyrimidine-5-carboxylate (100 mg, 0.20 mmol) in 1,4-dioxane (30 mL), (R)—N,N-dimethylpyrrolidin-3-amine (33.6 mg, 0.29 mmol) and diisopropylethylamine (50.6 mg, 0.40 mmol) were added. The reaction mixture was stirred at 120° C. for 18 hrs. Dichloromethane and water were added, and then the mixture solution was separated. The organic phase was successively washed with water and saturated brine, then dried over anhydrous sodium sulfate, filtered, and concentrated, and then the residue was separated by column chromatography [dichloromethane: methanol=10:1] to obtain isopropyl (R)-2-((4-(3-(dimethylamino) pyrrolidin-1-yl)-2-methoxy-5-nitrophenyl)amino)-4-(3,3,5-trimethyl-2,3-dihydro-1H-pyrrolo[3,2-b]pyridin-1-yl)pyrimidine-5-carboxylate (120 mg, yield: 95%). ESI-MS: 605.3 $[M+1]^+$.

Intermediates E22 to E77 were Prepared According to the Preparation Method for Intermediate E21:

| Intermediate No. | Structure | Chemical name | ESI-MS: $[M + 1]^+$ |
|---|---|---|---|
| E22 | 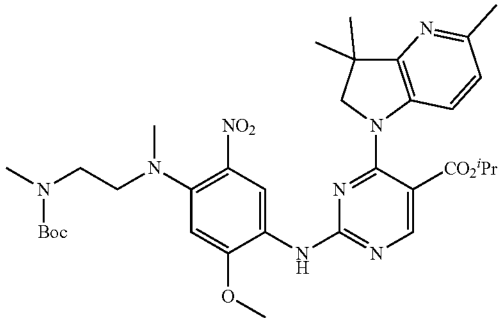 | isopropyl 2-((4-((2-((tert-butoxycarbonyl)(methyl)amino)ethyl)(methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate | 679.4 |
| E23 | 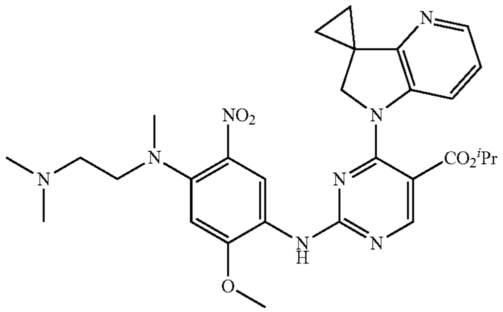 | isopropyl 2-((4-((2-(dimethylamino)ethyl)(methyl)amino)-2-methoxy-5-nitrophenyl)amino)-4-(spiro(cyclopropane-1,3'-pyrrolo[3,2-b]pyridin)-1'(2'H)-yl)pyrimidine-5-carboxylate | 577.2 |
| E24 | 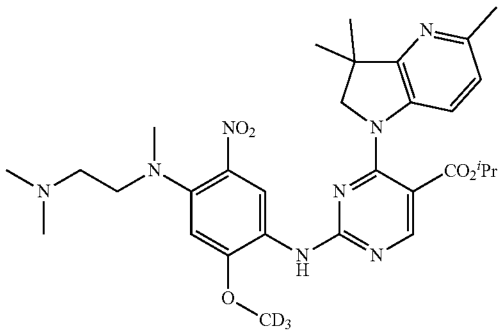 | isopropyl 2-((4-((2-(dimethylamino)ethyl)(methyl)amino)-2-(methoxy-$d_3$)-5-nitrophenyl)amino)-4-(3,3,5-trimethyl-2,3-dihydro-1H-pyrrolo[3,2-b]pyridin-1-yl)pyrimidine-5-carboxylate | 596.3 |

-continued

| Intermediate No. | Structure | Chemical name | ESI-MS: [M + 1]$^+$ |
|---|---|---|---|
| E25 | 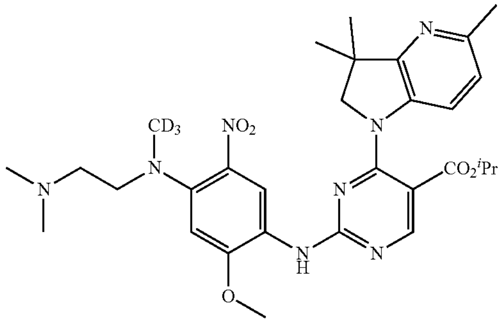 | isopropyl 2-((4-((2-(dimethylamino)ethyl)(methyl-$d_3$)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate | 596.2 |
| E26 | 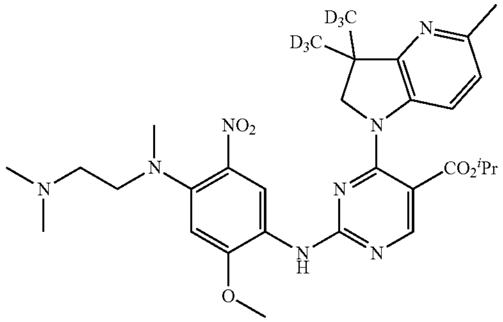 | isopropyl 2-((4-((2-(dimethylamino)ethyl)(methyl)amino)-2-methoxy-5-nitrophenyl)amino)-4-(5-methyl-3,3-bis(methyl-$d_3$)-2,3-dihydro-1H-pyrrolo[3,2-b]pyridin-1-yl)pyrimidine-5-carboxylate | 599.4 |
| E27 | 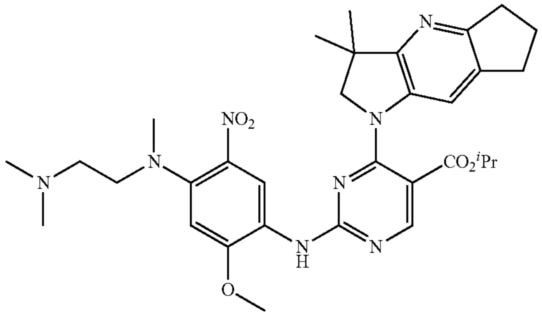 | isopropyl 4-(3,3-dimethyl-3,5,6,7-tetrahydrocyclopenta[b]pyrrolo[2,3-e]pyridin-1(2H)-yl)-2-((4-((2-(dimethylamino)ethyl)(methyl)amino)-2-methoxy-5-nitrophenyl)amino)pyrimidine-5-carboxylate | 619.4 |
| E28 | 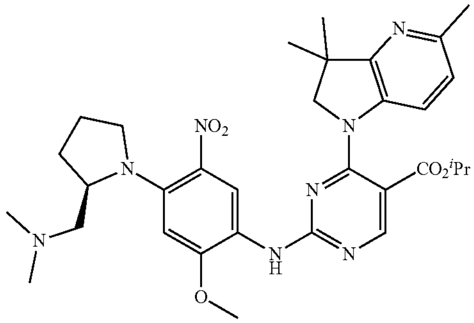 | isopropyl (R)-2-((4-(2-((dimethylamino)methyl)pyrrolidin-1-yl)-2-methoxy-5-nitrophenyl)amino)-4-(3,3,5-trimethyl-2,3-dihydro-1H-pyrrolo[3,2-b]pyridin-1-yl)pyrimidine-5-carboxylate | 619.4 |

-continued

| Intermediate No. | Structure | Chemical name | ESI-MS: $[M + 1]^+$ |
|---|---|---|---|
| E29 | 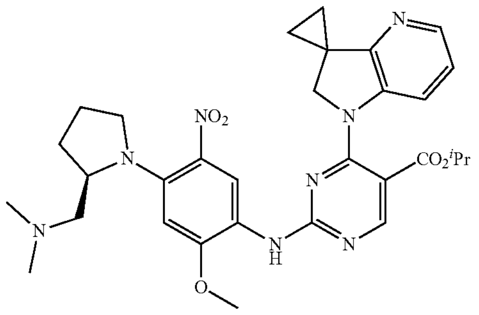 | isopropyl (R)-2-((4-(2-((dimethylamino) methyl)pyrrolidin-1-yl)-2-methoxy-5-nitrophenyl)amino)-4-(spiro(cyclopropane-1,3'-pyrrolo[3,2-b]pyridin)-1'(2'H)-yl)pyrimidine-5-carboxylate | 603.4 |
| E30 | 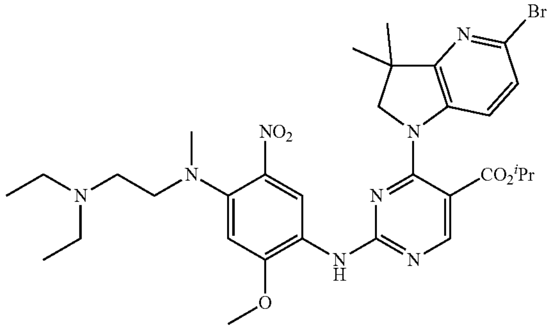 | isopropyl 4-(5-bromo-3,3-dimethyl-2,3-dihydro-1H-pyrrolo[3,2-b]pyridin-1-yl)-2-((4-((2-(diethylamino) ethyl)(methyl)amino)-2-methoxy-5-nitrophenyl)amino) pyrimidine-5-carboxylate | 685.3<br>687.3 |
| E31 | 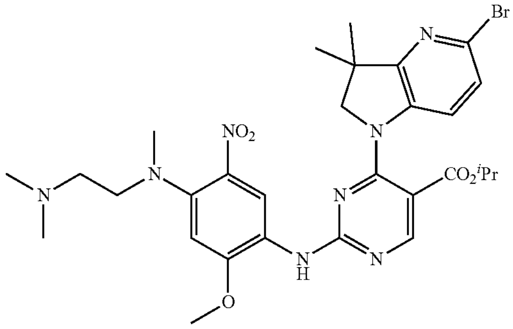 | isopropyl 4-(5-bromo-3,3-dimethyl-2,3-dihydro-1H-pyrrolo[3,2-b]pyridin-1-yl)-2-((4-((2-(dimethylamino) ethyl)(methyl)amino)-2-methoxy-5-nitrophenyl)amino)pyrimidine-5-carboxylate | 657.2<br>659.2 |
| E32 | 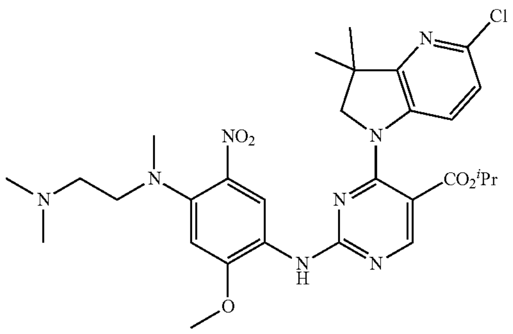 | isopropyl 4-(5-chloro-3,3-dimethyl-2,3-dihydro-1H-pyrrolo[3,2-b] pyridin-1-yl)-2-((4-((2-(dimethylamino)ethyl)(methyl) amino)-2-methoxy-5-nitrophenyl) amino)pyrimidine-5-carboxylate | 613.3 |

-continued

| Intermediate No. | Structure | Chemical name | ESI-MS: $[M + 1]^+$ |
|---|---|---|---|
| E33 | 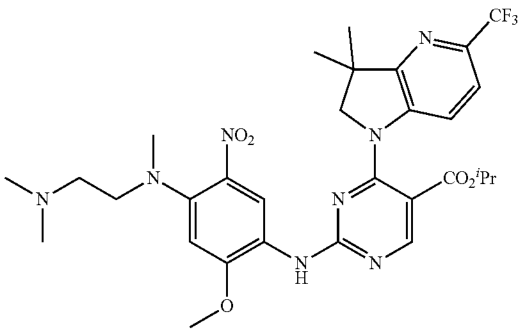 | isopropyl 4-(3,3-dimethyl-5-(trifluoro-methyl)-2,3-dihydro-1H-pyrrolo [3,2-b]pyridin-1-yl)-2-((4-((2-(dimethylamino)ethyl)(methyl) amino)-2-methoxy-5-nitrophenyl) amino)pyrimidine-5-carboxylate | 647.3 |
| E34 | 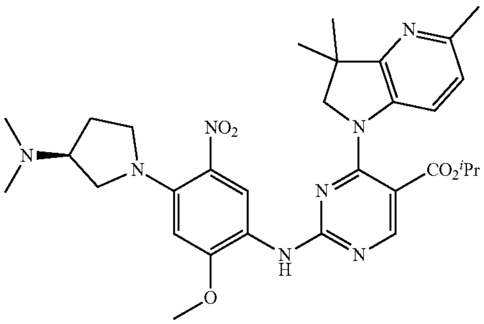 | isopropyl (S)-2-((4-(3-(dimethylamino) pyrrolidin-1-yl)-2-methoxy-5-nitrophenyl)amino)-4-(3,3,5-trimethyl-2,3-dihydro-1H-pyrrolo[3,2-b]pyridin-1-yl) pyrimidine-5-carboxylate | 605.3 |
| E35 | 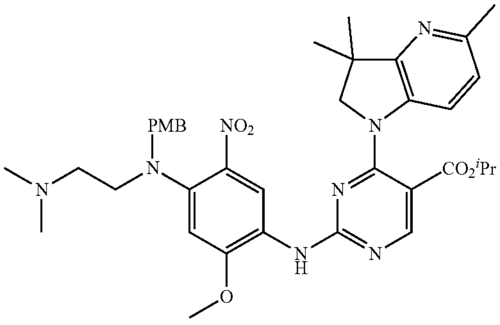 | isopropyl 2-((4-((2-(dimethylamino)ethyl) (4-methoxybenzyl)amino)-2-methoxy-5-nitrophenyl)amino)-4-(3,3,5-trimethyl-2,3-dihydro-1H-pyrrolo[3,2-b]pyridin-1-yl) pyrimidine-5-carboxylate | 699.4 |
| E36 | 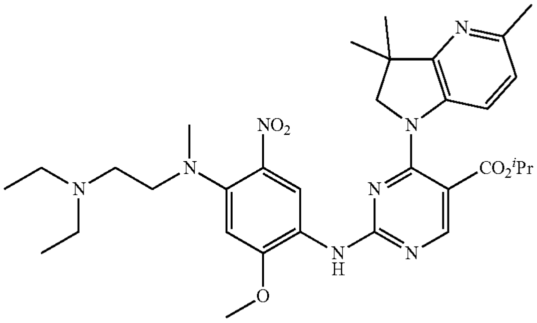 | isopropyl 2-((4-((2-(diethylamino)ethyl) (methyl)amino)-2-methoxy-5-nitrophenyl)amino)-4-(3,3,5-trimethyl-2,3-dihydro-1H-pyrrolo [3,2-b]pyridin-1-yl)pyrimidine-5-carboxylate | 621.4 |

-continued

| Intermediate No. | Structure | Chemical name | ESI-MS: [M + 1]+ |
| --- | --- | --- | --- |
| E37 | 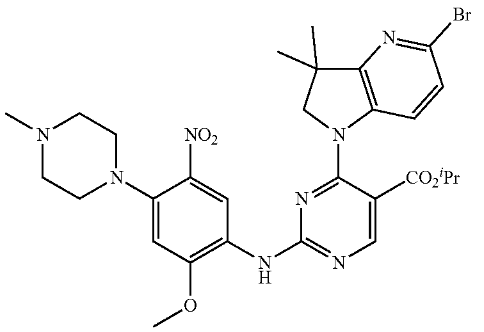 | isopropyl 4-(5-bromo-3,3-dimethyl-2,3-dihydro-1H-pyrrolo[3,2-b]pyridin-1-yl)-2-((2-methoxy-4-(4-methylpiperazin-1-yl)-5-nitrophenyl)amino)pyrimidine-5-carboxylate | 655.3 657.3 |
| E38 | 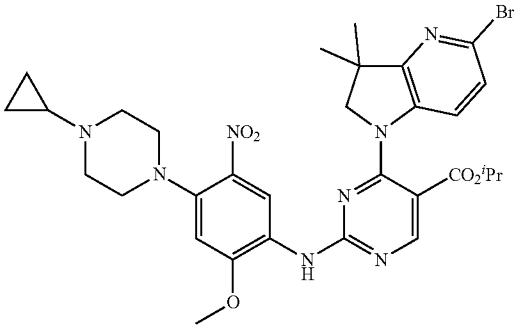 | isopropyl 4-(5-bromo-3,3-dimethyl-2,3-dihydro-1H-pyrrolo[3,2-b]pyridin-1-yl)-2-((4-(4-cyclopropylpiperazin-1-yl)-2-methoxy-5-nitrophenyl)amino) pyrimidine-5-carboxylate | 681.2 683.2 |
| E39 | 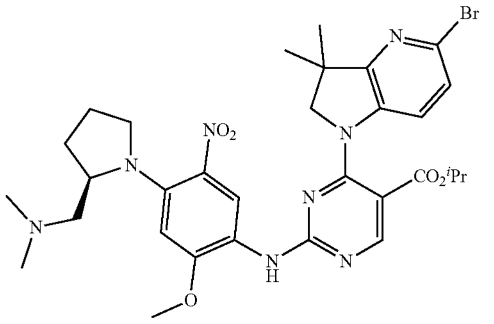 | isopropyl (R)-4-(5-bromo-3,3-dimethyl-2,3-dihydro-1H-pyrrolo[3,2-b]pyridin-1-yl)-2-((4-(2-((dimethylamino) methyl)pyrrolidin-1-yl)-2-methoxy-5-nitrophenyl)amino)pyrimidine-5-carboxylate | 683.3 685.3 |
| E40 | 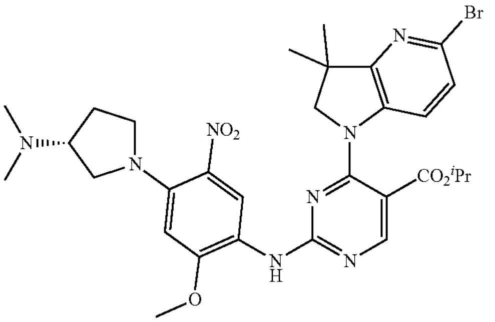 | isopropyl (R)-4-(5-bromo-3,3-dimethyl-2,3-dihydro-1H-pyrrolo[3,2-b]pyridin-1-yl)-2-((4-(3-(dimethylamino) pyrrolidin-1-yl)-2-methoxy-5-nitrophenyl)amino)pyrimidine-5-carboxylate | 669.3 671.3 |

-continued

| Intermediate No. | Structure | Chemical name | ESI-MS: [M + 1]+ |
|---|---|---|---|
| E41 | 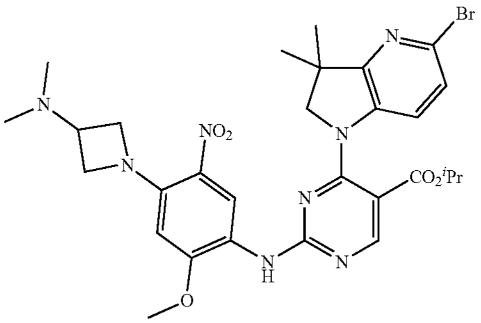 | isopropyl 4-(5-bromo-3,3-dimethyl-2,3-dihydro-1H-pyrrolo[3,2-b]pyridin-1-yl)-2-((4-(3-(dimethylamino)azetidin-1-yl)-2-methoxy-5-nitrophenyl)amino) pyrimidine-5-carboxylate | 655.3<br>657.3 |
| E42 | 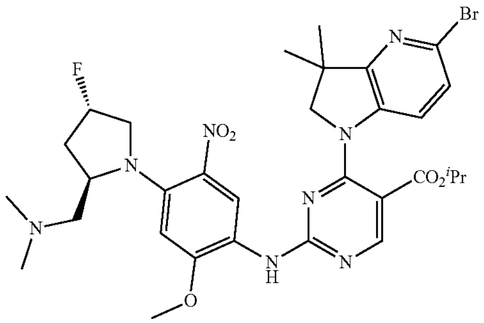 | isopropyl 4-(5-bromo-3,3-dimethyl-2,3-dihydro-1H-pyrrolo[3,2-b]pyridin-1-yl)-2-((4-((2R,4S)-2-((dimethylamino) methyl)-4-fluoropyrrolidin-1-yl)-2-methoxy-5-nitrophenyl)amino) pyrimidine-5-carboxylate | 701.3<br>703.3 |
| E43 | 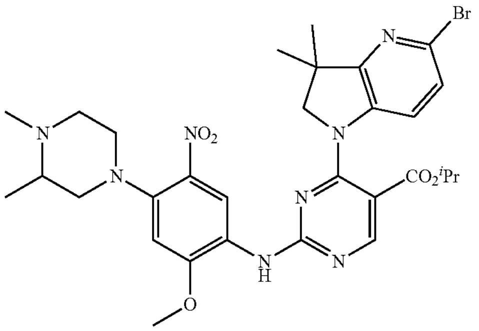 | isopropyl 4-(5-bromo-3,3-dimethyl-2,3-dihydro-1H-pyrrolo[3,2-b]pyridin-1-yl)-2-((4-(3,4-dimethylpiperazin-1-yl)-2-methoxy-5-nitrophenyl)amino) pyrimidine-5-carboxylate | 669.3<br>671.3 |
| E44 | 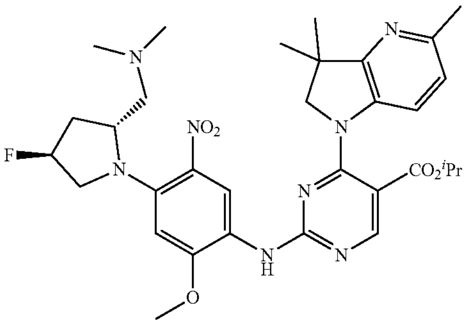 | isopropyl 2-((4-((2R,4S)-2-((dimethylamino) methyl)-4-fluoropyrrolidin-1-yl)-2-methoxy-5-nitrophenyl)amino)-4-(3,3,5-trimethyl-2,3-dihydro-1H-pyrrolo [3,2-b]pyridin-1-yl)pyrimidine-5-carboxylate | 637.3 |

-continued

| Intermediate No. | Structure | Chemical name | ESI-MS: $[M + 1]^+$ |
|---|---|---|---|
| E45 | 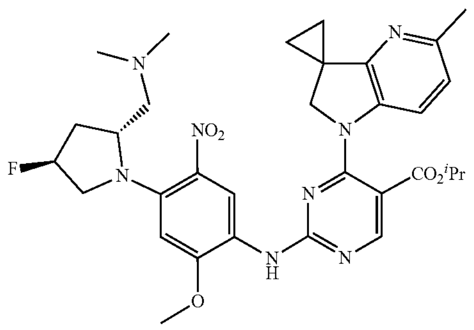 | isopropyl 2-((4-((2R,4S)-2-((dimethylamino) methyl)-4-fluoropyrrolidin-1-yl)-2-methoxy-5-nitrophenyl)amino)-4-(5'-methylspiro(cyclopropane-1,3'-pyrrolo[3,2-b]pyridin)-1'(2'H)-yl) pyrimidine-5-carboxylate | 635.3 |
| E46 | 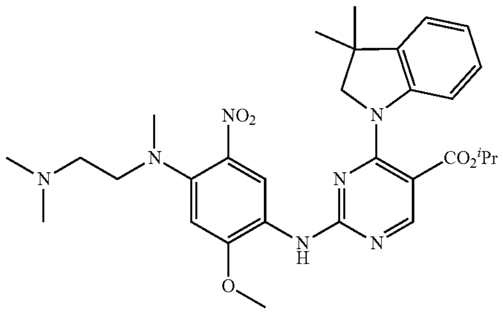 | isopropyl 2-((4-((2-(dimethylamino)ethyl) (methyl)amino)-2-methoxy-5-nitrophenyl)amino)-4-(3,3-dimethyl-indolin-1-yl)pyrimidine-5-carboxylate | 578.3 |
| E47 | 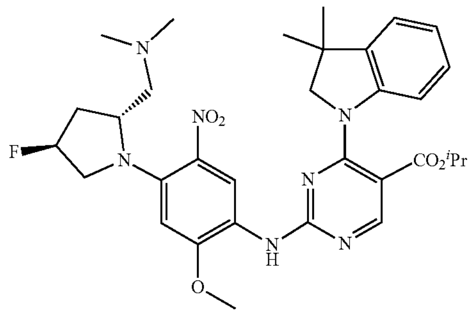 | isopropyl 2-((4-((2R,4S)-2-((dimethylamino) methyl)-4-fluoropyrrolidin-1-yl)-2-methxoy-5-nitrophenyl)amino)-4-(3,3-dimethylindolin-1-yl)pyrimidine-5-carboxylate | 622.5 |
| E48 | 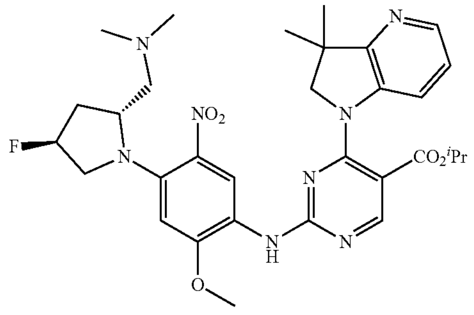 | isopropyl 4-(3,3-dimethyl-2,3-dihydro-1H-pyrrolo [3,2-b]pyridin-1-yl)-2-((4-((2R,4S)-2-((dimethylamino)methyl)-4-fluoropyrrolidin-1-yl)-2-methoxy-5-nitrophenyl)amino)pyrimidine-5-carboxylate | 623.3 |

-continued

| Intermediate No. | Structure | Chemical name | ESI-MS: $[M + 1]^+$ |
|---|---|---|---|
| E49 | 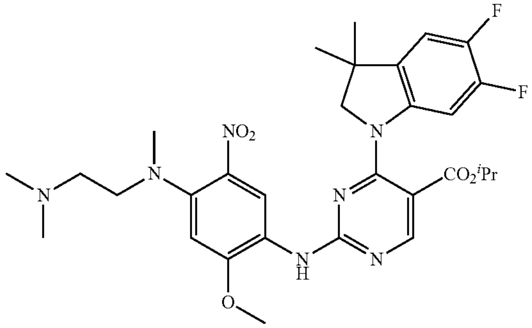 | isopropyl 4-(5,6-difluoro-3,3-dimethylindolin-1-yl)-2-((4-((2-(dimethylamino) ethyl)(methyl)amino)-2-methoxy-5-nitrophenyl)amino)pyrimidine-5-carboxylate | 614.3 |
| E50 | 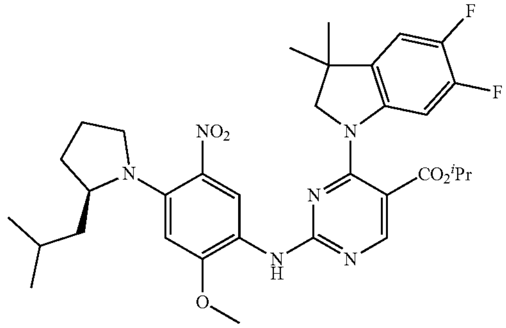 | isopropyl (R)-4-(5,6-difluoro-3,3-dimethylindolin-1-yl)-2-((4-(2-((dimethylamino) methyl)pyrrolidin-1-yl)-2-methoxy-5-nitrophenyl)amino)pyrimidine-5-carboxylate | 640.3 |
| E51 | 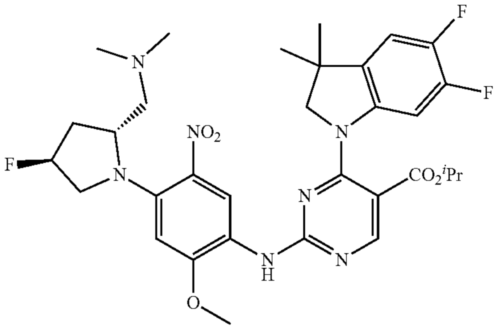 | isopropyl 4-(5,6-difluoro-3,3-dimethylindolin-1-yl)-2-((4-((2R,4S)-2-((dimethylamino) methyl)-4-fluoropyrrolidin-1-yl)-2-methoxy-5-nitrophenyl)amino) pyrimidine-5-carboxylate | 658.3 |
| E52 | 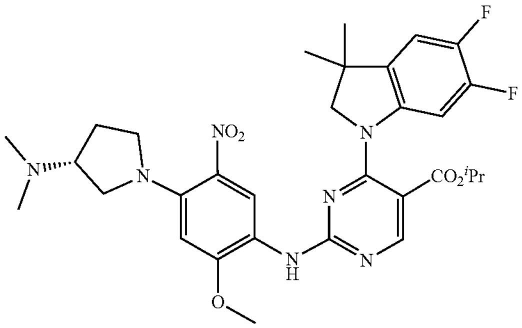 | isopropyl (R)-4-(5,6-difluoro-3,3-dimethylindolin-1-yl)-2-((4-(3-(dimethylamino) pyrrolidin-1-yl)-2-methoxy-5-nitrophenyl)amino)pyrimidine-5-carboxylate | 626.3 |

-continued

| Intermediate No. | Structure | Chemical name | ESI-MS: $[M + 1]^+$ |
|---|---|---|---|
| E53 | 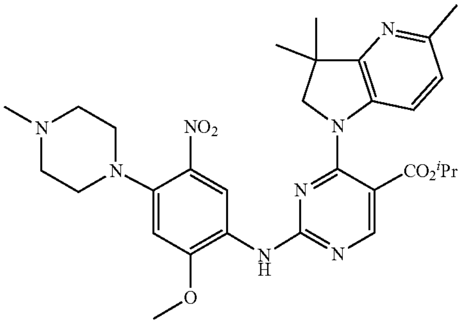 | isopropyl 2-((2-methoxy-4-(4-methylpiperazin-1-yl)-5-nitrophenyl)amino)-4-(3,3,5-trimethyl-2,3-dihydro-1H-pyrrolo [3,2-b]pyridin-1-yl)pyrimidine-5-carboxylate | 591.2 |
| E54 | 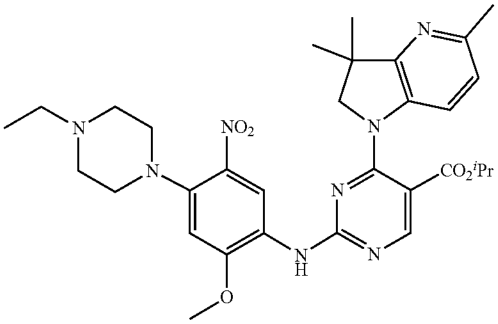 | isopropyl 2-((4-(4-ethylpiperazin-1-yl)-2-methoxy-5-nitrophenyl)amino)-4-(3,3,5-trimethyl-2,3-dihydro-1H-pyrrolo [3,2-b]pyridin-1-yl)pyrimidine-5-carboxylate | 605.4 |
| E55 | 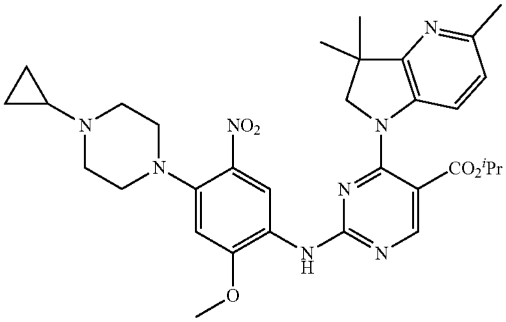 | isopropyl 2-((4-(4-cyclopropylpiperazin-1-yl)-2-methoxy-5-nitrophenyl)amino)-4-(3,3,5-trimethyl-2,3-dihydro-1H-pyrrolo[3,2-b]pyridin-1-yl) pyrimidine-5-carboxylate | 617.2 |
| E56 | 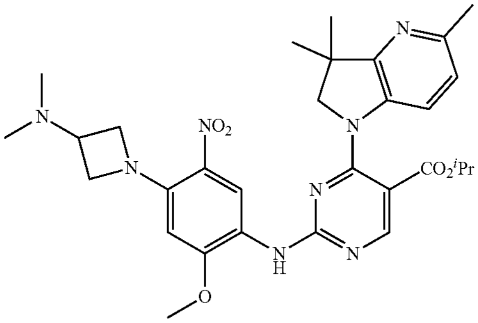 | isopropyl 2-((4-(3-(dimethylamino)azetidin-1-yl)-2-methoxy-5-nitrophenyl)amino)-4-(3,3,5-trimethyl-2,3-dihydro-1H-pyrrolo[3,2-b]pyridin-1-yl) pyrimidine-5-carboxylate | 591.2 |

-continued

| Intermediate No. | Structure | Chemical name | ESI-MS: $[M + 1]^+$ |
|---|---|---|---|
| E57 | 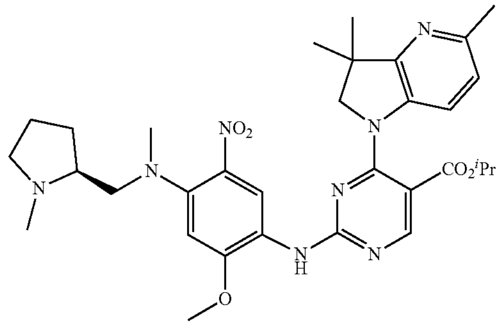 | isopropyl (S)-2-((2-methoxy-4-(methyl((1-methylpyrrolidin-2-yl)methyl)amino)-5-nitrophenyl)amino)-4-(3,3,5-trimethyl-2,3-dihydro-1H-pyrrolo[3,2-b]pyridin-1-yl)pyrimidine-5-carboxylate | 619.3 |
| E58 | 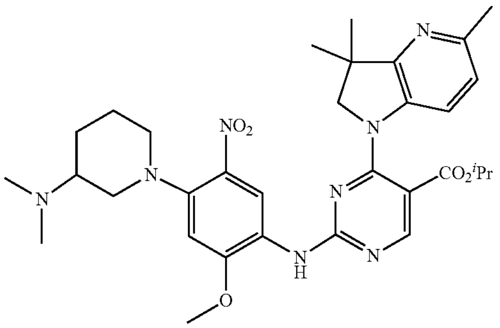 | isopropyl 2-((4-(3-(dimethylamino)piperidin-1-yl)-2-methoxy-5-nitrophenyl)amino)-4-(3,3,5-trimethyl-2,3-dihydro-1H-pyrrolo[3,2-b]pyridin-1-yl)pyrimidine-5-carboxylate | 691.2 |
| E59 | 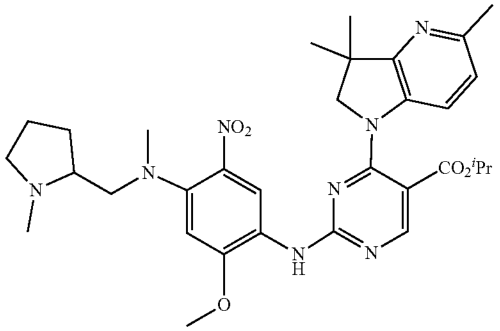 | isopropyl 2-((2-methoxy-4-(methyl((1-methyl-pyrrolidin-2-yl)methyl)amino)-5-nitrophenyl)amino)-4-(3,3,5-trimethyl-2,3-dihydro-1H-pyrrolo[3,2-b]pyridin-1-yl)pyrimidine-5-carboxylate | 619.3 |
| E60 | 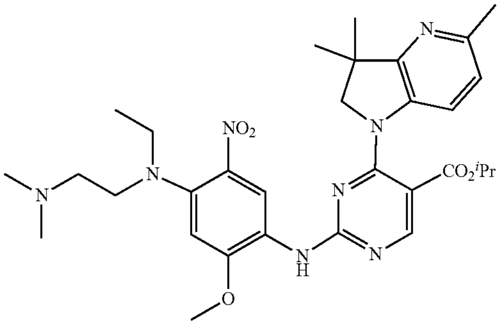 | isopropyl 2-((4-((2-(dimethylamino)ethyl)(ethyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate | 607.2 |

-continued

| Intermediate No. | Structure | Chemical name | ESI-MS: [M + 1]$^+$ |
|---|---|---|---|
| E61 | 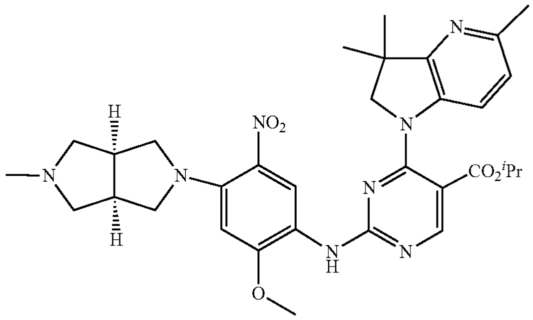 | isopropyl 2-((2-methoxy-4-((3aR,6aS)-5-methylhexahydropyrrolo[3,4-c]pyrrolo-2(1H)-yl)-5-nitrophenyl)amino)-4-(3,3,5-trimethyl-2,3-dihydro-1H-pyrrolo[3,2-b]pyridin-1-yl) pyrimidine-5-carboxylate | 617.4 |
| E62 | 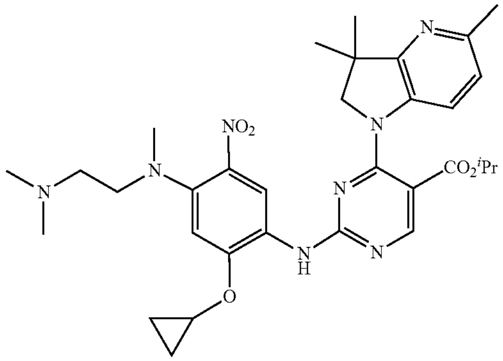 | isopropyl 2-((2-cyclopropoxy-4-((2-(dimethyl-amino)ethyl)(methyl)amino)-5-nitrophenyl)amino)-4-(3,3,5-trimethyl-2,3-dihydro-1H-pyrrolo[3,2-b]pyridin-1-yl)pyrimidine-5-carboxylate | 619.3 |
| E63 | 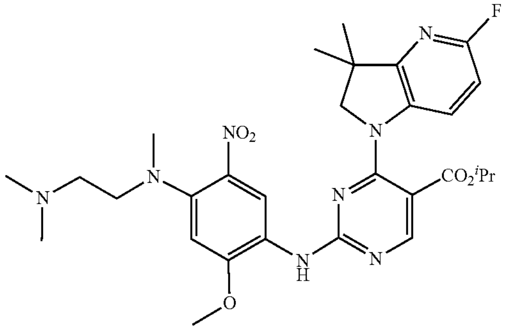 | isopropyl 2-((4-((2-(dimethylamino)ethyl) (methyl)amino)-2-methoxy-5-nitrophenyl)amino)-4-(5-fluoro-3,3-dimethyl-2,3-dihydro-1H-pyrrolo[3,2-b] pyridin-1-yl)pyrimidine-5-carboxylate | 597.2 |
| E64 | 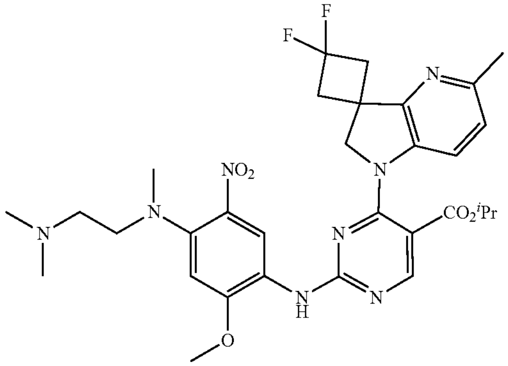 | isopropyl 4-(3,3-difluoro-5'-methylspiro (cyclobutane-1,3'-pyrrolo[3,2-b] pyridin)-1'(2'H)-yl)-2-((4-((2-(dimethylamino)ethyl)(methyl) amino)-2-methoxy-5-nitrophenyl) amino)pyrimidine-5-carboxylate | 641.2 |

-continued

| Intermediate No. | Structure | Chemical name | ESI-MS: $[M + 1]^+$ |
|---|---|---|---|
| E65 | 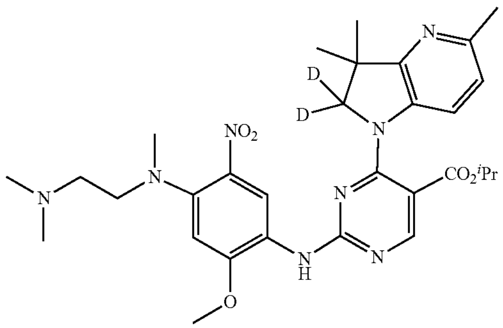 | isopropyl 2-((4-((2-(dimethylamino)ethyl)(methyl)amino)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 595.2 |
| E66 | 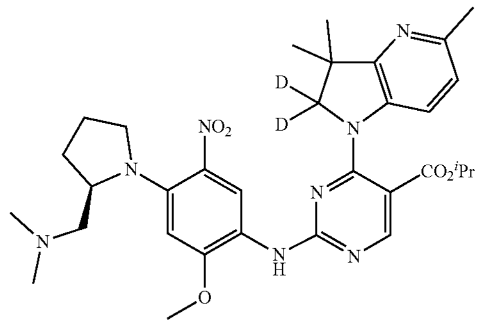 | isopropyl (R)-2-((4-(2-((dimethylamino)methyl)pyrrolidin-1-yl)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 621.3 |
| E67 | 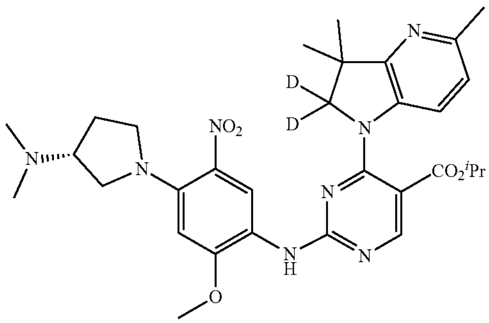 | isopropyl (R)-2-((4-(3-(dimethylamino)pyrrolidin-1-yl)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 607.3 |
| E68 | 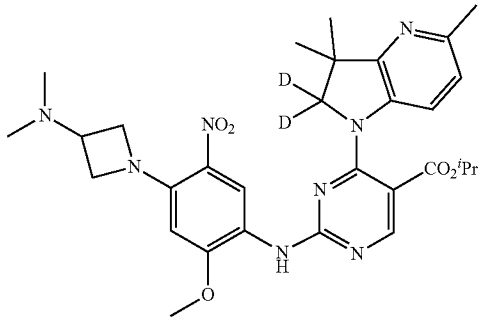 | isopropyl 2-((4-(3-(dimethylamino)azetidin-1-yl)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 593.2 |

-continued

| Intermediate No. | Structure | Chemical name | ESI-MS: $[M + 1]^+$ |
|---|---|---|---|
| E69 | 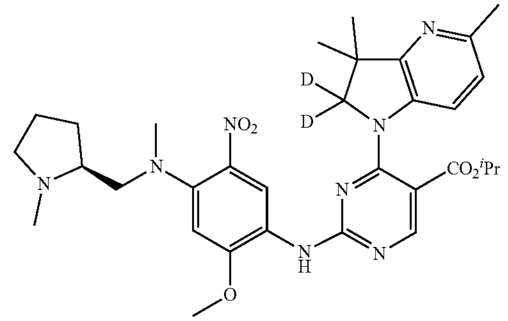 | isopropyl (S)-2-((2-methoxy-4-(methyl((1-methylpyrrolidin-2-yl)methyl)amino)-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 621.4 |
| E70 | 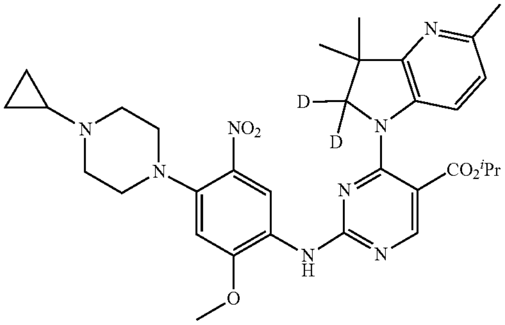 | isopropyl 2-((4-(4-cyclopropylpiperazin-1-yl)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 619.4 |
| E71 | 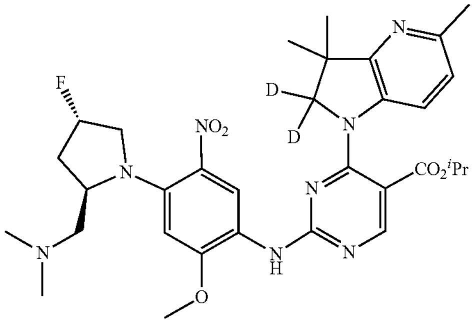 | isopropyl 2-((4-((2R,4S)-2-((dimethylamino)methyl)-4-fluoropyrrolidin-1-yl)-2-methoxy-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 639.4 |
| E72 | 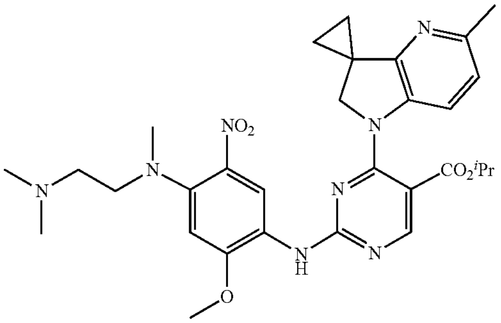 | isopropyl 2-((4-((2-(dimethylamino)ethyl)(methyl)amino)-2-methoxy-5-nitrophenyl)amino)-4-(5'-methylspiro(cyclopropane-1,3'-pyrrolo[3,2-b]pyridin)-1'(2'H)-yl)pyrimidine-5-carboxylate | 591.2 |

-continued

| Intermediate No. | Structure | Chemical name | ESI-MS: $[M + 1]^+$ |
|---|---|---|---|
| E73 | 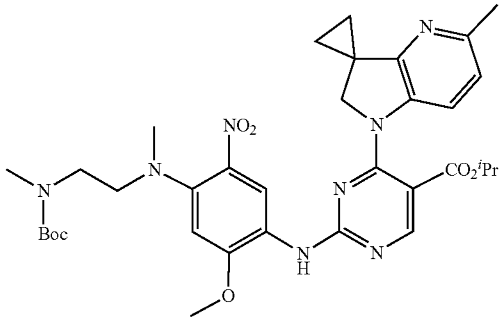 | isopropyl 2-((4-((2-((tert-butoxycarbonyl)(methyl)amino)ethyl)(methyl)amino)-2-methoxy-5-nitrophenyl)amino)-4-(5'-methylspiro(cyclopropane-1,3'-pyrrolo[3,2-b]pyridin)-1'(2'H)-yl)pyrimidine-5-carboxylate | 677.2 |
| E74 | 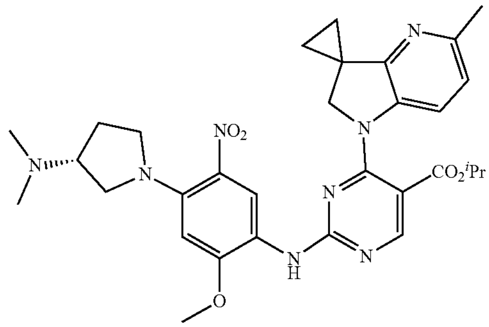 | isopropyl (R)-2-((4-(3-(dimethylamino)pyrrolidin-1-yl)-2-methoxy-5-nitrophenyl)amino)-4-(5'-methylspiro(cyclopropane-1,3'-pyrrolo[3,2-b]pyridin)-1'(2'H)-yl)pyrimidine-5-carboxylate | 603.2 |
| E75 | 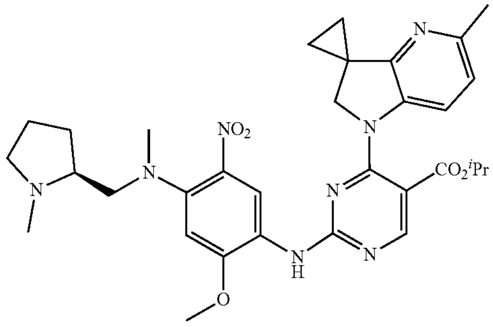 | isopropyl (S)-2-((2-methoxy-4-(methyl)((1-methylpyrrolidin-2-yl)methyl)amino)-5-nitrophenyl)amino)-4-(5'-methylspiro(cyclopropane-1,3'-pyrrolo[3,2-b]pyridin)-1'(2'H)-yl)pyrimidine-5-carboxylate | 617.2 |
| E76 | 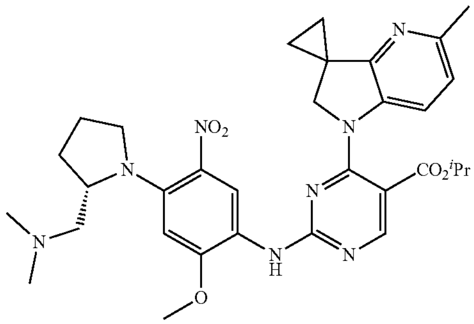 | isopropyl (S)-2-((4-(2-((dimethylamino)methyl)pyrrolidin-1-yl)-2-methoxy-5-nitrophenyl)amino)-4-(5'-methylspiro(cyclopropane-1,3'-pyrrolo[3,2-b]pyridin)-1'(2'H)-yl)pyrimidine-5-carboxylate | 617.2 |

-continued

| Intermediate No. | Structure | Chemical name | ESI-MS: [M + 1]$^+$ |
| --- | --- | --- | --- |
| E77 | 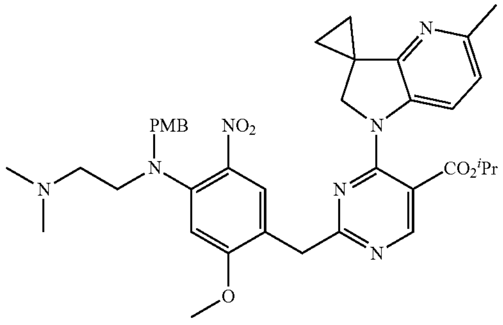 | isopropyl 2-((4-((2-(dimethylamino)ethyl)(4-methoxybenzyl)amino)-2-methoxy-5-nitrophenyl)amino)-4-(5'-methyl spiro(cyclopropane-1,3'-pyrrolo[3,2-b] pyridin)-1'(2'H)-yl)pyrimidine-5-carboxylate | 697.4 |

Intermediate E78: Preparation of isopropyl 4-(3,3-dimethyl-5-(prop-1-yn-1-yl)-2,3-dihydro-1H-pyrrolo [3,2-b]pyridin-1-yl)-2-((4-((2-(dimethylamino)ethyl) (methyl)amino)-2-methoxy-5-nitrophenyl)amino) pyrimidine-5-carboxylate

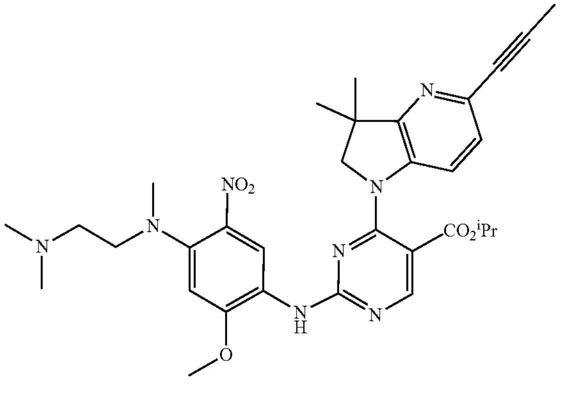

Isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (300 mg, 0.45 mmol), propyne (9 mL, 1 M, 9 mmol), tetrakis(triphenylphosphine)palladium (103 mg, 0.09 mmol) and CuI (17 mg, 0.09 mmol) were dissolved in 10 mL of a mixed solution of triethylamine and tetrahydrofuran (5:1). The reaction mixture was stirred at room temperature under nitrogen protection for 18 hrs, and after the reaction was completed, the reaction mixture was filtered through diatomaceous earth. The resulting filtrate was concentrated, and then the residue was separated by rapid silica gel column chromatography [dichloromethane:methanol=10:1] to obtain isopropyl 4-(3,3-dimethyl-5-(prop-1-yn-1-yl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (220 mg, yield: 79.5%). ESI-MS: 617.3 [M+1]$^+$.

Intermediates E79 to E88 were Prepared According to the Preparation Method for Intermediate E78:

| Intermediate No. | Structure | Chemical name | ESI-MS: [M + 1]$^+$ |
| --- | --- | --- | --- |
| E79 | 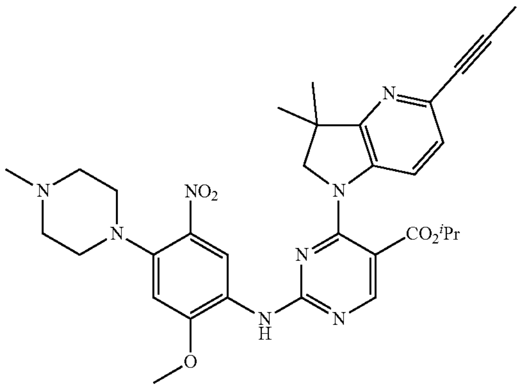 | isopropyl 4-(3,3-dimethyl-5-(prop-1-yn-1-yl)-2,3-dihydro-1H-pyrrolo [3,2-b]pyridin-1-yl)-2-((2-methoxy-4-(4-methylpiperazin-1-yl)-5-nitrophenyl)amino)pyrimidine 5-carboxylate | 615.4 |

-continued

| Intermediate No. | Structure | Chemical name | ESI-MS: $[M + 1]^+$ |
|---|---|---|---|
| E80 | 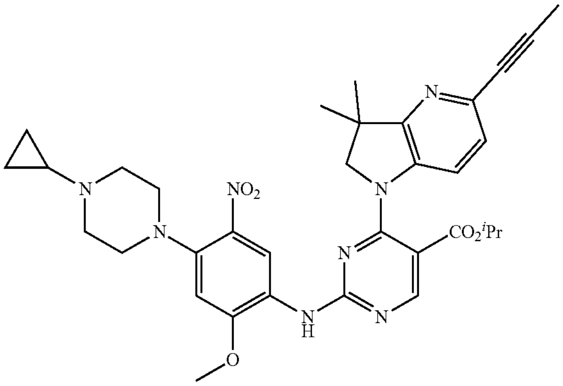 | isopropyl 2-((4-(4-cyclopropylpiperazin-1-yl)-2-methoxy-5-nitrophenyl) amino)-4-(3,3-dimethyl-5-(prop-1-yn-1-yl)-2,3-dihydro-1H-pyrrolo[3,2-b]pyridin-1-yl) pyrimidine-5-carboxylate | 641.4 |
| E81 | 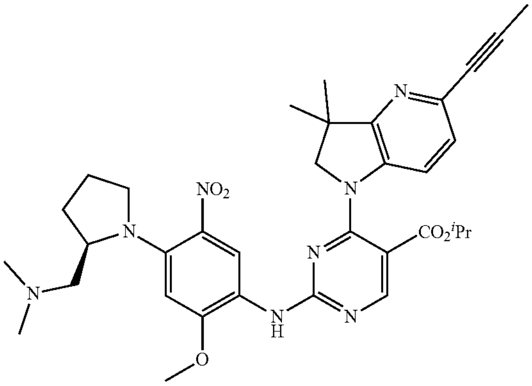 | isopropyl (R)-4-(3,3-dimethyl-5-(prop-1-yn-1-yl)-2,3-dihydro-1H-pyrrolo [3,2-b]pyridin-1-yl)-2-((4-(2-((dimethylamino)methyl)pyrrolidin-1-yl)-2-methoxy-5-nitrophenyl) amino)pyrimidine-5-carboxylate | 643.4 |
| E82 | 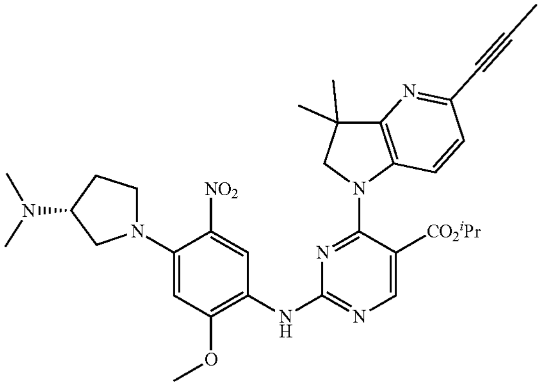 | isopropyl (R)-4-(3,3-dimethyl-5-(prop-1-yn-1-yl)-2,3-dihydro-1H-pyrrolo [3,2-b]pyridin-1-yl)-2-((4-(3-(dimethylamino)pyrrolidin-1-yl)-2-methoxy-5-nitrophenyl) amino)pyrimidine-5-carboxylate | 629.4 |
| E83 | 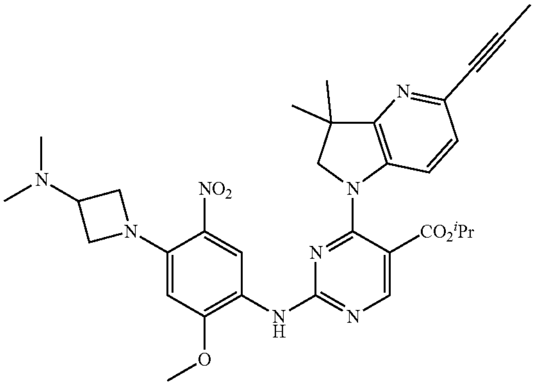 | isopropyl 4-(3,3-dimethyl-5-(prop-1-yn-1-yl)-2,3-dihydro-1H-pyrrolo[3,2-b]pyridin-1-yl)-2-((4-(3-(dimethylamino)azetidin-1-yl)-2-methoxy-5-nitrophenyl)amino) pyrimidine-5-carboxylate | 615.4 |

-continued

| Intermediate No. | Structure | Chemical name | ESI-MS: [M + 1]+ |
| --- | --- | --- | --- |
| E84 | 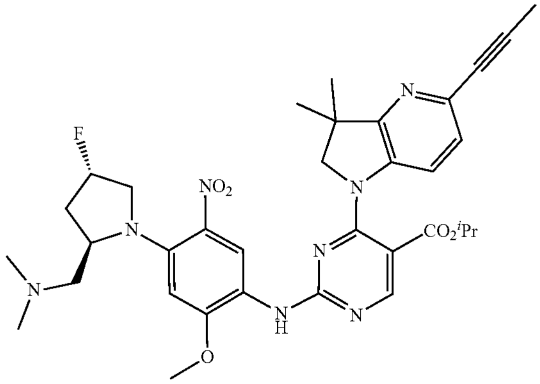 | isopropyl 4-(3,3-dimethyl-5-(prop-1-yn-1-yl)-2,3-dihydro-1H-pyrrolo[3,2-b]pyridin-1-yl)-2-((4-((2R,4S)-2-((dimethylamino)methyl)-4-fluoropyrrolidin-1-yl)-2-methoxy-5-nitrophenyl)amino) pyrimidine-5-carboxylate | 661.4 |
| E85 | 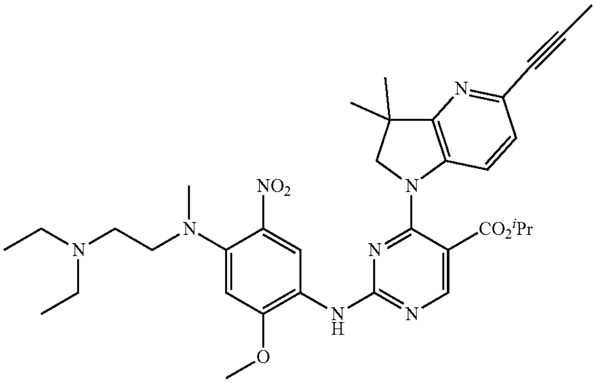 | isopropyl 2-((4-((2-(diethylamino)ethyl) (methyl)amino)-2-methoxy-5-nitrophenyl)amino)-4-(3,3-dimethy-5-(prop-1-yn-1-yl)-2,3-dihydro-1H-pyrrolo[3,2-b]pyridin-1-yl)pyrimidine-5-carboxylate | 645.3 |
| E86 | 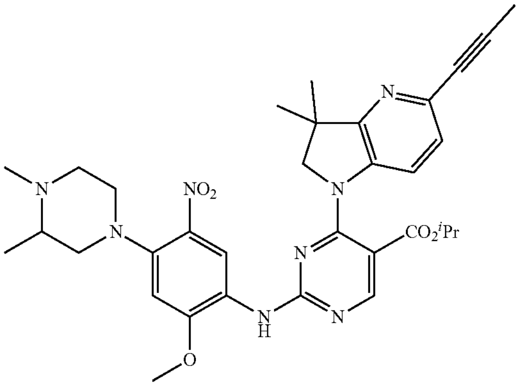 | isopropyl 4-(3,3-dimethyl-5-(prop-1-yn-1-yl)-2,3-dihydro-1H-pyrrolo[3,2-b]pyridin-1-yl)-2-((4-(3,4-dimethylpiperazin-1-yl)-2-methoxy-5-nitrophenyl)amino) pyrimidine-5-carboxylate | 629.3 |
| E87 | 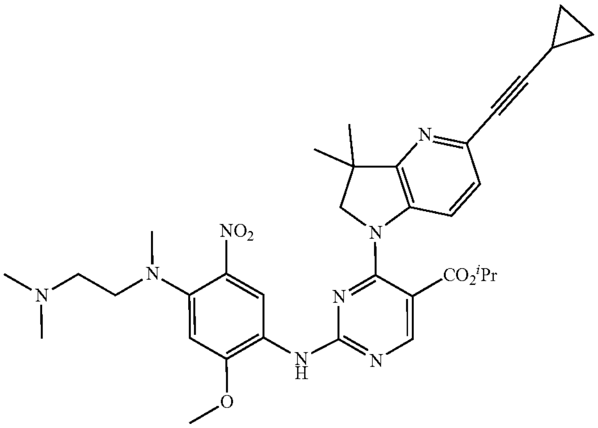 | isopropyl 4-(5-(cyclopropylethynyl)-3,3-dimethyl-2,3-dihydro-1H-pyrrolo[3,2-b]pyridin-1-yl)-2-((4-((2-(dimethylamino)ethyl)(methyl)-amino)-2-methoxy-5-nitrophenyl)amino)pyrimidine-5-carboxylate | 643.5 |

-continued

| Intermediate No. | Structure | Chemical name | ESI-MS: [M + 1]+ |
|---|---|---|---|
| E88 | 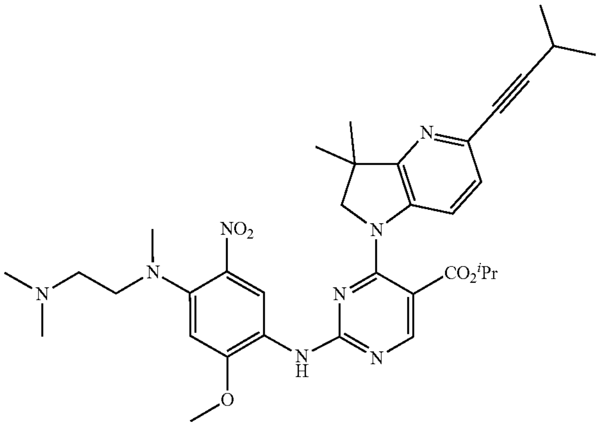 | isopropyl 4-(3,3-dimethyl-5-(3-methylbut-1-yn-1-yl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate | 645.4 |

Intermediate E89: Preparation of isopropyl 4-(3,3-dimethyl-5-vinyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate

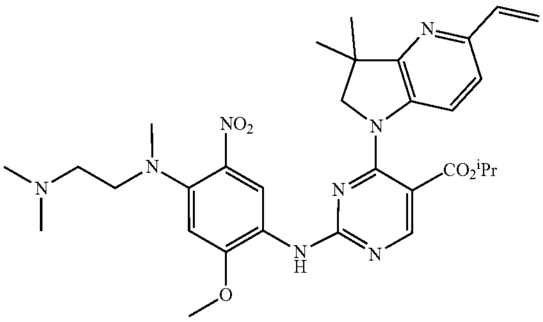

Isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (100 mg, 0.15 mmol), 2-vinyl-4,4,5,5-tetramethyl-1,3,2-dioxaborolane (46.8 mg, 0.3 mmol), sodium carbonate (48 mg, 0.45 mmol), palladium acetate (4 mg, 0.02 mmol) and triphenylphosphine (8 mg, 0.3 mmol) were dissolved in ethylene glycol dimethyl ether (5 mL) and water (1 mL), and the reaction mixture was stirred at 90° C. under nitrogen protection for 18 hrs. After the reaction was completed, the reaction mixture was filtered through diatomaceous earth. The resulting filtrate was concentrated, and then the residue was separated by rapid silica gel column chromatography [dichloromethane:methanol=10:1] to obtain isopropyl 4-(3,3-dimethyl-5-vinyl-2,3-dihydro-1H-pyrrolo[3,2-b]pyridin-1-yl)-2-((4-((2-(dimethyl amino)ethyl)(methyl)amino)-2-methoxy-5-nitrophenyl)amino)pyrimidine-5-carboxylate (66 mg, yield: 73.3%). ESI-MS: 605.3 $[M+1]^+$.

Intermediate E90 was Prepared According to the Preparation Method for Intermediate E89:

| Intermediate No. | Structure | Chemical name | ESI-MS: [M + 1]+ |
|---|---|---|---|
| E90 | 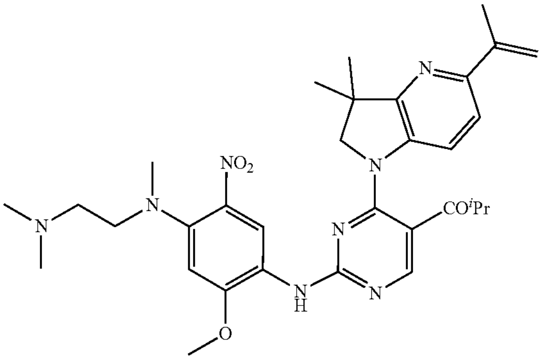 | isopropyl 4-(3,3-dimethyl-5-(prop-1-en-2-yl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate | 619.5 |

Preparation of Intermediate E91: isopropyl 4-(5-cyano-3,3-dimethyl-2,3-dihydro-1H-pyrrolo[3,2-b]pyridin-1-yl)-2-((4-((2-(dimethylamino)ethyl)(methyl) amino)-2-methoxy-5-nitrophenyl)amino)pyrimidine-5-carboxylate

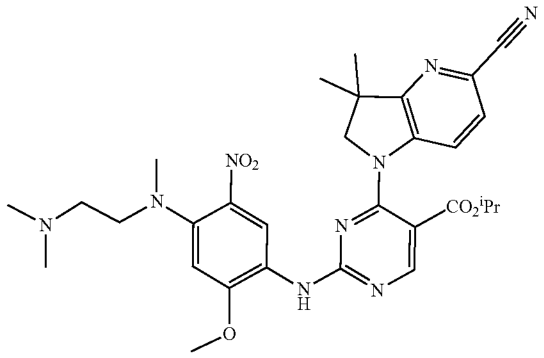

Isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (100 mg, 0.15 mmol), zinc cyanide (35.7 mg, 0.3 mmol) and tetrakis(triphenylphosphine)palladium (17.6 mg, 0.015 mmol) were dissolved in N,N-dimethylformamide (10 mL) and water (1 mL), and the reaction mixture was stirred at 90° C. under nitrogen protection for 2 hrs. After the reaction was completed, the reaction mixture was filtered through diatomaceous earth. The resulting filtrate was concentrated, and then the residue was separated by rapid silica gel column chromatography [dichloromethane: methanol=10:1] to obtain isopropyl 4-(5-cyano-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (82 mg, yield: 89.3%). ESI-MS: 604.2 $[M+1]^+$.

Preparation of Intermediate E92: isopropyl 4-(5-(azetidin-1-yl)-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate

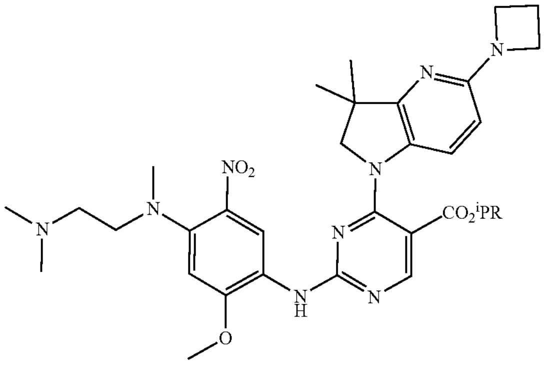

Isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (100 mg, 0.15 mmol), azetidine (10 mg, 1.7 mmol), 1,1'-binaphthyl-2,2'-bis(diphenylphosphine) (37.8 mg, 0.06 mmol), palladium acetate (6.8 mg, 0.03 mmol) and cesium carbonate (99 mg, 0.3 mmol) were dissolved in dioxane (12 mL), and the reaction mixture was stirred at 120° C. under nitrogen protection for 2 hrs. After the reaction was completed, the reaction mixture was filtered through diatomaceous earth. The resulting filtrate was concentrated, and then the residue was separated by rapid silica gel column chromatography [dichloromethane methanol=10:1] to obtain isopropyl 4-(5-(azetidin-1-yl)-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (52 mg, yield: 53.9%). ESI-MS: 634.5 $[M+1]^+$.

Preparation of Intermediate E93-1: isopropyl 2-((4-((2-hydroxyethyl)(methyl) amino)-2-methoxy-5-nitrophenyl)amino)-4-(3,3,5-trimethyl-2,3-dihydro-1H-pyrrolo [3,2-b]pyridin-1-yl)pyrimidine-5-carboxylate

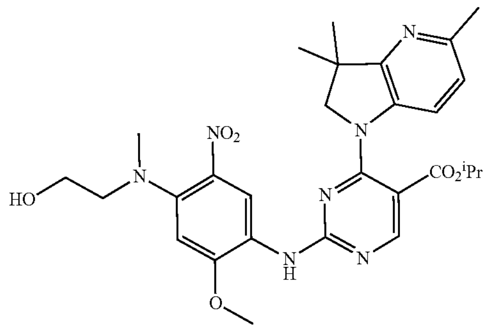

To a solution of isopropyl 2-((4-fluoro-2-methoxy-5-nitrophenyl)amino)-4-(3,3,5-trimethyl-2,3-dihydro-1H-pyrrolo[3,2-b]pyridin-1-yl)pyrimidine-5-carboxylate (400 mg, 0.78 mmol) in 1,4-dioxane (30 mL), 2-(methylamino)ethan-1-ol (0.10 mL, 1.18 mmol) and diisopropylethylamine (0.26 mL, 1.57 mmol) were added. The reaction mixture was stirred at 120° C. for 18 hrs. Dichloromethane and water were added, and then the mixture solution was separated. The organic phase was successively washed with water and saturated brine, then dried over anhydrous sodium sulfate, filtered, and concentrated, and then the residue was separated by column chromatography [dichloromethane:methanol=10:1] to obtain isopropyl 2-((4-((2-hydroxyethyl)(methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate (120 mg, yield: 95%). ESI-MS: 566.3 $[M+1]^+$.

Intermediates E95-1 to E97-1 and Intermediate E99-1 were Prepared According to the Preparation Method for Intermediate E93-1:

| Intermediate No. | Structure | Chemical name | ESI-MS: $[M + 1]^+$ |
|---|---|---|---|
| E95-1 | 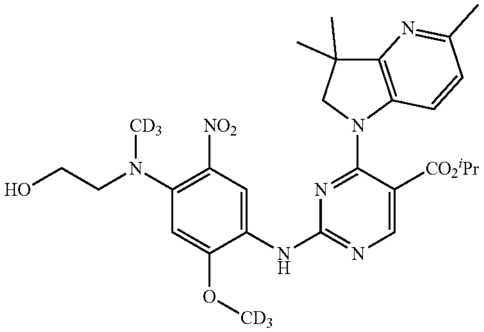 | isopropyl 2-((4-((2-hydroxyethyl)(methyl-$d_3$) amino)-2-(methoxy-$d_3$)-5-nitrophenyl) amino)-4-(3,3,5-trimethyl-2,3-dihydro-1H-pyrrolo[3,2-b] pyridin-1-yl)pyrimidine-5-carboxylate | 572.4 |
| E96-1 | 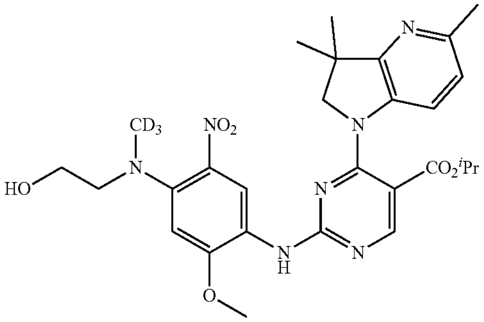 | isopropyl 2-((4-((2-hydoxyethyl)(methyl-$d_3$)amino)-2-methoxy-5-nitro-phenyl)amino)-4-(3,3,5-trimethyl-2,3-dihydro-1H-pyrrolo[3,2-b]pyridin-1-yl)pyrimidine-5-carboxylate | 569.3 |
| E97-1 | 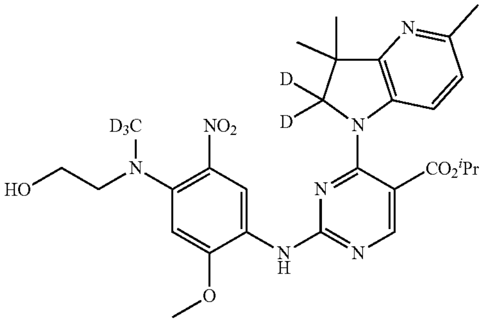 | isopropyl 2-((4-((2-hydroxyethyl)(methyl-$d_3$)amino-2-methoxy-5-nitrophenyl) amino)-4-(3,3,5-trimethyl-2,3-dihydro-1H-pyrrolo[3,2-b]pyridin-1-yl)-2,2-$d_2$)pyrimidine-5-carboxylate | 571.4 |
| E99-1 | 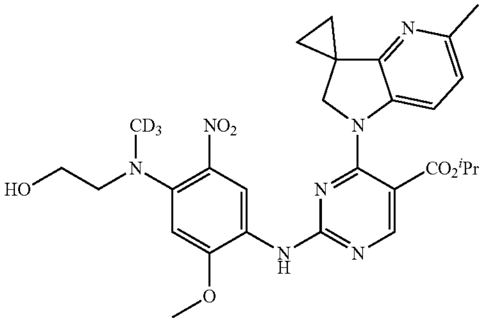 | isopropyl 2-((4-((2-hydroxyethyl)(methyl-$d_3$)amino)-2-methoxy-5-nitrophenyl)amino)-4-(5'-methylspiro (cyclopropane-1,3'-pyrrolo[3,2-b] pyridin)-1'(2'H)-yl)pyrimidine-5-carboxylate | 567.4 |

Preparation of Intermediate E93-2: isopropyl 2-((2-methoxy 4-(methyl(2-((methanesulfonyl)oxy)ethyl) amino)-5-nitrophenyl)amino)-4-(3,3,5-trimethyl-2,3-dihydro-1H-pyrrolo[3,2-b]pyridin-1-yl)pyrimidine-5-carboxylate

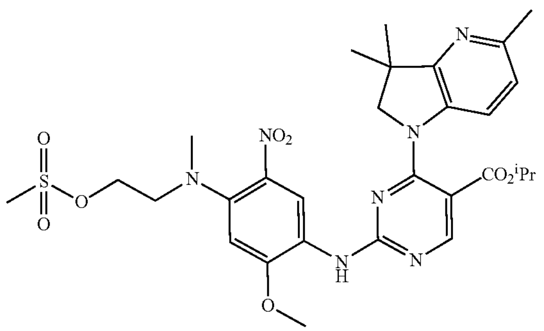

A solution of isopropyl 2-((4-((2-hydroxyethyl)(methyl) amino)-2-methoxy-5-nitrophenyl)amino)-4-(3,3,5-trimethyl-2,3-dihydro-1H-pyrrolo[3,2-b]pyridin-1-yl)pyrimidine-5-carboxylate (410 mg, 0.73 mmol) in dichloromethane (10 mL) was cooled to 0° C. and N,N-diisopropylethylamine (0.36 mL, 2.18 mmol) and methanesulfonyl chloride (0.07 mL, 0.87 mmol) were added. The reaction mixture was stirred at 0° C. for 0.5 hrs. After the solvent was removed, the residue was separated by silica gel column chromatography [dichloromethane:methanol=10:1] to obtain isopropyl 2-((2-methoxy-4-(methyl(2-((methanesulfonyl)oxy)ethyl)amino)-5-nitrophenyl)amino)-4-(3,3,5-trimethyl-2,3-dihydro-1H-pyrrolo[3,2-b]pyridin-1-yl)pyrimidine-5-carboxylate (470 mg, yield: 89%). ESI-MS: 644.3 $[M+1]^+$.

Intermediates E95-2 to E97-2 and Intermediate E99-2 were Prepared According to the Preparation Method for Intermediate E93-2:

| Intermediate No. | Structure | Chemical name | ESI-MS: $[M+1]^+$ |
|---|---|---|---|
| E95-2 | 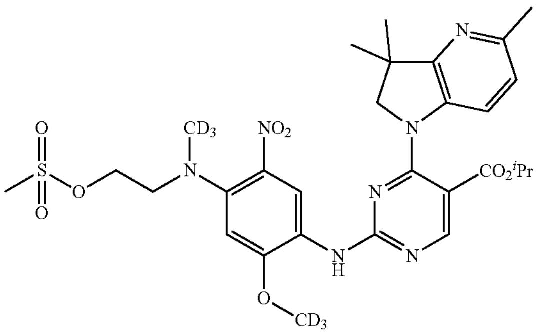 | isopropyl 2-((2-(methoxy-$d_3$)-4-((methyl-$d_3$)(2-((methanesulfonyl)oxy) ethyl)amino)-5-nitrophenyl) amino)-4-(3,3,5-trimethyl-2,3-dihydro-1H-pyrrolo[3,2-b] pyridin-1-yl)pyrimidine-5-carboxylate | 650.4 |
| E96-2 | 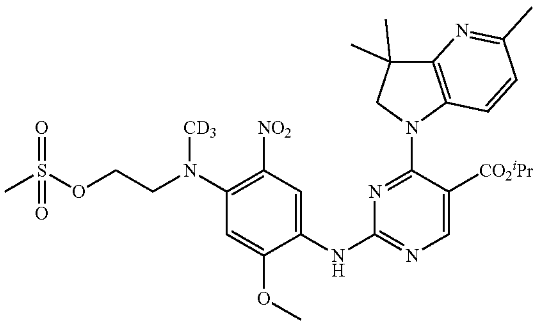 | isopropyl 2-((2-methoxy-4-((methyl-$d_3$) (2-((methanesulfonyl)oxy) ethyl)amino)-5-nitrophenyl) amino)-4-(3,3,5-trimethyl-2,3-dihydro-1H-pyrrolo[3,2-b] pyridin-1-yl)pyrimidine-5-carboxylate | 647.4 |

-continued

| Intermediate No. | Structure | Chemical name | ESI-MS: $[M + 1]^+$ |
| --- | --- | --- | --- |
| E97-2 | 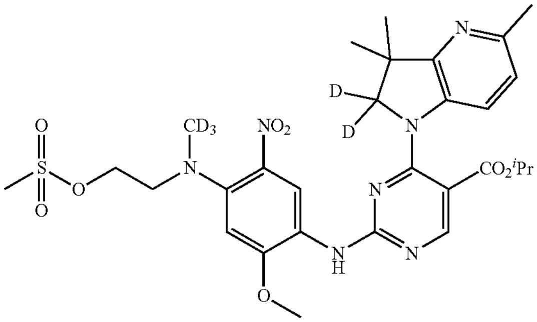 | isopropyl 2-((2-methoxy-4-((methyl-$d_3$)(2-((methanesulfonyl)oxy)ethyl)amino)-5-nitrophenyl)amino)-4-(3,3,5-trimethyl-2,3-dihydro-1H-pyrrolo[3,2-b]pyridin-1-yl-2,2-$d_2$)pyrimidine-5-carboxylate | 649.4 |
| E99-2 | 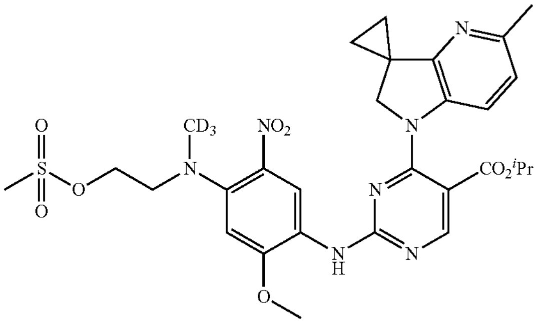 | isopropyl 2-((2-methoxy-4-((methyl-$d_3$)(2-((methanesulfonyl)oxy)ethyl)amino)-5-nitrophenyl)amino)-4-(5'-methylspiro(cyclopropane-1,3'-pyrrolo[3,2-b]pyridin)-1'(2'H)-yl)pyrimidine-5-carboxylate | 645.4 |

Preparation of Intermediate E93: isopropyl 2-((2-methoxy-4-(methyl(2-(pyrrolidin-1-yl) ethyl) amino)-5-nitrophenyl)amino) 4-(3,3,5-trimethyl-2,3-dihydro-1H-pyrrolo [3,2-b]pyridin-1-yl)pyrimidine-5-carboxylate

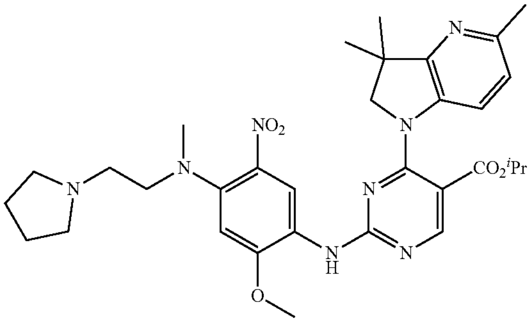

To a solution of isopropyl 2-((2-methoxy-4-(methyl(2-((methanesulfonyl)oxy) ethyl)amino)-5-nitrophenyl) amino)-4-(3,3,5-trimethyl-2,3-dihydro-1H-pyrrolo[3,2-b] pyridin-1-yl)pyrimidine-5-carboxylate (1.0 g, 4.5 mmol) in acetonitrile (30 mL), pyrrolidine (0.03 mL, 0.37 mmol) and potassium carbonate (1.2 g, 9.0 mmol) were added. The reaction mixture was stirred at 50° C. for 18 hrs. After the solvent was removed, the residue was separated by silica gel column chromatography [dichloromethane:methanol=10:1] to obtain isopropyl 2-((2-methoxy-4-(methyl(2-(pyrrolidin-1-yl)ethyl)amino)-5-nitrophenyl)amino)-4-(3,3,5-trimethyl-2,3-dihydro-1H-pyrrolo[3,2-b]pyridin-1-yl)pyrimidine-5-carboxylate (40 mg, yield: 31.7%). ESI-MS: 310.3 $[M/2+1]^+$.

Intermediates E94 to E100 were Prepared According to the Preparation Method for Intermediate E93:

| Intermediate No. | Structure | Chemical name | ESI-MS: $[M + 1]^+$ |
|---|---|---|---|
| E94 | 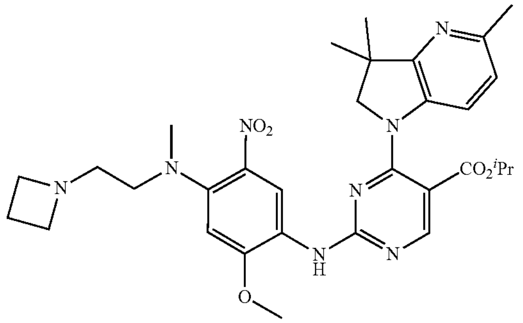 | isopropyl 2-((4-((2-(azetidin-1-yl)ethyl) (methyl)amino)-2-methoxy-5-nitro-phenyl)amino)-4-(3,3,5-trimethyl-2,3-dihydro-1H-pyrrolo[3,2-b]pyridin-1-yl)pyrimidine-5-carboxylate | 605.4 |
| E95 | 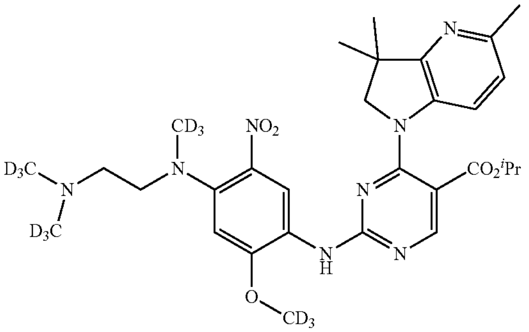 | isopropyl 2-((4-((2-(bis(methyl-$d_3$)amino) ethyl)(methyl-$d_3$)amino-2-(methoxy-$d_3$)-5-nitrophenyl)amino)-4-(3,3,5-trimethyl-2,3-dihydro-1H-pyrrolo [3,2-b]pyridin-1-yl)pyrimidine-5-carboxylate | 605.4 |
| E96 | 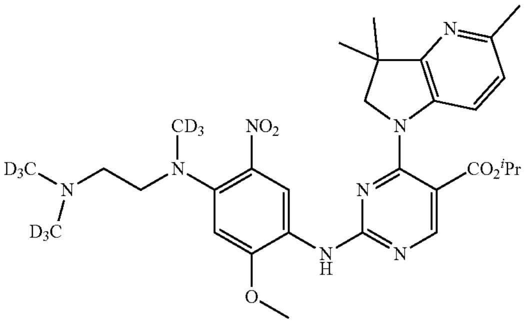 | isopropyl 2-((4-((2-(bis(methyl-$d_3$)amino) ethyl)(methyl-$d_3$)amino)-2-methoxy-5-nitrophenyl)amino)-4-(3,3,5-trimethyl-2,3-dihydro-1H-pyrrolo [3,2-b]pyridin-1-yl)pyrimidine-5-carboxylate | 602.4 |
| E97 | 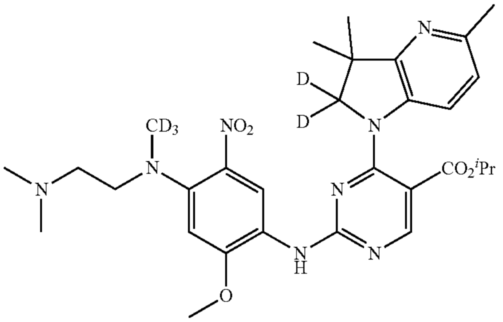 | isopropyl 2-((4-((2-(dimethylamino)ethyl) (methyl-$d_3$)amino)-2-methoxy-5-nitrophenyl)amino)-4-(3,3,5-trimethyl-2,3-dihydro-1H-pyrrolo[3,2-b] pyridin-1-yl-2,2-$d_2$)pyrimidine-5-carboxylate | 598.4 |

-continued

| Intermediate No. | Structure | Chemical name | ESI-MS: [M + 1]+ |
|---|---|---|---|
| E98 | 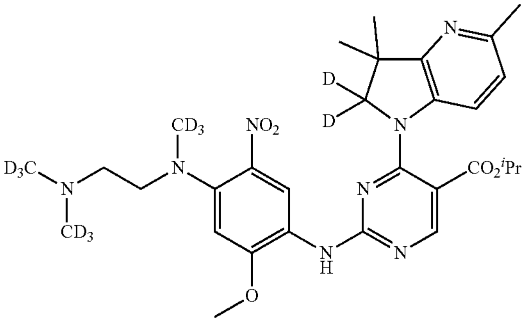 | isopropyl 2-((4-((2-(bis(methyl-$d_3$)amino) ethyl)(methyl-$d_3$)amino)-2-methoxy-5-nitrophenyl)amino)-4-(3,3,5-trimethyl-2,3-dihydro-1H-pyrrolo [3,2-b]pyridin-1-yl-2,2-$d_2$)pyrimidine-5-carboxylate | 604.4 |
| E99 | 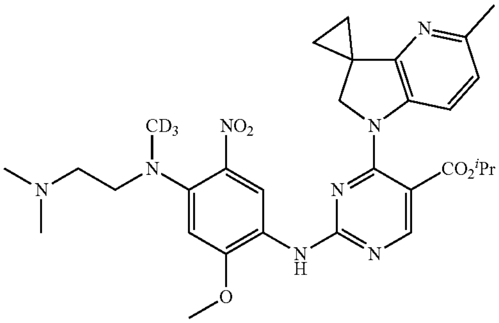 | isopropyl 2-((4-((2-(dimethylamino)ethyl) (methyl-$d_3$)amino)-2-methoxy-5-nitrophenyl)amino)-4-(5'-methylspiro (cyclopropane-1,3'-pyrrolo[3,2-b] pyridin-1'(2'H)-yl)pyrimidine-5-carboxylate | 594.4 |
| E100 | 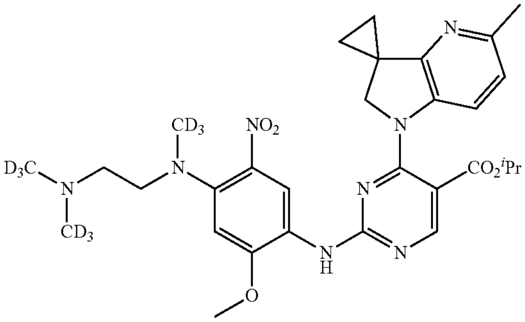 | isopropyl 2-((4-((2-(bis(methyl-$d_3$)amino) ethyl)(methyl-$d_3$)amino)-2-methoxy-5-nitrophenyl)amino)-4-(5'-methyl spiro(cyclopropane-1,3'-pyrrolo[3,2-b] pyridin)-1'(2'H)-yl)pyrimidine-5-carboxylate | 600.4 |

Preparation of Intermediate F1: isopropyl 2-((5-amino-4-((2-(dimethylamino) ethyl)(methyl)amino)-2-methoxyphenyl)amino-4-(3,3,5-trimethyl-2,3-dihydro-1H-pyrrolo[3,2-b]pyridin-1-yl)pyrimidine-5-carboxylate

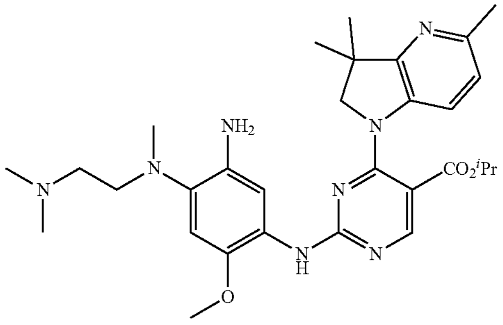

To a solution of isopropyl 2-((4-((2-(dimethylamino) ethyl)(methyl)amino)-2-methoxy-5-nitrophenyl)amino)-4-(3,3,5-trimethyl-2,3-dihydro-1H-pyrrolo[3,2-b]pyridin-1-yl)pyrimidine-5-carboxylate (72 mg, 0.11 mmol) in methanol (20 mL), 10% palladium on carbon (10 mg) was added. The reaction mixture was stirred at room temperature for 0.5 hrs, then filtered, and concentrated to obtain isopropyl 2-((5-amino-4-((2-(dimethylamino)ethyl)(methyl) amino)-2-methoxyphenyl)amino)-4-(3,3,5-trimethyl-2,3-dihydro-1H-pyrrolo[3,2-b]pyridin-1-yl)pyrimidine-5-carboxylate (65 mg, yield: 86.3%). ESI-MS: 563.3 $[M+1]^+$.

Preparation of Intermediate F2: isopropyl 2-((5-amino-4-((2-(dimethylamino) ethyl)(methyl)amino)-2-isopropoxyphenyl)amino)-4-(3,3,5-trimethyl-2,3-dihydro-1H-pyrrolo[3,2-b]pyridin-1-yl)pyrimidine-5-carboxylate

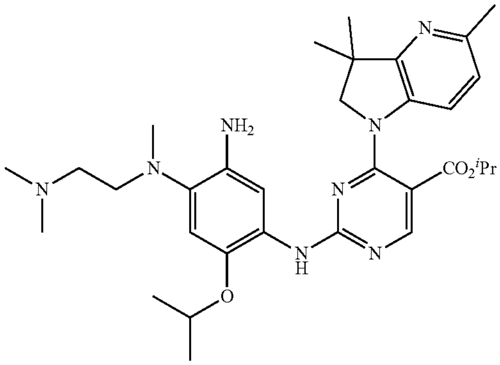

To a mixed solution of isopropyl 2-((4-((2-(dimethylamino)ethyl)(methyl)amino)-2-isopropoxy-5-nitrophenyl) amino)-4-(3,3,5-trimethyl-2,3-dihydro-1H-pyrrolo[3,2-b] pyridin-1-yl)pyrimidine-5-carboxylate (129 mg, 0.21 mmol) in methanol/water [methanol:water (v/v)=2:1] (30 mL), iron powder (104 mg, 1.87 mmol) and ammonium chloride (101 mg, 1.87 mmol) were added. The reaction mixture was stirred at 100° C. for 1 hr and filtered. Ethyl acetate and water were added to the resulting solution, and then the mixture solution was separated. The organic phase was successively washed with water and saturated brine, then dried over anhydrous sodium sulfate, filtered, and concentrated to obtain isopropyl 2-((5-amino-4-((2-(dimethylamino)ethyl)(methyl)amino)-2-isopropoxyphenyl)amino)-4-(3,3,5-trimethyl-2,3-dihydro-1H-pyrrolo[3,2-b]pyridin-1-yl)pyrimidine-5-carboxylate (92 mg, yield: 74.6%). ESI-MS: 591.4 $[M+1]^+$.

Intermediates F3 to F93 were prepared according to the preparation method for intermediate F1 or F2:

| Intermediate No. | Structure | Chemical name | ESI-MS: $[M + 1]^+$ |
|---|---|---|---|
| F3 | 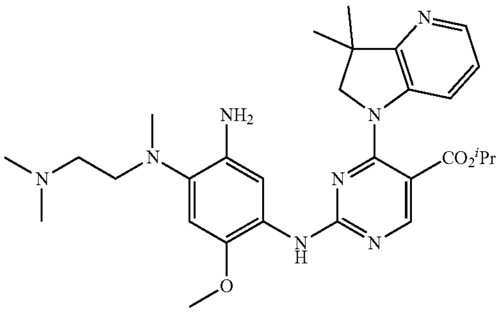 | isopropyl 2-((5-amino-4-((2-(dimethyl-amino)ethyl)(methyl)amino)-2-methoxyphenyl)amino)-4-(3,3-dimethyl-2,3-dihydro-1H-pyrrolo [3,2-b]pyridin-1-yl)pyrimidine-5-carboxylate | 549.2 |

-continued

| Intermediate No. | Structure | Chemical name | ESI-MS: $[M + 1]^+$ |
|---|---|---|---|
| F4 | 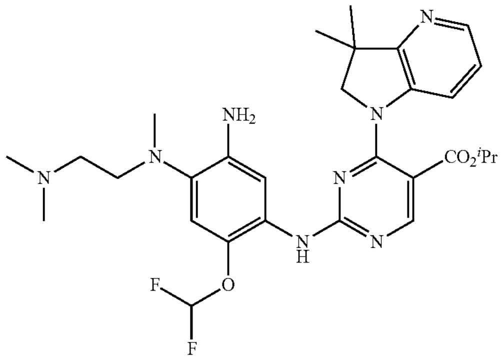 | isopropyl 2-((5-amino-2-(difluoromethoxy)-4-((2-(dimethylamino)ethyl)(methyl)amino)phenyl)amino)-4-(3,3-dimethyl-2,3-dihydro-1H-pyrrolo[3,2-b]pyridin-1-yl)pyrimidine-5-carboxylate | 585.2 |
| F5 | 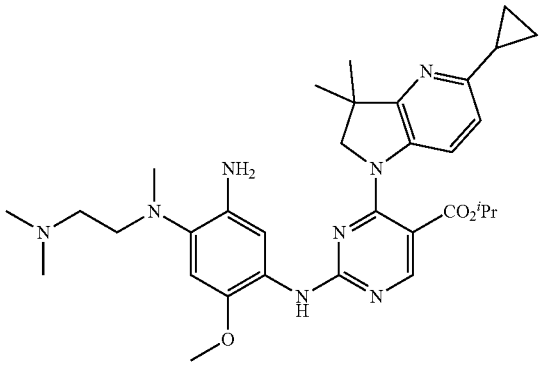 | isopropyl 2-((5-amino-4-((2-(dimethylamino)ethyl)(methyl)amino)-2-methoxyphenyl)amino)-4-(5-cyclopropyl-3,3-dimethyl-2,3-dihydro-1H-pyrrolo[3,2-b]pyridin-1-yl)pyrimidine-5-carboxylate | 589.5 |
| F6 | 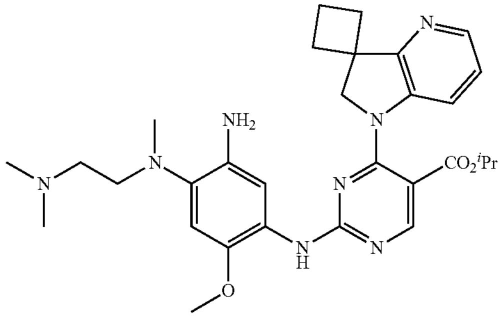 | isopropyl 2-((5-amino-4-((2-(dimethylamino)ethyl)(methyl)amino)-2-methoxyphenyl)amino)-4-(5'-methylspiro(cyclobutane-1,3'-pyrrolo[3,2-b]pyridin)-1'(2'H)-yl)pyrimidine-5-carboxylate | 575.3 |
| F7 | 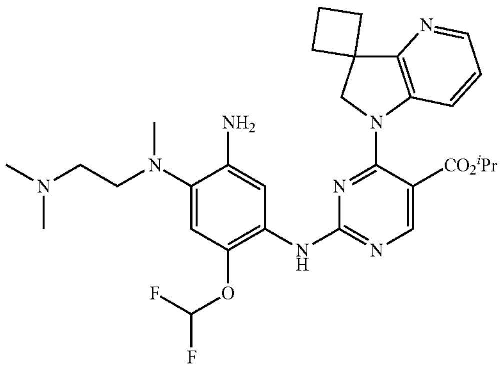 | isopropyl 2-((5-amino-2-(difluoromethoxy)-4-((2-(dimethylamino)ethyl)(methyl)amino)phenyl)amino)-4-(spiro(cyclobutane-1,3'-pyrrolo[3,2-b]pyridin)-1'(2'H)-yl)pyrimidine-5-carboxylate | 597.2 |

-continued

| Intermediate No. | Structure | Chemical name | ESI-MS: $[M + 1]^+$ |
|---|---|---|---|
| F8 | 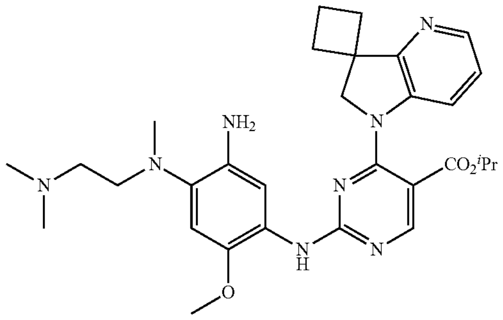 | isopropyl 2-((5-amino-4-((2-(dimethylamino) ethyl)(methyl)amino)-2-methoxyphenyl)amino)-4-(spiro (cyclobutane-1,3'-pyrrolo[3,2-b] pyridin)-1'(2'H)-yl)pyrimidine-5-carboxylate | 561.3 |
| F9 | 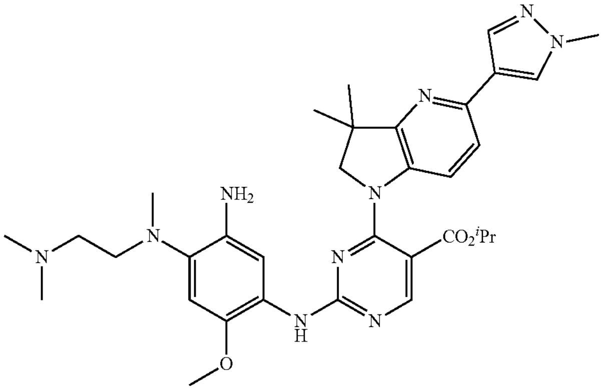 | isopropyl 2-((5-amino-4-((2-(dimethylamino) ethyl)(methyl)amino)-2-methoxy-phenyl)amino)-4-(3,3-dimethyl-5-(1-methyl-1H-pyrazol-4-yl)-2,3-dihydro-1H-pyrrolo[3,2-b] pyridin-1-yl)pyrimidine-5-carboxylate | 629.4 |
| F10 | 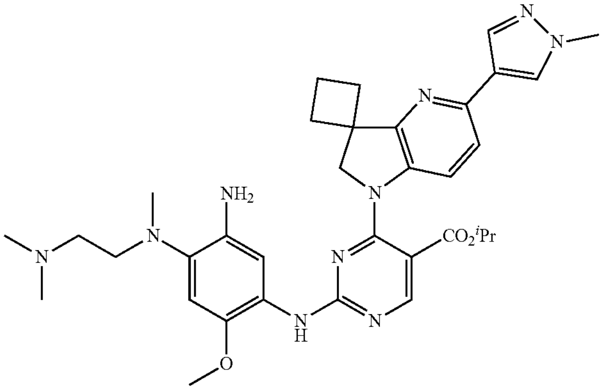 | isopropyl 2-((5-amino-4-((2-(dimethylamino) ethyl)(methyl)amino)-2-methoxy-phenyl)amino)-4-(5'-(1-methyl-1H-pyrazol-4-yl)spiro (cyclobutane-1,3'-pyrrolo[3,2-b] pyridin)-1'(2'H)-yl)pyrimidine-5-carboxylate | 641.4 |
| F11 | 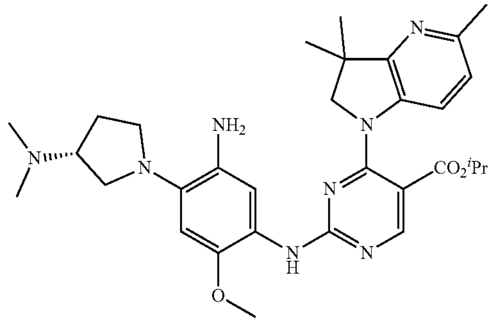 | isopropyl (R)-2-((5-amino-4-(3-(dimethylamino) pyrrolidin-1-yl)-2-methoxy-phenyl)amino)-4-(3,3,5-trimethyl-2,3-dihydro-1H-pyrrolo[3,2-b] pyridin-1-yl)pyrimidine-5-carboxylate | 575.2 |

-continued

| Intermediate No. | Structure | Chemical name | ESI-MS: $[M + 1]^+$ |
|---|---|---|---|
| F12 | 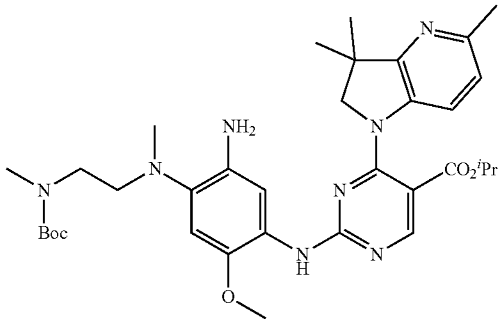 | isopropyl 2-((5-amino-4-((2-((tert-butoxy-carbonyl)(methyl)amino)ethyl)(methyl)amino)-2-methoxyphenyl)amino)-4-(3,3,5-trimethyl-2,3-dihydro-1H-pyrrolo[3,2-b]pyridin-1-yl)pyrimidine-5-carboxylate | 649.4 |
| F13 | 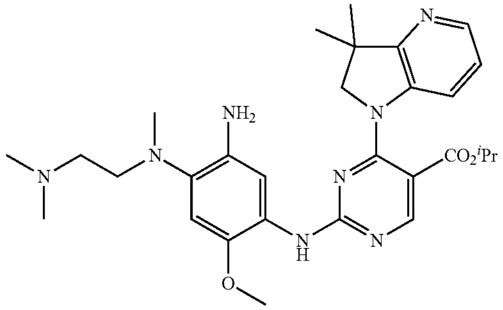 | isopropyl 2-((5-amino-4-((2-(dimethylamino)ethyl)(methyl)amino)-2-methoxyphenyl)amino)-4-(spiro(cyclopropane-1,3'-pyrrolo[3,2-b]pyridin)-1'(2'H)-yl)pyrimidine-5-carboxylate | 547.2 |
| F14 | 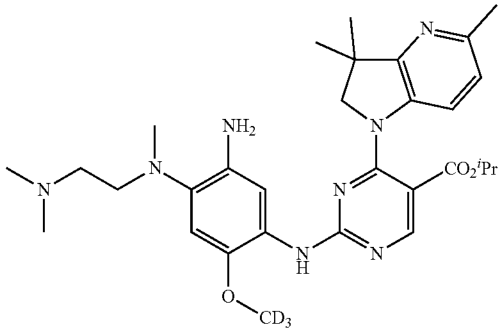 | isopropyl 2-((5-amino-4-((2-(dimethylamino)ethyl)(methyl)amino)-2-(methoxy-$d_3$)phenyl)amino)-4-(3,3,5-trimethyl-2,3-dihydro-1H-pyrrolo[3,2-b]pyridin-1-yl)pyrimidine-5-carboxylate | 566.3 |
| F15 | 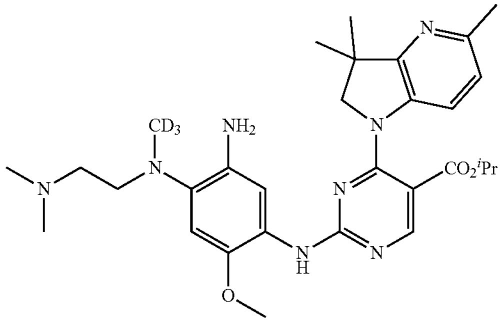 | isopropyl 2-((5-amino-4-((2-(dimethylamino)ethyl)(methyl-$d_3$)amino)-2-methoxyphenyl)amino)-4-(3,3,5-trimethyl-2,3-dihydro-1H-pyrrolo[3,2-b]pyridin-1-yl)pyrimidine-5-carboxylate | 566.2 |

-continued

| Intermediate No. | Structure | Chemical name | ESI-MS: $[M + 1]^+$ |
|---|---|---|---|
| F16 | 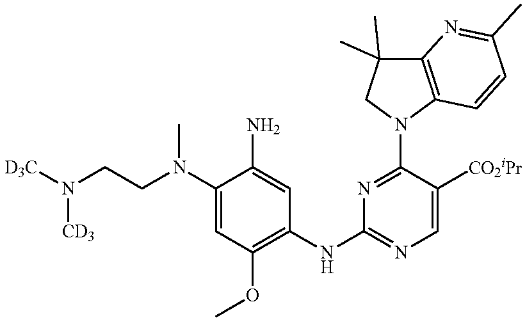 | isopropyl 2-((5-amino-4-((2-(bis(methyl-$d_3$)amino)ethyl)(methyl)amino)-2-methoxyphenyl)amino)-4-(3,3,5-trimethyl-2,3-dihydro-1H-pyrrolo[3,2-b]pyridin-1-yl) pyrimidine-5-carboxylate | 569.4 |
| F17 | 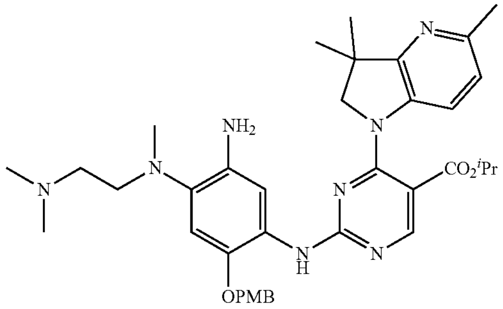 | isopropyl 2-((5-amino-4-((2-(dimethylamino) ethyl)(methyl)amino)-2-((4-methoxybenzyl)oxy)phenyl) amino)-4-(3,3,5-trimethyl-2,3-dihydro-1H-pyrrolo[3,2-b]pyridin-1-yl)pyrimidine-5-carboxylate | 669.4 |
| F18 | 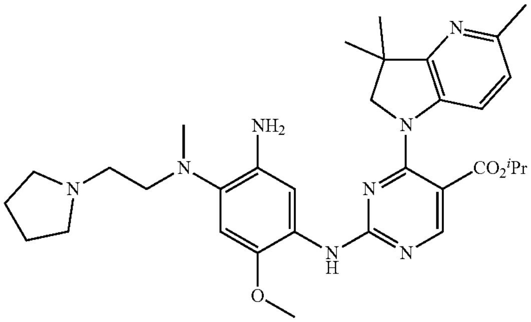 | isopropyl 2-((5-amino-2-methoxy-4-(methyl (2-(pyrrolidin-1-yl)ethyl) amino)phenyl)amino)-4-(3,3,5-trimethyl-2,3-dihydro-1H-pyrrolo [3,2-b]pyridin-1-yl)pyrimidine-5-carboxylate | 589.5 |
| F19 | 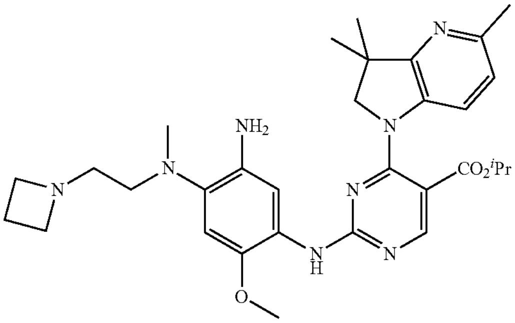 | isopropyl 2-((5-amino-4-((2-(azetidin-1-yl)ethyl)(methyl)amino)-2-methoxyphenyl)amino)-4-(3,3,5-trimethyl-2,3-dihydro-1H-pyrrolo [3,2-b]pyridin-1-yl)pyrimidine-5-carboxylate | 575.4 |

-continued

| Intermediate No. | Structure | Chemical name | ESI-MS: $[M + 1]^+$ |
|---|---|---|---|
| F20 | 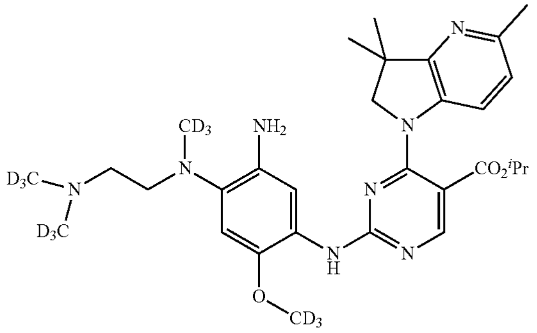 | isopropyl 2-((5-amino-4-((2-(bis(methyl-$d_3$)amino)ethyl)(methyl-$d_3$) amino)-2-(methoxy-$d_3$)phenyl) amino)-4-(3,3,5-trimethyl-2,3-dihydro-1H-pyrrolo[3,2-b]pyridin-1-yl)pyrimidine-5-carboxylate | 575.4 |
| F21 | 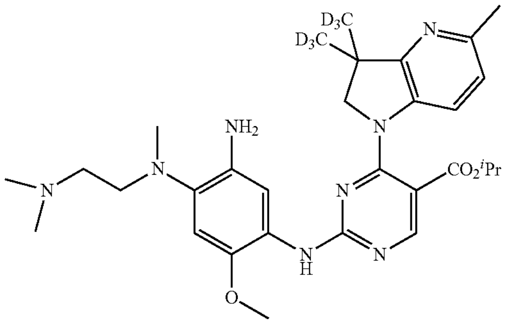 | isopropyl 2-((5-amino-4-((2-(dimethylamino) ethyl)(methyl)amino)-2-methoxyphenyl)amino)-4-(5-methyl-3,3-bis(methyl-$d_3$)-2,3-dihydro-1H-pyrrolo[3,2-b]pyridin-1-yl)pyrimidine-5-carboxylate | 569.4 |
| F22 | 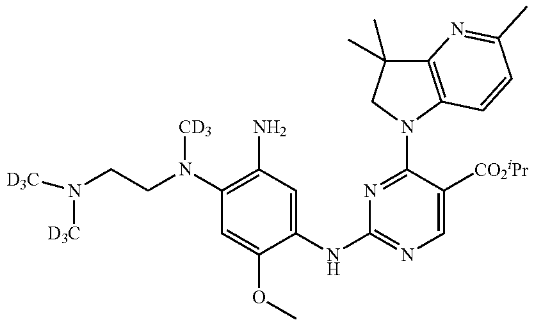 | isopropyl 2-((5-amino-4-((2-(bis(methyl-$d_3$)amino)ethyl)(methyl-$d_3$) amino)-2-methoxyphenyl)amino)-4-(3,3,5-trimethyl-2,3-dihydro-1H-pyrrolo[3,2-b]pyridin-1-yl) pyrimidine-5-carboxylate | 572.4 |
| F23 | 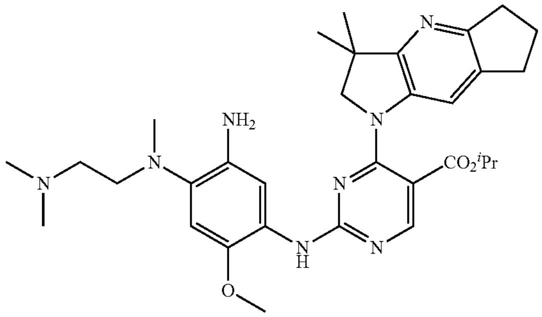 | isopropyl 2-((5-amino-4-((2-(dimethylamino) ethyl)(methyl)amino)-2-methoxyphenyl)amino)-4-(3,3-dimethyl-3,5,6,7-tetrahydrocyclo penta[b]pyrrolo[2,3-e]pyridin-1(2H)-yl)pyrimidine-5-carboxylate | 589.4 |

-continued

| Intermediate No. | Structure | Chemical name | ESI-MS: [M + 1]+ |
|---|---|---|---|
| F24 | 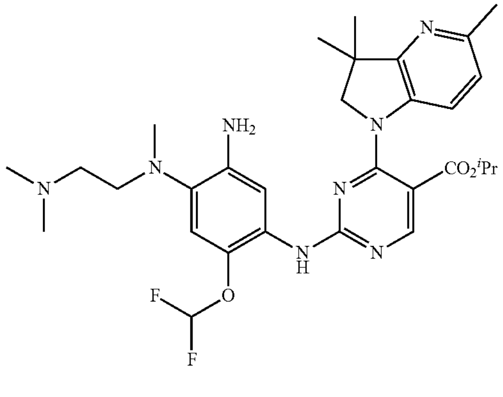 | isopropyl 2-((5-amino-2-(difluoromethoxy) 4-((2-(dimethylamino)ethyl) (methyl)amino)phenyl)amino)-4-(3,3,5-trimethyl-2,3-dihydro-1H-pyrrolo[3,2-b]pyridin-1-yl) pyrimidine-5-carboxylate | 599.4 |
| F25 | 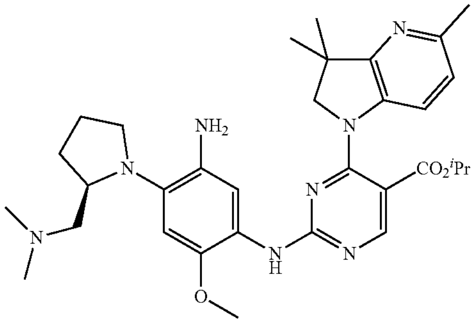 | isopropyl (R)-2-((5-amino-4-(2-((dimethyl-amino)methyl)pyrrolidin-1-yl)-2-methoxyphenyl)amino)-4-(3,3,5-trimethyl-2,3-dihydro-1H-pyrrolo[3,2-b]pyridin-1-yl) pyrimidine-5-carboxylate | 589.4 |
| F26 | 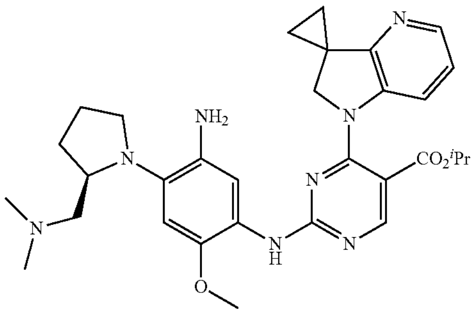 | isopropyl (R)-2-((5-amino-4-((2-((dimethyl-amino)methyl)pyrrolidin-1-yl)-2-methoxyphenyl)amino)-4-(spiro(cyclopropane-1,3'-pyrrolo [3,2-b]pyridin)-1'(2'H)-yl) pyrimidine-5-carboxylate | 573.4 |
| F27 | 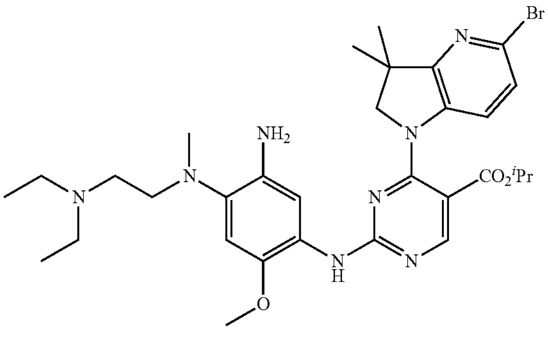 | isopropyl 2-((5-amino-4-((2-(diethylamino) ethyl)(methyl)amino)-2-methoxyphenyl)amino)-4-(5-bromo-3,3-dimethyl-2,3-dihydro-1H-pyrrolo[3,2-b]pyridin-1-yl) pyrimidine-5-carboxylate | 655.2<br>657.2 |

-continued

| Intermediate No. | Structure | Chemical name | ESI-MS: $[M + 1]^+$ |
|---|---|---|---|
| F28 | 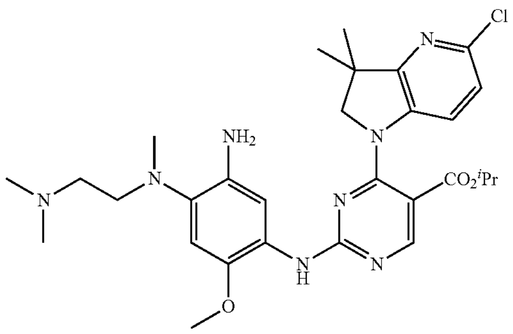 | isopropyl 2-((5-amino-4-((2-(dimethylamino) ethyl)(methyl)amino)-2-methoxy-phenyl)amino)-4-(5-chloro-3,3-dimethyl-2,3-dihydro-1H-pyrrolo[3,2-b]pyridin-1-yl) pyrimidine-5-carboxylate | 583.3 |
| F29 | 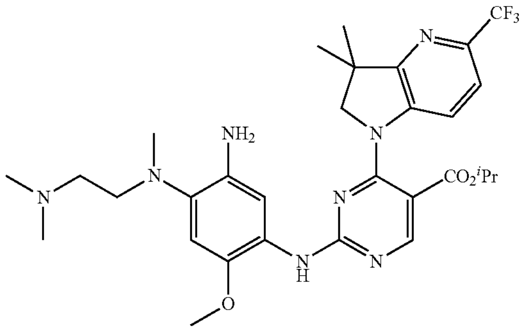 | isopropyl 2-((5-amino-4-((2-(dimethylamino) ethyl)(methyl)amino)-2-methoxy-phenyl)amino)-4-(3,3-dimethyl-5-(trifluoromethyl)-2,3-dihydro-1H-pyrrolo[3,2-b]pyridin-1-yl) pyrimidine-5-carboxylate | 617.3 |
| F30 | 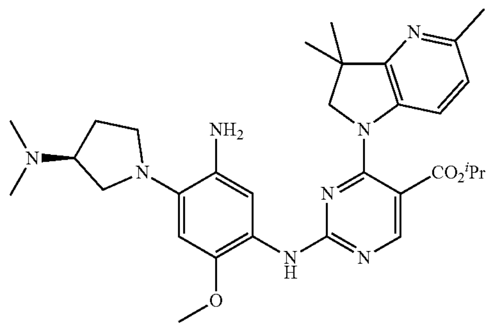 | isopropyl (S)-2-((5-amino-4-(3-(dimethyl-amino)pyrrolidin-1-yl)-2-methoxy-phenyl)amino)-4-(3,3,5-trimethyl-2,3-dihydro-1H-pyrrolo [3,2-b]pyridin-1-yl)pyrimidine-5-carboxylate | 575.3 |
| F31 | 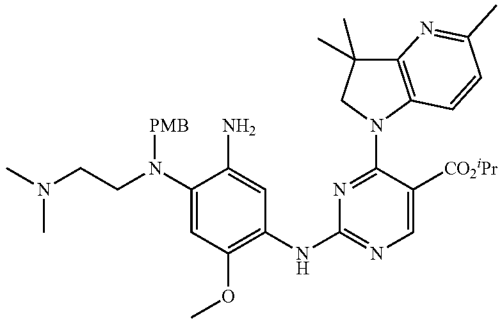 | isopropyl 2-((5-amino-4-((2-(dimethylamino) ethyl)(4-methoxybenzyl) amino)-2-methoxyphenyl)amino)-4-(3,3,5-trimethyl-2,3-dihydro-1H-pyrrolo[3,2-b]pyridin-1-yl) pyrimidine-5-carboxylate | 669.4 |

-continued

| Intermediate No. | Structure | Chemical name | ESI-MS: $[M + 1]^+$ |
|---|---|---|---|
| F32 | 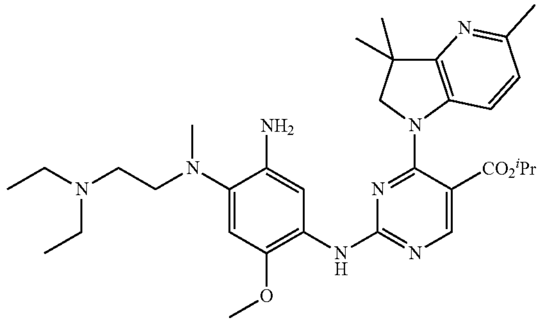 | isopropyl 2-((5-amino-4-((2-(diethylamino) ethyl)(methyl)amino)-2-methoxyphenyl)amino)-4-(3,3,5-trimethyl-2,3-dihydro-1H-pyrrolo [3,2-b]pyridin-1-yl)pyrimidine-5-carboxylate | 591.3 |
| F33 | 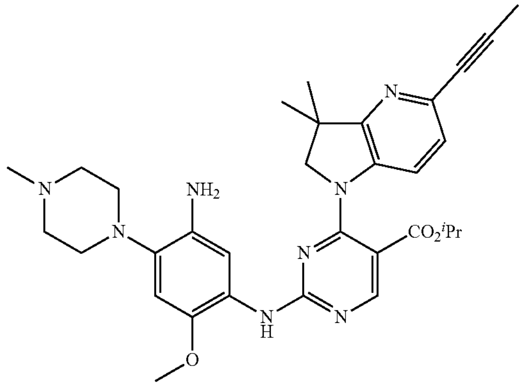 | isopropyl 2-((5-amino-2-methoxy-4-(4-methylpiperazin-1-yl)phenyl) amino)-4-(3,3-dimethyl-5-(prop-1-yn-1-yl)-2,3-dihydro-1H-pyrrolo [3,2-b]pyridin-1-yl)pyrimidine-5-carboxylate | 585.3 |
| F34 | 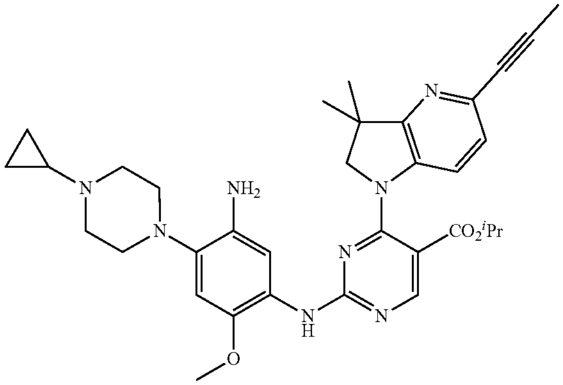 | isopropyl 2-((5-amino-4-(4-cyclopropyl-piperazin-1-yl)-2-methoxyphenyl) amino)-4-(3,3-dimethyl-5-(prop-1-yn-1-yl)-2,3-dihydro-1H-pyrrolo[3,2-b]pyridin-1-yl) pyrimidine-5-carboxylate | 611.4 |
| F35 | 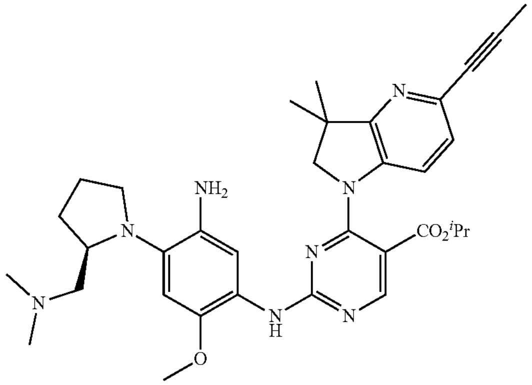 | isopropyl (R)-2-((5-amino-4-(2-((dimethyl-amino)methyl)pyrrolidin-1-yl)-2-methoxyphenyl)amino)-4-(3,3-dimethyl-5-(prop-1-yn-1-yl)-2,3-dihydro-1H-pyrrolo[3,2-b] pyridin-1-yl)pyrimidine-5-carboxylate | 613.4 |

-continued

| Intermediate No. | Structure | Chemical name | ESI-MS: $[M + 1]^+$ |
|---|---|---|---|
| F36 | 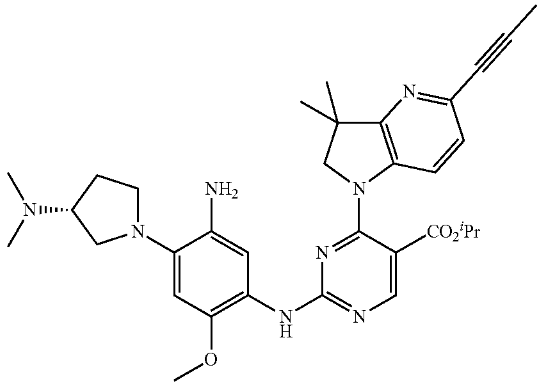 | isopropyl (R)-2-((5-amino-4-(3-(dimethyl-amino)pyrrolidin-1-yl)-2-methoxy-phenyl)amino)-4-(3,3-dimethyl-5-(prop-1-yn-1-yl)-2,3-dihydro-1H-pyrrolo[3,2-b]pyridin-1-yl) pyrimidine-5-carboxylate | 599.4 |
| F37 | 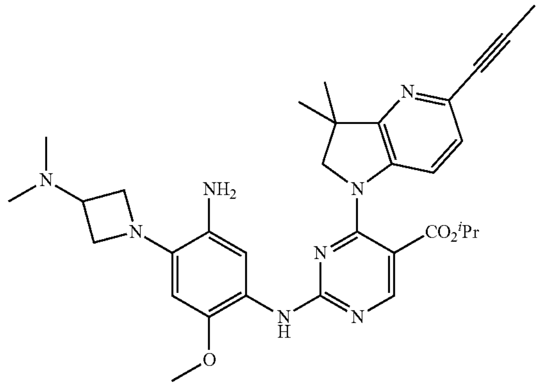 | isopropyl 2-((5-amino-4-(3-(dimethylamino) azetidin-1-yl)-2-methoxyphenyl) amino)-4-(3,3-dimethyl-5-(prop-1-yn-1-yl)-2,3-dihydro-1H-pyrrolo[3,2-b]pyridin-1-yl) pyrimidine-5-carboxylate | 585.4 |
| F38 | 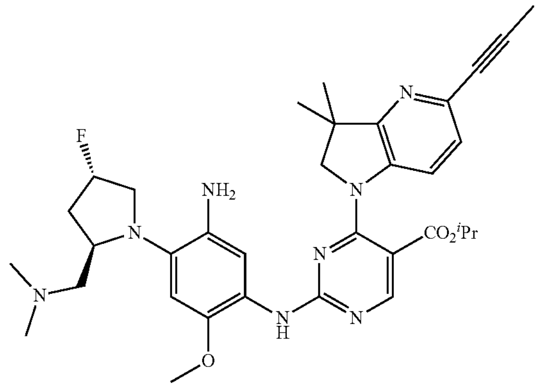 | isopropyl 2-((5-amino-4-((2R,4S)-2-((dimethylamino)methyl)-4-fluoro pyrrolidin-1-yl)-2-methoxyphenyl) amino)-4-(3,3-dimethyl-5-(prop-1-yn-1-yl)-2,3-dihydro-1H-pyrrolo [3,2-b]pyridin-1-yl)pyrimidine-5-carboxylate | 631.4 |
| F39 | 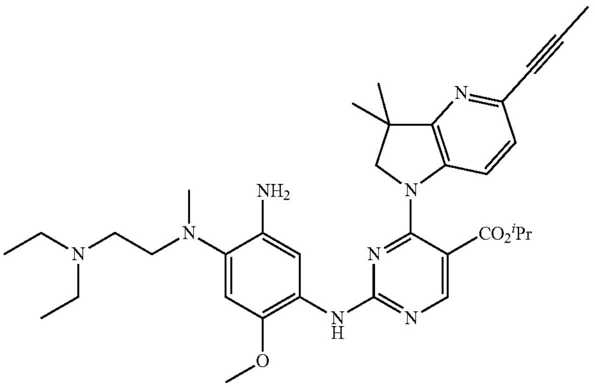 | isopropyl 2-((5-amino-4-((2-(diethylamino) ethyl)(methyl)amino)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 615.4 |

-continued

| Intermediate No. | Structure | Chemical name | ESI-MS: [M + 1]+ |
| --- | --- | --- | --- |
| F40 | 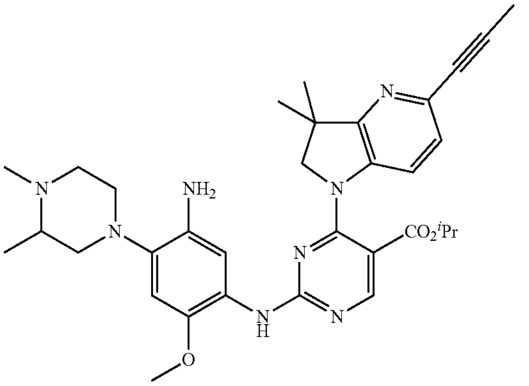 | isopropyl 2-((5-amino-4-(3,4-dimethyl-piperazin-1-yl)-2-methoxyphenyl) amino)-4-(3,3-dimethyl-5-(prop-1-yn-1-yl)-2,3-dihydro-1H-pyrrolo[3,2-b]pyridin-1-yl) pyrimidine-5-carboxylate | 599.3 |
| F41 | 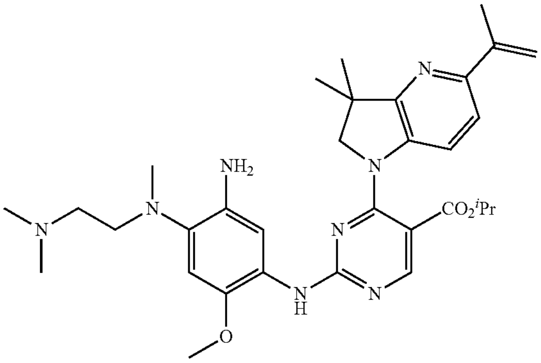 | isopropyl 2-((5-amino-4-((2-(dimethylamino) ethyl)(methyl)amino)-2-methoxyphenyl)amino)-4-(3,3-dimethyl-5-(prop-1-en-2-yl)-2,3-dihydro-1H-pyrrolo[3,2-b]pyridin-1-yl)pyrimidine-5-carboxylate | 589.5 |
| F42 | 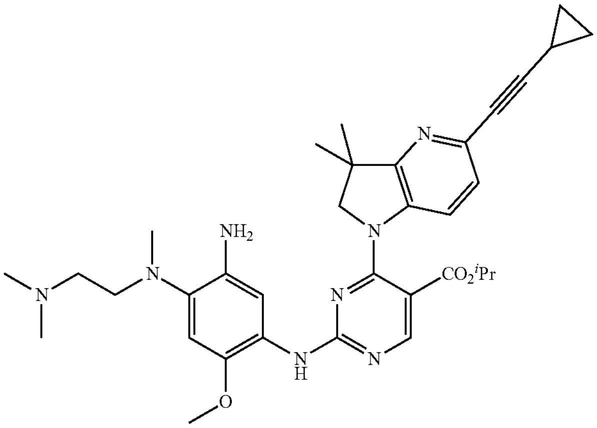 | isopropyl 2-((5-amino-4-((2-(dimethylamino) ethyl)(methyl)amino)-2-methoxyphenyl)amino)-4-(5-(cyclopropylethynl)-3,3-dimethyl-2,3-dihydro-1H-pyrrolo[3,2-b] pyridin-1-yl)pyrimidine-5-carboxylate | 613.2 |

-continued

| Intermediate No. | Structure | Chemical name | ESI-MS: $[M + 1]^+$ |
|---|---|---|---|
| F43 | 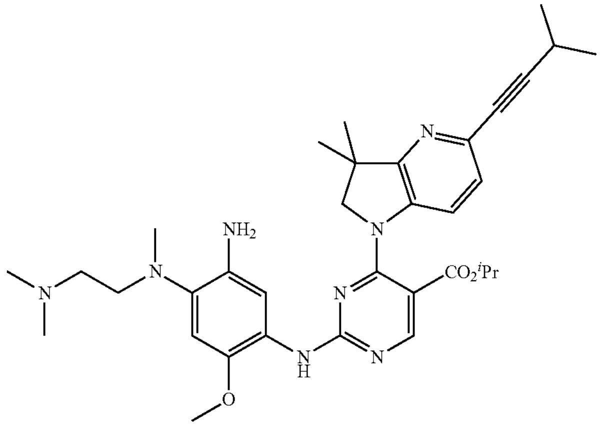 | isopropyl 2-((5-amino-4-((2-(dimethylamino) ethyl)(methyl)amino)-2-methoxyphenyl)amino)-4-(3,3-dimethyl-5-(3-methylbut-1-yn-1-yl)-2,3-dihydro-1H-pyrrolo[3,2-b] pyridin-1-yl)pyrimidine-5-carboxylate | 615.4 |
| F44 | 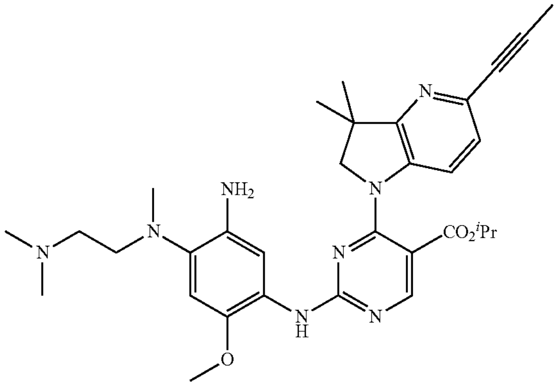 | isopropyl 2-((5-amino-4-((2-(dimethylamino) ethyl)(methyl)amino)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 587.3 |
| F45 | 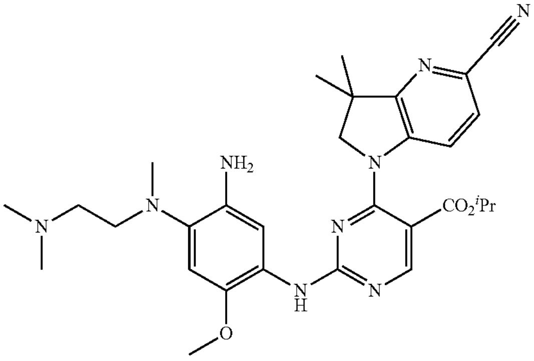 | isopropyl 2-((5-amino-4-((2-(dimethylamino) ethyl)(methyl)amino)-2-methoxyphenyl)amino)-4-(5-cyano-3,3-dimethyl-2,3-dihydro-1H-pyrrolo[3,2-b]pyridin-1-yl) pyrimidine-5-carboxylate | 574.2 |
| F46 | 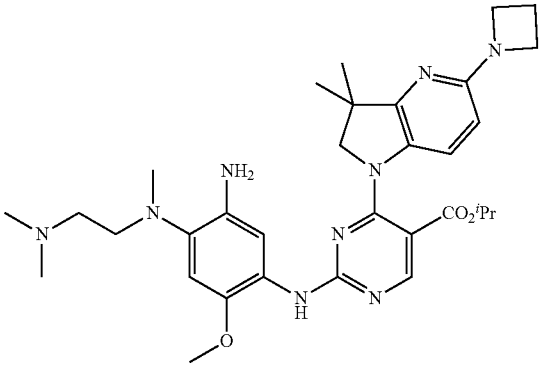 | isopropyl 2-((5-amino-4-((2-(dimethylamino) ethyl)(methyl)amino)-2-methoxyphenyl)amino)-4-(5-(azetidin-1-yl)-3,3-dimethyl-2,3-dihydro-1H-pyrrolo[3,2-b]pyridin-1-yl)pyrimidine-5-carboxylate | 604.3 |

-continued

| Intermediate No. | Structure | Chemical name | ESI-MS: $[M + 1]^+$ |
|---|---|---|---|
| F47 | 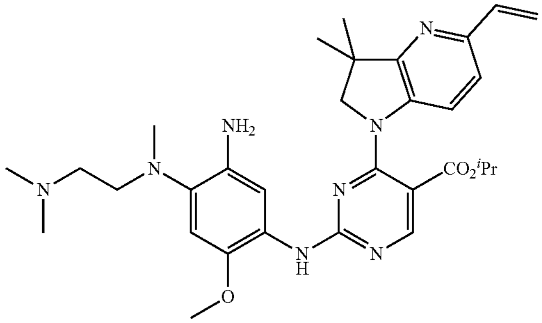 | isopropyl 2-((5-amino-4-((2-(dimethylamino) ethyl)(methyl)amino)-2-methoxyphenyl)amino)-4-(3,3-dimethyl-5-vinyl-2,3-dihydro-1H-pyrrolo[3,2-b]pyridin-1-yl) pyrimidine-5-carboxylate | 575.3 |
| F48 | 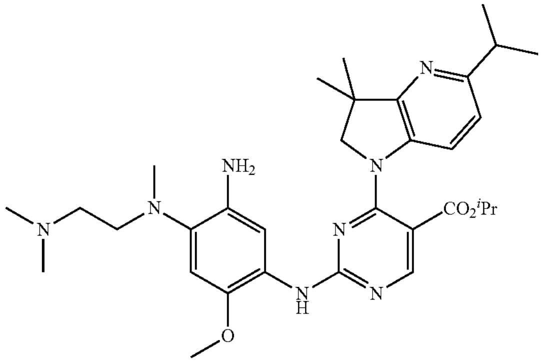 | isopropyl 2-((5-amino-4-((2-(dimethylamino) ethyl)(methyl)amino)-2-methoxyphenyl)amino)-4-(5-isopropyl-3,3-dimethyl-2,3-dihydro-1H-pyrrolo[3,2-b]pyridin-1-yl) pyrimidine-5-carboxylate | 591.4 |
| F49 | 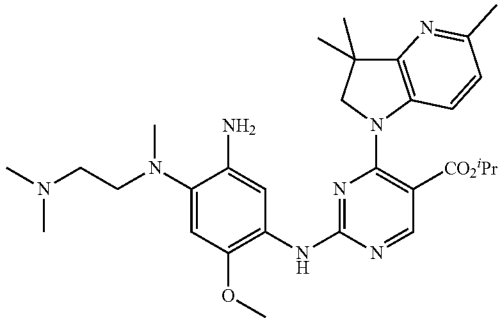 | isopropyl 2-((5-amino-6-((2-(dimethylamino) ethyl)(methyl)amino)-2-methoxypyridin-3-yl)amino)-4-(3,3,5-trimethyl-2,3-dihydro-1H-pyrrolo[3,2-b]pyridin-1-yl) pyrimidine-5-carboxylate | 564.2 |
| F50 | 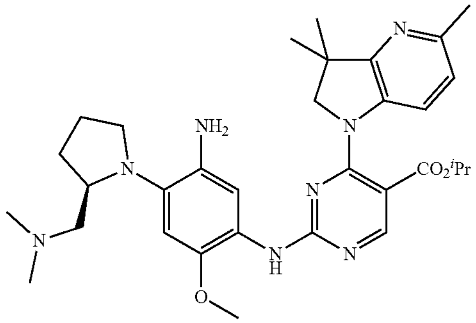 | isopropyl (R)-2-((5-amino-6-(2-((dimethyl-amino)methyl)pyrrolidin-1-yl)-2-methoxypyridin-3-yl)amino)-4-(3,3,5-trimethyl-2,3-dihydro-1H-pyrrolo[3,2-b]pyridin-1-yl)pyrimidine-5-carboxylate | 590.2 |

-continued

| Intermediate No. | Structure | Chemical name | ESI-MS: [M + 1]+ |
|---|---|---|---|
| F51 | 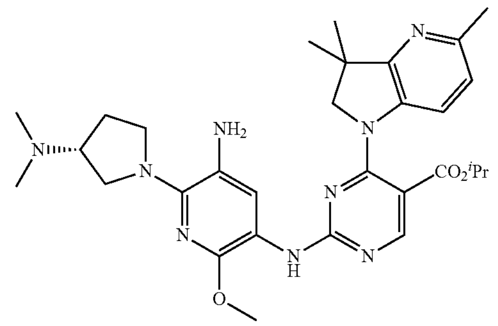 | isopropyl (R)-2-((5-amino-6-(3-(dimethyl-amino)pyrrolidin-1-yl)-2-methoxy-pyridin-3-yl)amino)-4-(3,3,5-trimethyl-2,3-dihydro-1H-pyrrolo[3,2-b]pyridin-1-yl) pyrimidine-5-carboxylate | 576.4 |
| F52 | 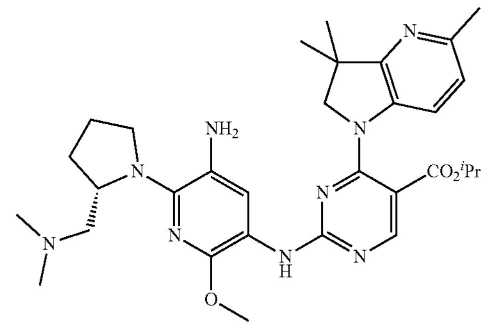 | isopropyl (S)-2-((5-amino-6-(2-((dimethyl-amino)methyl)pyrrolidin-1-yl)-2-methoxypyridin-3-yl)amino)-4-(3,3,5-trimethyl-2,3-dihydro-1H-pyrrolo[3,2-b]pyridin-1-yl) pyrimidine-5-carboxylate | 590.3 |
| F53 | 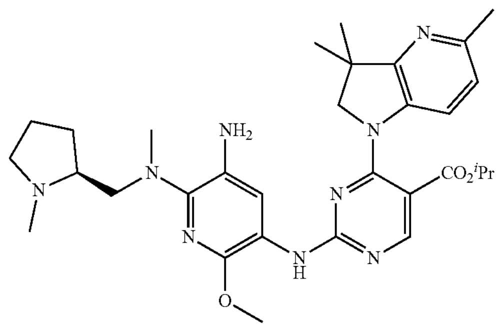 | isopropyl (S)-2-((5-amino-2-methoxy-6-(methyl((1-methylpyrrolidin-2-yl)methyl)amino)pyridin-3-yl) amino)-4-(3,3,5-trimethyl-2,3-dihydro-1H-pyrrolo[3,2-b] pyridin-1-yl)pyrimidine-5-carboxylate | 590.3 |
| F54 | 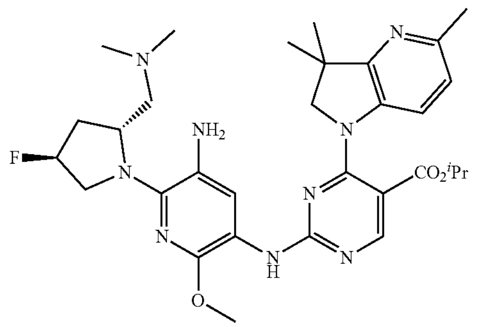 | isopropyl 2-((5-amino-6-((2R,4S)-2-((dimethylamino)methyl)-4-fluoro pyrrolidin-1-yl)-2-methoxy-pyridin-3-yl)amino)-4-(3,3,5-trimethyl-2,3-dihydro-1H-pyrrolo[3,2-b]pyridin-1-yl) pyrimidine-5-carboxylate | 608.4 |

-continued

| Intermediate No. | Structure | Chemical name | ESI-MS: [M + 1]+ |
|---|---|---|---|
| F55 | 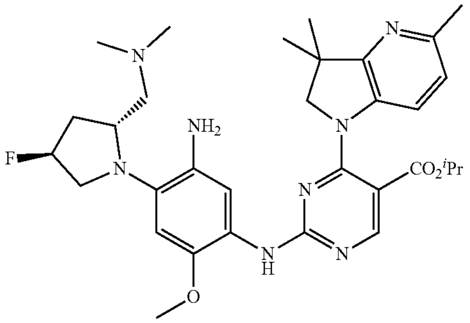 | isopropyl 2-((5-amino-4-((2R,4S)-2-((dimethylamino)methyl)-4-fluoro pyrrolidin-1-yl)-2-methoxyphenyl) amino)-4-(3,3,5-trimethyl-2,3-dihydro-1H-pyrrolo[3,2-b] pyridin-1-yl)pyrimidine-5-carboxylate | 607.4 |
| F56 | 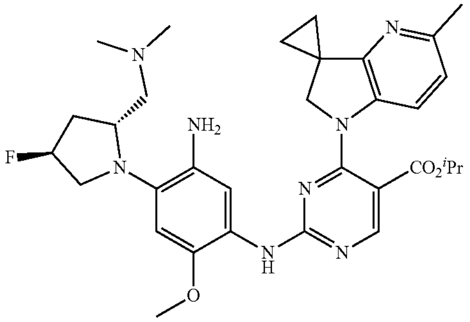 | isopropyl 2-((5-amino-4-((2R,4S)-2-((dimethylamino)methyl)-4-fluoro pyrrolidin-1-yl)-2-methoxyphenyl) amino)-4-(5'-methylspiro (cyclopropane-1,3'-pyrrolo[3,2-b] pyridin)-1'(2'H)-yl)pyrimidine-5-carboxylate | 605.4 |
| F57 | 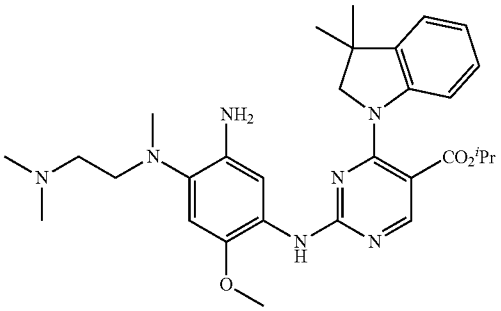 | isopropyl 2-((5-amino-4-((2-(dimethylamino) ethyl)(methyl)amino)-2-methoxyphenyl)amino)-4-(3,3-dimethylindolin-1-yl)pyrimidine-5-carboxylate | 548.3 |
| F58 | 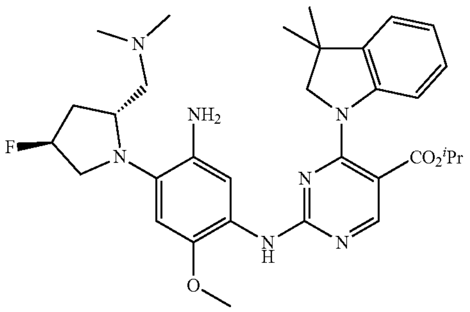 | isopropyl 2-((5-amino-4-((2R,4S)-2-((dimethylamino)methyl)-4-fluoro pyrrolidin-1-yl)-2-methoxyphenyl) amino)-4-(3,3-dimethylindolin-1-yl)pyrimidine-5-carboxylate | 592.4 |

-continued

| Intermediate No. | Structure | Chemical name | ESI-MS: [M + 1]+ |
|---|---|---|---|
| F59 | 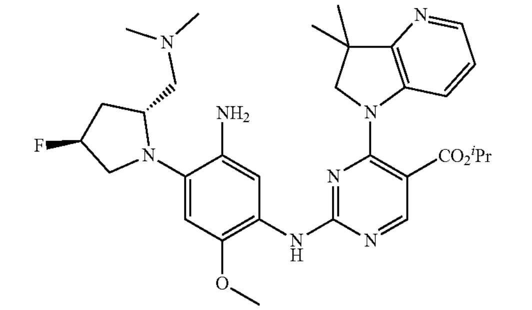 | isopropyl 2-((5-amino-4-((2R,4S)-2-((dimethylamino)methyl)-4-fluoro pyrrolidin-1-yl)-2-methoxyphenyl) amino)-4-(3,3-dimethyl-2,3-dihydro-1H-pyrrolo[3,2-b] pyridin-1-yl)pyrimidine-5-carboxylate | 593.4 |
| F60 | 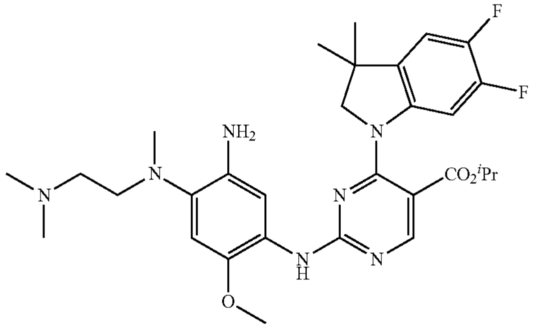 | isopropyl 2-((5-amino-4-((2-(dimethylamino) ethyl)(methyl)amino)-2-methoxy-phenyl)amino)-4-(5,6-difluoro-3,3-dimethylindolin-1-yl) pyrimidine-5-carboxylate | 584.4 |
| F61 | 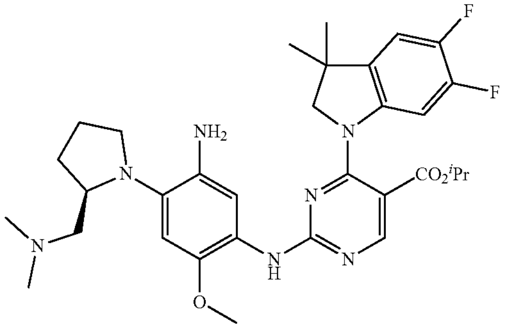 | isopropyl (R)-2-((5-amino-4-(2-((dimethyl-amino)methyl)pyrrolidin-1-yl)-2-methoxyphenyl)amino)-4-(5,6-difluoro-3,3-dimethylindolin-1-yl)pyrimidine-5-carboxylate | 610.4 |
| F62 | 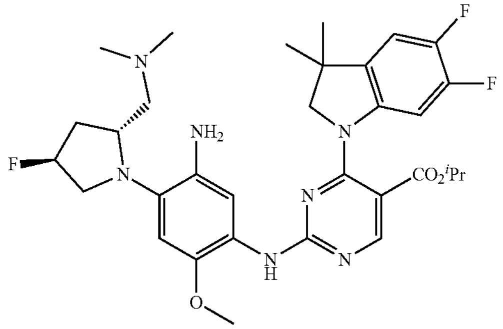 | isopropyl 2-((5-amino-4-((2R,4S)-2-((dimethylamino)methyl)-4-fluoro pyrrolidin-1-yl)-2-methoxyphenyl) amino)-4-(5,6-difluoro-3,3-dimethylindolin-1-yl)pyrimidine-5-carboxylate | 628.4 |

-continued

| Intermediate No. | Structure | Chemical name | ESI-MS: $[M + 1]^+$ |
|---|---|---|---|
| F63 | 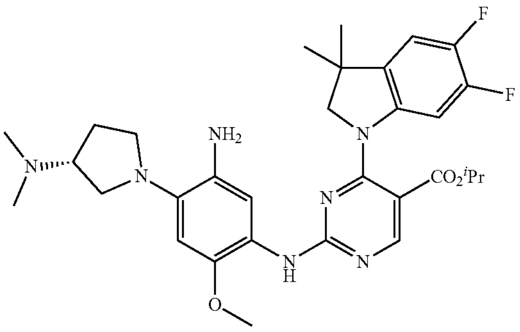 | isopropyl (R)-2-((5-amino-4-(3-(dimethyl-amino)pyrrolidin-1-yl)-2-methoxy-phenyl)amino)-4-(5,6-difluoro-3,3-dimethylindolin-1-yl) pyrimidine-5-carboxylate | 596.4 |
| F64 | 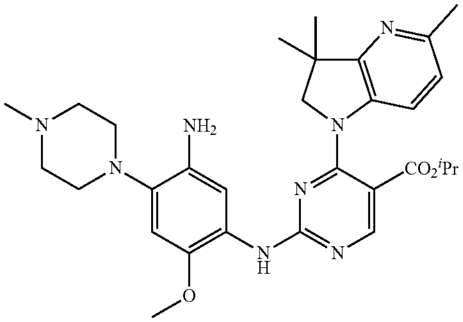 | isopropyl 2-((5-amino-2-methoxy-4-(4-methylpiperazin-1-yl)phenyl) amino)-4-(3,3,5-trimethyl-2,3-dihydro-1H-pyrrolo[3,2-b]pyridin-1-yl)pyrimidine-5-carboxylate | 561.2 |
| F65 | 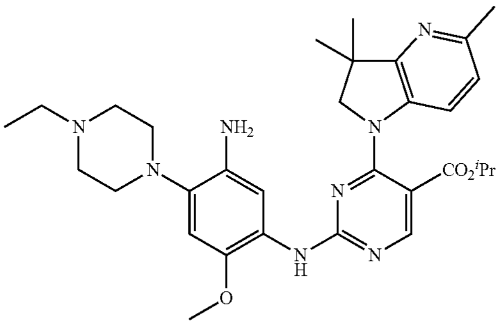 | isopropyl 2-((5-amino-4-(4-ethylpiperazin-1-yl)-2-methoxyphenyl)amino)-4-(3,3,5-trimethyl-2,3-dihydro-1H-pyrrolo[3,2-b]pyridin-1-yl) pyrimidine-5-carboxylate | 575.3 |
| F66 | 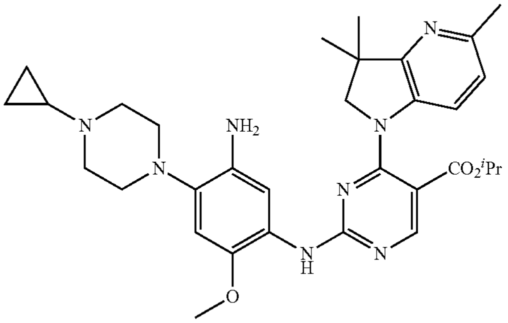 | isopropyl 2-((5-amino-4-(4-cyclopropyl-piperazin-1-yl)-2-methoxyphenyl) amino)-4-(3,3,5-trimethyl-2,3-dihydro-1H-pyrrolo[3,2-b] pyridin-1-yl)pyrimidine-5-carboxylate | 587.3 |

-continued

| Intermediate No. | Structure | Chemical name | ESI-MS: [M + 1]+ |
|---|---|---|---|
| F67 | 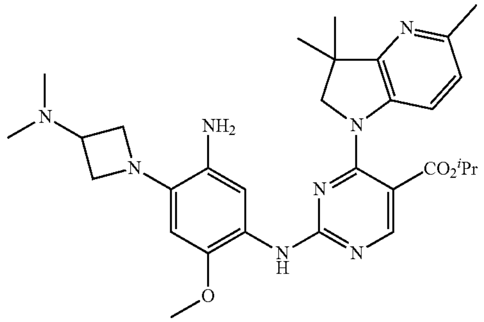 | isopropyl 2-((5-amino-4-(3-(dimethylamino) azetidin-1-yl)-2-methoxyphenyl) amino)-4-(3,3,5-trimethyl-2,3-dihydro-1H-pyrrolo[3,2-b] pyridin-1-yl)pyrimidine-5-carboxylate | 561.2 |
| F68 | 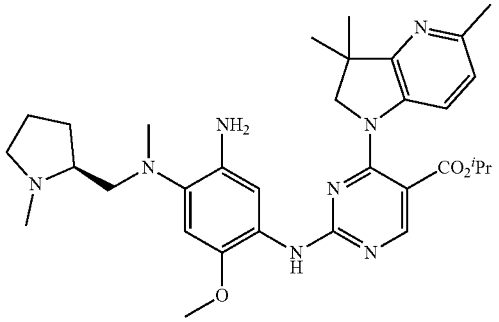 | isopropyl (S)-2-((5-amino-2-methoxy-4-(methyl((1-methylpyrrolidin-2-yl)methyl)amino)phenyl)amino)-4-(3,3,5-trimethyl-2,3-dihydro-1H-pyrrolo[3,2-b]pyridin-1-yl) pyrimidine-5-carboxylate | 589.4 |
| F69 | 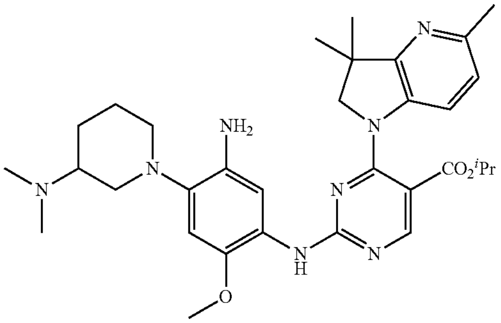 | isopropyl 2-((5-amino-4-(3-(dimethylamino) piperidin-1-yl)-2-methoxyphenyl) amino)-4-(3,3,5-trimethyl-2,3-dihydro-1H-pyrrolo[3,2-b] pyridin-1-yl)pyrimidine-5-carboxylate | 589.4 |
| F70 | 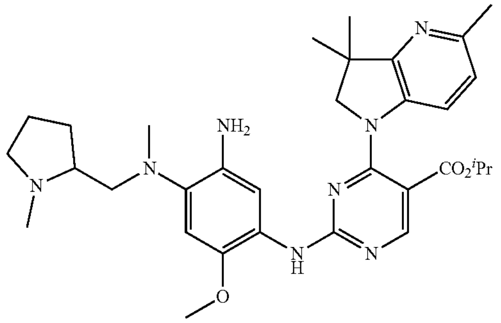 | isopropyl 2-((5-amino-2-methoxy-4-(methyl((1-methylpyrrolidin-2-yl)methyl)amino)phenyl)amino)-4-(3,3,5-trimethyl-2,3-dihydro-1H-pyrrolo[3,2-b]pyridin-1-yl) pyrimidine-5-carboxylate | 589.4 |

-continued

| Intermediate No. | Structure | Chemical name | ESI-MS: [M + 1]+ |
|---|---|---|---|
| F71 | 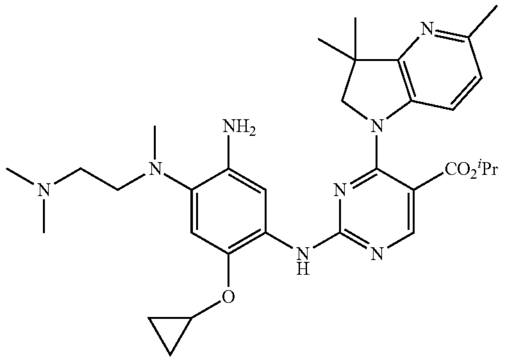 | isopropyl 2-((5-amino-2-cyclopropoxy-4-((2-(dimethylamino)ethyl)(methyl)amino)phenyl)amino)-4-(3,3,5-trimethyl-2,3-dihydro-1H-pyrrolo[3,2-b]pyridin-1-yl)pyrimidine-5-carboxylate | 589.4 |
| F72 | 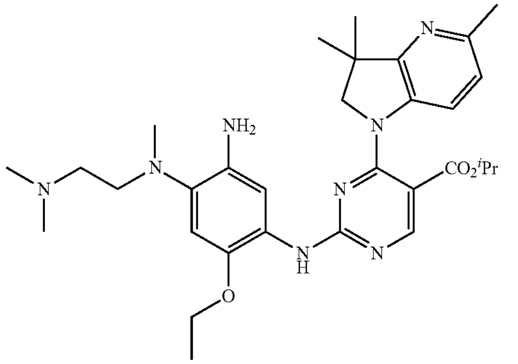 | isopropyl 2-((5-amino-4-((2-(dimethylamino)ethyl)(methyl)amino)-2-ethoxyphenyl)amino)-4-(3,3,5-trimethyl-2,3-dihydro-1H-pyrrolo[3,2-b]pyridin-1-yl)pyrimidine-5-carboxylate | 577.3 |
| F73 | 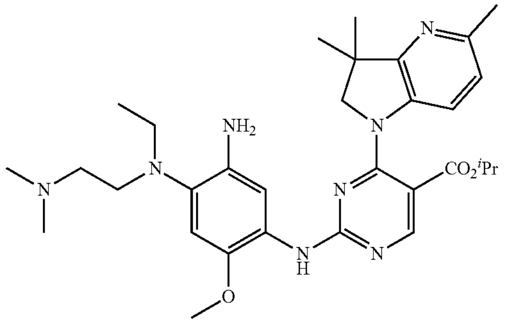 | isopropyl 2-((5-amino-4-((2-(dimethylamino)ethyl)(ethyl)amino)-2-methoxyphenyl)amino)-4-(3,3,5-trimethyl-2,3-dihydro-1H-pyrrolo[3,2-b]pyridin-1-yl)pyrimidine-5-carboxylate | 577.4 |
| F74 | 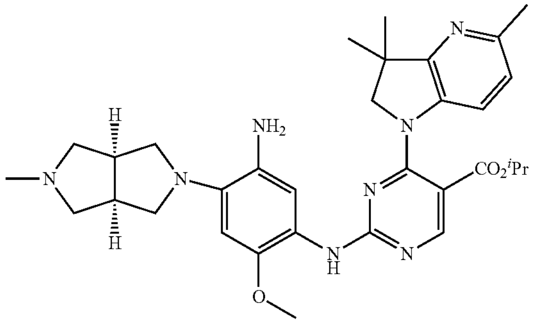 | isopropyl 2-((5-amino-2-methoxy-4-((3aR,6aS)-5-methylhexahydropyrrolo[3,4-c]pyrrol-2(1H)-yl)phenyl)amino)-4-(3,3,5-trimethyl-2,3-dihydro-1H-pyrrolo[3,2-b]pyridin-1-yl)pyrimidine-5-carboxylate | 587.4 |

-continued

| Intermediate No. | Structure | Chemical name | ESI-MS: [M + 1]+ |
|---|---|---|---|
| F75 | 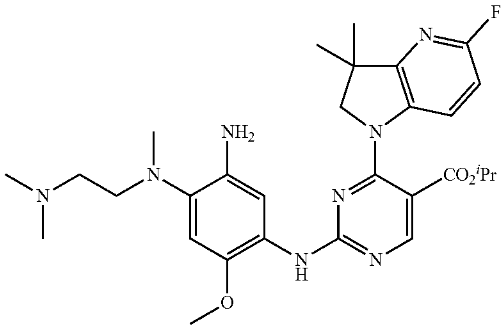 | isopropyl 2-((5-amino-4-((2-(dimethylamino) ethyl)(methyl)amino)-2-methoxyphenyl)amino)-4-(5-fluoro-3,3-dimethyl-2,3-dihydro-1H-pyrrolo[3,2-b]pyridin-1-yl) pyrimidine-5-carboxylate | 567.2 |
| F76 | 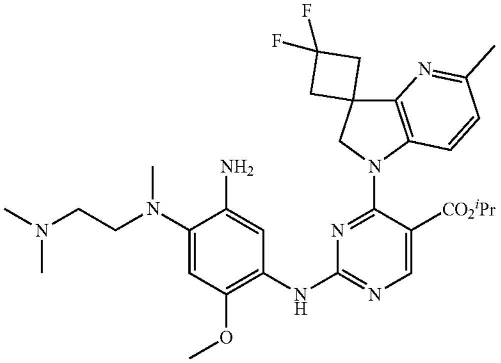 | isopropyl 2-((5-amino-4-((2-(dimethylamino) ethyl)(methyl)amino)-2-methoxyphenyl)amino)-4-(3,3-difluoro-5'-methylspiro(cyclobutane-1,3'-pyrrolo[3,2-b]pyridin)-1'(2'H)-yl)pyrimidine-5-carboxylate | 611.3 |
| F77 | 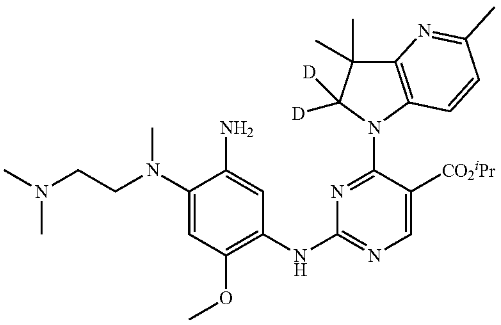 | isopropyl 2-((5-amino-4-((2-(dimethylamino) ethyl)(methyl)amino)-2-methoxyphenyl)amino)-4-(3,3,5-trimethyl-2,3-dihydro-1H-pyrrolo [3,2-b]pyridin-1-yl-2,2-$d_2$) pyrimidine-5-carboxylate | 565.4 |
| F78 | 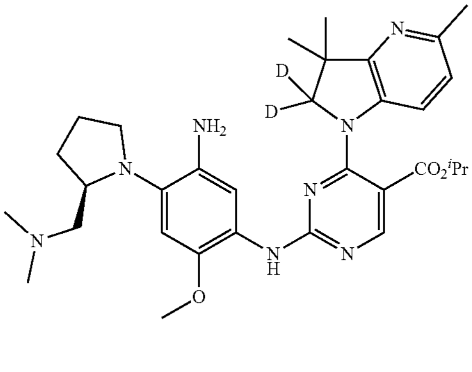 | isopropyl (R)-2-((5-amino-4-(2-((dimethyl-amino)methyl)pyrrolidin-1-yl)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 591.4 |

-continued

| Intermediate No. | Structure | Chemical name | ESI-MS: $[M + 1]^+$ |
|---|---|---|---|
| F79 | 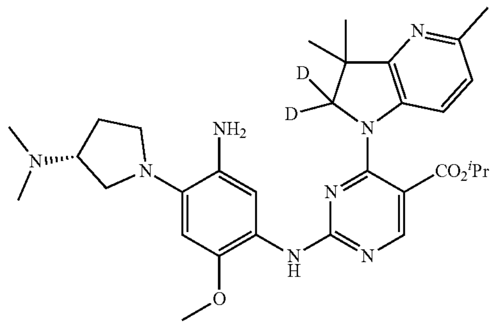 | isopropyl (R)-2-((5-amino-4-(3-(dimethyl-amino)pyrrolidin-1-yl)-2-methoxy-phenyl)amino)-4-(3,3,5-trimethyl-2,3-dihydro-1H-pyrrolo[3,2-b] pyridin-1-yl-2,2-$d_2$)pyrimidine-5-carboxylate | 577.3 |
| F80 | 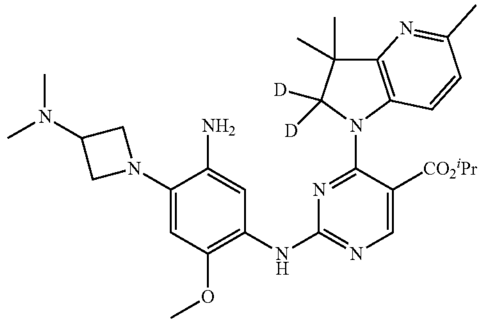 | isopropyl 2-((5-amino-4-(3-(dimethylamino) azetidin-1-yl)-2-methoxyphenyl) amino)-4-(3,3,5-trimethyl-2,3-dihydro-1H-pyrrolo[3,2-b] pyridin-1-yl-2,2-$d_2$)pyrimidine-5-carboxylate | 563.2 |
| F81 | 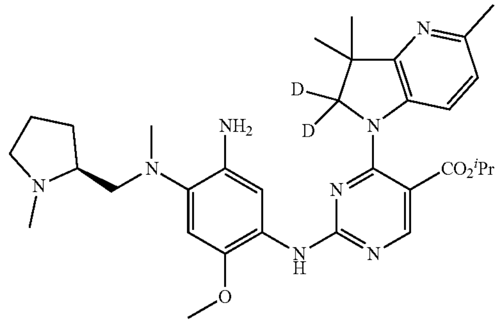 | isopropyl (S)-2-((5-amino-2-methoxy-4-(methyl((1-methylpyrrolidin-2-yl) methyl)amino)phenyl)amino)-4-(3,3,5-trimethyl-2,3-dihydro-1H-pyrrolo[3,2-b]pyridin-1-yl-2,2-$d_2$) pyrimidine-5-carboxylate | 591.4 |
| F82 | 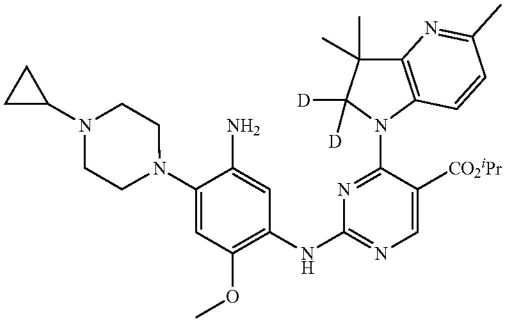 | isopropyl 2-((5-amino-4-(4-cyclopropyl-piperazin-1-yl)-2-methoxyphenyl) amino)-4-(3,3,5-trimethyl-2,3-dihydro-1H-pyrrolo[3,2-b]pyridin-1-yl-2,2-$d_2$)pyrimidine-5-carboxylate | 589.4 |

-continued

| Intermediate No. | Structure | Chemical name | ESI-MS: $[M + 1]^+$ |
|---|---|---|---|
| F83 | 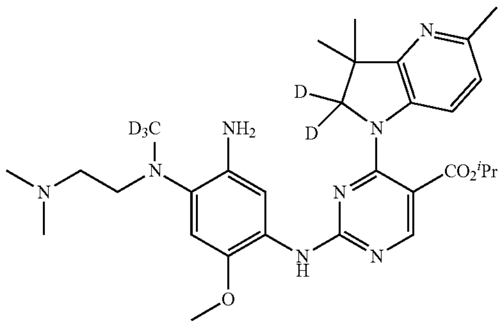 | isopropyl 2-((5-amino-4-((2-(dimethylamino) ethyl)(methyl-$d_3$)amino)-2-methoxyphenyl)amino)-4-(3,3,5-trimethyl-2,3-dihydro-1H-pyrrolo[3,2-b]pyridin-1-yl-2,2-$d_2$) pyrimidine-5-carboxylate | 568.4 |
| F84 | 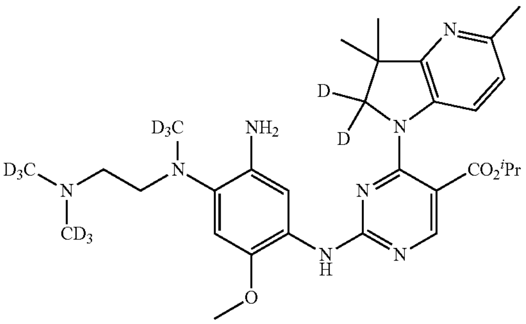 | isopropyl 2-((5-amino-4-((2-(bis(methyl-$d_3$)amino)ethyl)(methyl-$d_3$) amino)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 574.4 |
| F85 | 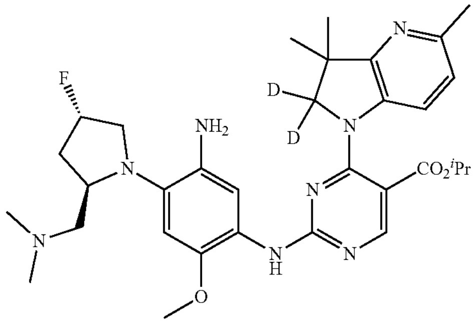 | isopropyl 2-((5-amino-4-((2R,4S)-2-((dimethylamino)methyl)-4-fluoro pyrrolidin-1-yl)-2-methoxyphenyl) amino)-4-(3,3,5-trimethyl-2,3-dihydro-1H-pyrrolo[3,2-b]pyridin-1-yl-2,2-$d_2$)pyrimidine-5-carboxylate | 609.4 |
| F86 | 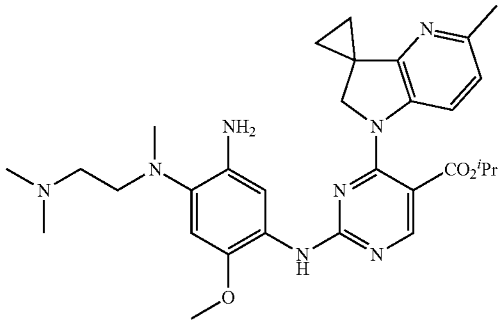 | isopropyl 2-((5-amino-4-((2-(dimethylamino) ethyl)(methyl)amino)-2-methoxyphenyl)amino)-4-(5'-methylspiro(cyclopropane-1,3'-pyrrolo[3,2-b]pyridin)-1'(2'H)-yl) pyrimidine-5-carboxylate | 561.2 |

-continued

| Intermediate No. | Structure | Chemical name | ESI-MS: $[M + 1]^+$ |
|---|---|---|---|
| F87 | 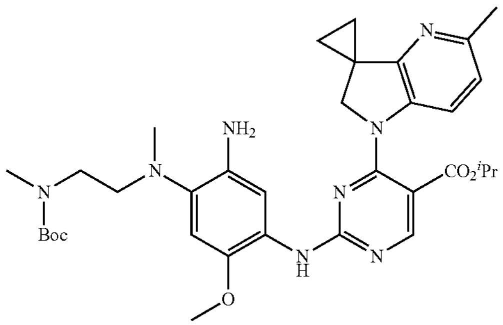 | isopropyl 2-((5-amino-4-((2-((tert-butoxy-carbonyl)(methyl)amino)ethyl)(methyl)amino)-2-methoxyphenyl)amino)-4-(5'-methylspiro(cyclo-propane-1,3'-pyrrolo[3,2-b]pyridin)-1'(2'H)-yl)pyrimidine-5-carboxylate | 647.2 |
| F88 | 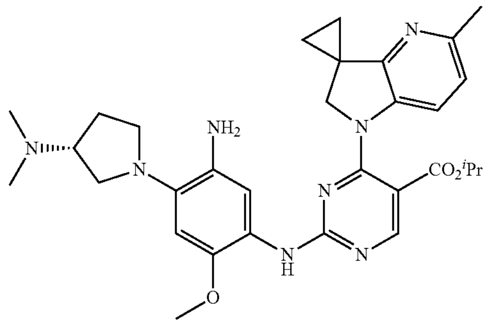 | isopropyl (R)-2-((5-amino-4-(3-(dimethyl-amino)pyrrolidin-1-yl)-2-methoxyphenyl)amino)-4-(5'-methylspiro(cyclopropane-1,3'-pyrrolo[3,2-b]pyridin)-1'(2'H)-yl)pyrimidine-5-carboxylate | 573.2 |
| F89 | 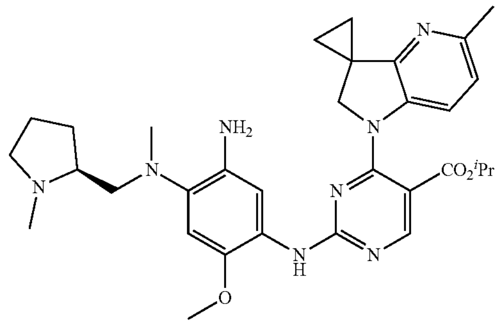 | isopropyl (S)-2-((5-amino-2-methoxy-4-(methyl((1-methylpyrrolidin-2-yl)methyl)amino)phenyl)amino)-4-(5'-methylspiro(cyclopropane-1,3'-pyrrolo[3,2-b]pyridin)-1'(2'H)-yl)pyrimidine-5-carboxylate | 587.2 |
| F90 | 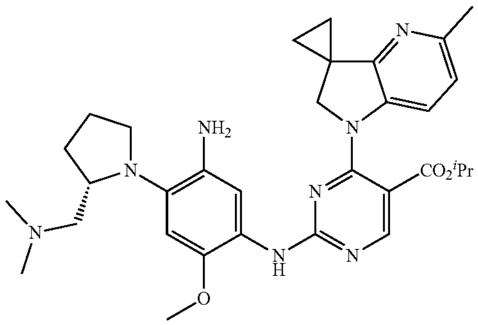 | isopropyl (S)-2-((5-amino-4-(2-((dimethyl-amino)methyl)pyrrolidin-1-yl)-2-methoxyphenyl)amino)-4-(5'-methylspiro(cyclopropane-1,3'-pyrrolo[3,2-b]pyridin)-1'(2'H)-yl)pyrimidine-5-carboxylate | 587.2 |

-continued

| Intermediate No. | Structure | Chemical name | ESI-MS: $[M+1]^+$ |
|---|---|---|---|
| F91 | 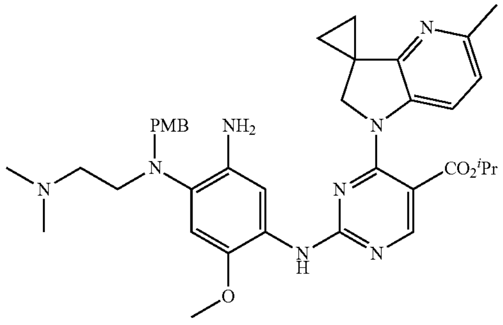 | isopropyl 2-((5-amino-4-((2-(dimethylamino) ethyl)(4-methoxybenzyl) amino)-2-methoxyphenyl)amino)-4-(5'-methylspiro(cyclopropane-1,3'-pyrrolo[3,2-b]pyridin)-1'(2'H)-yl)pyrimidine-5-carboxylate | 667.4 |
| F92 | 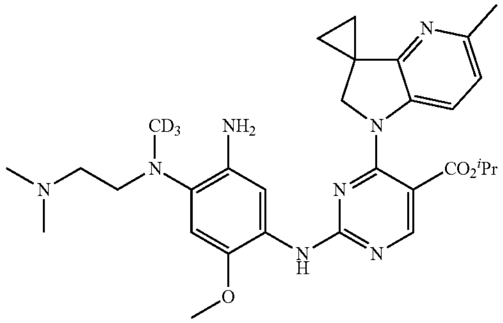 | isopropyl 2-((5-amino-4-((2-(dimethylamino) ethyl)(methyl-$d_3$)amino)-2-methoxyphenyl)amino)-4-(5'-methylspiro(cyclopropane-1,3'-pyrrolo[3,2-b]pyridin)-1'(2'H)-yl)pyrimidine-5-carboxylate | 564.4 |
| F93 | 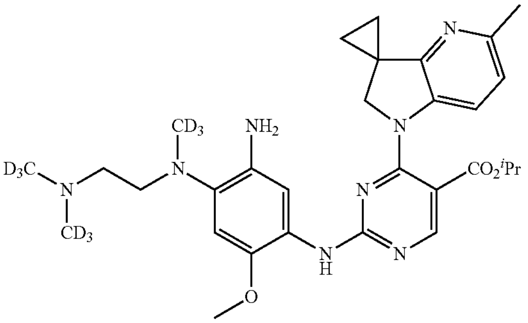 | isopropyl 2-((5-amino-4-((2-(bis(methyl-$d_3$)amino)ethyl)(methyl-$d_3$) amino)-2-methoxyphenyl)amino)-4-(5'-methylspiro(cyclopropane-1,3'-pyrrolo[3,2-b]pyridin)-1'(2'H)-yl)pyrimidine-5-carboxylate | 570.4 |

Preparation of Intermediate G1: isopropyl 2-((5-acrylamido-4-((2-((tert-butoxycarbonyl)(methyl) amino)ethyl)(methyl)amino)-2-methoxyphenyl) amino)-4-(3,3,5-trimethyl-2,3-dihydro-1H-pyrrolo[3,2-b]pyridin-1-yl)pyrimidine-5-carboxylate

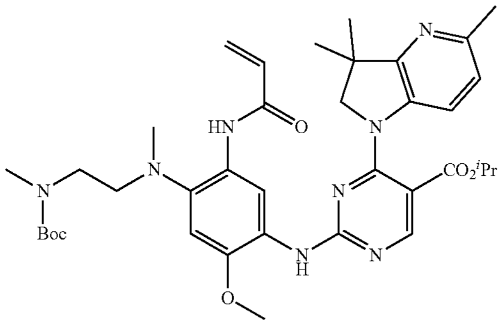

Isopropyl 2-((5-amino-4-((2-((tert-butoxycarbonyl) (methyl)amino)ethyl)(methyl) amino)-2-methoxyphenyl) amino)-4-(3,3,5-trimethyl-2,3-dihydro-1H-pyrrolo[3,2-b] pyridin-1-yl)pyrimidine-5-carboxylate (120 mg, 0.19 mmol) was dissolved in anhydrous acetonitrile/water (3 mL/1 mL). N,N-Diisopropylethylamine (71.7 mg, 0.56 mmol) was added to the solution. Acryloyl chloride (33.5 mg, 0.37 mmol) was added to the reaction mixture at 0° C. After the mixture was stirred for 30 min, dichloromethane and water were added, and then the mixture solution was separated. The organic phase was successively washed with water and saturated brine, then dried over anhydrous sodium sulfate, filtered, and concentrated, and then the residue was separated by reversed-phase column chromatography [40-50% acetonitrile/water] to obtain isopropyl 2-((5-acrylamido-4-((2-((tert-butoxycarbonyl)(methyl)amino)ethyl)(methyl) amino)-2-methoxyphenyl)amino)-4-(3,3,5-trimethyl-2,3-dihydro-1H-pyrrolo[3,2-b]pyridin-1-yl)pyrimidine-5-carboxylate (110 mg, yield: 64.3%). ESI-MS: 703.4 $[M+1]^+$.

Intermediates G2 to G5 were Prepared According to the Preparation Method for Intermediate G1:

| Intermediate No. | Structure | Chemical name | ESI-MS: [M + 1]+ |
|---|---|---|---|
| G2 | 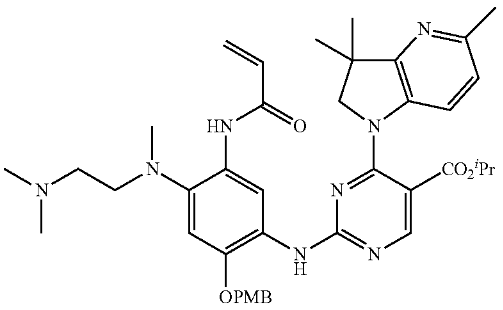 | isopropyl 2-((5-acrylamido-4-((2-(dimethylamino)ethyl)(methyl)amino)-2-((4-methoxybenzyl)oxy)phenyl)amino)-4-(3,3,5-trimethyl-2,3-dihydro-1H-pyrrolo[3,2-b]pyridin-1-yl)pyrimidine-5-carboxylate | 723.4 |
| G3 | 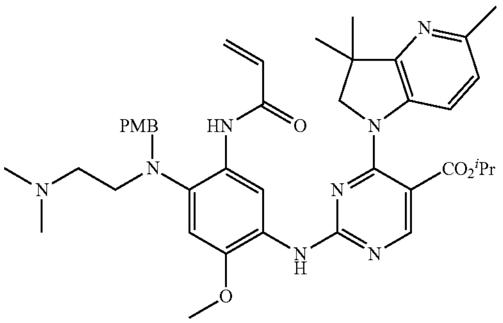 | isopropyl 2-((5-acrylamido-4-((2-(dimethylamino)ethyl)(4-methoxybenzyl)amino)-2-methoxyphenyl)amino)-4-(3,3,5-trimethyl-2,3-dihydro-1H-pyrrolo[3,2-b]pyridin-1-yl)pyrimidine-5-carboxylate | 723.4 |
| G4 | 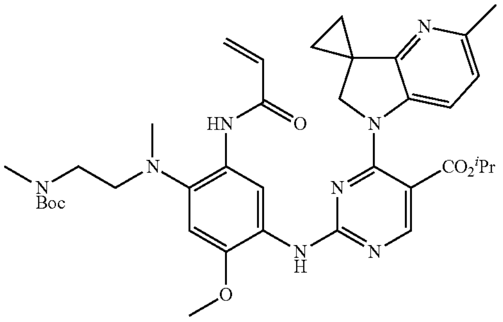 | isopropyl 2-((5-acrylamido-4-((2-((tert-butoxycarbonyl)(methyl)amino)ethyl)(methyl)amino)-2-methoxyphenyl)amino)-4-(5'-methylspiro(cyclopropane-1,3'-pyrrolo[3,2-b]pyridin)-1'(2'H)-yl)pyrimidine-5-carboxylate | 701.4 |
| G5 | 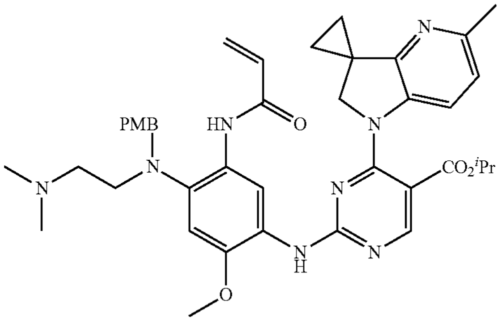 | isopropyl 2-((5-acrylamido-4-((2-(dimethylamino)ethyl)(4-methoxybenzyl)amino)-2-methoxyphenyl)amino)-4-(5'-methylspiro(cyclopropane-1,3'-pyrrolo[3,2-b]pyridin)-1'(2'H)-yl)pyrimidine-5-carboxylate | 721.4 |

II. PREPARATION OF SPECIFIC EXAMPLES

Example 1: Preparation of isopropyl 2-((5-acrylamido-4-((2-(dimethylamino)ethyl)(methyl)amino)-2-methoxyphenyl)amino)-4-(3,3,5-trimethyl-2,3-dihydro-1H-pyrrolo[3,2-b]pyridin-1-yl)pyrimidine-5-carboxylate

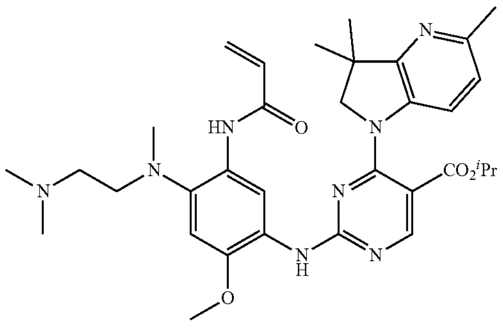

Isopropyl 2-((5-amino-4-((2-(dimethylamino)ethyl)(methyl)amino)-2-methoxyphenyl)amino)-4-(3,3,5-trimethyl-2,3-dihydro-1H-pyrrolo[3,2-b]pyridin-1-yl)pyrimidine-5-carboxylate (65 mg, 0.1 mmol, 1 eq.) was dissolved in acetonitrile/water (3 mL/1 mL). N,N-Diisopropylethylamine (20 mg, 0.15 mmol, 1.5 eq.) was added to the solution. Acryloyl chloride (12 mg, 0.13 mmol, 1.3 eq.) was added to the reaction mixture at 0° C. The reaction mixture was stirred at 0° C. for 10 min and concentrated, and then the residue was separated by reversed-phase column chromatography [40-50% acetonitrile/water] to obtain isopropyl 2-((5-acrylamido-4-((2-(dimethylamino)ethyl)(methyl)amino)-2-methoxyphenyl)amino)-4-(3,3,5-trimethyl-2,3-dihydro-1H-pyrrolo[3,2-b]pyridin-1-yl)pyrimidine-5-carboxylate (7.2 mg, yield: 11.2%). ESI-MS: 617.4$[M+1]^+$.

$^1H$ NMR (MeOH-$d_4$) δ 8.97 (s, 1H), 8.55 (s, 1H), 7.11 (d, J=8.2 Hz, 1H), 6.92-6.79 (nm, 2H), 6.53-6.39 (m, 1H), 6.26 (dd, J=17.0, 1.9 Hz, 1H), 5.70 (dd, J=10.1, 1.9 Hz, 1H), 4.98-4.81 (m, 1H), 3.94 (s, 2H), 3.83 (s, 3H), 2.95 (t, J=6.0 Hz, 2H), 2.59 (s, 3H), 2.37 (d, J=6.0 Hz, 5H), 2.20 (s, 6H), 1.31 (s, 6H), 1.05 (d, J=6.2 Hz, 6H).

The following examples were prepared according to the preparation method of Example 1. Among them, Examples 60 to 62 were obtained by chiral separation. Separation conditions were as follows: chiral column: IC column, column temperature: 40° C. mobile phase: n-hexane (0.1% diethylamine): ethanol (0.1% diethylamine)=50:50 or 60:40; flow rate: 1 mL per minute.

| Example No. | Structure | Chemical name | ESI-MS: $[M+1]^+$ |
|---|---|---|---|
| 2 | 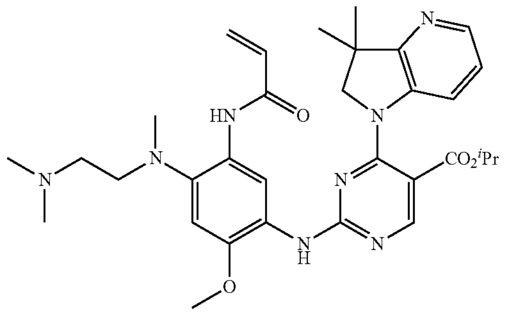 | isopropyl 2-((5-acrylamido-4-((2-(dimethylamino)ethyl)(methyl)amino)-2-methoxyphenyl)amino)-4-(3,3-dimethyl-2,3-dihydro-1H-pyrrolo[3,2-b]pyridin-1-yl)pyrimidine-5-carboxylate | 603.4 |
| 3 | 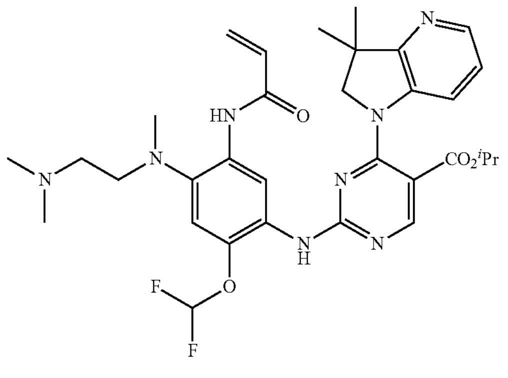 | isopropyl 2-((5-acrylamido-2-(difluoromethoxy)-4-((2-(dimethylamino)ethyl)(methyl)amino)phenyl)amino)-4-(3,3-dimethyl-2,3-dibydro-1H-pyrrolo[3,2-b]pyridin-1-yl)pyrimidine-5-carboxylate | 639.3 |

-continued

| Example No. | Structure | Chemical name | ESI-MS: $[M + 1]^+$ |
|---|---|---|---|
| 4 | 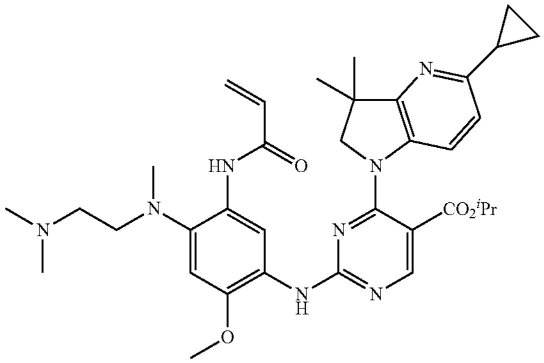 | isopropyl 2-((5-acrylamido-4-((2-(dimethylamino)ethyl)(methyl)amino)-2-methoxyphenyl)amino)-4-(5-cyclopropyl-3,3-dimethyl-2,3-dihydro-1H-pyrrolo[3,2-b]pyridin-1-yl)pyrimidine-5-carboxylate | 643.2 |
| 5 | 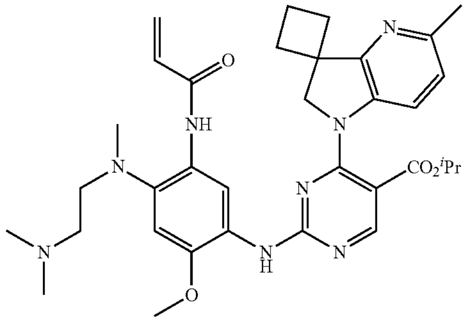 | isopropyl 2-((5-acrylamido-4-((2-(dimethylamino)ethyl)(methyl)amino)-2-methoxyphenyl)amino)-4-(5'-methylspiro(cyclobutane-1,3'-pyrrolo[3,2-b]pyridin)-1'(2'H)-yl)pyrimidine-5-carboxylate | 629.4 |
| 6 | 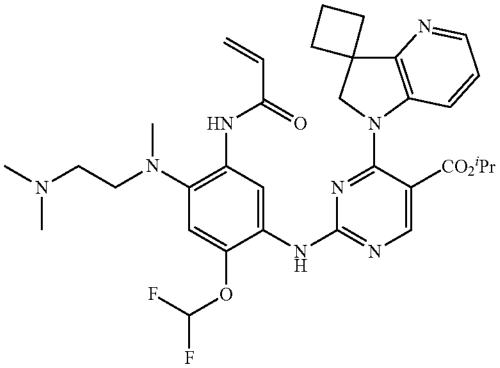 | isopropyl 2-((5-acrylamido-2-(difluoromethoxy)-4-((2-(dimethylamino)ethyl)(methyl)amino)phenyl)amino)-4-(spiro(cyclobutane-1,3'-pyrrolo[3,2-b]pyridin)-1'(2'H)-yl)pyrimidine-5-carboxylate | 651.4 |
| 7 | 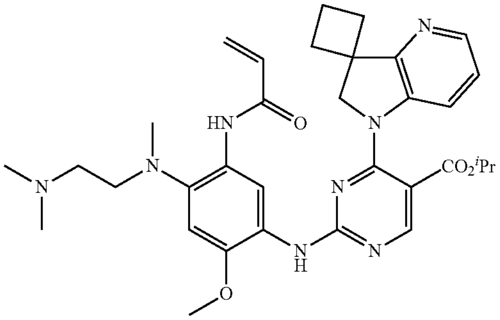 | isopropyl 2-((5-acrylamido-4-((2-(dimethylamino)ethyl)(methyl)amino)-2-methoxyphenyl)amino)-4-(spiro(cyclobutane-1,3'-pyrrolo[3,2-b]pyridin)-1'(2'H)-yl)pyrimidine-5-carboxylate | 615.4 |

-continued

| Example No. | Structure | Chemical name | ESI-MS: [M + 1]+ |
|---|---|---|---|
| 8 | 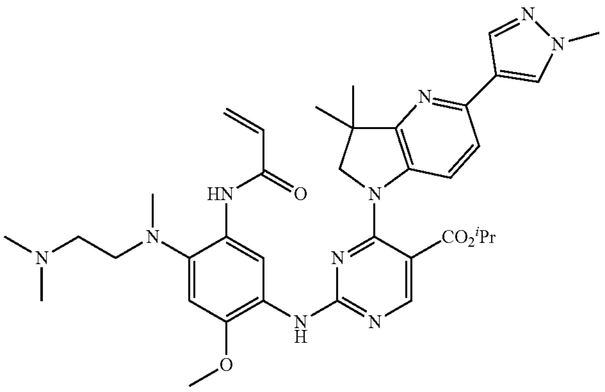 | isopropyl 2-((5-acrylamido-4-((2-(dimethylamino)ethyl)(methyl)amino)-2-methoxyphenyl)amino)-4-(3,3-dimethyl-5-(1-methyl-1H-pyrazol-4-yl)-2,3-dihydro-1H-pyrrolo[3,2-b]pyridin-1-yl)pyrimidine-5-carboxylate | 683.4 |
| 10 | 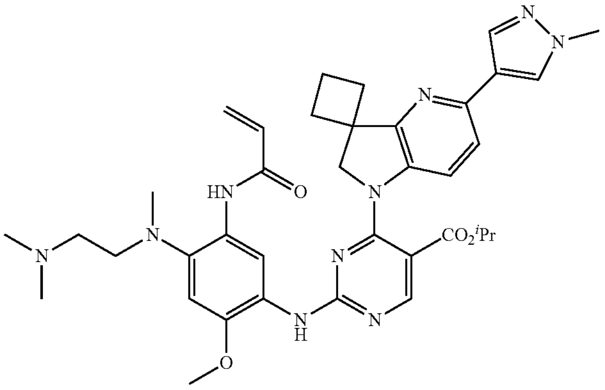 | isopropyl 2-((5-acrylamido-4-((2-(dimethylamino)ethyl)(methyl)amino)-2-methoxyphenyl)amino)-4-(5'-(1-methyl-1H-pyrazol-4-yl)spiro(cyclobutane-1,3'-pyrrolo[3,2-b]pyridin)-1'(2'H)-yl)pyrimidine-5-carboxylate | 695.4 |
| 11 | 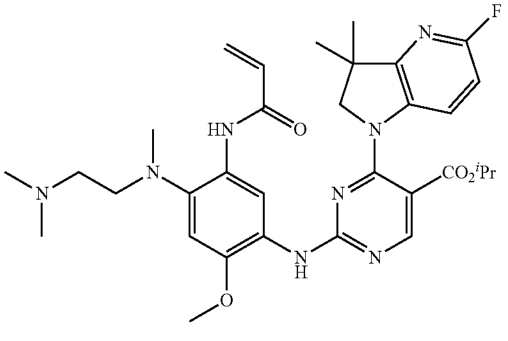 | isopropyl 2-((5-acrylamido-4-((2-(dimethylamino)ethyl)(methyl)amino)-2-methoxyphenyl)amino)-4-(5-fluoro-3,3-dimethyl-2,3-dihydro-1H-pyrrolo[3,2-b]pyridin-1-yl)pyrimidine-5-carboxylate | 621.3 |
| 12 | 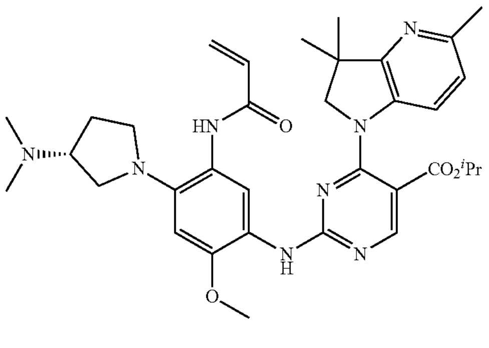 | isopropyl (R)-2-((5-acrylamido-4-(3-(dimethylamino)pyrrolidin-1-yl)-2-methoxyphenyl)amino)-4-(3,3,5-trimethyl-2,3-dihydro-1H-pyrrolo[3,2-b]pyridin-1-yl)pyrimidine-5-carboxylate | 629.4 |

-continued

| Example No. | Structure | Chemical name | ESI-MS: [M + 1]+ |
|---|---|---|---|
| 13 | 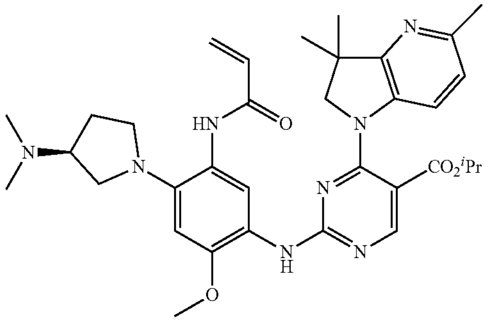 | isopropyl (S)-2-((5-acrylamido-4-(3-(dimethylamino)pyrrolidin-1-yl)-2-methoxyphenyl)amino)-4-(3,3,5-trimethyl-2,3-dihydro-1H-pyrrolo[3,2-b]pyridin-1-yl)pyrimidine-5-carboxylate | 629.4 |
| 14 | 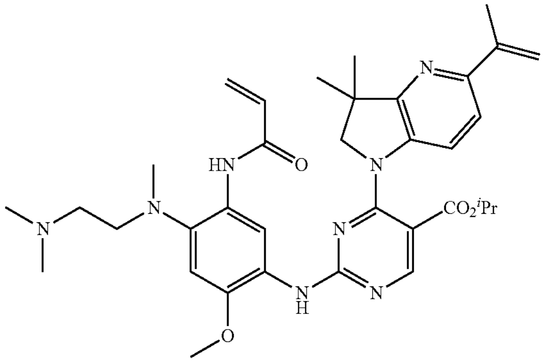 | isopropyl 2-((5-acrylamido-4-((2-(dimethylamino)ethyl)(methyl)amino)-2-methoxyphenyl)amino)-4-(3,3-dimethyl-5-(prop-1-en-2-yl)-2,3-dihydro-1H-pyrrolo[3,2-b]pyridin-1-yl)pyrimidine-5-carboxylate | 643.5 |
| 16 | 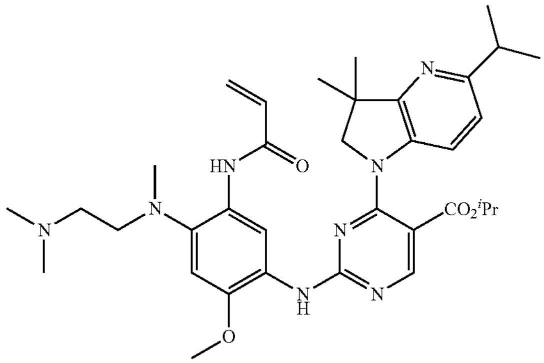 | isopropyl 2-((5-acrylamido-4-((2-(dimethylamino)ethyl)(methyl)amino)-2-methoxyphenyl)amino)-4-(5-isopropyl-3,3-dimethyl-2,3-dihydro-1H-pyrrolo[3,2-b]pyridin-1-yl)pyrimidine-5-carboxylate | 645.5 |
| 17 | 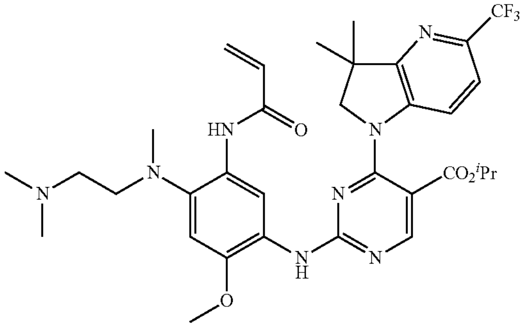 | isopropyl 2-((5-acrylamido-4-((2-(dimethylamino)ethyl)(methyl)amino)-2-methoxyphenyl)amino)-4-(3,3-dimethyl-5-(trifluoromethyl)-2,3-dibydro-1H-pyrrolo[3,2-b]pyridin-1-yl)pyrimidine-5-carboxylate | 671.3 |

-continued

| Example No. | Structure | Chemical name | ESI-MS: [M + 1]+ |
| --- | --- | --- | --- |
| 18 | 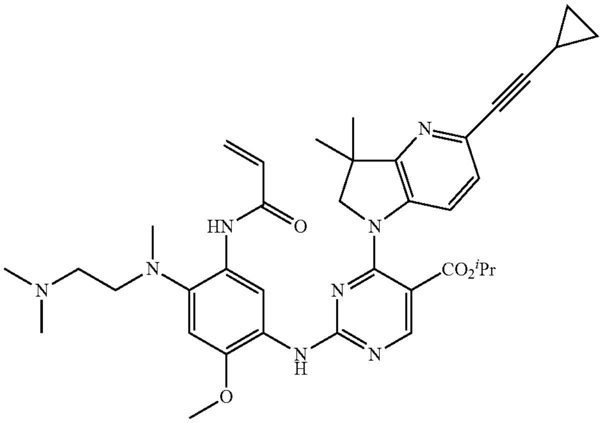 | isopropyl 2-((5-acrylamido-4-((2-(dimethylamino)ethyl)(methyl)amino)-2-methoxyphenyl)amino)-4-(5-(cyclopropylethynyl)-3,3-dimethyl-2,3-dihydro-1H-pyrrolo[3,2-b]pyridin-1-yl)pyrimidine-5-carboxylate | 667.3 |
| 19 | 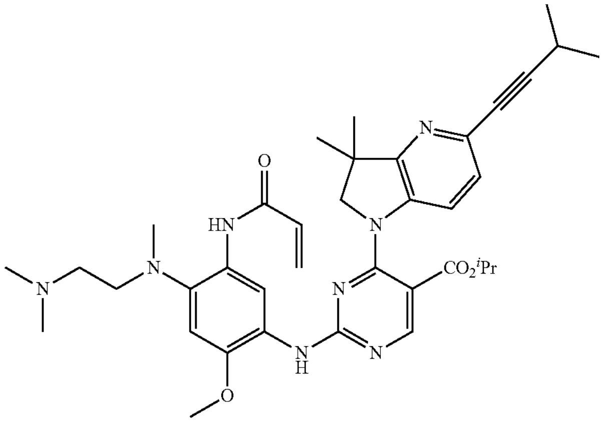 | isopropyl 2-((5-acrylamido-4-((2-(dimethylamino)ethyl)(methyl)amino)-2-methoxyphenyl)amino)-4-(3,3-dimethyl-5-(3-methylbut-1-yn-1-yl)-2,3-dihydro-1H-pyrrolo[3,2-b]pyridin-1-yl)pyrimidine-5-carboxylate | 669.5 |
| 20 | 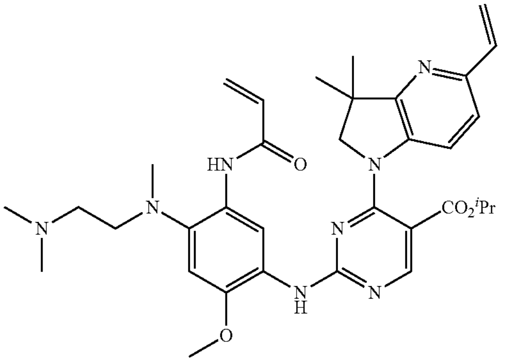 | isopropyl 2-((5-acrylamido-4-((2-(dimethylamino)ethyl)(methyl)amino)-2-methoxyphenyl)amino)-4-(3,3-dimethyl-5-vinyl-2,3-dihydro-1H-pyrrolo[3,2-b]pyridin-1-yl)pyrimidine-5-carboxylate | 629.3 |
| 21 | 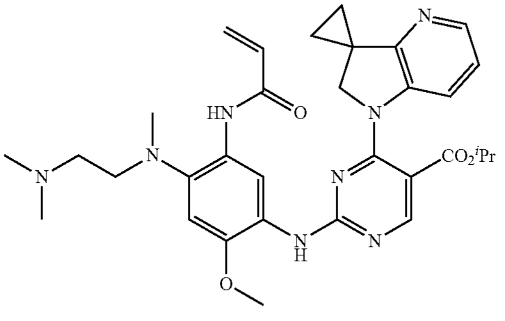 | isopropyl 2-((5-acrylamido-4-((2-(dimethylamino)ethyl)(methyl)amino)-2-methoxyphenyl)amino)-4-(spiro(cyclopropane-1,3'-pyrrolo[3,2-b]pyridin)-1'(2'H)-yl)pyrimidine-5-carboxylate | 601.3 |

-continued

| Example No. | Structure | Chemical name | ESI-MS: [M + 1]+ |
|---|---|---|---|
| 22 | 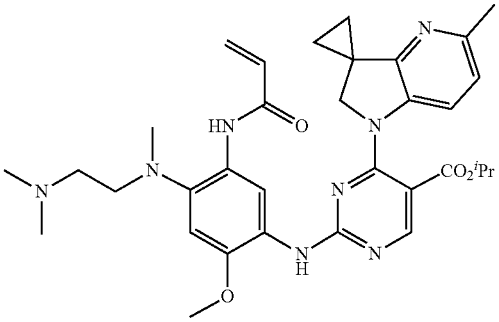 | isopropyl 2-((5-acrylamido-4-((2-(dimethylamino)ethyl)(methyl)amino)-2-methoxyphenyl)amino)-4-(5'-methy lspiro(cyclopropane-1,3'-pyrrolo[3,2-b]pyridin)-1'(2'H)-yl)pyrimidine-5-carboxylate | 615.2 |
| 23 | 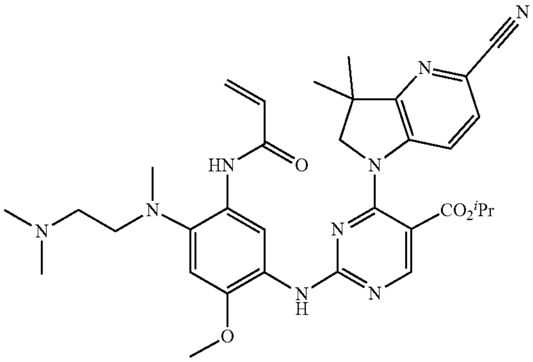 | isopropyl 2-((5-acrylamido-4-((2-(dimethylamino)ethyl)(methyl)amino)-2-methoxyphenyl)amino)-4-(5-cyano-3,3-dimethyl-2,3-dihydro-1H-pyrrolo[3,2-b]pyridin-1-yl)pyrimidine-5-carboxylate | 628.3 |
| 24 | 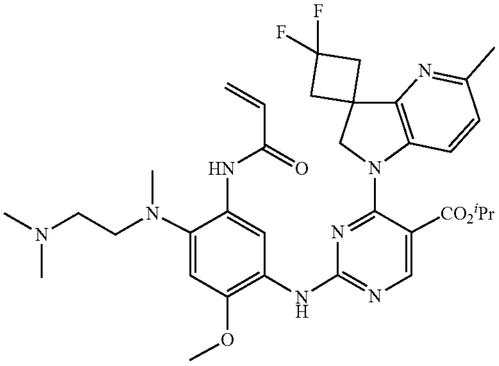 | isopropyl 2-((5-acrylamido-4-((2-(dimethylamino)ethyl)(methyl)amino)-2-methoxyphenyl)amino)-4-(3,3-difluoro-5'-methylspiro(cyclobutane-1,3'-pyrrolo[3,2-b]pyridin)-1'(2'H)-yl)pyrimidine-5-carboxylate | 665.4 |
| 26 | 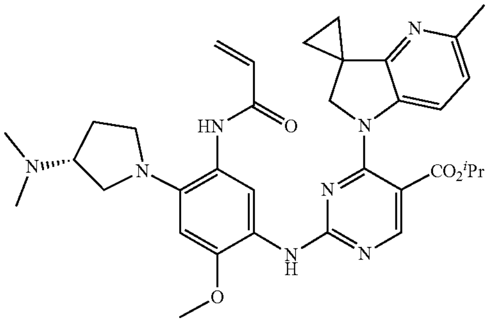 | isopropyl (R)-2-((5-acrylamido-4-(3-(dimethylamino)pyrrolidin-1-yl)-2-methoxyphenyl)amino)-4-(5'-methylspiro(cyclopropane-1,3'-pyrrolo[3,2-b]pyridin)-1'(2'H)-yl)pyrimidine-5-carboxylate | 627.4 |

-continued

| Example No. | Structure | Chemical name | ESI-MS: [M + 1]+ |
|---|---|---|---|
| 27 | 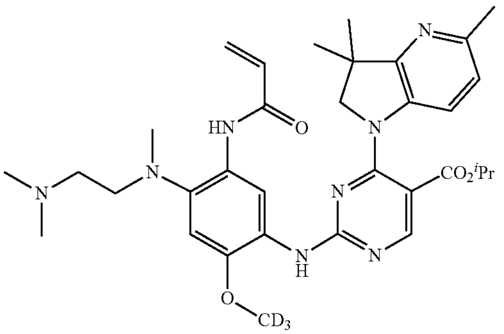 | isopropyl 2-((5-acrylamido-4-((2-(dimethylamino)ethyl)(methyl)amino)-2-(methoxy-$d_3$)phenyl)amino)-4-(3,3,5-trimethyl-2,3-dihydro-1H-pyrrolo[3,2-b]pyridin-1-yl)pyrimidine-5-carboxylate | 620.4 |
| 28 | 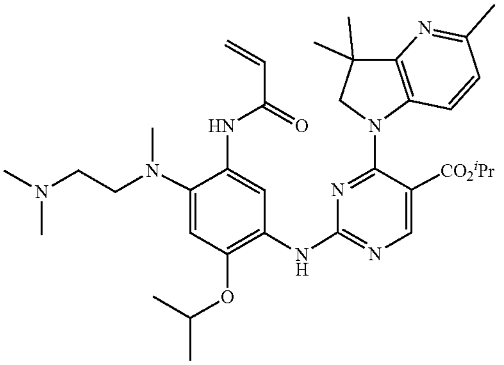 | isopropyl 2-((5-acrylamido-4-((2-(dimethylamino)ethyl)(methyl)amino)-2-isopropoxyphenyl)amino)-4-(3,3,5-trimethyl-2,3-dihydro-1H-pyrrolo[3,2-b]pyridin-1-yl)pyrimidine-5-carboxylate | 645.4 |
| 29 | 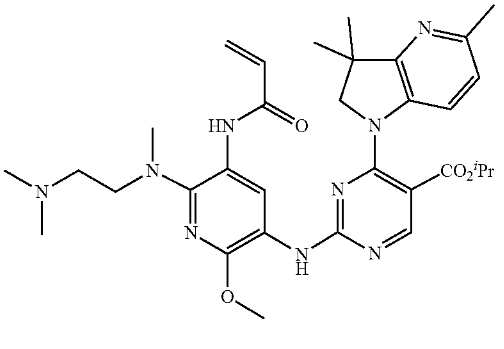 | isopropyl 2-((5-acrylamido-6-((2-(dimethylamino)ethyl)(methyl)amino)-2-methoxypyridin-3-yl)amino)-4-(3,3,5-trimethyl-2,3-dihydro-1H-pyrrolo[3,2-b]pyridin-1-yl)pyrimidine-5-carboxylate | 618.3 |
| 30 | 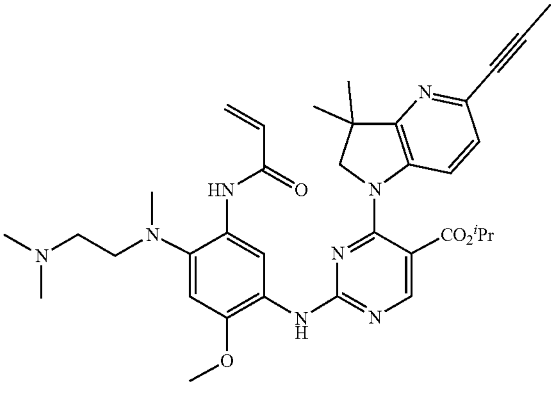 | isopropyl 2-((5-acrylamido-4-((2-(dimethylamino)ethyl)(methyl)amino)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 641.4 |

-continued

| Example No. | Structure | Chemical name | ESI-MS: $[M + 1]^+$ |
|---|---|---|---|
| 31 | 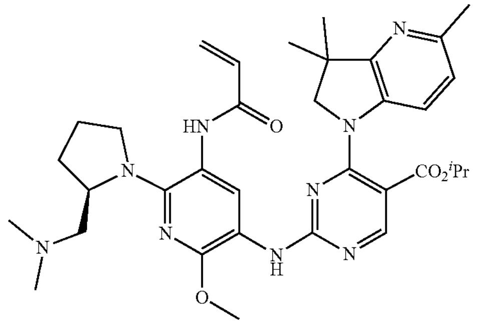 | isopropyl (R)-2-((5-acrylamido-6-(2-((dimethylamino)methyl)pyrrolidin-1-yl)-2-methoxypyridin-3-yl)amino)-4-(3,3,5-trimethyl-2,3-dihydro-1H-pyrrolo[3,2-b]pyridin-1-yl)pyrimidine-5-carboxylate | 644.4 |
| 32 | 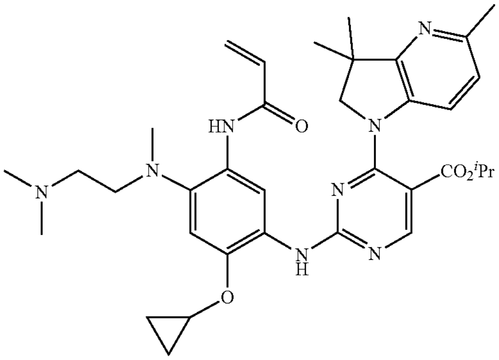 | isopropyl 2-((5-acrylamido-2-cyclopropoxy-4-((2-(dimethylamino)ethyl)(methyl)amino)phenyl)amino)-4-(3,3,5-trimethyl-2,3-dihydro-1H-pyrrolo[3,2-b]pyridin-1-yl)pyrimidine-5-carboxylate | 643.4 |
| 33 | 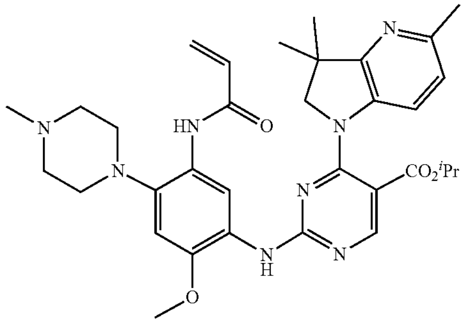 | isopropyl 2-((5-acrylamido-2-methoxy-4-(4-methylpiperazin-1-yl)phenyl)amino)-4-(3,3,5-trimethyl-2,3-dihydro-1H-pyrrolo[3,2-b]pyridin-1-yl)pyrimidine-5-carboxylate | 615.2 |
| 34 | 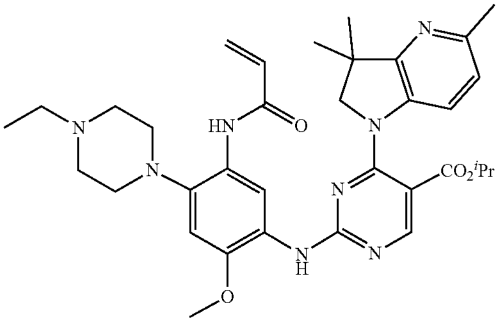 | isopropyl 2-((5-acrylamido-4-(4-ethylpiperazin-1-yl)-2-methoxyphenyl)amino)-4-(3,3,5-trimethyl-2,3-dihydro-1H-pyrrolo[3,2-b]pyridin-1-yl)pyrimidine-5-carboxylate | 629.4 |

-continued

| Example No. | Structure | Chemical name | ESI-MS: $[M + 1]^+$ |
| --- | --- | --- | --- |
| 35 | 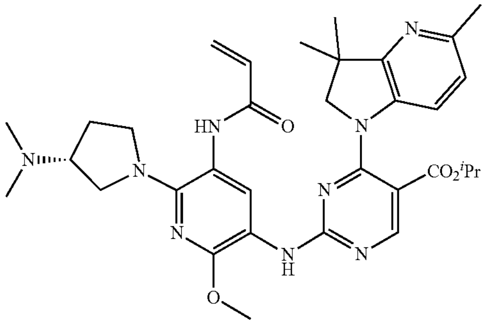 | isopropyl (R)-2-((5-acrylamido-6-(3-(dimethyl-amino)pyrrolidin-1-yl)-2-methoxy-pyridin-3-yl)amino)-4-(3,3,5-trimethyl-2,3-dihydro-1H-pyrrolo[3,2-b]pyridin-1-yl)pyrimidine-5-carboxylate | 630.3 |
| 36 | 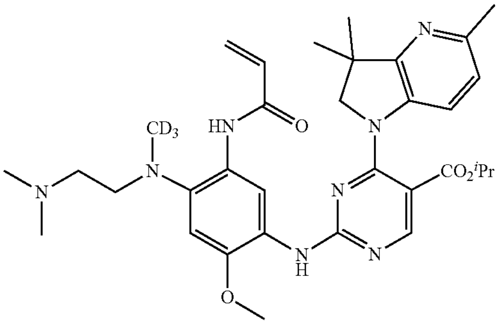 | isopropyl 2-((5-acrylamido-4-((2-(dimethylami-no)ethyl)(methyl-$d_3$)amino)-2-methoxy-phenyl)amino)-4-(3,3,5-trimethyl-2,3-dihydro-1H-pyrrolo[3,2-b]pyridin-1-yl)pyrimidine-5-carboxylate | 620.4 |
| 37 | 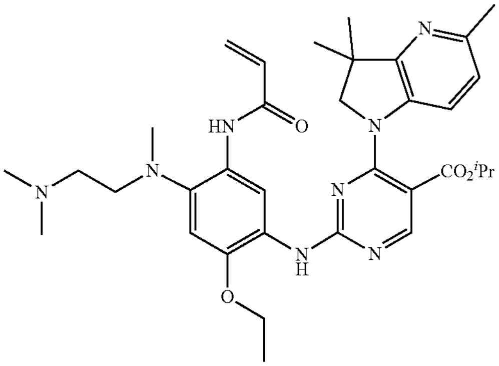 | isopropyl 2-((5-acrylamido-4-((2-(dimethylami-no)ethyl)(methyl)amino)-2-ethoxy-phenyl)amino)-4-(3,3,5-trimethyl-2,3-dihydro-1H-pyrrolo[3,2-b]pyridin-1-yl)pyrimidine-5-carboxylate | 631.4 |
| 38 | 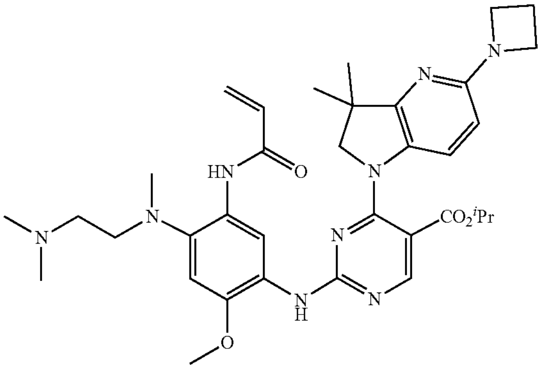 | isopropyl 2-((5-acrylamido-4-((2-(dimethylami-no)ethyl)(methyl)amino)-2-methoxy-phenyl)amino)-4-(5-(azetidin-1-yl)-3,3-dimethyl-2,3-dihydro-1H-pyrrolo[3,2-b]pyridin-1-yl)pyrimidine-5-carboxylate | 658.8 |

-continued

| Example No. | Structure | Chemical name | ESI-MS: [M + 1]+ |
|---|---|---|---|
| 39 | 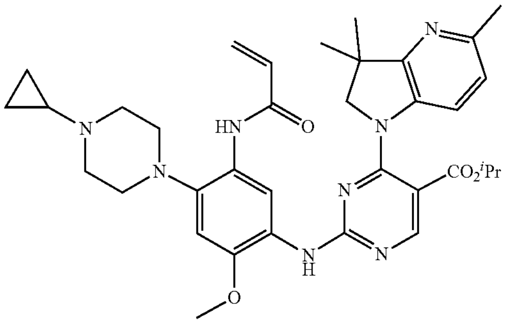 | isopropyl 2-((5-acrylamido-4-(4-cyclopropyl-piperazin-1-yl)-2-methoxy-phenyl)amino)-4-(3,3,5-trimethyl-2,3-dihydro-1H-pyrrolo[3,2-b]pyridin-1-yl)pyrimidine-5-carboxylate | 641.4 |
| 40 | 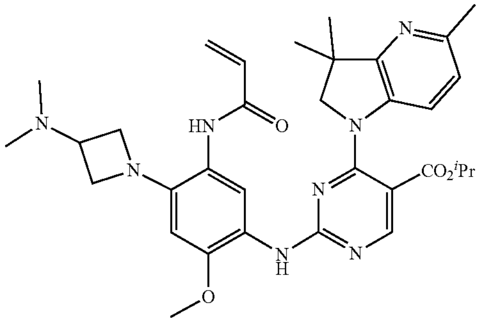 | isopropyl 2-((5-acrylamido-4-(3-(dimethylamino)azetidin-1-yl)-2-methoxyphenyl)amino)-4-(3,3,5-trimethyl-2,3-dihydro-1H-pyrrolo[3,2-b]pyridin-1-yl)pyrimidine-5-carboxylate | 615.2 |
| 41 | 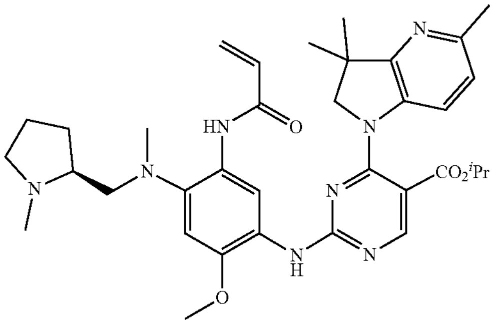 | isopropyl (S)-2-((5-acrylamido-2-methoxy-4-(methyl((1-methylpyrrolidin-2-yl)methyl)amino)phenyl)amino)-4-(3,3,5-trimethyl-2,3-dihydro-1H-pyrrolo[3,2-b]pyridin-1-yl)pyrimidine-5-carboxylate | 643.4 |
| 42 | 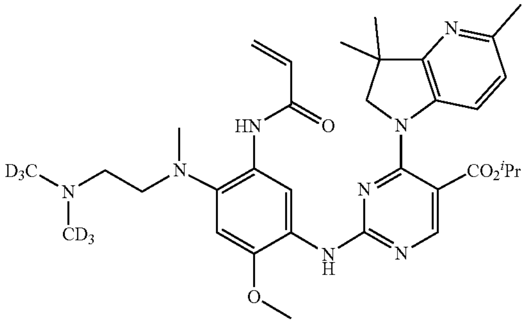 | isopropyl 2-((5-acrylamido-4-((2-(bis(methyl-$d_3$)amino)ethyl)(methyl)amino)-2-methoxyphenyl)amino)-4-(3,3,5-trimethyl-2,3-dihydro-1H-pyrrolo[3,2-b]pyridin-1-yl)pyrimidine-5-carboxylate | 623.4 |

-continued

| Example No. | Structure | Chemical name | ESI-MS: [M + 1]$^+$ |
|---|---|---|---|
| 43 | 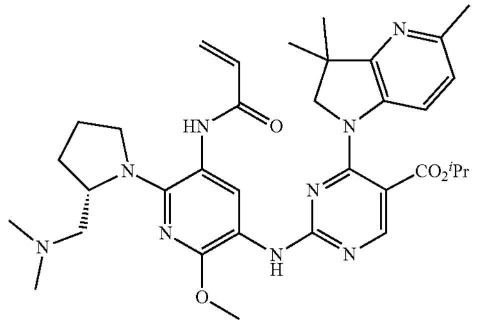 | isopropyl (S)-2-((5-acrylamido-6-(2-((dimethyl-amino)methyl)pyrrolidin-1-yl)-2-meth-oxypyridin-3-yl)amino)-4-(3,3,5-tri-methyl-2,3-dihydro-1H-pyrrolo[3,2-b]pyridin-1-yl)pyrimidine-5-carboxylate | 644.4 |
| 44 | 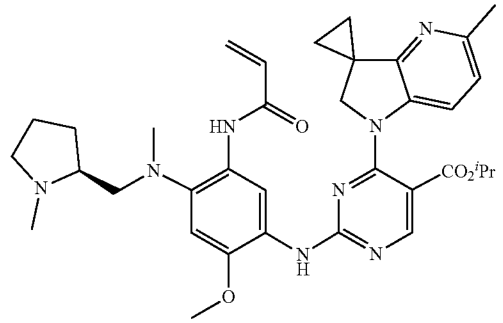 | isopropyl (S)-2-((5-acrylamido-2-methoxy-4-(methyl((1-methylpyrrolidin-2-yl)methyl)amino)phenyl)amino)-4-(5'-methylspiro(cyclopropane-1,3'-pyrrolo[3,2-b]pyridin)-1'(2'H)-yl)pyrimidine-5-carboxylate | 641.4 |
| 45 | 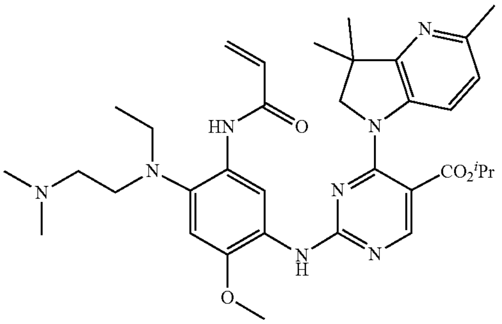 | isopropyl 2-((5-acrylamido-4-((2-(dimethylami-no)ethyl)(ethyl)amino)-2-methoxy-phenyl)amino)-4-(3,3,5-trimethyl-2,3-dihydro-1H-pyrrolo[3,2-b]pyridin-1-yl)pyrimidine-5-carboxylate | 631.4 |
| 46 | 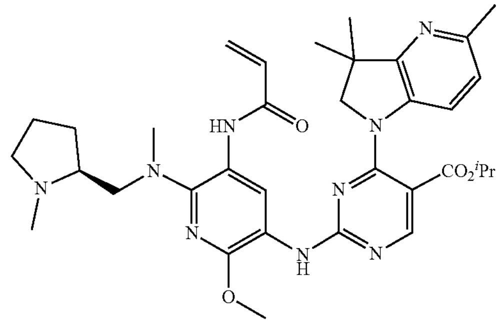 | isopropyl (S)-2-((5-acrylamido-2-methoxy-6-(methyl((1-methylpyrrolidin-2-yl)methyl)amino)pyridin-3-yl)amino)-4-(3,3,5-trimethyl-2,3-dihydro-1H-pyrrolo[3,2-b]pyridin-1-yl)pyrimidine-5-carboxylate | 644.3 |

-continued

| Example No. | Structure | Chemical name | ESI-MS: [M + 1]+ |
|---|---|---|---|
| 47 | 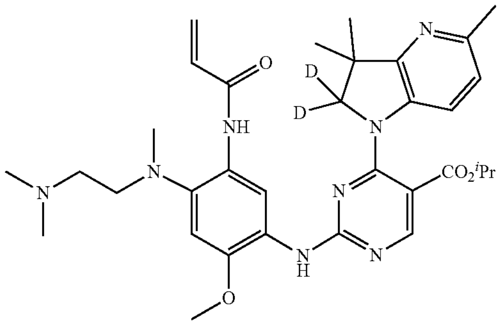 | isopropyl 2-((5-acrylamido-4-((2-(dimethylamino)ethyl)(methyl)amino)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 619.4 |
| 48 | 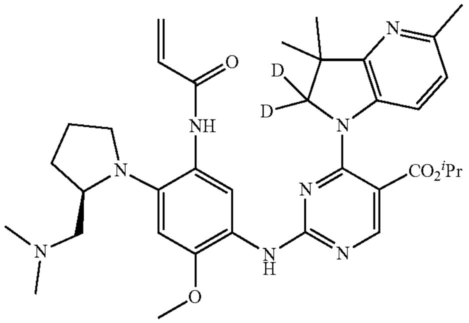 | isopropyl (R)-2-((5-acrylamido-4-(2-((dimethylamino)methyl)pyrrolidin-1-yl)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 645.4 |
| 49 | 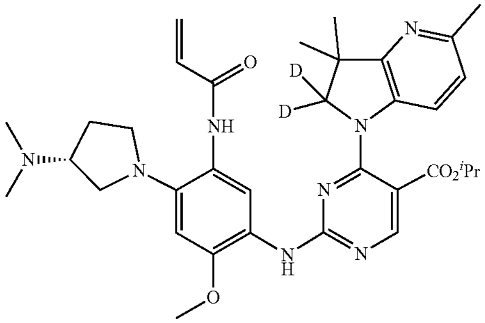 | isopropyl (R)-2-((5-acrylamido-4-(3-(dimethylamino)pyrrolidin-1-yl)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 631.4 |
| 50 | 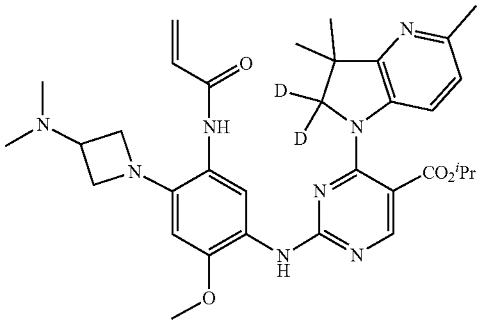 | isopropyl 2-((5-acrylamido-4-(3-(dimethylamino)azetidin-1-yl)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 617.4 |

-continued

| Example No. | Structure | Chemical name | ESI-MS: $[M + 1]^+$ |
| --- | --- | --- | --- |
| 51 | 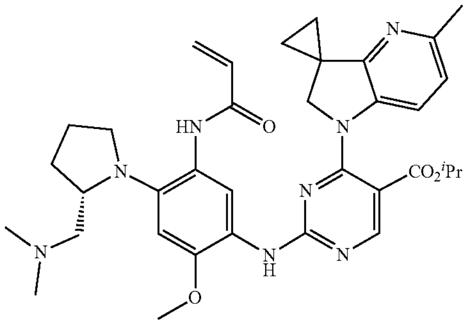 | isopropyl (S)-2-((5-acrylamido-4-(2-((dimethylamino)methyl)pyrrolidin-1-yl)-2-methoxyphenyl)amino)-4-(5'-methyl-spiro(cyclopropane-1,3'-pyrrolo[3,2-b]pyridin)-1'(2'H)-yl)pyrimidine-5-carboxylate | 641.4 |
| 52 | 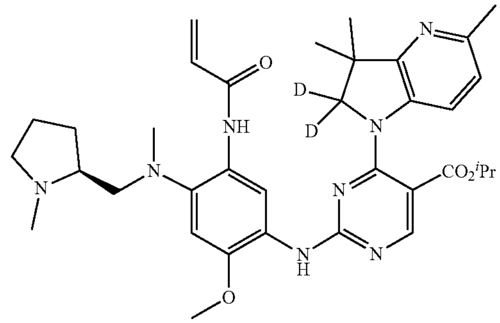 | isopropyl (S)-2-((5-acrylamido-2-methoxy-4-(methyl((1-methylpyrrolidin-2-yl)methyl)amino)phenyl)amino)-4-(3,3,5-trimethyl-2,3-dihydro-1H-pyrrolo[3,2-b]pyridin-1-yl-2,2-$d_2$)pyrimidine-5-carboxylate | 645.4 |
| 53 | 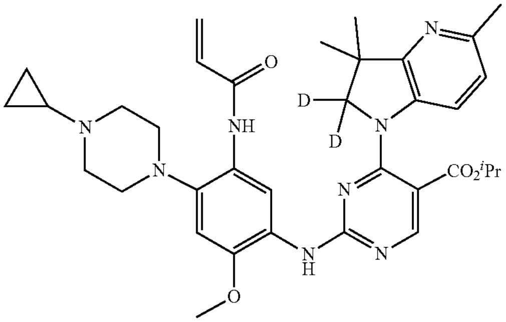 | isopropyl 2-((5-acrylamido-4-(4-cyclopropyl-piperazin-1-yl)-2-methoxy-phenyl)amino)-4-(3,3,5-trimethyl-2,3-dihydro-1H-pyrrolo[3,2-b]pyridin-1-yl-2,2-$d_2$)pyrimidine-5-carboxylate | 643.4 |
| 56 | 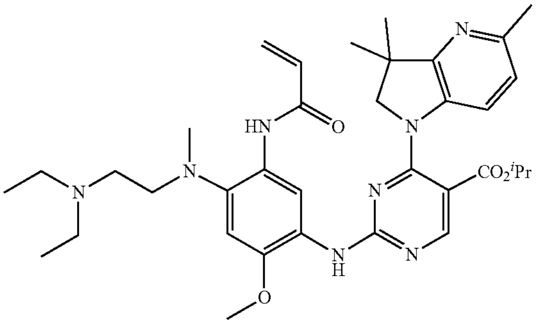 | isopropyl 2-((5-acrylamido-4-((2-(diethylamino)ethyl)(methyl)amino)-2-methoxy-phenyl)amino)-4-(3,3,5-trimethyl-2,3-dihydro-1H-pyrrolo[3,2-b]pyridin-1-yl)pyrimidine-5-carboxylate | 645.4 |

-continued

| Example No. | Structure | Chemical name | ESI-MS: [M + 1]+ |
|---|---|---|---|
| 57 | 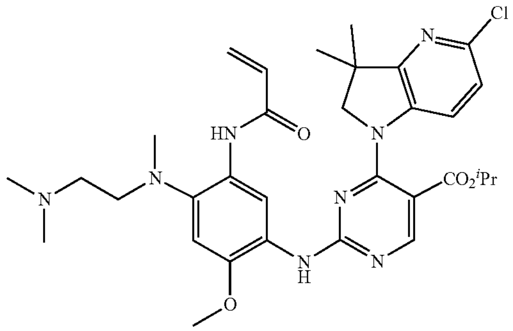 | isopropyl 2-((5-acrylamido-4-((2-(dimethylamino)ethyl)(methyl)amino)-2-methoxyphenyl)amino)-4-(5-chloro-3,3-dimethyl-2,3-dihydro-1H-pyrrolo[3,2-b]pyridin-1-yl)pyrimidine-5-carboxylate | 637.4 |
| 58 | 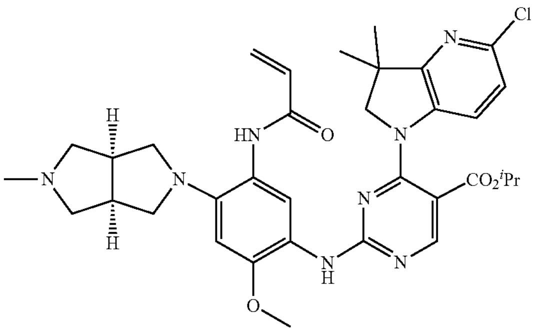 | isopropyl 2-((5-acrylamido-2-methoxy-4-((3aR,6aS)-5-methylhexahydropyrrolo[3,4-c]pyrrol-2(1H)-yl)phenyl)amino)-4-(3,3,5-trimethyl-2,3-dihydro-1H-pyrrolo[3,2-b]pyridin-1-yl)pyrimidine-5-carboxylate | 641.4 |
| 59 | 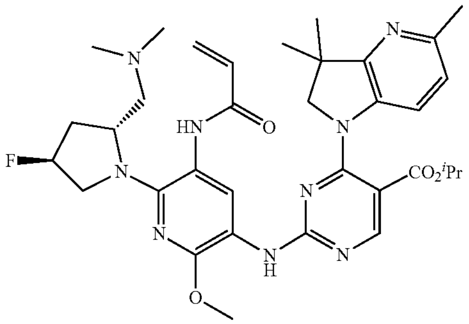 | isopropyl 2-((5-acrylamido-6-((2R,4S)-2-((dimethylamino)methyl)-4-fluoropyrrolidin-1-yl)-2-methoxypyridin-3-yl)amino)-4-(3,3,5-trimethyl-2,3-dihydro-1H-pyrrolo[3,2-b]pyridin-1-yl)pyrimidine-5-carboxylate | 662.4 |
| 60 | 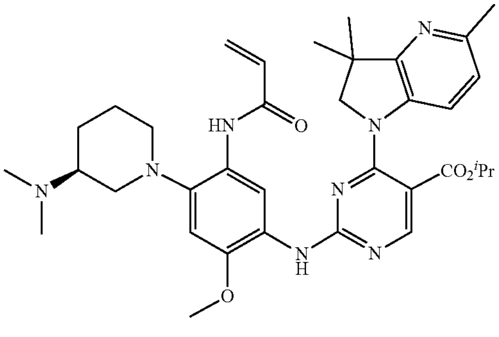 | isopropyl (S)-2-((5-acrylamido-4-(3-(dimethylamino)piperidin-1-yl)-2-methoxyphenyl)amino)-4-(3,3,5-trimethyl-2,3-dihydro-1H-pyrrolo[3,2-b]pyridin-1-yl)pyrimidine-5-carboxylate | 643.4 |

-continued

| Example No. | Structure | Chemical name | ESI-MS: [M + 1]+ |
|---|---|---|---|
| 61 | 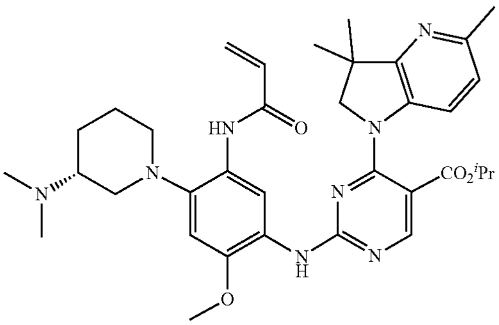 | isopropyl (R)-2-((5-acrylamido-4-(3-(dimethyl-amino)piperidin-1-yl)-2-methoxy-phenyl)amino)-4-(3,3,5-trimethyl-2,3-dihydro-1H-pyrrolo[3,2-b]pyridin-1-yl)pyrimidine-5-carboxylate | 643.4 |
| 62 | 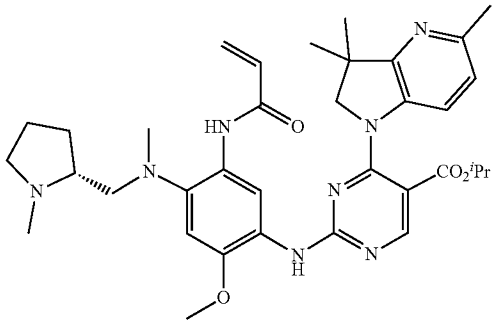 | isopropyl (R)-2-((5-acrylamido-2-methoxy-4-(methyl((1-methylpyrrolidin-2-yl)methyl)amino)phenyl)amino)-4-(3,3,5-trimethyl-2,3-dihydro-1H-pyrrolo[3,2-b]pyridin-1-yl)pyrimidine-5-carboxylate | 643.4 |
| 63 | 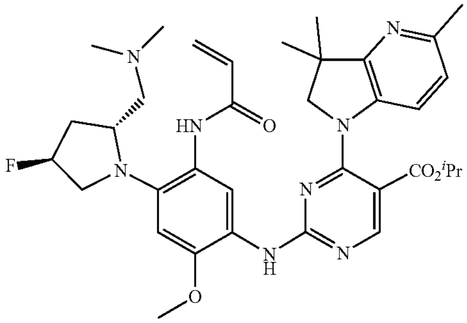 | isopropyl 2-((5-acrylamido-4-((2R,4S)-2-((dimethylamino)methyl)-4-fluoro-pyrrolidin-1-yl)-2-methoxy-phenyl)amino)-4-(3,3,5-trimethyl-2,3-dihydro-1H-pyrrolo[3,2-b]pyridin-1-yl)pyrimidine-5-carboxylate | 661.4 |
| 64 | 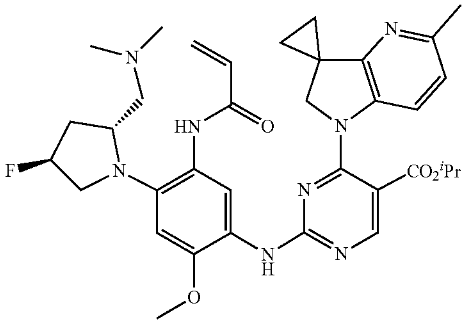 | isopropyl 2-((5-acrylamido-4-((2R,4S)-2-((di-methylamino)methyl)-4-fluoro-pyrrolidin-1-yl)-2-methoxy-phenyl)amino)-4-(5'-methyl-spiro(cyclopropane-1,3'-pyrrolo[3,2-b]pyridin)-1'(2'H)-yl)pyrimidine-5-carboxylate | 659.4 |

-continued

| Example No. | Structure | Chemical name | ESI-MS: [M + 1]+ |
|---|---|---|---|
| 66 | 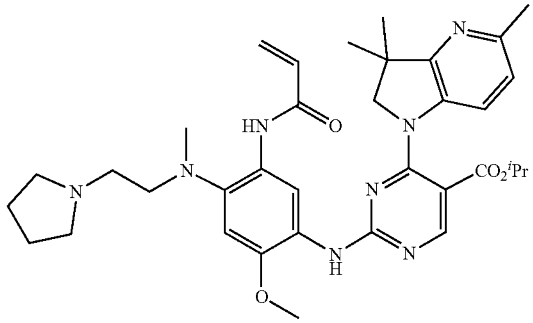 | isopropyl 2-((5-acrylamido-2-methoxy-4-(methyl(2-(pyrrolidin-1-yl)ethyl)amino)phenyl)amino)-4-(3,3,5-trimethyl-2,3-dihydro-1H-pyrrolo[3,2-b]pyridin-1-yl)pyrimidine-5-carboxylate | [M/2 + 1]+ |
| 67 | 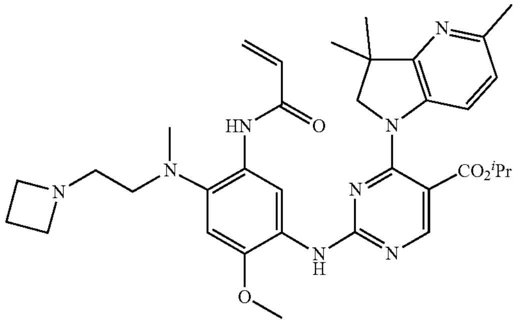 | isopropyl 2-((5-acrylamido-4-((2-(azetidin-1-yl)ethyl)(methyl)amino)-2-methoxy-phenyl)amino)-4-(3,3,5-trimethyl-2,3-dihydro-1H-pyrrolo[3,2-b]pyridin-1-yl)pyrimidine-5-carboxylate | 629.4 |
| 68 | 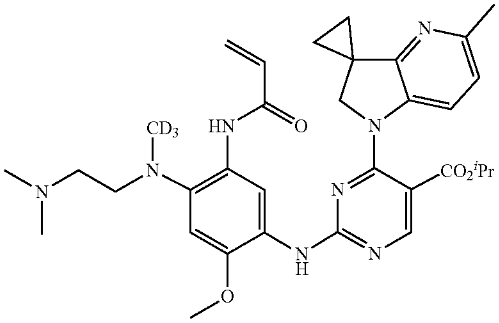 | isopropyl 2-((5-acrylamino-4-((2-(dimethylamino)ethyl)(methyl-$d_3$)amino)-2-methoxyphenyl)amino)-4-(5'-methylspiro(cyclopropane-1,3'-pyrrolo[3,2-b]pyridin)-1'(2'H)-yl)pyrimidine-5-carboxylate | 618.4 |
| 69 | 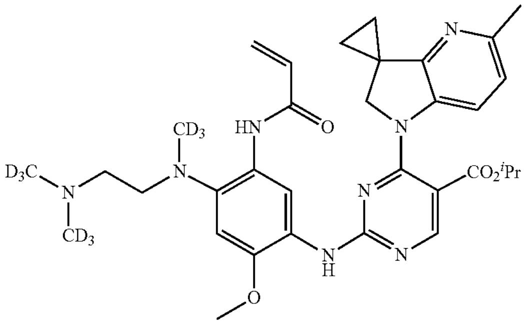 | isopropyl 2-((5-acrylamido-4-((2-(bis(methyl-$d_3$)amino)ethyl)(methyl-$d_3$)amino)-2-methoxyphenyl)amino)-4-(5'-methylspiro(cyclopropane-1,3'-pyrrolo[3,2-b]pyridin)-1'(2'H)-yl)pyrimidine-5-carboxylate | 624.4 |

-continued

| Example No. | Structure | Chemical name | ESI-MS: [M + 1]+ |
|---|---|---|---|
| 70 | 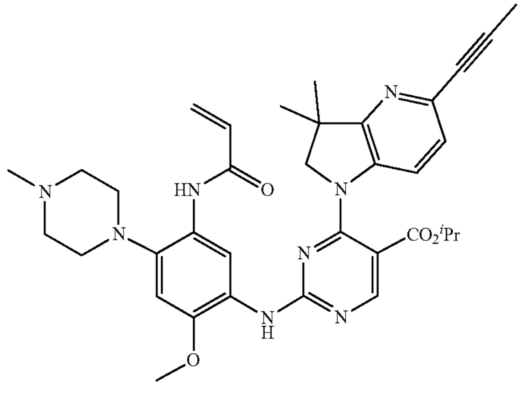 | isopropyl 2-((5-acrylamido-2-methoxy-4-(4-methylpiperazin-1-yl)phenyl)amino)-4-(3,3-dimethyl-5-(prop-1-yn-1-yl)-2,3-dihydro-1H-pyrrolo[3,2-b]pyridin-1-yl)pyrimidine-5-carboxylate | 639.4 |
| 71 | 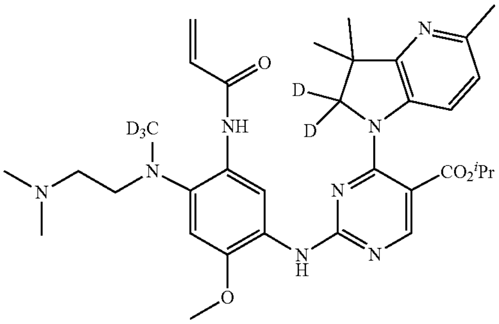 | isopropyl 2-((5-acrylamido-4-((2-(dimethylamino)ethyl)(methyl-$d_3$)amino)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 622.4 |
| 72 | 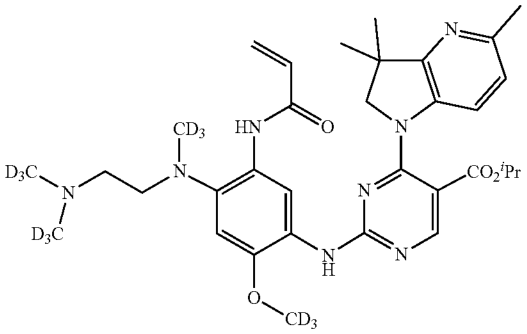 | isopropyl 2-((5-acrylamido-4-((2-(bis(methyl-$d_3$)amino)ethyl)(methyl-$d_3$)amino)-2-(methoxy-$d_3$)phenyl)amino)-4-(3,3,5-trimethyl-2,3-dihydro-1H-pyrrolo[3,2-b]pyridin-1-yl)pyrimidine-5-carboxylate | 629.6 |
| 73 | 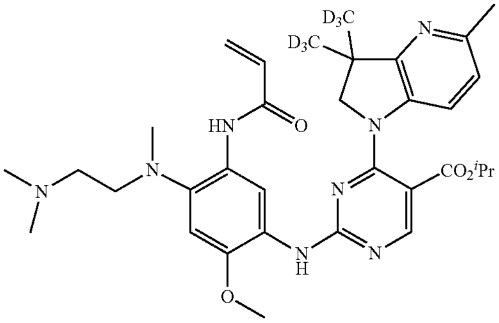 | isopropyl 2-((5-acrylamido-4-((2-(dimethylamino)ethyl)(methyl)amino)-2-methoxyphenyl)amino)-4-(5-methyl-3,3-bis(methyl-$d_3$)-2,3-dihydro-1H-pyrrolo[3,2-b]pyridin-1-yl)pyrimidine-5-carboxylate | 623.4 |

-continued

| Example No. | Structure | Chemical name | ESI-MS: [M + 1]+ |
|---|---|---|---|
| 74 | 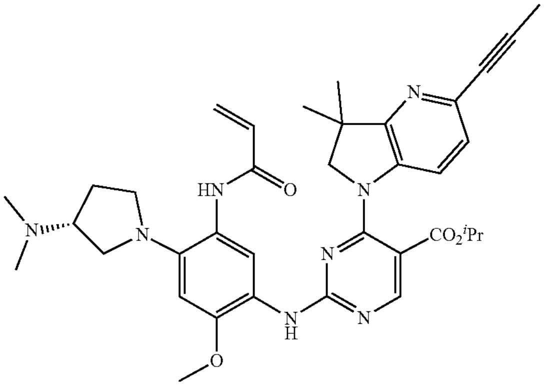 | isopropyl (R)-2-((5-acrylamido-4-(3-(dimethyl-amino)pyrrolidin-1-yl)-2-methoxy-phenyl)amino)-4-(3,3-dimethyl-5-(prop-1-yn-1-yl)-2,3-dihydro-1H-pyrrolo[3,2-b]pyridin-1-yl)pyrimidine-5-carboxylate | 653.4 |
| 75 | 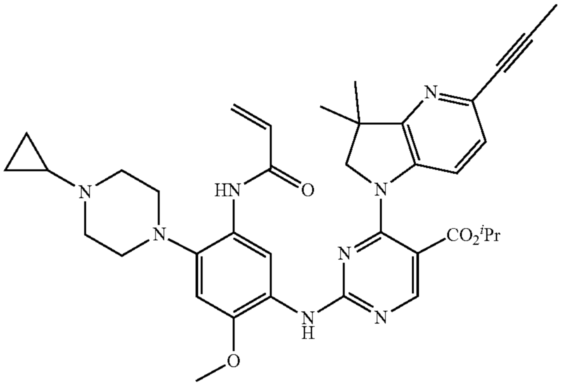 | isopropyl 2-((5-acrylamido-4-(4-cyclopropyl-piperazin-1-yl)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 665.4 |
| 76 | 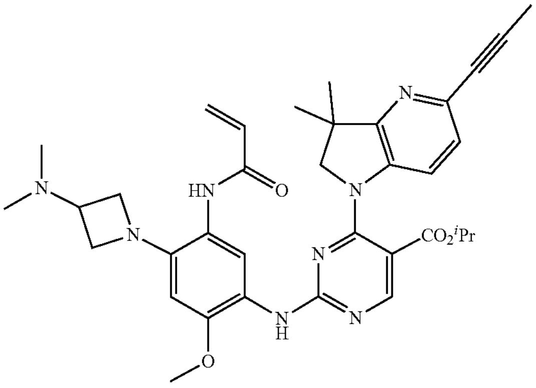 | isopropyl 2-((5-acrylamido-4-(3-(dimethylamino)azetidin-1-yl)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 639.4 |
| 77 | 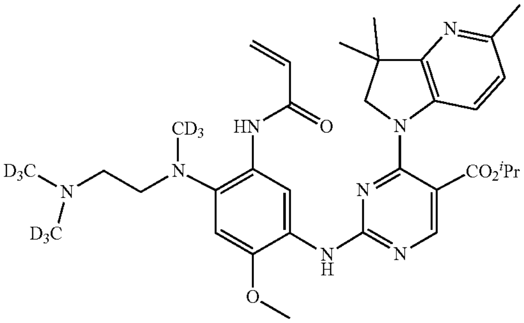 | isopropyl 2-((5-acrylamido-4-((2-(bis(methyl-$d_3$)amino)ethyl)(methyl-$d_3$)amino)-2-methoxyphenyl)amino)-4-(3,3,5-trimethyl-2,3-dihydro-1H-pyrrolo[3,2-b]pyridin-1-yl)pyrimidine-5-carboxylate | 626.5 |

-continued

| Example No. | Structure | Chemical name | ESI-MS: $[M + 1]^+$ |
| --- | --- | --- | --- |
| 78 | 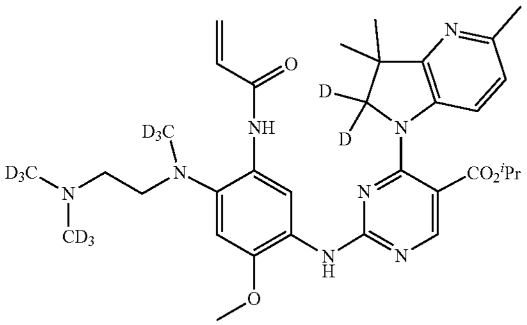 | isopropyl 2-((5-acrylamido-4-((2-(bis(methyl-$d_3$)amino)ethyl)(methyl-$d_3$)amino)-2-methoxyphenyl)amino)-4-(3,3,5-trimethyl-2,3-dihydro-1H-pyrrolo[3,2-b]pyridin-1-yl-2,2-$d_2$)pyrimidine-5-carboxylate | 628.5 |
| 79 | 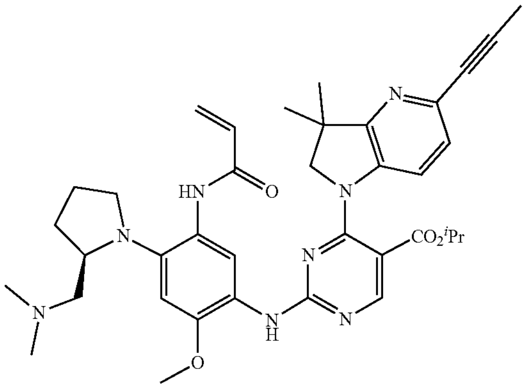 | isopropyl (R)-2-((5-acrylamido-4-(2-((dimethylamino)methyl)pyrrolidin-1-yl)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 667.5 |
| 80 | 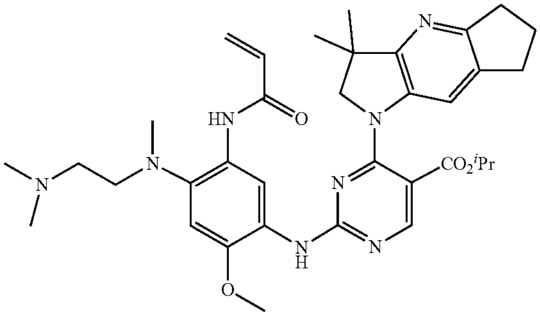 | isopropyl 2-((5-acrylamido-4-((2-(dimethylamino)ethyl)(methyl)amino)-2-methoxyphenyl)amino)-4-(3,3-dimethyl-3,5,6,7-tetrahydrocyclopenta[b]pyrrolo[2,3-e]pyridin-1(2H)-yl)pyrimidine-5-carboxylate | 643.4 |
| 81 | 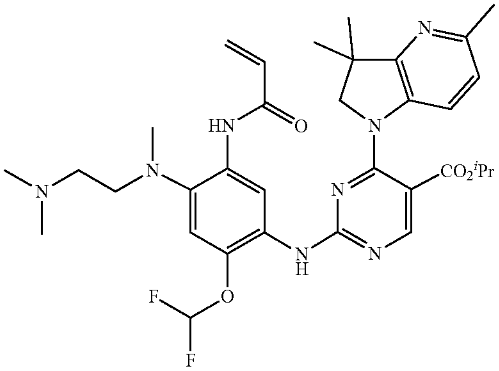 | isopropyl 2-((5-acrylamido-2-(difluoromethoxy)-4-((2-(dimethylamino)ethyl)(methyl)amino)phenyl)amino)-4-(3,3,5-trimethyl-2,3-dihydro-1H-pyrrolo[3,2-b]pyridin-1-yl)pyrimidine-5-carboxylate | 653.4 |

-continued

| Example No. | Structure | Chemical name | ESI-MS: $[M + 1]^+$ |
|---|---|---|---|
| 82 | 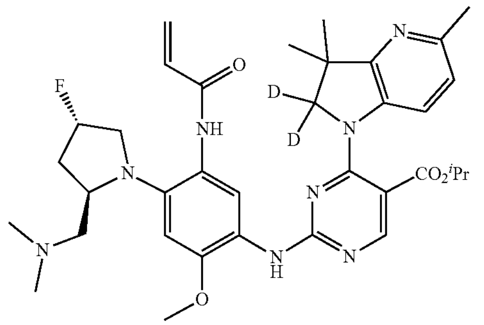 | isopropyl 2-((5-acrylamido-4-((2R,4S)-2-((dimethylamino)methyl)-4-fluoro-pyrrolidin-1-yl)-2-methoxy-phenyl)amino)-4-(3,3,5-trimethyl-2,3-dihydro-1H-pyrrolo[3,2-b]pyridin-1-yl-2,2-$d_2$)pyrimidine-5-carboxylate | 663.4 |
| 83 | 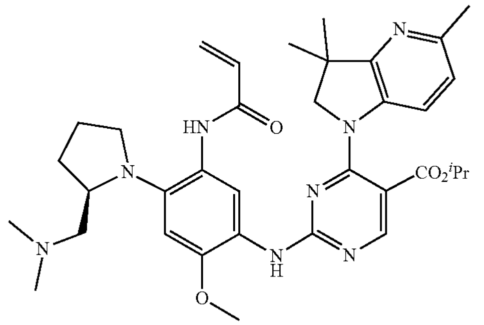 | isopropyl (R)-2-((5-acrylamido-4-(2-((dimethyl-amino)methyl)pyrrolidin-1-yl)-2-methoxyphenyl)amino)-4-(3,3,5-trimethyl-2,3-dihydro-1H-pyrrolo[3,2-b]pyridin-1-yl)pyrimidine-5-carboxylate | 643.4 |
| 84 | 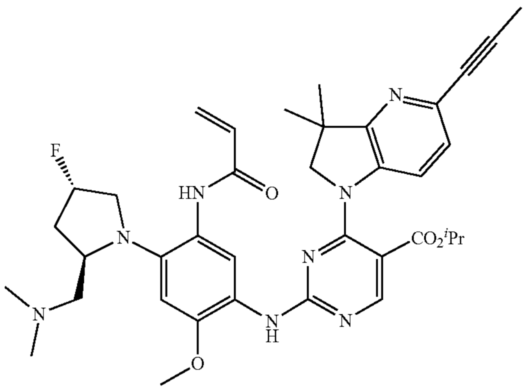 | isopropyl 2-((5-acrylamido-4-((2R,4S)-2-((dimethylamino)methyl)-4-fluoro-pyrrolidin-1-yl)-2-methoxy-phenyl)amino)-4-(3,3-dimethyl-5-(prop-1-yn-1-yl)-2,3-dihydro-1H-pyrrolo[3,2-b]pyridin-1-yl)pyrimidine-5-carboxylate | 685.4 |
| 85 | 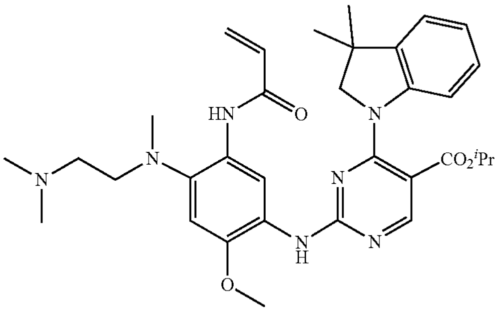 | isopropyl 2-((5-acrylamido-4-((2-(dimethylamino)ethyl)(methyl)amino)-2-methoxy-phenyl)amino)-4-(3,3-dimethylindolin-1-yl)pyrimidine-5-carboxylate | 602.4 |

-continued

| Example No. | Structure | Chemical name | ESI-MS: [M + 1]+ |
|---|---|---|---|
| 86 | 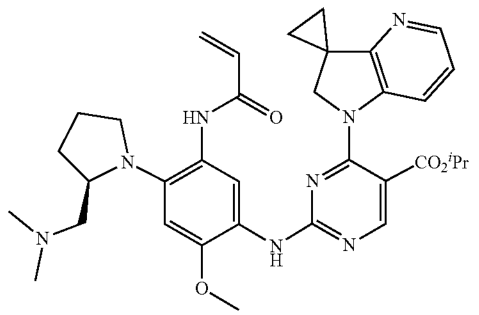 | isopropyl (R)-2-((5-acrylamido-4-(2-((dimethyl-amino)methyl)pyrrolidin-1-yl)-2-meth-oxyphenyl)amino)-4-(spiro(cyclopro-pane-1,3'-pyrrolo[3,2-b]pyridin)-1'(2'H)-yl)pyrimidine-5-carboxylate | 627.4 |
| 87 | 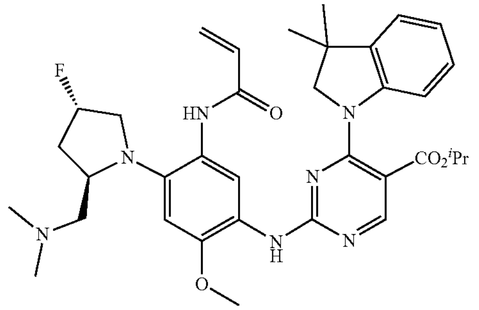 | isopropyl 2-((5-acrylamido-4-((2R,4S)-2-((di-methylamino)methyl)-4-fluoro-pyrrolidin-1-yl)-2-methoxy-phenyl)amino)-4-(3,3-dimethyl-indolin-1-yl)pyrimidine-5-carboxylate | 646.4 |
| 88 | 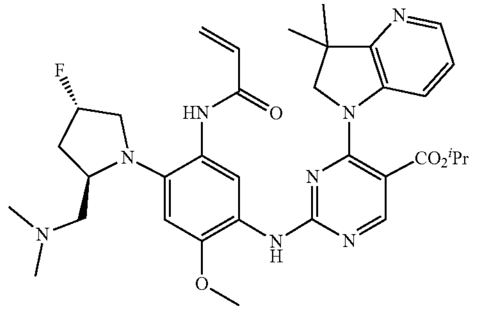 | isopropyl 2-((5-acrylamido-4-((2R,4S)-2-((di-methylamino)methyl)-4-fluoro-pyrrolidin-1-yl)-2-methoxy-phenyl)amino)-4-(3,3-dimethyl-2,3-dihydro-1H-pyrrolo[3,2-b]pyridin-1-yl)pyrimidine-5-carboxylate | 647.4 |
| 89 | 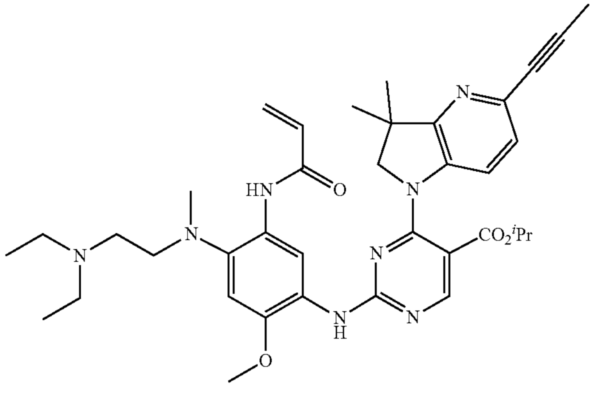 | isopropyl 2-((5-acrylamido-4-((2-(diethyl-amino)ethyl)(methyl)amino)-2-methoxyphenyl)amino)-4-(3,3-dimethyl-5-(prop-1-yn-1-yl)-2,3-dihydro-1H-pyrrolo[3,2-b]pyridin-1-yl)pyrimidine-5-carboxylate | 669.4 |

-continued

| Example No. | Structure | Chemical name | ESI-MS: [M + 1]$^+$ |
|---|---|---|---|
| 90 | 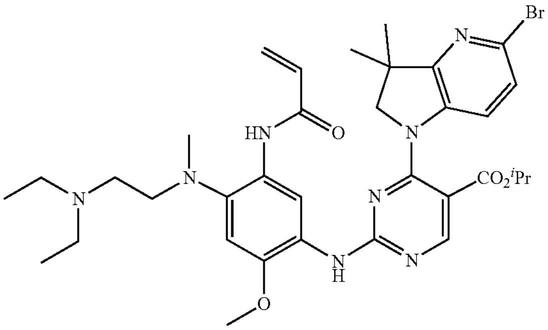 | isopropyl 2-((5-acrylamido-4-((2-(diethyl-amino)ethyl)(methyl)amino)-2-methoxyphenyl)amino)-4-(5-bromo-3,3-dimethyl-2,3-dihydro-1H-pyrrolo[3,2-b]pyridin-1-yl)pyrimidine-5-carboxylate | 709.2 711.2 |
| 91 | 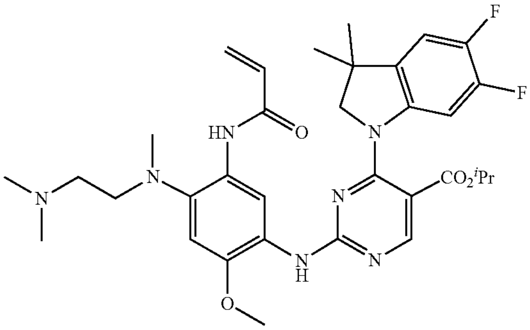 | isopropyl 2-((5-acrylamido-4-((2-(dimethylami-no)ethyl)(methyl)amino)-2-methoxy-phenyl)amino)-4-(5,6-difluoro-3,3-dimethylindolin-1-yl)pyrimidine-5-carboxylate | 638.4 |
| 92 | 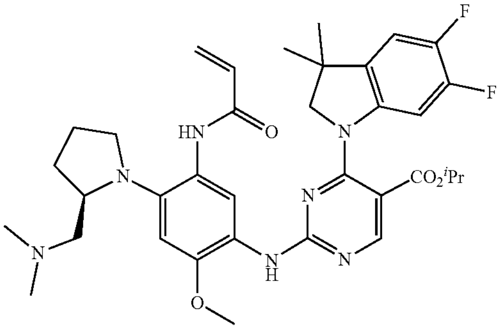 | isopropyl (R)-2-((5-acrylamido-4-(2-((dimethyl-amino)methyl)pyrrolidin-1-yl)-2-meth-oxyphenyl)amino)-4-(5,6-difluoro-3,3-dimethylindolin-1-yl)pyrimidine-5-carboxylate | 664.4 |
| 93 | 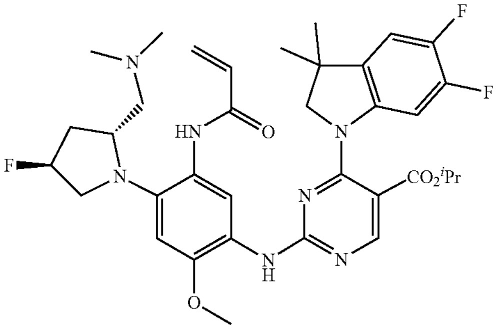 | isopropyl 2-((5-acrylamido-4-((2R,4S)-2-((di-methylamino)methyl)-4-fluoro-pyrrolidin-1-yl)-2-methoxy-phenyl)amino)-4-(5,6-difluoro-3,3-dimethylindolin-1-yl)pyrimidine-5-carboxylate | 682.4 |

-continued

| Example No. | Structure | Chemical name | ESI-MS: [M + 1]+ |
|---|---|---|---|
| 94 | 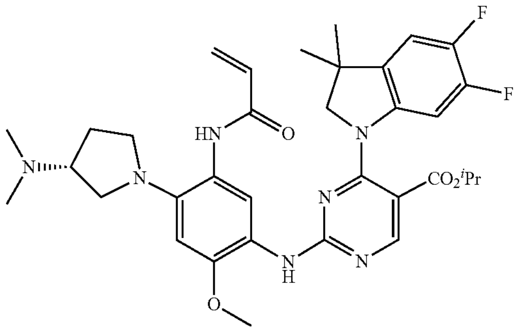 | isopropyl (R)-2-((5-acrylamido-4-(3-(dimethyl-amino)pyrrolidin-1-yl)-2-methoxy-phenyl)amino)-4-(5,6-difluoro-3,3-dimethylindolin-1-yl)pyrimidine-5-carboxylate | 650.4 |
| 95 | 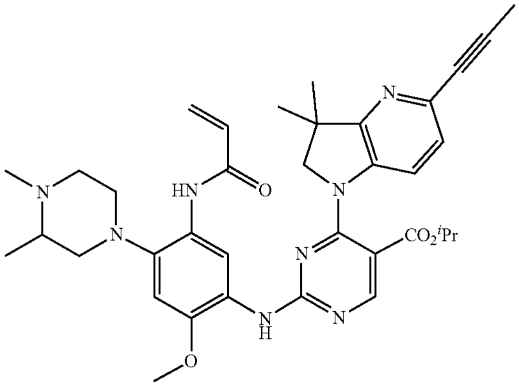 | isopropyl 2-((5-acrylamido-4-(3,4-dimethyl-piperazin-1-yl)-2-methoxy-phenyl)amino)-4-(3,3-dimethyl-5-(prop-1-yn-1-yl)-2,3-dihydro-1H-pyrrolo[3,2-b]pyridin-1-yl)pyrimidine-5-carboxylate | 653.4 |

$^1$H NMR data of the compounds prepared in the above examples are as follows:

| Example No. | $^1$H NMR |
|---|---|
| 2 | (DMSO-$d_6$) δ 10.08 (s, 1H), 8.79 (s, 1H), 8.60 (d, J = 1.6 Hz, 2H), 8.03 (dd, J = 4.9, 1.3 Hz, 1H), 7.26 (s, 1H), 6.99 (d, J = 14.0 Hz, 2H), 6.43-6.31 (m, 1H), 6.23 (dd, J = 16.9, 2.2 Hz, 1H), 5.75 (dd, J = 10.0, 2.2 Hz, 1H), 4.90 (p, J = 6.2 Hz, 1H), 3.91 (s, 2H), 3.81 (s, 3H), 2.87 (t, J = 5.9 Hz, 2H), 2.72 (s, 3H), 2.30 (t, J = 5.9 Hz, 2H), 2.20 (s, 6H), 1.28 (s, 6H), 1.09 (d, J = 6.2 Hz, 6H). |
| 3 | (DMSO-$d_6$) δ 10.18 (s, 1H), 9.08 (s, 1H), 8.73 (s, 1H), 8.60 (d, J = 1.2 Hz, 1H), 8.09-7.94 (m, 1H), 7.36-6.84 (m, 4H), 6.48-6.21 (m, 2H), 5.80 (dt, J = 10.1, 1.5 Hz, 1H), 4.99-4.86 (m, 1H), 3.84 (s, 2H), 2.85 (t, J = 5.8 Hz, 2H), 2.73-2.68 (m, 3H), 2.34 (t, J = 5.8 Hz, 2H), 2.21 (d, J = 1.2 Hz, 6H), 1.29-1.25 (m, 6H), 1.12 (dd, J = 6.2, 1.3 Hz, 6H). |
| 4 | (DMSO-$d_6$) δ 10.07 (s, 1H), 8.77 (s, 1H), 8.54 (dd, J = 14.9, 3.9 Hz, 2H), 7.17 (s, 1H), 7.00 (d, J = 3.5 Hz, 1H), 6.81 (dd, J = 8.7, 3.6 Hz, 1H), 6.46-6.37 (m, 1H), 6.22 (dd, J = 16.9, 4.1 Hz, 1H), 5.75 (dt, J = 10.1, 2.8 Hz, 1H), 5.01-4.74 (m, 1H), 3.83 (dd, J = 21.1, 3.7 Hz, 5H), 2.87 (d, J = 5.3 Hz, 2H), 2.71 (d, J = 3.6 Hz, 3H), 2.31 (t, J = 5.6 Hz, 2H), 2.20 (d, J = 3.5 Hz, 6H), 1.98 (dq, J = 8.4, 4.7, 4.2 Hz, 1H), 1.22 (d, J = 3.6 Hz, 6H), 1.11 (t, J = 4.9 Hz, 6H), 0.89-0.79 (m, 4H). |
| 5 | (DMSO-$d_6$) δ 10.08 (s, 1H), 8.73 (s, 1H), 8.57 (s, 2H), 7.24 (s, 1H), 7.02 (s, 1H), 6.82 (d, J = 8.3 Hz, 1H), 6.42 (dd, J = 16.9, 10.1 Hz, 1H), 6.23 (dd, J = 16.9, 2.1 Hz, 1H), 5.75 (dd, J = 10.0, 2.2 Hz, 1H), 4.93 (p, J = 6.2 Hz, 1H), 4.16 (s, 2H), 3.80 (s, 3H), 2.88 (t, J = 5.9 Hz, 2H), 2.72 (s, 3H), 2.43-2.39 (m, 5H), 2.31 (t, J = 5.9 Hz, 2H), 2.21 (s, 6H), 2.18-2.15 (m, 2H), 2.07-1.92 (m, 2H), 1.16 (d, J = 6.2 Hz, 6H). |
| 6 | (DMSO-$d_6$) δ 10.20 (s, 1H), 9.09 (s, 1H), 8.70 (s, 1H), 8.60 (s, 1H), 8.09 (dd, J = 5.0, 1.3 Hz, 1H), 7.46-7.32 (m, 1H), 7.16 (s, 1H), 7.02 (t, J = 76.0 Hz, 1H), 6.97 (dd, J = 8.2, 4.9 Hz, 1H), 6.44 (dd, J = 16.9, 10.0 Hz, 1H), 6.26 (dd, J = 17.0, 2.1 Hz, 1H), 5.80 (dd, J = 10.1, 2.1 Hz, 1H), 4.95 (p, J = 6.2 Hz, 1H), 4.13 (s, 2H), 2.86 (t, J = 5.7 Hz, 2H), 2.71 (s, 3H), 2.44-2.30 (m, 4H), 2.21 (s, 6H), 2.21-2.12 (m, 2H), 2.12-1.94 (m, 2H), 1.16 (d, J = 6.3 Hz, 6H). |

-continued

| Example No. | $^1H$ NMR |
|---|---|
| 7 | (DMSO-$d_6$) δ 10.09 (s, 1H), 8.75 (s, 1H), 8.62 (s, 1H), 8.59 (s, 1H), 8.09 (dd, J = 4.9, 1.3 Hz, 1H), 7.28 (d, J = 8.5 Hz, 1H), 7.02 (s, 1H), 6.98 (dd, J = 8.0, 4.8 Hz, 1H), 6.42 (dd, J = 16.9, 10.1 Hz, 1H), 6.23 (dd, J = 16.9, 2.1 Hz, 1H), 5.75 (dd, J = 10.0, 2.2 Hz, 1H), 4.92 (p, J = 6.2 Hz, 1H), 4.19 (s, 2H), 3.80 (s, 3H), 2.88 (t, J = 5.8 Hz, 2H), 2.72 (s, 3H), 2.40 (ddd, J = 11.5, 9.0, 7.0 Hz, 2H), 2.31 (t, J = 5.9 Hz, 2H), 2.20 (s, 8H), 2.11-1.84 (m, 2H), 1.13 (d, J = 6.3 Hz, 6H). |
| 8 | (DMSO-$d_6$) δ 10.06 (s, 1H), 8.79 (s, 1H), 8.59 (s, 1H), 8.56 (s, 1H), 8.12 (s, 1H), 7.85 (s, 1H), 7.25 (s, 2H), 7.02 (s, 1H), 6.48-6.35 (m, 1H), 6.23 (dd, J = 16.9, 2.2 Hz, 1H), 5.75 (dd, J = 10.0, 2.2 Hz, 1H), 4.98-4.88 (m, 1H), 3.92 (s, 2H), 3.87 (s, 3H), 3.81 (s, 3H), 2.88 (t, J = 5.9 Hz, 2H), 2.72 (s, 3H), 2.30 (t, J = 6.0 Hz, 2H), 2.19 (s, 6H), 1.31 (s, 6H), 1.11 (d, J = 6.2 Hz, 6H). |
| 10 | (DMSO-$d_6$) δ 10.07 (s, 1H), 8.75 (s, 1H), 8.58 (d, J = 4.2 Hz, 2H), 8.17 (s, 1H), 7.89 (s, 1H), 7.24 (d, J = 8.0 Hz, 2H), 7.03 (s, 1H), 6.42 (dd, J = 16.9, 10. 1 Hz, 1H), 6.23 (dd, J = 16.9, 2.1 Hz, 1H), 5.81-5.69 (m, 1H), 4.93 (p, J = 6.1 Hz, 1H), 4.20 (s, 2H), 3.88 (s, 3H), 3.81 (s, 3H), 2.89 (t, J = 5.8 Hz, 2H), 2.73 (s, 3H), 2.42 (d, J = 7.8 Hz, 2H), 2.30 (d, J = 5.8 Hz, 2H), 2.19 (s, 8H), 1.99 (d, J = 9.6 Hz, 2H), 1.15 (d, J = 6.2 Hz, 6H). |
| 11 | (DMSO-$d_6$) δ 10.05 (s, 1H), 8.67 (d, J = 5.9 Hz, 2H), 8.60 (s, 1H), 7.57 (s, 1H), 7.01 (s, 1H), 6.72 (d, J = 8.7 Hz, 1H), 6.40 (dd, J = 16.9, 10.1 Hz, 1H), 6.21 (dd, J = 16.9, 2.2 Hz, 1H), 5.75 (dd, J = 10.0, 2.2 Hz, 1H), 4.97 (p, J = 6.2 Hz, 1H), 3.89 (s, 2H), 3.79 (s, 3H), 2.88 (t, J = 5.9 Hz, 2H), 2.72 (s, 3H), 2.31 (t, J = 5.9 Hz, 2H), 2.20 (s, 6H), 1.26 (s, 6H), 1.17 (d, J = 6.2 Hz, 6H) |
| 12 | (DMSO-$d_6$) δ 9.31 (s, 1H), 8.53 (s, 1H), 8.44 (s, 1H), 7.76 (s, 1H), 7.22 (s, 1H), 6.86 (d, J = 8.3 Hz, 1H), 6.58-6.45 (m, 2H), 6.19 (dd, J = 17.0, 2.2 Hz, 1H), 5.70 (dd, J = 10.2, 2.1 Hz, 1H), 4.92 (p, J = 6.2 Hz, 1H), 3.78 (d, J = 11.5 Hz, 5H), 3.41-3.35 (m, 1H), 3.20 (t, J = 8.9 Hz, 3H), 2.72-2.66 (m, 1H), 2.39 (s, 3H), 2.17 (s, 6H), 2.09 (s, 1H), 1.82-1.66 (m, 1H), 1.25 (s, 6H), 1.13 (dd, J = 6.2, 2.2 Hz, 6H). |
| 13 | (DMSO-$d_6$) δ 9.32 (s, 1H), 8.54 (s, 1H), 8.44 (s, 1H), 7.77 (s, 1H), 7.22 (s, 1H), 6.86 (d, J = 8.3 Hz, 1H), 6.62-6.43 (m, 2H), 6.25-6.14 (m, 1H), 5.73-5.64 (m, 1H), 4.92 (p, J = 6.2 Hz, 1H), 3.78 (d, J = 11.3 Hz, 5H), 3.20 (t, J = 8.0 Hz, 3H), 2.68 (d, J = 8.0 Hz, 1H), 2.39 (s, 3H), 2.17 (s, 6H), 2.13-2.04 (m, 1H), 1.79-1.66 (m, 1H), 1.25 (s, 6H), 1.15-1.10 (m, 6H). |
| 14 | (DMSO-$d_6$) δ 10.04 (s, 1H), 8.75 (s, 1H), 8.65-8.48 (m, 2H), 7.34-7.14 (m, 2H), 7.02 (s, 1H), 6.42 (s, 1H), 6.28-6.15 (m, 1H), 5.85-5.70 (m, 2H), 5.14 (d, J = 2.0 Hz, 1H), 5.02-4.84 (m, 1H), 3.86 (d, J = 42.4 Hz, 5H), 2.90 (s, 2H), 2.71 (s, 3H), 2.42-2.17 (m, 8H), 2.10 (s, 3H), 1.29 (s, 6H), 1.12 (d, J = 6.0 Hz, 6H). |
| 16 | (DMSO-$d_6$) δ 8.56 (s, 1H), 8.47 (s, 1H), 7.75 (s, 1H), 7.13 (s, 1H), 6.88 (d, J = 11.9 Hz, 2H), 6.29-6.11 (m, 2H), 5.64-5.41 (m, 2H), 4.94-4.82 (m, 1H), 4.61 (d, J = 9.8 Hz, 1H), 3.86 (s, 3H), 3.83-3.70 (m, 2H), 3.20 (s, 3H), 2.98-2.88 (m, 3H), 2.69 (s, 3H), 2.37-2.25 (m, 2H), 2.10 (s, 6H), 1.26 (d, J = 13.0 Hz, 6H), 1.20 (d, J = 7.0 Hz, 6H), 1.06 (t, J = 6.0 Hz, 6H). |
| 17 | (DMSO-$d_6$) δ 10.10 (s, 1H), 8.73 (d, J = 37.2 Hz, 3H), 7.51-7.33 (m, 2H), 7.03 (s, 1H), 6.48-6.17 (m, 2H), 5.75 (dd, J = 10.0, 2.2 Hz, 1H), 4.94 (p, J = 6.2 Hz, 1H), 4.01 (s, 2H), 3.82 (s, 3H), 2.88 (t, J = 5.8 Hz, 2H), 2.72 (s, 3H), 2.30 (t, J = 5.8 Hz, 2H), 2.20 (s, 6H), 1.32 (s, 6H), 1.12 (d, J = 6.2 Hz, 6H). $^{19}F$ NMR δ 64.88. |
| 18 | (DMSO-$d_6$) δ 10.07 (s, 1H), 8.77-8.60 (m, 3H), 7.20 (d, J = 8.7 Hz, 1H), 7.06-6.92 (m, 2H), 6.41 (dd, J = 16.9, 10.0 Hz, 1H), 6.23 (dd, J = 16.9, 2.1 Hz, 1H), 5.75 (dd, J = 10.1, 2.1 Hz, 1H), 4.94 (tt, J = 12.4, 6.1 Hz, 1H), 3.90 (s, 2H), 3.80 (s, 3H), 2.88 (t, J = 5.8 Hz, 2H), 2.71 (s, 3H), 2.32 (t, J = 5.9 Hz, 2H), 2.21 (s, 6H), 1.54 (tt, J = 8.5, 5.0 Hz, 1H), 1.27 (d, J = 5.2 Hz, 6H), 1.12 (d, J = 6.1 Hz, 6H), 0.95-0.83 (m, 2H), 0.74 (dd, J = 5.2, 2.4 Hz, 2H). |
| 19 | (DMSO-$d_6$) δ 10.08 (s, 1H), 8.74 (s, 1H), 8.63 (d, J = 17.0 Hz, 2H), 7.21 (s, 1H), 7.03 (d, J = 8.7 Hz, 2H), 6.40 (dd, J = 16.9, 10.1 Hz, 1H), 6.22 (dd, J = 16.9, 2.2 Hz, 1H), 5.75 (dd, J = 10.0, 2.2 Hz, 1H), 4.93 (p, J = 6.3 Hz, 1H), 3.90 (s, 2H), 3.80 (s, 3H), 2.89 (d, J = 6.0 Hz, 2H), 2.82-2.77 (m, 1H), 2.72 (s, 3H), 2.31 (t, J = 5.9 Hz, 2H), 2.21 (s, 6H), 1.26 (s, 6H), 1.21 (d, J = 6.9 Hz, 6H), 1.13 (d, J = 6.2 Hz, 6H). |
| 20 | (DMSO-$d_6$) δ 10.07 (s, 1H), 8.78 (s, 1H), 8.60 (s, 2H), 7.21 (s, 1H), 7.10 (d, J = 8.3 Hz, 1H), 7.01 (s, 1H), 6.79-6.65 (m, 1H), 6.51-6.32 (m, 1H), 6.29-6.16 (m, 1H), 6.05 (d, 1H), 5.75 (d, J = 10.0, 2.2 Hz, 1H), 5.32-5.27 (m, 1H), 4.95-4.86 (m, 1H), 3.93 (s, 2H), 3.81 (s, 3H), 2.88 (t, J = 5.9 Hz, 2H), 2.72 (s, 3H), 2.30 (t, J = 6.0 Hz, 2H), 2.19 (s, 6H), 1.29 (s, 6H), 1.11 (d, J = 6.2 Hz, 6H). |
| 21 | (DMSO-$d_6$) δ 10.05 (s, 1H), 8.69 (s, 1H), 8.60 (s, 2H), 7.91 (dd, J = 4.9, 1.3 Hz, 1H), 7.41 (s, 1H), 7.02 (s, 1H), 6.86 (s, 1H), 6.40 (dd, J = 16.9, 10.1 Hz, 1H), 6.20 (dd, J = 16.9, 2.1 Hz, 1H), 5.74 (dd, J = 10.1, 2.1 Hz, 1H), 4.96 (p, J = 6.3 Hz, 1H), 4.12 (s, 2H), 3.79 (s, 3H), 2.87 (d, J = 5.9 Hz, 2H), 2.72 (s, 3H), 2.31 (t, J = 5.9 Hz, 2H), 2.20 (s, 6H), 1.20 (d, J = 6.2 Hz, 6H), 1.12 (dt, J = 17.8, 2.6 Hz, 4H). |
| 22 | ($CDCl_3$) δ 10.01 (s, 1H), 9.41 (s, 1H), 8.73 (s, 1H), 7.73 (s, 1H), 7.15-6.99 (m, 1H), 6.77 (s, 1H), 6.73 (d, J = 8.2 Hz, 1H), 6.43-6.27 (m, 2H), 5.74-5.64 (m, 1H), 5.00 (p, J = 6.2 Hz, 1H), 4.44 (s, 2H), 3.86 (s, 3H), 2.89 (t, J = 5.4 Hz, 2H), 2.70 (s, 3H), 2.42 (s, 3H), 2.32(s, 2H), 2.28 (s, 6H), 1.82 (s, 2H), 1.36 (q, J = 4.2 Hz, 2H), 1.17 (s, 3H), 1.15 (s, 3H). |
| 23 | (DMSO-$d_6$) δ 10.06 (s, 1H), 8.81 (s, 1H), 8.78-8.73 (m, 1H), 8.70 (s, 1H), 7.63 (d, J = 8.4 Hz, 1H), 7.31 (s, 1H), 7.02 (s, 1H), 6.51-6.34 (m, 1H), 6.25-6.17 (m, 1H), 5.75 (d, J = 10.0, 2.1 Hz, 1H), 4.95 (p, J = 6.2 Hz, 1H), 4.01 (s, 2H), 3.82 (s, 3H), 2.88 (t, J = 5.8 Hz, 2H), 2.72 (s, 3H), 2.30 (t, J = 5.9 Hz, 2H), 2.20 (s, 6H), 1.31 (s, 6H), 1.13 (d, J = 6.3 Hz, 6H). |

-continued

| Example No. | $^1$H NMR |
|---|---|
| 24 | (DMSO-$d_6$) δ 10.06 (s, 1H), 8.65 (d, J = 11.1 Hz, 2H), 8.59 (s, 1H), 7.37 (s, 1H), 7.02 (s, 1H), 6.87 (d, J = 8.3 Hz, 1H), 6.40 (dd, J = 16.9, 10.1 Hz, 1H), 6.21 (dd, J = 16.9, 2.1 Hz, 1H), 5.74 (dd, J = 10.1, 2.1 Hz, 1H), 4.97 (p, J = 6.3 Hz, 1H), 4.25 (s, 2H), 3.79 (s, 3H), 3.06-2.82 (m, 6H), 2.72 (s, 3H), 2.41 (s, 3H), 2.31 (t, J = 5.9 Hz, 2H), 2.20 (s, 6H), 1.20 (d, J = 6.2 Hz, 6H). |
| 26 | (DMSO-$d_6$) δ 9.34 (s, 1H), 8.55 (d, J = 9.4 Hz, 2H), 7.56 (s, 1H), 7.40-7.12 (m, 1H), 6.76 (s, 1H), 6.58-6.42 (m, 2H), 6.17 (dd, J = 17.0, 2.2 Hz, 1H), 5.69 (dd, J = 10.2, 2.2 Hz, 1H), 4.97 (p, J = 6.2 Hz, 1H), 4.08-3.92 (m, 2H), 3.78 (s, 3H), 3.21 (t, J = 8.5 Hz, 3H), 2.68 (p, J = 7.5 Hz, 1H), 2.32 (s, 3H), 2.17 (s, 6H), 2.10-1.94 (m, 1H), 1.73 (p, J = 9.2 Hz, 1H), 1.22 (d, J = 6.3 Hz, 6H), 1.12 (d, J = 2.8 Hz, 2H), 1.07 (d, J = 3.1 Hz, 2H). |
| 27 | (DMSO-$d_6$) δ 10.07 (s, 1H), 8.77 (s, 1H), 8.57 (s, 1H), 8.53 (s, 1H), 7.21 (s, 1H), 7.00 (s, 1H), 6.83 (d, J = 8.3 Hz, 1H), 6.41 (dd, J = 16.9, 10.1 Hz, 1H), 6.23 (dd, J = 16.9, 2.2 Hz, 1H), 5.75 (dd, J = 10.0, 2.2 Hz, 1H), 5.00-4.85 (m, 1H), 3.87 (s, 2H), 2.87 (d, J = 6.0 Hz, 2H), 2.72 (s, 3H), 2.38 (s, 3H), 2.30 (t, J = 5.8 Hz, 2H), 2.20 (s, 6H), 1.26 (s, 6H), 1.12 (d, J = 6.3 Hz, 6H). |
| 28 | (DMSO-$d_6$) δ 10.06 (s, 1H), 8.90 (s, 1H), 8.59 (s, 1H), 8.32 (s, 1H), 7.13 (d, J = 8.2 Hz, 1H), 7.00 (s, 1H), 6.85 (d, J = 8.2 Hz, 1H), 6.42 (dd, J = 16.9, 10.0 Hz, 1H), 6.24 (dd, J = 16.9. 2.2 Hz, 1H), 5.76 (dd, J = 10.0, 2.2 Hz, 1H), 4.89 (p, J = 6.2 Hz, 1H), 4.61 (p, J = 6.0 Hz, 1H), 3.93 (s, 2H), 2.86 (t, J = 5.8 Hz, 2H), 2.69 (s, 3H), 2.38 (s, 3H), 2.29 (t, J = 5.8 Hz, 2H), 2.20 (s, 6H), 1.36-1.23 (m, 12H), 1.09 (d, J = 6.3 Hz, 6H). |
| 29 | (DMSO-$d_6$) δ 9.78 (s, 1H), 8.68 (s, 1H), 8.55 (s, 1H), 8.36 (s, 1H), 7.24 (s, 1H), 6.84 (d, J = 8.3 Hz, 1H), 6.46 (dd, J = 17.0, 10.1 Hz, 1H), 6.22 (dd, J = 17.0, 2.1 Hz, 1H), 5.75 (dd, J = 10.1, 2.1 Hz, 1H), 4.99-4.86 (m, 1H), 3.83 (s, 3H), 3.78 (s, 2H), 3.18 (t, J = 6.7 Hz, 2H), 2.86 (s, 3H), 2.45 (d, J = 6.7 Hz, 2H), 2.39 (s, 3H), 2.19 (s, 6H), 1.25 (s, 6H), 1.14 (d, J = 6.2 Hz, 6H). |
| 30 | (DMSO-$d_6$) δ 10.08 (s, 1H), 8.76 (s, 1H), 8.63 (d, J = 18.3 Hz, 2H), 7.20 (s, 1H), 7.03 (d, J = 19.7 Hz, 2H), 6.44-6.35 (m, 1H), 6.26-6.17 (m, 1H), 5.76 (d, 1H), 4.97-4.83 (m, 1H), 3.91 (s, 2H), 3.80 (s, 3H), 2.87 (t, J = 5.9 Hz, 2H), 2.72 (s, 3H), 2.31 (t, J = 5.9 Hz, 2H), 2.20 (s, 6H), 2.04 (s, 3H), 1.26 (s, 6H), 1.11 (d, J = 6.2 Hz, 6H). |
| 31 | (DMSO-$d_6$) δ 9.52 (s, 1H), 8.64 (s, 1H), 8.53 (s, 1H), 7.78 (s, 1H), 7.24 (s, 1H), 6.84 (s, 1H), 6.45 (dd, J = 17.0, 10.2 Hz, 1H), 6.20 (dd, J = 17.1, 2.1 Hz, 1H), 5.71 (dd, J = 10.1, 2.2 Hz, 1H), 4.94 (p, J = 6.2 Hz, 1H), 4.48-4.37 (m, 1H), 3.81 (s, 3H), 3.73 (s, 2H), 3.60 (dt, J = 9.7, 6.7 Hz, 2H), 2.48-2.43 (m, 1H), 2.39 (s, 3H), 2.18 (s, 6H), 2.16-2.09 (m, 1H), 1.95 (dtd, J = 32.8, 11.1, 10.3, 7.0 Hz, 2H), 1.79 (td, J = 10.6, 8.7, 4.4 Hz, 2H), 1.30-1.22 (m, 6H), 1.15 (d, J = 6.2 Hz, 6H). |
| 32 | (DMSO-$d_6$) δ 10.05 (s, 1H), 8.76 (s, 1H), 8.56 (s, 1H), 8.44 (s, 1H), 7.22 (s, 2H), 6.82 (d. J = 8.3 Hz, 1H), 6.42 (dd, J = 16.9, 10.1 Hz, 1H), 6.23 (dd, J = 16.9, 2.2 Hz, 1H), 5.76 (dd, J = 10.0, 2.2 Hz, 1H), 4.91 (p, J = 6.2 Hz, 1H), 3.93-3.83 (m, 3H), 3.32 (s, 31H), 2.88 (t, J = 5.8 Hz, 2H), 2.72 (s, 3H), 2.38 (s, 3H), 2.33 (t, J = 5.9 Hz, 2H), 2.21 (s, 6H), 1.26 (s, 6H), 1.12 (d, J = 6.3 Hz, 6H), 0.75 (d, J = 5.2 Hz, 1H), 0.65 (t, J = 2.8 Hz, 2H). |
| 33 | ($CDCl_3$) δ 9.41 (s, 1H), 8.66 (s, 1H), 8.43 (s, 1H), 7.70 (s, 1H), 6.93 (s, 1H), 6.83-6.64 (m, 2H), 6.45-6.28 (m, 1H), 6.25-6.15 (m, 1H), 5.69 (dd, J = 9.9, 1.7 Hz, 1H), 5.03-4.78 (m, 1H), 4.13 (s, 2H), 3.80 (d, J = 1.5 Hz, 3H), 2.85 (d, J = 4.8 Hz, 4H), 2.57 (bts, 4H), 2.42 (d, J = 1.4 Hz, 4H), 2.34 (d, J = 1.7 Hz, 3H), 1.37 (d, J = 1.5 Hz, 6H), 1.01 (d, J = 6.2 Hz, 6H). |
| 34 | ($CDCl_3$) δ 9.49 (s, 1H), 8.73 (s, 1H), 8.53 (s, 1H), 7.77 (s, 1H), 7.00 (s, 1H), 6.87-6.72 (m, 2H), 6.41 (dd, J = 16.9, 1.5 Hz, 1H), 6.28 (dd, J = 16.8, 10.0 Hz, 1H), 5.76 (dd, J = 9.9, 1.6 Hz, 1H), 5.00-4.94 (m, 1H), 4.20 (s, 2H), 3.86 (s, 3H), 2.94 (d, J = 4.8 Hz, 4H), 2.67 (s, 4H), 2.54 (br, 4H), 2.49 (s, 3H), 1.44 (s, 6H), 1.17 (t, J = 7.2 Hz, 3H), 1.08 (d, J = 6.3 Hz, 6H). |
| 35 | (DMSO-$d_6$) δ 9.50 (s, 1H), 8.66 (s, 1H), 8.52 (s, 1H), 7.61 (s, 1H), 7.19 (s, 1H), 6.82 (s, 1H), 6.43 (dd, J = 17.0, 10.2 Hz, 1H), 6.20 (dd, J = 17.1, 2.1 Hz, 1H), 5.72 (dd, J = 10.2, 2.1 Hz, 1H), 4.94 (p, J = 6.2 Hz, 1H), 3.79 (s, 3H), 3.71 (s, 2H), 3.57 (dd, J = 10.1, 7.1 Hz, 3H), 3.37 (d, J = 12.1 Hz, 1H), 2.65 (q, J = 7.7, 6.9 Hz, 1H), 2.39 (s, 3H), 2.16 (s, 6H), 2.10-2.03 (m, 1H), 1.69 (p, J = 9.9 Hz, 1H), 1.25 (s, 6H), 1.15 (d, J = 6.2 Hz, 6H). |
| 36 | (DMSO-$d_6$) δ 10.09 (s, 1H), 8.77 (s, 1H), 8.57 (s, 2H), 7.21 (s, 1H), 7.00 (s, 1H), 6.83 (d, J = 8.3 Hz, 1H), 6.41 (dd, J = 16.8, 10.1 Hz, 1H), 6.23 (d, J = 16.8 Hz, 1H), 5.75 (d, J = 10.0 Hz, 1H), 5.01-4.82 (m, 1H), 3.86 (s, 2H), 3.80 (s, 3H), 2.91-2.83 (m, 2H), 2.37 (s, 3H), 2.30 (t, J = 6.0 Hz, 2H), 2.20 (s, 6H), 1.26 (s, 6H), 1.12 (d, J = 6.2 Hz, 6H). |
| 37 | (DMSO-$d_6$) δ 10.09 (s, 1H), 8.84 (s, 1H), 8.58 (s, 1H), 8.47 (s, 1H), 7.17 (s, 1H), 6.99 (s, 1H), 6.84 (d, J = 8.3 Hz, 1H), 6.41 (dd, J = 16.9, 10.0 Hz, 1H), 6.23 (dd, J = 16.9, 2.0 Hz, 1H), 5.77-5.75 (m, 1H), 4.92-4.89 (m, 1H), 4.09-4.04 (m, 2H), 3.90 (s, 2H), 2.86 (t, J = 5.9 Hz, 2H), 2.70 (s, 3H), 2.38 (s, 3H), 2.29 (t, J = 5.8 Hz, 2H), 2.20 (s, 6H), 1.31 (t, J = 6.9 Hz, 3H), 1.27 (s, 6H), 1.10 (d, J = 6.3 Hz, 6H). |
| 38 | (DMSO-$d_6$) δ 10.03 (s, 1H), 8.68 (s, 1H), 8.50 (s, 1H), 8.43 (s, 1H), 7.31 (s, 1H), 7.00 (s, 1H), 6.43 (s, 1H), 6.29-6.18 (m, 1H), 5.93 (d, J = 8.8 Hz, 1H), 5.76 (d, J = 10.0, 2.2 Hz, 1H), 4.98-4.87 (m, 1H), 3.86 (d, J = 7.3 Hz, 4H), 3.77 (d, J = 16.3 Hz, 5H), 2.93-2.86 (m, 2H), 2.71 (s, 3H), 2.31-2.21 (m, 8H), 2.05-1.92 (m, 2H), 1.21-1.16 (m, 12H). |

-continued

| Example No. | $^1H$ NMR |
|---|---|
| 39 | (DMSO-$d_6$) δ 9.00 (s, 1H), 8.54 (s, 1H), 8.52 (brs, 2H), 7.18 (s, 1H), 6.87 (t, J = 4.1 Hz, 2H), 6.65 (dd, J = 16.9, 10.1 Hz, 1H), 6.22 (dd, J = 16.9, 2.0 Hz, 1H), 5.75 (d, J = 10.2 Hz, 1H), 4.91 (p, J = 6.2 Hz, 1H), 3.85 (s, 2H), 3.80 (s, 3H), 2.82 (d, J = 4.8 Hz, 4H), 2.76 (brs, 4H), 2.39 (s, 3H), 1.776-1.68 (m, 1H), 1.26 (s, 6H), 1.11 (d, J = 6.2 Hz, 6H), 0.51-0.41 (m, 2H), 0.37-0.27 (m, 2H). |
| 40 | (DMSO-$d_6$) δ 9.28 (s, 1H), 8.51 (d, J = 14.6 Hz, 2H), 7.60 (s, 1H), 7.23 (s, 1H), 6.88 (d, J = 8.3 Hz, 1H), 6.49 (dd, J = 17.0, 10.2 Hz, 1H), 6.25-6.00 (m, 2H), 5.69 (dd, J = 10.1, 2.2 Hz, 1H), 4.93 (p, J = 6.2 Hz, 1H), 3.97 (t, J = 7.0 Hz, 2H), 3.77 (s, 3H), 3.73 (s, 2H), 3.55 (t, J = 6.7 Hz, 2H), 3.06 (p, J = 6.4 Hz, 1H), 2.39 (s, 4H), 2.08 (s, 6H), 1.24 (s, 6H), 1.15 (d, J = 6.2 Hz, 6H). |
| 41 | (DMSO-$d_6$) δ 10.00 (s, 1H), 8.84 (s, 1H), 8.70-8.42 (m, 2H), 7.23 (s, 1H), 6.90 (s, 1H), 6.79 (d, J = 8.3 Hz, 1H), 6.42 (dd, J = 16.9, 10.1 Hz, 1H), 6.29-6.16 (m, 1H), 5.88-5.47 (m, 1H), 4.92 (p, J = 6.2 Hz, 1H), 3.89-3.82 (m, 2H), 3.79 (d, J = 0.9 Hz, 3H), 3.08-3.00 (m, 1H), 2.85-2.76 (m, 1H), 2.76 (s, 3H), 2.72-2.64 (m, 2H), 2.37 (s, 3H), 2.35-2.27 (m, 1H), 1.99-1.86 (m, 1H), 1.73-1.55 (m, 2H), 1.40-1.32 (m, 1H), 1.25 (d, J = 3.5 Hz, 6H), 1.13 (dd, J = 6.3, 3.3 Hz, 6H). |
| 42 | (DMSO-$d_6$) δ 10.13 (s, 1H), 8.77 (s, 1H), 8.57 (d, J = 1.5 Hz, 2H), 7.21 (s, 1H), 7.01 (s, 1H), 6.83 (d, J = 8.3 Hz, 1H), 6.40 (dd, J = 16.9, 10.0 Hz, 1H), 6.23 (dd, J = 16.9, 2.2 Hz, 1H), 5.76 (dd, J = 10.0, 2.2 Hz, 1H), 4.91 (p, J = 6.2 Hz, 1H), 3.86 (s, 2H), 3.80 (s, 3H), 2.87 (t, J = 5.9 Hz, 2H), 2.72 (s, 3H), 2.37 (s, 3H), 2.30 (t, J = 5.9 Hz, 2H), 1.26 (s, 6H), 1.12 (d, J = 6.2 Hz, 6H). |
| 43 | (DMSO-$d_6$) δ 9.54 (s, 1H), 8.67 (s, 1H), 8.53 (s, 1H), 7.78 (s, 1H), 7.22 (s, 1H), 6.84 (s, 1H), 6.45 (dd, J = 17.0, 10.2 Hz, 1H), 6.20 (dd, J = 17.1, 2.1 Hz, 1H), 5.71 (dd, J = 10.1, 2.1 Hz, 1H), 4.94 (p, J = 6.2 Hz, 1H), 4.42 (d, J = 7.1 Hz, 1H), 3.81 (s, 3H), 3.72 (s, 2H), 3.63-3.58 (m, 1H), 3.28-3.22 (m, 1H), 2.46 (dd, J = 11.5, 4.0 Hz, 1H), 2.39 (s, 3H), 2.18 (s, 6H), 2.13 (t, J = 10.6 Hz, 1H), 2.03-1.97(m, 1H), 1.95-1.89 (m, 1H), 1.83-1.78 (m, 2H), 1.25 (s, 6H), 1.15 (d, J = 6.2 Hz, 6H). |
| 44 | (MeOH-$d_4$) δ 9.03 (s, 1H), 8.63 (s, 1H), 7.22 (d, J = 8.4 Hz, 1H), 6.96 (s, 1H), 6.81 (d, J = 8.3 Hz, 1H), 6.51 (dd, J = 16.8, 10.1 Hz, 1H), 6.31 (dd, J = 17.0, 1.8 Hz, 1H), 5.79 (dd, J = 10.1, 1.8 Hz, 1H), 5.00 (p, J = 6.2 Hz, 1H), 4.27 (s, 2H), 3.91 (s, 3H), 3.06 (dd, J = 13.0, 6.8 Hz, 2H), 2.81 (dd, J = 12.9, 6.5 Hz, 1H), 2.74 (s, 3H), 2.58 (t, J = 7.2 Hz, 1H), 2.46 (s, 3H), 2.39 (s, 3H), 2.02 (dq, J = 12.6, 8.4 Hz, 2H), 1.76 (q, J = 8.8, 7.1 Hz, 2H), 1.65-1.47 (m, 2H), 1.21 (s, 3H), 1.19 (s, 3H), 1.13 (q, J = 4.1 Hz, 2H). |
| 45 | (DMSO-$d_6$) δ 10.24 (s, 1H), 8.78 (s, 1H), 8.53 (d, J = 3.5 Hz, 2H), 7.15 (br, 1H), 6.98 (s, 1H), 6.75 (d, J = 8.3 Hz, 1H), 6.29 (dd, J = 16.9, 9.9 Hz, 1H), 6.16 (dd, J = 16.8, 2.1 Hz, 1H), 5.69 (dd, J = 10.0, 2.1 Hz, 1H), 4.88-4.82 (m, 1H), 3.81 (s, 2H), 3.73 (s, 3H), 3.03-2.79 (m, 4H), 2.30 (s, 3H), 2.11 (s, 9H), 1.20 (s, 6H), 1.06 (d, J = 6.2 Hz, 6H), 0.79 (t, J = 7.0 Hz, 3H). |
| 46 | (DMSO-$d_6$) δ 10.21 (s, 1H), 8.72 (s, 2H), 8.55 (s, 1H), 7.22 (s, 1H), 6.80 (s, 1H), 6.39 (dd, J = 17.0, 10.1 Hz, 1H), 6.23 (dd, J = 17.0, 2.2 Hz, 1H), 5.77 (dd, J = 10.0, 2.2 Hz, 1H), 4.94 (h, J = 6.2 Hz, 1H), 3.84 (s, 3H), 3.78 (d, J = 2.4 Hz, 2H), 3.29-3.20 (m, 1H), 3.13-3.05 (m, 1H), 2.98-2.91 (m, 1H), 2.89 (s, 3H), 2.78 (s, 1H), 2.53 (d, J = 3.2 Hz, 1H), 2.47 (s, 3H), 2.38 (s, 3H), 2.35-2.27 (m, 1H), 1.99-1.89 (m, 1H), 1.71-1.59 (m, 2H), 1.42-1.39 (m, 1H), 1.25 (s, 6H), 1.14 (dd, J = 6.2, 3.8 Hz, 6H). |
| 47 | (DMSO-$d_6$) δ 10.09 (s, 1H), 8.76 (s, 1H), 8.57 (d, J = 3.9 Hz, 2H), 7.22 (s, 1H), 7.01 (s, 1H), 6.83 (d, J = 8.2 Hz, 1H), 6.41 (dd, J = 16.9, 10.1 Hz, 1H), 6.22 (dd, J = 16.9, 2.2 Hz, 1H), 5.76 (dd, J = 9.9, 2.2 Hz, 1H), 4.92 (p, J = 6.2 Hz, 1H), 3.80 (s, 3H), 2.87 (t, J = 5.8 Hz, 2H), 2.72 (s, 3H), 2.37 (s, 3H), 2.30 (t, J = 5.9 Hz, 2H), 2.20 (s, 6H), 1.26 (s, 6H), 1.12 (d, J = 6.2 Hz, 6H). |
| 48 | (DMSO-$d_6$) δ 9.47 (s, 1H), 8.54 (d, J = 13.2 Hz, 2H), 8.29 (s, 1H), 7.23 (s, 1H), 6.85 (d, J = 8.2 Hz, 1H), 6.77 (s, 1H), 6.56 (dd, J = 17.0, 10.1 Hz, 1H), 6.20 (dd, J = 17.0, 2.1 Hz, 1H), 5.71 (dd, J = 10.2, 2.1 Hz, 1H), 4.97-4.86 (m, 1H), 3.78 (s, 3H), 3.66 (s, 1H), 3.42-3.38 (m, 1H), 2.93 (q, J = 7.6 Hz, 1H), 2.38 (s, 3H), 2.27-2.23(m, 1H), 2.17-2.05 (m, 8H), 1.90-1.86 (m, 2H), 1.70-1.66 (m, 1H), 1.25 (s, 6H), 1.13 (dd, J = 6.2, 4.5 Hz, 6H). |
| 49 | (DMSO-$d_6$) δ 9.33 (s, 1H), 8.50 (d, J = 27.4 Hz, 2H), 7.75 (s, 1H), 7.22 (s, 1H), 6.86 (d, J = 8.2 Hz, 1H), 6.58-6.45 (m, 2H), 6.19 (dd, J = 17.0, 2.1 Hz, 1H), 5.70 (dd, J = 10.2, 2.1 Hz, 1H), 4.92 (p, J = 6.3 Hz, 1H), 3.79 (s, 3H), 3.43-3.37 (m, 1H), 3.23-3.13 (m, 3H), 2.72-2.64 (m, 1H), 2.39 (s, 3H), 2.17 (s, 6H), 2.12-2.04 (m, 1H), 1.74 (q, J = 10.4, 9.7 Hz, 1H), 1.25 (s, 6H), 1.13 (dd, J = 6.3, 2.1 Hz, 6H). |
| 50 | (DMSO-$d_6$) δ 9.27 (s, 1H), 8.51 (d, J = 16.2 Hz, 2H), 7.59 (s, 1H), 7.24 (s, 1H), 6.88 (d, J = 8.2 Hz, 1H), 6.49 (dd, J = 17.0, 10.2 Hz, 1H), 6.24-6.13 (m, 2H), 5.69 (dd, J = 10.2, 2.2 Hz, 1H), 4.94 (p, J = 6.2 Hz, 1H), 3.97 (t, J = 7.0 Hz, 2H), 3.77 (s, 3H), 3.55 (t, J = 6.7 Hz, 2H), 3.10-3.02 (m, 1H), 2.39 (s, 3H), 2.08 (s, 6H), 1.24 (s, 6H), 1.15 (d, J = 6.2 Hz, 6H). |
| 51 | (DMSO-$d_6$) δ 9.47 (s, 1H), 8.62 (s, 1H), 8.56 (s, 1H), 8.08 (s, 1H), 7.37 (s, 1H), 6.77 (s, 1H), 6.55 (dd, J = 16.9, 10.2 Hz, 1H), 6.17 (dd, J = 17.1, 2.1 Hz, 1H), 5.70 (dd, J = 10.1, 2.1 Hz, 1H), 4.97 (p, J = 6.2 Hz, 1H), 4.04 (s, 2H), 3.77 (s, 3H), 3.69 (s, OH), 2.93 (td, J = 9.0, 8.5, 5.3 Hz, 1H), 2.31 (s, 3H), 2.12 (s, 6H), 1.95-1.79 (m, 1H), 1.68 (dq, J = 13.8. 7.2 Hz, 1H), 1.22 (d, J = 6.3 Hz, 6H), 1.12 (t, J = 2.9 Hz, 2H), 1.06 (q, J = 4.6, 3.8 Hz, 2H). |

-continued

| Example No. | $^1$H NMR |
|---|---|
| 52 | (DMSO-$d_6$) δ 10.01 (s, 1H), 8.83 (s, 1H), 8.58 (d, J = 18.9 Hz, 2H), 7.24 (s, 1H), 6.90 (s, 1H), 6.79 (d, J = 8.2 Hz, 1H), 6.43 (dd, J = 16.9, 10.1 Hz, 1H), 6.23 (dd, J = 16.9, 2.2 Hz, 1H), 5.77 (dd, J = 10.0, 2.2 Hz, 1H), 4.93 (p, J = 6.2 Hz, 1H), 3.80 (s, 3H), 3.08-3.00 (m, 1H), 2.76 (s, 4H), 2.71-2.64 (m, 2H), 2.49 (s, 3H), 2.37 (s, 3H), 2.35-2.27 (m, 1H), 1.99-1.89 (m, 1H), 1.74-1.55 (m, 2H), 1.36 (td, J = 8.6, 4.2 Hz, 1H), 1.25 (d, J = 3.6 Hz, 6H), 1.14 (dd, J = 6.2, 3.3 Hz, 6H). |
| 53 | (DMSO-$d_6$) δ 9.01 (s, 1H), 8.54 (d, J = 17.6 Hz, 3H), 7.19 (s, 1H), 6.87 (s, 2H), 6.65 (dd, J = 16.9, 10.2 Hz, 1H), 6.22 (dd, J = 17.0, 2.0 Hz, 1H), 5.79-5.71 (m, 1H), 4.91 (p, J = 6.2 Hz, 1H), 3.80 (s, 3H), 2.89-2.70 (m, 8H), 2.39 (s, 3H), 1.72 (s, 1H), 1.26 (s, 6H), 1.11 (d, J = 6.1 Hz, 6H), 0.51-0.42 (m, 2H), 0.33 (d, J = 2.9 Hz, 2H). |
| 56 | (DMSO-$d_6$) δ 9.62 (s, 1H), 8.93 (s, 1H), 8.61 (d, J = 13.1 Hz, 2H), 8.32 (s, 1H), 7.30 (s, 1H), 6.98 (s, 1H), 6.91 (d, J = 8.2 Hz, 1H), 6.65 (dd, J = 16.9, 10.2 Hz, 1H), 6.29 (dd, J = 17.0, 1.9 Hz, 1H), 5.90-5.75 (m, 1H), 4.93 (p, J = 6.3 Hz, 1H), 3.84 (d, J = 15.2 Hz, 5H), 3.33 (t, J = 6.3 Hz, 2H), 3.22 (d, J = 5.5 Hz, 2H), 3.14 (s, 4H), 2.64 (s, 3H), 2.40 (s, 3H), 1.27 (s, 6H), 1.15 (t, J = 7.5 Hz, 12H). |
| 57 | (DMSO-$d_6$) δ 10.10 (s, 1H), 8.73 (d, J = 8.5 Hz, 2H), 8.63 (s, 1H), 7.37 (s, 1H), 7.05 (d, J = 20.0 Hz, 2H), 6.51-6.35 (m, 1H), 6.28-6.17 (m, 1H), 5.80-5.70 (m, 1H), 5.02-4.87 (m, 1H), 3.92 (s, 2H), 3.81 (s, 3H), 2.88 (t, J = 5.8 Hz, 2H), 2.72 (s, 3H), 2.32 (t, J = 5.8 Hz, 2H), 2.21 (s, 6H), 1.28 (s, 7H), 1.16 (d, J = 6.2 Hz, 6H). |
| 58 | (DMSO-$d_6$) δ 9.19 (s, 1H), 8.54 (d, J = 13.4 Hz, 2H), 8.26 (s, 1H), 7.19 (s, 1H), 6.86 (d, J = 8.2 Hz, 1H), 6.73 (s, 1H), 6.55 (dd, J = 17.0, 10.2 Hz, 1H), 6.22 (d, J = 17.0 Hz, 1H), 5.74 (d, J = 10.2 Hz, 1H), 4.91 (p, J = 6.2 Hz, 1H), 3.81 (d, J = 6.7 Hz, 5H), 3.26-3.23 (m, 4H), 2.77 (d, J = 8.9 Hz, 4H), 2.39 (s, 3H), 2.26 (s, 3H), 1.26 (s, 7H), 1.12 (d, J = 6.3 Hz, 7H). |
| 59 | (DMSO-$d_6$) δ 9.64 (s, 1H), 8.79 (s, 1H), 8.54 (s, 1H), 7.79 (s, 1H), 7.24 (s, 1H), 6.83 (s, 1H), 6.51 (t. J = 14.1 Hz, 1H), 6.22 (dd, J = 17.0, 2.1 Hz, 1H), 5.74 (d, J = 10.2 Hz, 1H), 5.35 (d, J = 53.4 Hz, 1H), 4.96 (p, J = 6.2 Hz, 1H), 4.66 (s, 1H), 3.84 (s, 3H), 3.71 (s, 3H), 2.98-2.62 (m, 4H), 2.44 (s, 2H), 2.37 (s, 3H), 2.20 (s, 3H), 2.00 (d, J = 7.5 Hz, 2H), 1.24 (s, 6H), 1.17 (d, J = 6.2 Hz, 6H). |
| 60 | (DMSO-$d_6$) δ 10.21 (s, 0H), 9.35 (s, 1H), 8.56 (d, J = 5.4 Hz, 2H), 7.32-7.10 (m, 1H), 7.00-6.75 (m, 3H), 6.23 (dd, J = 17.0, 2.2 Hz, 1H), 5.74 (dd, J = 10.2, 2.1 Hz, 1H), 4.91 (p, J = 6.2 Hz, 1H), 3.84 (s, 2H), 3.83 (s, 3H), 3.20 (d, J = 10.6 Hz, 1H), 2.77 (brs, 4H), 2.39 (s, 3H), 2.03-1.88 (m, 3H), 1.71 (brs, 1H), 1.26 (d, J = 2.1 Hz, 6H), 1.12 (dd, J = 6.3, 1.7 Hz, 6H). |
| 61 | (DMSO-$d_6$) δ 10.26 (s, 0H), 9.34 (s, 1H), 8.56 (d, J = 5.7 Hz, 2H), 7.25-7.10 (m, 1H), 7.00-6.85 (m, 3H), 6.23 (dd, J = 17.0, 2.1 Hz, 1H), 5.74 (dd, J = 10.2, 2.1 Hz, 1H), 4.91 (p, J = 6.2 Hz, 1H), 3.84 (s, 2H), 3.83 (s, 3H), 3.19 (d, J = 10.8 Hz, 1H), 2.78 (brs, 4H), 2.39 (s, 3H), 2.15-1.85 (m, 3H), 1.71 (brs, 1H), 1.26 (d, J = 2.1 Hz, 6H), 1.12 (dd, J = 6.3, 1.9 Hz, 6H). |
| 62 | (DMSO-$d_6$) δ 10.02 (s, 1H), 8.86 (brs 1H), 8.61 (s, 1H), 8.56 (s, 1H), 7.23 (s, 1H), 6.90 (s, 1H), 6.79 (d, J = 8.3 Hz, 1H), 6.42 (dd, J = 16.8, 10.1 Hz, 1H), 6.23 (dd, J = 17.0, 2.2 Hz, 1H), 5.77 (dd, J = 10.0, 2.2 Hz, 1H), 4.92 (p, J = 6.2 Hz, 1H), 3.92-3.81 (m, 2H), 3.80 (s, 3H), 3.08-2.98 (m, J, 1H), 2.85-2.74 (m, 4H), 2.71-2.64 (m, 2H), 2.37 (s, 3H), 2.36-2.27 (m, 1H), 2.01-1.85 (m, 1H), 177-1.55 (m, 2H), 1.40-1.30 (m, 1H), 1.25 (d, J = 3.7 Hz, 6H), 1.13 (dd, J = 6.3, 3.6 Hz, 6H). |
| 63 | (DMSO-$d_6$) δ 9.31 (s, 1H), 8.56 (d, J = 6.4 Hz, 2H), 8.04 (s, 1H), 7.23 (s, 1H), 6.85 (d, J = 8.7 Hz, 1H), 6.74 (s, 1H), 6.58 (dd, J = 17.0, 10.2 Hz, 1H), 6.20 (dd, J = 16.9, 2.2 Hz, 1H), 5.71 (dd, J = 10.1, 2.1 Hz, 1H), 5.34 (d, J = 54.3 Hz, 1H), 4.92 (p, J = 6.2 Hz, 1H), 4.05-3.98 (m, 1H), 3.86 (dd, J = 12.5, 3.7 Hz, 1H), 3.80 (d, J = 2.4 Hz, 1H), 3.78 (d, J = 3.0 Hz, 3H), 3.43-3.37 (m, 1H), 3.05 (dd, J = 26.9, 12.2 Hz, 1H), 2.46-2.41 (m, 1H), 2.38 (s, 3H), 2.34-2.32 (m, 1H), 2.15 (s, 6H), 2.03-1.97 (m, 1H), 1.93-1.88 (m, 1H), 1.25 (s, 6H), 1.14 (dd, J = 6.2, 4.0 Hz, 6H). |
| 64 | (DMSO-$d_6$) δ 9.30 (s, 1H), 8.66 (s, 1H), 8.55 (s, 1H), 7.82 (s, 1H), 7.36 (s, 1H), 6.74 (s, 2H), 6.57 (dd, J = 17.0, 10.2 Hz, 1H), 6.18 (dd, J = 16.9, 2.1 Hz, 1H), 5.70 (dd, J = 10.1, 2.1 Hz, 1H), 5.34 (d, J = 54.5 Hz, 1H), 4.98 (p, J = 6.2 Hz, 1H), 4.01 (s, 3H), 3.76 (s, 3H), 3.42-3.37 (m, 1H), 3.05 (dd, J = 26.9, 12.3 Hz, 1H), 2.44 (d. J = 5.6 Hz, 1H), 2.37 (dd, J = 12.0, 3.4 Hz, 1H), 2.31 (d, J = 8.2 Hz, 3H), 2.15 (s, 6H), 2.01 (t, J = 7.8 Hz, 1H), 1.90 (s, 1H), 1.23 (d, J = 6.3 Hz, 6H), 1.16-1.01 (m, 4H). |
| 66 | (DMSO-$d_6$) δ 9.79 (s, 1H), 8.72 (s, 1H), 8.58 (d, J = 5.7 Hz, 2H), 7.22 (s, 1H), 7.00 (s, 1H), 6.83 (d, J = 8.3 Hz, 1H), 6.47 (dd, J = 16.9, 10.2 Hz, 1H), 6.22 (dd, J = 17.0, 2.0 Hz, 1H), 5.75 (dd, J = 10.0, 2.1 Hz, 1H), 4.92 (q, J = 6.2 Hz, 1H), 3.86 (s, 2H), 3.81 (s, 3H), 3.33 (d, J = 2.3 Hz, 3H), 2.95 (t, J = 6.1 Hz, 2H), 2.71 (s, 3H), 2.47 (t, J = 6.5 Hz, 6H), 2.38 (s, 3H), 1.72 (q, J = 3.3 Hz, 4H), 1.26 (s, 6H), 1.12 (d, J = 6.2 Hz, 6H). |
| 67 | (DMSO-$d_6$) δ 10.76 (s, 1H), 9.78 (s, 1H), 8.77-8.34 (m, 3H), 7.17 (dd, J = 17.0, 10.1 Hz, 1H), 6.97 (d, J = 8.3 Hz, 1H), 6.88 (s, 1H), 6.25 (dd, J = 17.0, 2.2 Hz, 1H), 5.74 (dd, J = 10.1, 2.2 Hz, 1H), 4.93 (p, J = 6.2 Hz, 1H), 4.01 (ddd, J = 16.3, 11.0, 6.1 Hz, 4H), 3.84 (d, J = 3.8 Hz, 5H), 3.37-3.32 (m, 6H), 3.14 (t, J = 5.5 Hz, 2H), 2.54 (s, 3H), 2.41 (s, 3H), 1.27 (s, 6H), 1.13 (d, J = 6.3 Hz, 6H). |
| 68 | (DMSO-$d_6$) δ 10.09 (s, 1H), 8.69 (s, 1H), 8.57 (s, 1H), 7.35 (s, 1H), 7.01 (s, 1H), 6.71 (d, J = 8.0 Hz, 1H), 6.40 (dd, J = 16.8, 10.0 Hz, 1H), 6.20 (dd, J = 16.9, 2.1 Hz, 1H), 5.75 (dd, J = 10.1, 2.1 Hz, 1H), 5.32 (t, J = 4.9 Hz, 1H), 4.97 (p, J = 6.2 Hz, 1H), 4.07 (s, 2H), 3.79 (s, 3H), 2.88 (t, J = 5.9 Hz, 2H), 2.30 (s, 3H), 2.20 (s, 6H), 1.99 (dt, J = 13.2, 6.9 Hz, 3H), 1.23 (s, 2H), 1.21 (s, 3H), 1.12 (t, J = 3.0 Hz, 2H), 1.06 (t, J = 3.1 Hz, 2H). |

-continued

| Example No. | $^1$H NMR |
|---|---|
| 69 | (DMSO-$d_6$) δ 10.12 (s, 1H), 8.69 (s, 1H), 8.57 (s, 2H), 7.35 (s, 1H), 7.02 (s, 1H), 6.71 (d, J = 9.4 Hz, 1H), 6.40 (dd, J = 16.9, 10.1 Hz, 1H), 6.20 (dd, J = 16.9, 2.2 Hz, 1H), 5.75 (dd, J = 10.1, 2.2 Hz, 1H), 5.32 (t, J = 4.8 Hz, 0H), 4.97 (p, J = 6.2 Hz, 1H), 4.07 (s, 2H), 3.79 (s, 3H), 2.87 (t, J = 5.8 Hz, 2H), 2.30 (s, 4H), 1.99 (dt, J = 13.3, 7.0 Hz, 2H), 1.23 (s, 2H), 1.21 (s, 3H), 1.12 (t, J = 2.9 Hz, 2H), 1.06 (t, J = 3.0 Hz, 2H). |
| 70 | (DMSO-$d_6$) δ 9.01 (s, 1H), 8.62 (d, J = 15.3 Hz, 2H), 8.46 (s, 1H), 7.12 (t, J = 16.0 Hz, 2H), 6.85 (s, 1H), 6.63 (dd, J = 16.9, 10.2 Hz, 1H), 6.22 (dd, J = 16.9, 2.0 Hz, 1H), 5.74 (dd, J = 10.2, 2.1 Hz, 1H), 4.90 (p, J = 6.2 Hz, 1H), 3.85 (d, J = 30.9 Hz, 5H), 2.87 (t, J = 4.6 Hz, 4H), 2.54 (s, 4H), 2.26 (s, 3H), 2.05 (s, 3H), 1.27 (s, 6H), 1.10 (d, J = 6.3 Hz, 6H). |
| 71 | (DMSO-$d_6$) δ 10.10 (s, 1H), 8.76 (s, 1H), 8.58 (d, J = 4.6 Hz, 2H), 7.22 (s, 1H), 7.01 (s, 1H), 6.83 (d, J = 8.3 Hz, 1H), 6.41 (dd, J = 16.9, 10.1 Hz, 1H), 6.23 (dd, J = 17.0, 2.2 Hz, 1H), 5.76 (dd, J = 9.9, 2.2 Hz, 1H), 4.92 (p, J = 6.2 Hz, 1H), 3.80 (s, 3H), 2.87 (t, J = 5.9 Hz, 2H), 2.37 (s, 3H), 2.31 (t, J = 5.9 Hz, 2H), 2.20 (s, 6H), 1.25 (s, 6H), 1.12 (d, J = 6.2 Hz, 6H). |
| 72 | (DMSO-$d_6$) δ 10.13 (s, 1H), 8.76 (s, 1H), 8.57 (d, J = 2.7 Hz, 2H), 7.21 (s, 1H), 7.00 (s, 1H), 6.83 (d, J = 8.2 Hz, 1H), 6.41 (dd, J = 17.0, 10.0 Hz, 1H), 6.23 (dd, J = 17.0, 2.2 Hz, 1H), 5.76 (dd, J = 10.0, 2.2 Hz, 1H), 4.91 (p, J = 6.2 Hz, 1H), 3.86 (s, 2H), 2.87 (t, J = 5.8 Hz, 2H), 2.37 (s, 3H), 2.31 (q, J = 5.7, 4.8 Hz, 2H), 1.26 (s, 6H), 1.12 (d, J = 6.2 Hz, 6H). |
| 73 | (DMSO-$d_6$) δ 10.10 (s, 1H), 8.76 (s, 1H), 8.57 (d, J = 1.9 Hz, 2H), 7.21 (s, 1H), 7.01 (s, 1H), 6.83 (d, J = 8.3 Hz, 1H), 6.41 (dd, J = 16.9, 10.0 Hz, 1H), 6.23 (dd, J = 17.0, 2.2 Hz, 1H), 5.76 (dd, J = 10.0, 2.2 Hz, 1H), 4.91 (p, J = 6.2 Hz, 1H), 3.86 (s, 2H), 3.80 (s, 3H), 2.88 (t, J = 5.6 Hz, 2H), 2.72 (s, 3H), 2.37 (s, 3H), 2.35-2.28 (m, 2H), 2.21 (s, 6H), 1.12 (d, J = 6.2 Hz, 6H). |
| 74 | (DMSO-$d_6$) δ 9.36 (s, 1H), 8.59 (d, J = 20.4 Hz, 2H), 7.68 (s, 1H), 7.14 (d, J = 55.1 Hz, 2H), 6.57-6.44 (m, 2H), 6.24-6.09 (m, 1H), 5.74-5.65 (m, 1H), 4.99-4.85 (m, 1H), 3.78 (d, J = 7.1 Hz, 5H), 3.31-3.04 (m, 4H), 2.68 (t, J = 7.9 Hz, 1H), 2.17 (s, 6H), 2.05 (s, 4H), 1.80-1.66 (m, 1H), 1.25 (s, 6H), 1.13 (d, 6H). |
| 75 | (DMSO-$d_6$) δ 9.02 (d, J = 3.5 Hz, 1H), 8.61 (dd, J = 10.1, 3.6 Hz, 2H), 8.56-8.37 (m, 1H), 7.30-7.04 (m, 2H), 6.86 (d, J = 3.6 Hz, 1H), 6.65 (ddd, J = 15.9, 10.2, 3.6 Hz, 1H), 6.22 (dd, J = 16.9, 3.2 Hz, 1H), 5.75 (dd, J = 10.3, 3.1 Hz, 1H), 4.91 (dt, J = 11.2, 5.8 Hz, 1H), 3.84 (dd, J = 40.1, 3.5 Hz, 5H), 2.91-2.67 (m, 8H), 2.04 (d, J = 3.7 Hz, 3H), 1.76-1.67 (m, 1H), 1.27 (d, J = 3.5 Hz, 6H), 1.20-1.01 (m, 6H), 0.39 (dt, J = 50.3, 3.7 Hz, 4H). |
| 76 | (DMSO-$d_6$) δ 9.30 (s, 1H), 8.58 (d, J = 15.8 Hz, 2H), 7.60 (s, 1H), 7.23 (s, 1H), 7.10 (d, J = 8.2 Hz, 1H), 6.49 (dd, J = 17.0, 10.2 Hz, 1H), 6.28-6.12 (m, 2H), 5.70 (dd, J = 10.2, 2.1 Hz, 1H), 4.93 (p, J = 6.2 Hz, 1H), 3.97 (t, J = 7.1 Hz, 2H), 3.78 (d, J = 2.9 Hz, 5H), 3.57 (t, J = 6.7 Hz, 2H), 3.08 (q, J = 6.4 Hz, 1H), 2.07 (d, J = 13.8 Hz, 9H), 1.25 (s, 6H), 1.13 (d, J = 6.2 Hz, 6H). |
| 77 | (DMSO-$d_6$) δ 10.13 (s, 1H), 8.77 (s, 1H), 8.58 (d, J = 2.5 Hz, 2H), 7.21 (s, 1H), 7.00 (s, 1H), 6.83 (d, J = 8.0 Hz, 1H), 6.40 (dd, J = 16.9, 10.0 Hz, 1H), 6.23 (dd, J = 16.9, 2.2 Hz, 1H), 5.76 (dd, J = 10.0, 2.2 Hz, 1H), 4.91 (p, J = 6.2 Hz, 1H), 3.86 (s, 2H), 3.80 (s, 3H), 2.86 (t, J = 5.9 Hz, 2H), 2.37 (s, 3H), 2.30 (t, J = 5.8 Hz, 2H), 1.26 (s, 6H), 1.12 (d, J = 6.2 Hz, 6H) |
| 78 | (DMSO-$d_6$) δ 10.12 (s, 1H), 8.76 (s, 1H), 8.57 (s, 2H), 7.22 (s, 1H), 7.00 (s, 1H), 6.83 (d, J = 8.1 Hz, 1H), 6.40 (dd, J = 16.9, 10.0 Hz, 1H), 6.22 (dd, J = 16.9, 2.2 Hz, 1H), 5.76 (dd, J = 10.0, 2.2 Hz, 1H), 4.92 (p, J = 6.2 Hz, 1H), 3.80 (s, 3H), 2.86 (t, J = 5.9 Hz, 2H), 2.37 (s, 3H), 2.30 (t, J = 5.9 Hz, 2H), 1.26 (s, 6H), 1.12 (d, J = 6.2 Hz, 6H). |
| 79 | (DMSO-$d_6$) δ 9.49 (s, 1H), 8.62 (d, J = 27.6 Hz, 2H), 8.23 (s, 1H), 7.23 (s, 1H), 7.07 (d, J = 8.4 Hz, 1H), 6.77 (s, 1H), 6.56 (dd, J = 17.0, 10.2 Hz, 1H), 6.20 (dd, J = 16.9, 2.2 Hz, 1H), 5.71 (dd, J = 10.2, 2.1 Hz, 1H), 4.92 (p, J = 6.2 Hz, 1H), 3.85 (d, J = 2.2 Hz, 2H), 3.77 (s, 3H), 3.68 (t, J = 6.2 Hz, 1H), 3.41 (dt, J = 9.9, 6.7 Hz, 2H), 2.94 (td, J = 9.2, 8.6, 5.4 Hz, 1H), 2.26 (d, J = 4.9 Hz, 2H), 2.12 (s, 6H), 2.04 (s, 3H), 1.95-1.83 (m, 2H), 1.67 (dt, J = 13.8, 6.9 Hz, 1H), 1.26 (d, J = 2.1 Hz, 6H), 1.12 (dd, J = 6.3, 4.1 Hz, 6H). |
| 80 | (DMSO-$d_6$) δ 10.08 (s, 1H), 8.81 (s, 1H), 8.56 (d, J = 2.7 Hz, 2H), 7.18 (s, 1H), 7.01 (s, 1H), 6.40 (dd, J = 16.9, 10.0 Hz, 1H), 6.22 (dd, J = 16.9, 2.2 Hz, 1H), 5.75 (dd, J = 10.0, 2.2 Hz, 1H), 4.92 (p, J = 6.2 Hz, 1H), 3.88 (s, 2H), 3.81 (s, 3H), 2.86 (t, J = 5.8 Hz, 2H), 2.81 (t, J = 7.6 Hz, 2H), 2.71 (s, 3H), 2.69 (d, J = 7.7 Hz, 2H), 2.31 (t, J = 5.9 Hz, 2H), 2.20 (s, 6H), 2.08-1.97 (m, 2H), 1.25 (s, 6H), 1.14 (d, J = 6.2 Hz, 6H). |
| 81 | (DMSO-$d_6$) δ 10.20 (s, 1H), 9.06 (s, 1H), 8.72 (s, 1H), 8.58 (s, 1H), 7.26 (s, 1H), 7.24-6.99 (m, 2H), 6.88-6.75 (m, 1H), 6.43 (dd, J = 16.9, 10.1 Hz, 1H), 6.25 (dd, J = 16.9, 2.1 Hz, 1H), 5.80 (dd, J = 10.0, 2.1 Hz, 1H), 4.94 (p, J = 6.2 Hz, 1H), 3.80 (s, 2H), 2.85 (t, J = 5.7 Hz, 2H), 2.71 (s, 3H), 2.37 (s, 3H), 2.34 (t, J = 5.8 Hz, 2H), 2.21 (s, 6H), 1.24 (s, 6H), 1.14 (d, J = 6.2 Hz, 6H). |
| 82 | (DMSO-$d_6$) δ 9.30 (s, 1H), 8.56 (d, J = 5.4 Hz, 2H), 8.03 (s, 1H), 7.24 (s, 1H), 6.84 (d, J = 8.3 Hz, 1H), 6.74 (s, 1H), 6.58 (dd, J = 17.0, 10.2 Hz, 1H), 6.20 (dd, J = 17.0, 2.2 Hz, 1H), 5.71 (dd, J = 10.1, 2.1 Hz, 1H), 5.34 (d, J = 54.3 Hz, 1H), 4.99-4.86 (m, 1H), 4.02 (s, 1H), 3.88-3.75 (m, 4H), 3.05 (dd, J = 27.0, 12.3 Hz, 1H), 2.37 (s, 3H), 2.35-2.32 (m, 1H), 2.17-2.12 (m, 7H), 2.03-1.88 (m, 2H), 1.25 (s, 6H), 1.14 (dd, J = 6.3, 3.9 Hz, 6H). |

-continued

| Example No. | $^1$H NMR |
|---|---|
| 83 | (DMSO-$d_6$) δ 9.48 (s, 1H), 8.55 (d, J = 4.5 Hz, 2H), 8.28 (s, 1H), 7.22 (s, 1H), 6.85 (d, J = 8.3 Hz, 1H), 6.76 (s, 1H), 6.56 (dd, J = 16.9, 10.2 Hz, 1H), 6.20 (dd, J = 16.9, 2.1 Hz, 1H), 5.71 (d, J = 10.0 Hz, 1H), 4.91 (p, J = 6.2 Hz, 1H), 3.81 (s, 2H), 3.78 (s, 3H), 3.66 (d, J = 7.5 Hz, 1H), 3.41 (d, J = 8.7 Hz, 1H), 3.01-2.88 (m, 1H), 2.38 (s, 3H), 2.24 (dd, J = 12.1, 4.8 Hz, 1H), 2.11 (s, 8H), 1.87 (d, J = 16.2 Hz, 2H), 1.67 (dd, J = 12.7, 6.5 Hz, 1H), 1.25 (s, 6H), 1.12 (t, J = 5.6 Hz, 6H). |
| 84 | (DMSO-$d_6$) δ 9.34 (s, 1H), 8.70 (s, 1H), 8.58 (s, 1H), 8.02 (s, 1H), 7.38-6.97 (m, 2H), 6.73 (s, 1H), 6.64-6.51 (m, 1H), 6.28-6.15 (m, 1H), 5.71 (d, J = 10.0, 2.2 Hz, 1H), 5.26 (s, 1H), 4.99-4.84 (m, 1H), 4.02 (s, 1H), 3.80 (d, J = 18.9 Hz, 7H), 3.05 (dd, J = 26.8, 12.3 Hz, 1H), 2.43-2.28 (m, 2H), 2.14 (d, J = 4.2 Hz, 6H), 2.03 (s, 3H), 1.90 (t, J = 11.6 Hz, 1H), 1.24 (d, J = 8.3 Hz, 6H), 1.18-1.09 (m, 6H). $^{19}$F NMR δ 170.86. |
| 85 | (DMSO-$d_6$) δ 10.11 (s, 1H), 8.90 (s, 1H), 8.5 (s, 1H), 8.44 (s, 1H), 7.22 (dd, J = 7.4, 1.3 Hz, 1H), 7.01 (d, J = 4.5 Hz, 2H), 6.92 (td, J = 9.1, 8.5, 4.1 Hz, 2H), 6.41 (dd, J = 16.9, 10.0 Hz, 1H), 6.24 (dd, J = 16.9, 2.2 Hz, 1H), 5.76 (dd, J = 10.0, 2.2 Hz, 1H), 4.82 (p, J = 6.2 Hz, 1H), 3.89 (s, 2H), 3.82 (s, 3H), 2.86 (t, J = 5.7 Hz, 2H), 2.71 (s, 3H), 2.29 (t, J = 5.8 Hz, 2H), 2.20 (s, 6H), 1.28 (s, 6H), 0.99 (d, J = 6.2 Hz, 6H). |
| 86 | (DMSO-$d_6$) δ 9.46 (s, 1H), 8.71 (s, 1H), 8.58 (s, 1H), 8.07 (s, 1H), 7.91 (d, J = 4.9 Hz, 1H), 7.42 (s, 1H), 6.89 (s, 1H), 6.77 (s, 1H), 6.55 (dd, J = 17.0, 10.2 Hz, 1H), 6.18 (dd, J = 17.0, 2.1 Hz, 1H), 5.70 (dd, J = 10.1, 2.1 Hz, 1H), 4.96 (p, J = 6.2 Hz, 1H), 4.07 (s, 2H), 3.77 (s, 3H), 3.70 (q, J = 6.8 Hz, 1H), 3.45-3.38 (m, 1H), 3.31-3.23 (m, 1H), 2.94 (q, J = 8.5, 7.9 Hz, 1H), 2.23 (dd, J = 12.0, 4.8 Hz, 1H), 2.11 (s, 7H), 1.96-1.81 (m, 2H), 1.68 (dd, J = 12.7, 6.4 Hz, 1H), 1.21 (d, J = 6.2 Hz, 6H), 1.16-1.06 (m, 4H). |
| 87 | (DMSO-$d_6$) δ 9.31 (s, 1H), 8.54 (s, 1H), 8.41 (s, 1H), 8.27 (s, 1H), 7.22 (d, J = 7.2 Hz, 1H), 7.04 (t, J = 7.5 Hz, 1H), 6.92 (t, J = 7.5 Hz, 2H), 6.75 (s, 1H), 6.59 (dd, J = 17.0, 10.1 Hz, 1H), 6.22 (dd, J = 17.0, 2.2 Hz, 1H), 5.72 (dd, J = 10.1, 2.2 Hz, 1H), 5.33 (d, J = 54.5 Hz, 1H), 4.82 (p, J = 6.2 Hz, 1H), 4.00 (d, J = 8.4 Hz, 1H), 3.85 (dd, J = 12.7, 3.9 Hz, 1H), 3.81 (s, 4H), 3.75 (dd, J = 12.3, 4.0 Hz, 1H), 3.04 (dd, J = 27.1, 12.2 Hz, 1H), 2.48-2.29 (m, 3H), 2.14 (s, 6H), 2.02-1.86 (m, 1H), 1.28 (s, 6H), 1.00 (t, J = 6.5 Hz, 6H). |
| 88 | (DMSO-$d_6$) δ 9.32 (s, 1H), 8.62 (s, 1H), 8.58 (s, 1H), 8.08 (s, 1H), 8.02 (dd, J = 4.8, 1.3 Hz, 1H), 7.27 (s, 1H), 7.01 (s, 1H), 6.74 (s, 1H), 6.59 (dd, J = 17.0, 10.2 Hz, 1H), 6.21 (dd, J = 16.9, 2.2 Hz, 1H), 5.71 (dd, J = 10.1, 2.2 Hz, 1H), 5.33 (d, J = 54.5 Hz, 1H), 4.92 (b, J = 6.3 Hz, 1H), 4.02 (d, J = 7.6 Hz, 1H), 3.81 (d, J = 20.6 Hz, 6H), 3.05 (dd, J = 26.8, 12.3 Hz, 1H), 2.49-2.29 (m, 3H), 2.14 (s, 6H), 2.04-1.88 (m, 1H), 1.28 (s, 6H), 1.10 (dd, J = 6.2, 4.4 Hz, 6H). |
| 89 | (DMSO-$d_6$) δ 9.75 (s, 1H), 8.65 (d, J = 34.8 Hz, 3H), 7.21 (s, 1H), 7.02 (d, J = 33.4 Hz, 2H), 6.48 (dd, J = 16.8, 10.1 Hz, 1H), 6.23 (dd, J = 16.9, 2.2 Hz, 1H), 5.76 (dd, J = 10.0, 2.1 Hz, 1H), 4.91 (p, J = 6.2 Hz, 1H), 3.85 (d, J = 33.0 Hz, 5H), 2.86 (s, 2H), 2.71 (s, 3H), 2.54 (s, 6H), 2.04 (s, 3H), 1.26 (s, 6H), 1.11 (d, J = 6.3 Hz, 6H), 0.95 (t, J = 7.1 Hz, 7H). |
| 90 | (DMSO-$d_6$) δ 9.75 (s, 1H), 8.76 (s, 1H), 8.63 (d, J = 6.6 Hz, 2H), 7.23 (d, J = 42.1 Hz, 2H), 6.99 (s, 1H), 6.47 (dd, J = 16.9, 10.1 Hz, 1H), 6.22 (dd, J = 16.9, 2.1 Hz, 1H), 5.76 (dd, J = 10.1, 2.1 Hz, 1H), 4.96 (p, J = 6.3 Hz, 1H), 3.84 (d, J = 31.0 Hz, SH), 2.86 (s, 2H), 2.71 (s, 3H), 2.64-2.52 (m, 6H), 1.26 (s, 6H), 1.16 (d, J = 6.2 Hz, 6H), 0.95 (t, J = 7.0 Hz, 6H). |
| 91 | (DMSO-$d_6$) δ 10.07 (s, 1H), 8.72 (s, 1H), 8.69 (s, 1H), 8.58 (s, 1H), 7.34 (dd, J = 10.1, 8.1 Hz, 1H), 7.11 (s, 1H), 7.00 (s, 1H), 6.38 (dd, J = 16.9, 10.1 Hz, 1H), 6.20 (dd, J = 16.9, 2.2 Hz, 1H), 5.77-5.68 (m, 1H), 4.98 (p, J = 6.2 Hz, 1H), 3.80 (d, J = 2.1 Hz, 5H), 2.86 (t, J = 5.7 Hz, 2H), 2.71 (s, 3H), 2.31 (t, J = 5.8 Hz, 2H), 2.20 (s, 6H), 1.25 (s, 6H), 1.18 (d, J = 6.3 Hz, 6H). |
| 92 | (DMSO-$d_6$) δ 9.46 (s, 1H), 8.69 (s, 1H), 8.55 (d, J = 2.9 Hz, 1H), 8.20 (s, 1H), 7.34 (dd, J = 10.2, 8.1 Hz, 1H), 7.11 (s, 1H), 6.77 (s, 1H), 6.53 (dd, J = 16.9, 10.2 Hz, 1H), 6.18 (dd, J = 16.9, 2.1 Hz, 1H), 5.69 (dd, J = 10.1, 2.2 Hz, 1H), 4.97 (p, J = 6.2 Hz, 1H), 3.77 (d, J = 3.4 Hz, SH), 3.68-3.59 (m, 1H), 3.43-3.36 (m, 1H), 2.94 (dt, J = 8.7, 6.2 Hz, 1H), 2.27-2.15 (m, 2H), 2.10 (s, 6H), 2.07-2.00 (m, 1H), 1.93-1.81 (m, 2H), 1.67 (dq, J = 13.7, 7.2 Hz, 1H), 1.25 (s, 6H), 1.17 (dd, J = 6.2, 2.5 Hz, 6H). |
| 93 | (DMSO-$d_6$) δ 9.27 (s, 1H), 8.69 (s, 1H), 8.55 (d, J = 1.4 Hz, 1H), 8.05 (s, 1H), 7.35 (dd, J = 10.1, 8.1 Hz, 1H), 7.10 (s, 1H), 6.76 (s, 1H), 6.58 (dd, J = 16.9, 10.2 Hz, 1H), 6.19 (dd, J = 17.0, 2.2 Hz, 1H), 5.69 (dd, J = 10.2, 2.1 Hz, 1H), 5.33 (d, J = 54.8 Hz, 1H), 4.96 (p, J = 6.2 Hz, 1H), 3.98 (s, 1H), 3.79 (d, J = 2.2 Hz, 3H), 3.77-3.75 (m, 2H), 3.73 (d, J = 3.6 Hz, 1H), 3.12-3.06 (m, 1H), 3.01 (d, J = 12.2 Hz, 1H), 2.41 (q, J = 7.7, 7.0 Hz, 1H), 2.36-2.29 (m, 1H), 2.13 (s, 6H), 2.03-1.86 (m, 1H), 1.26 (d, J = 2.4 Hz, 6H), 1.16 (dd, J = 6.2, 2.2 Hz, 6H). |
| 94 | (DMSO-$d_6$) δ 9.30 (s, 1H), 8.66 (s, 1H), 8.53 (s, 1H), 7.60 (s, 1H), 7.40-7.30 (m, 1H), 7.04 (s, 1H), 6.55-6.43 (m, 2H), 6.18 (dd, J = 17.0, 2.2 Hz, 1H), 5.68 (dd, J = 10.2, 2.2 Hz, 1H), 4.96 (p, J = 6.2 Hz, 1H), 3.78 (s, 3H), 3.76-3.67 (m, 2H), 3.38-3.35 (m, 1H), 3.20 (d. J = 7.7 Hz, 2H), 3.18-3.11 (m, 1H), 2.71-2.63 (m, 1H), 2.16 (s, 6H), 2.07 (d, J = 8.8 Hz, 1H), 1.78-1.64 (m, 1H), 1.25 (d, J = 4.5 Hz, 6H), 1.16 (d, J = 6.3 Hz, 6H). |
| 95 | (DMSO-$d_6$) δ 9.02 (s, 1H), 8.63 (d, J = 26.6 Hz, 2H), 8.44 (s, 1H), 7.23-7.02 (m, 2H), 6.85 (s, 1H), 6.62 (dd, J = 16.9, 10.2 Hz, 1H), 6.22 (dd, J = 16.9, 2.1 Hz, 1H), 5.74 (dd, J = 10.1, 2.1 Hz, 1H), 4.91 (p, J = 6.2 Hz, 1H), 3.84 (d, J = 28.3 Hz, 5H), 2.95-2.80 (m, 4H), 2.50 (d, J = 1.9 Hz, 3H), 2.27 (s, 3H), 2.04 (s, 3H), 1.26 (s, 7H), 1.11 (d, J = 6.3 Hz, 6H), 1.03 (d, J = 6.0 Hz, 3H). |

Example 9: Preparation of isopropyl 2-((5-acrylamido-4-((2-(dimethylamino)ethyl)(methyl)amino)-2-methoxyphenyl)amino)-4-(5-ethynyl-3,3-dimethyl-2,3-dihydro-1H-pyrrolo[3,2-b]pyridin-1-yl)pyrimidine-5-carboxylate

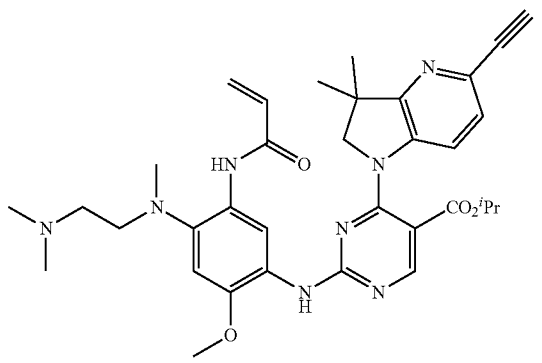

Step 1: Synthesis of ethyl 4-(5-bromo-3,3-dimethyl-2,3-dihydro-1H-pyrrolo [3,2-b]pyridin-1-yl)-2-(methylthio)pyrimidine-5-carboxylate

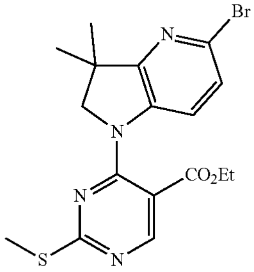 [SMILES: CCOC(=O)c1cnc(SC)nc1N1CC(C)(C)c2nc(Br)ccc21]

5-bromo-3,3-dimethyl-2,3-dihydro-1H-pyrrolo[3,2-b]pyridine (800 mg, 3.5 mmol, 1 eq.) and ethyl 4-chloro-2-(methylthio)pyrimidine-5-carboxylate (819 mg, 3.5 mmol, 1 eq.) were dissolved in N,N-dimethylformamide (10 mL). Sodium hydride (253.66 mg, 10.6 mmol, 3 eq.) was added to the reaction mixture at 0° C. The reaction mixture was stirred at room temperature for 1 hr. Ethyl acetate and water were added, and then the mixture solution was separated. The organic phase was successively washed with water and saturated brine, then dried over anhydrous sodium sulfate, filtered, and concentrated, and then the residue was separated by silica gel column chromatography [petroleum ether: ethyl acetate=4:1] to obtain ethyl 4-(5-bromo-3,3-dimethyl-2,3-dihydro-1H-pyrrolo[3,2-b]pyridin-1-yl)-2-(methylthio)pyrimidine-5-carboxylate (660 mg, yield: 44%). ESI-MS: 423.0, 425.0 $[M+1]^+$.

Step 2: Synthesis of 4-(5-bromo-3,3-dimethyl-2,3-dihydro-1H-pyrrolo[3,2-b]pyridin-1-yl)-2-(methylthio)pyrimidine-5-carboxylic acid

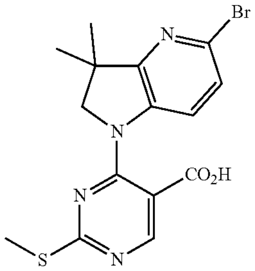 [SMILES: CSc1ncc(C(=O)O)c(N2CC(C)(C)c3nc(Br)ccc32)n1]

Ethyl 4-(5-bromo-3,3-dimethyl-2,3-dihydro-1H-pyrrolo[3,2-b]pyridin-1-yl)-2-(methylthio)pyrimidine-5-carboxylate (660 mg, 1.6 mmol, 1 eq.) and lithium hydroxide (382 mg, 7.8 mmol, 5 eq.) were dissolved in methanol/water/tetrahydrofuran (3 mL/3 mL/6 mL). The reaction mixture was stirred at room temperature overnight, adjusted to acidic with a 1 N hydrochloric acid solution, and then extracted with dichloromethane. The organic phase was successively washed with water and saturated brine, then dried over anhydrous sodium sulfate, filtered, and concentrated to obtain 4-(5-bromo-3,3-dimethyl-2,3-dihydro-1H-pyrrolo[3,2-b]pyridin-1-yl)-2-(methylthio)pyrimidine-5-carboxylic acid (440 mg, yield: 71%). ESI-MS: 395.1, 397.1 $[M+1]^+$.

Step 3: Synthesis of isopropyl 4-(5-bromo-3,3-dimethyl-2,3-dihydro-1H-pyrrolo[3,2-b]pyridin-1-yl)-2-(methylthio)pyrimidine-5-carboxylate

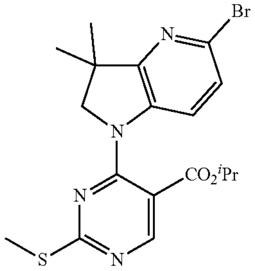

To a solution of 4-(5-bromo-3,3-dimethyl-2,3-dihydro-1H-pyrrolo[3,2-b]pyridin-1-yl)-2-(methylthio)pyrimidine-5-carboxylic acid (440 mg, 1.1 mmol) in dichloromethane (15 mL), N,N-dimethylformamide (0.05 mL, 0.68 mmol) and oxalyl chloride (0.20 mL, 2.28 mmol) were added. After the reaction mixture was stirred at room temperature for 1 hr, isopropanol (6 mL) was added to the above reaction mixture, and the mixture was heated to 60° C. and stirred for 1 hr. Ethyl acetate and water were added, and then the mixture solution was separated. The organic phase was successively washed with water and saturated brine, then dried over anhydrous sodium sulfate, filtered, and concentrated, and then the residue was separated by silica gel column chromatography [petroleum ether:ethyl acetate=3:1] to obtain isopropyl 4-(5-bromo-3,3-dimethyl-2,3-dihydro-1H-pyrrolo[3,2-b]pyridin-1-yl)-2-(methylthio)pyrimidine-5-carboxylate (200 mg, yield; 40%). ESI-MS: 437.0, 439.0 $[M+1]^+$.

Step 4: Synthesis of isopropyl 4-(5-bromo-3,3-dimethyl-2,3-dihydro-1H-pyrrolo[3,2-b]pyridin-1-yl)-2-(methylsulfonyl)pyrimidine-5-carboxylate

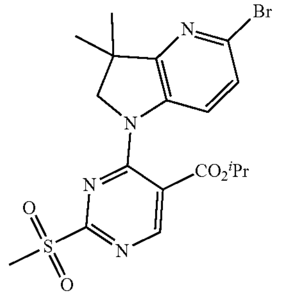

To a solution of isopropyl 4-(5-bromo-3,3-dimethyl-2,3-dihydro-1H-pyrrolo[3,2-b]pyridin-1-yl)-2-(methylthio)pyrimidine-5-carboxylate (200 mg, 0.46 mmol, 1 eq.) in tetrahydrofuran/water (6 mL/0.6 mL), potassium monopersulfate (562 mg, 0.92 mmol, 2 eq.) was added, and the reaction mixture was stirred at room temperature for 3 hrs. Ethyl acetate and water were added, and then the mixture solution was separated. The organic phase was successively washed with water and saturated brine, then dried over anhydrous sodium sulfate, filtered, and concentrated, and then the residue was separated by silica gel column chromatography [petroleum ether:ethyl acetate=5:1] to obtain isopropyl 4-(5-bromo-3,3-dimethyl-2,3-dihydro-1H-pyrrolo[3,2-b]pyridin-1-yl)-2-(methylsulfonyl)pyrimidine-5-carboxylate (42 mg, yield: 20%). ESI-MS: 469.1, 471.1 $[M+1]^+$.

Step 5: Synthesis of isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate

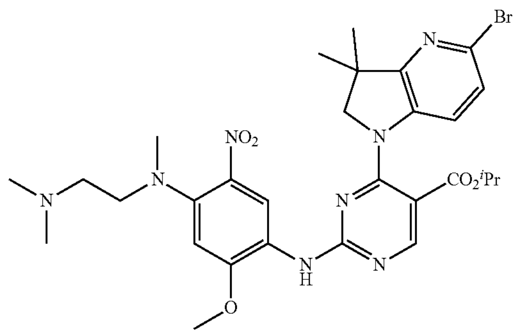

Isopropyl 4-(5-bromo-3,3-dimethyl-2,3-dihydro-1H-pyrrolo[3,2-b]pyridin-1-yl)-2-(methanesulfonyl)pyrimidine-5-carboxylate (42 mg, 0.09 mmol, 1 eq.) and N-(4-((2-(dimethylamino)ethyl)(methyl)amino)-2-methoxy-5-nitrophenyl)formamide (32 mg, 0.11 mmol, 1.2 eq.) were dissolved in N,N-dimethylacetamide (5 mL). Sodium hydride (25 mg, 0.61 mmol, 3 eq.) was added to the reaction mixture at 0° C. The reaction mixture was stirred at room temperature for 1 hr. Water was added, and the reaction mixture was stirred for another 0.5 hrs. Ethyl acetate and water were added, and then the mixture solution was separated. The organic phase was successively washed with water and saturated brine, then dried over anhydrous sodium sulfate, filtered, and concentrated, and then the residue was separated by silica gel column chromatography [petroleum ether:ethyl acetate=4:1] to obtain isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (46 mg, yield: 78%). ESI-MS: 657.3, 659.3 $[M+1]^+$.

Step 6: Synthesis of isopropyl 4-(3,3-dimethyl-5-((trimethylsilyl)ethynyl)-2,3-dihydro-1H-pyrrolo[3,2-b]pyridin-1-yl)-2-((4-((2-(dimethylamino)ethyl)(methyl) amino)-2-methoxy-5-nitrophenyl)amino)pyrimidine-5-carboxylate

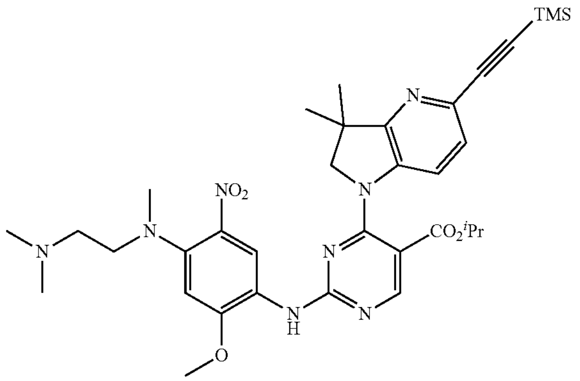

Isopropyl 4-(5-bromo-3,3-dimethyl-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (46 mg, 0.07 mmol, 1 eq.), trimethylsilylacetylene (21 mg, 0.21 mmol, 3 eq.), triethylamine (21 mg, 0.21 mmol, 3 eq.), bis(triphenylphosphine) palladium(II) dichloride (21 mg, 0.28 mmol, 0.4 eq.) and cuprous iodide (5 mg, 0.28 mmol, 0.4 eq.) were dissolved in tetrahydrofuran (6 mL), and the reaction mixture was stirred at room temperature under nitrogen protection for 3 hrs. After the reaction was completed, the reaction mixture was filtered through diatomaceous earth. The resulting filtrate was concentrated, and the residue was separated by rapid silica gel column chromatography [dichloromethane:methanol=10:1] to obtain isopropyl 4-(3,3-dimethyl-5-((trimethylsilyl) ethynyl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (36 mg, yield: 76.21%). ESI-MS: 675.3 $[M+1]^+$.

Step 7: Synthesis of isopropyl 2-((S-amino-4-((2-(dimethylamino)ethyl)(methyl) amino)-2-methoxy-phenyl)amino)-4-(3,3-dimethyl-5-((trimethylsilyl) ethynyl)-2,3-dihydro-1H-pyrrolo[3,2-b]pyridin-1-yl) pyrimidine-5-carboxylate

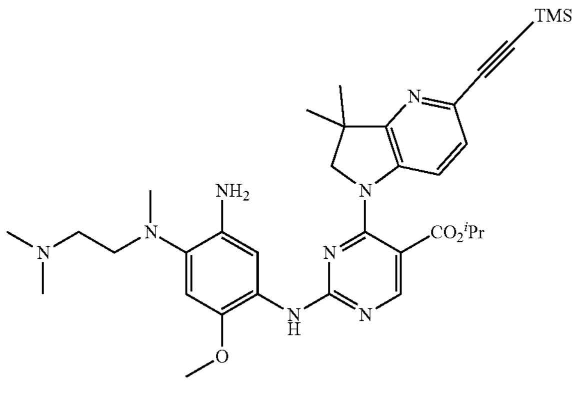

To a suspension of isopropyl 4-(3,3-dimethyl-5-((trimethylsilyl) ethynyl)-2,3-dihydro-1H-pyrrolo[3,2-b]pyridin-1-yl)-2-((4-((2-(dimethylamino)ethyl)(methyl)amino)-2-methoxy-5-nitrophenyl)amino)pyrimidine-5-carboxylate (36 mg, 0.05 mmol, 1 eq.) in ethanol/water (3 mL/3 mL), iron powder (30 mg, 0.53 mmol, 10 eq.) and ammonium chloride (29 mg, 0.53 mmol, 10 eq.) were added. The reaction mixture was stirred at reflux at 95° C. for 2 hrs. Dichloromethane and water were added, and then the mixture solution was separated. The organic phase was successively washed with water and saturated brine, then dried over anhydrous sodium sulfate, filtered, and concentrated to obtain isopropyl 2-((5-amino-4-((2-(dimethylamino)ethyl) (methyl)amino)-2-methoxyphenyl)amino)-4-(3,3-dimethyl-5-((trimethylsilyl)ethynyl)-2,3-dihydro-1H-pyrrolo[3,2-b] pyridin-1-yl)pyrimidine-5-carboxylate (30 mg, yield: 73.17%). ESI-MS: 645.4 $[M+1]^+$.

Step 8: Synthesis of isopropyl 2-((5-acrylamido-4-((2-(dimethylamino)ethyl) (methyl)amino)-2-methoxyphenyl)amino)-4-(5-ethynyl-3,3-dimethyl-2,3-dihydro-1H-pyrrolo[3,2-b]pyridin-1-yl) pyrimidine-5-carboxylate

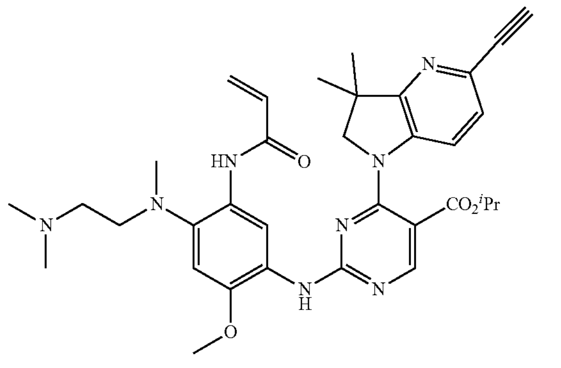

Isopropyl 2-((5-amino-4-((2-(dimethylamino)ethyl) (methyl)amino)-2-methoxyphenyl)amino)-4-(3,3-dimethyl-5-((trimethylsilyl)ethynyl)-2,3-dihydro-1H-pyrrolo[3,2-b] pyridin-1-yl)pyrimidine-5-carboxylate (30 mg, 0.05 mmol, 1 eq.) was dissolved in anhydrous acetonitrile/water (3 mL/3 mL). N,N-diisopropylethylamine (31 mg, 0.25 mmol, 5 eq.) was added to the solution. Acryloyl chloride (9 mg, 0.1 mmol, 2 eq.) was added to the reaction mixture at 0° C. After the reaction mixture was stirred for 30 mm, potassium carbonate (35 mg, 0.25 mmol, 5 eq.) and ethanol (3 mL) were added to the reaction mixture, and the above reaction mixture was stirred at room temperature for 30 min. Dichloromethane and water were added, and then the mixture solution was separated. The organic phase was successively washed with water and saturated brine, then dried over anhydrous sodium sulfate, filtered, and concentrated, and then the residue was separated by reversed-phase column chromatography [40-50% acetonitrile/water] to obtain isopropyl 2-((5-acrylamido-4-((2-(dimethylamino)ethyl) (methyl)amino)-2-methoxyphenyl)amino)-4-(5-ethynyl-3,3-dimethyl-2,3-dihydro-1H-pyrrolo[3,2-b]pyridin-1-yl)pyrimidine-5-carboxylate (7.6 mg, yield: 24%). ESI-MS: 627.3 $[M+1]^+$.

$^1H$ NMR (DMSO-$d_6$) δ 10.08 (s, 1H), 8.83-8.57 (m, 3H), 7.19 (t, J=14.6 Hz, 2H), 7.01 (s, 1H), 6.41 (dd, J=16.9, 10.1 Hz, 1H), 6.23 (dd, J=16.9, 2.2 Hz, 1H), 5.75 (dd, J=10.1, 2.2 Hz, 1H), 4.93 (p, J=6.2 Hz, 1H), 4.16 (s, 1H), 3.93 (s, 2H), 3.81 (s, 3H), 2.88 (t, J=5.8 Hz, 2H), 2.72 (s, 3H), 2.30 (d, J=5.8 Hz, 2H), 2.20 (s, 6H), 1.28 (s, 6H), 1.12 (d, J=6.2 Hz, 6H).

Example 15: Preparation of isopropyl 2-((5-acrylamido-2-methoxy-4-(methyl (2-(methylamino) ethyl)amino)phenyl)amino)-4-(3,3,5-trimethyl-2,3-dihydro-1H-pyrrolo[3,2-b]pyridin-1-yl)pyrimidine-5-carboxylate

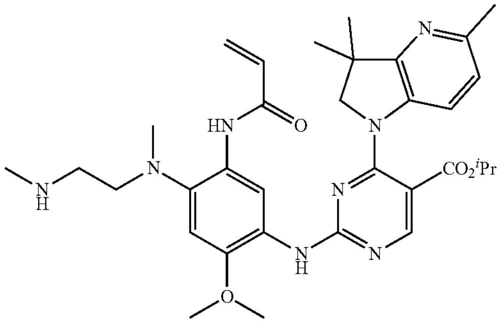

Isopropyl 2-((5-acrylamido-4-((2-((tert-butoxycarbonyl) (methyl)amino)ethyl) (methyl)amino)-2-methoxyphenyl) amino)-4-(3,3,5-trimethyl-2,3-dihydro-1H-pyrrolo[3,2-b] pyridin-1-yl)pyrimidine-5-carboxylate (110 mg, 0.16 mmol) was dissolved in anhydrous dichloromethane (5 mL). Trifluoroacetic acid (1 mL) was added to the solution. The reaction mixture was stirred at room temperature for 1 hr and distilled under reduced pressure to remove the solvent, and then the residue was separated by reversed-phase column chromatography to obtain isopropyl 2-((5-acrylamido-2-methoxy-4-(methyl(2-(methylamino)ethyl)amino)phenyl) amino)-4-(3,3,5-trimethyl-2,3-dihydro-1H-pyrrolo[3,2-b] pyridin-1-yl)pyrimidine-5-carboxylate (19.1 mg, yield: 19.0%). ESI-MS: 603.4 $[M+1]^+$.

$^1$H NMR (DMSO-$d_6$) δ 10.33 (s, 1H), 8.81 (s, 1H), 8.55 (d, J=10.6 Hz, 2H), 7.20 (s, 1H), 6.94 (s, 1H), 6.82 (d, J=8.3 Hz, 1H), 6.55 (dd, J=16.9, 10.1 Hz, 1H), 6.22 (dd, J=17.0, 2.2 Hz, 1H), 5.72 (dd, J=10.1, 2.2 Hz, 1H), 4.92 (p, J=6.2 Hz, 1H), 3.86 (s, 2H), 3.80 (s, 3H), 2.88-2.81 (m, 2H), 2.70 (s, 3H), 2.59 (t, J=5.4 Hz, 2H), 2.36 (d, J=17.4 Hz, 6H), 1.26 (s, 6H), 1.12 (d, J=6.3 Hz, 6H).

The following examples were prepared according to the preparation method of Example 15:

| Example No. | Structure | Chemical name | ESI-MS: $[M + 1]^+$ |
|---|---|---|---|
| 25 | 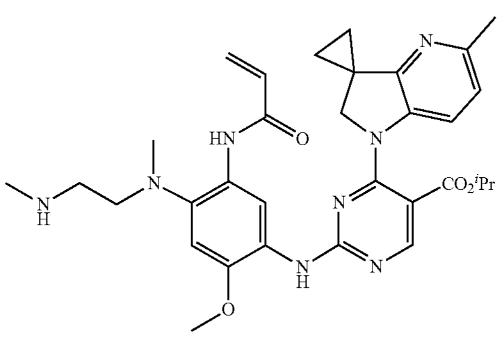 | isopropyl 2-((5-acrylamido-2-methoxy-4-(methyl(2-(methylamino)ethyl)amino)phenyl)amino)-4-(5'-methyl-spiro(cyclopropane-1,3'-pyrrolo[3,2-b]pyridin)-1'(2'H)-yl)pyrimidine-5-carboxylate | 601.2 |
| 54 | 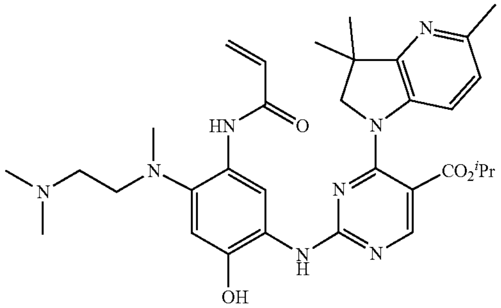 | isopropyl 2-((5-acrylamido-4-((2-(dimethylamino)ethyl)(methyl)amino)-2-hydroxy-phenyl)amino)-4-(3,3,5-trimethyl-2,3-dihydro-1H-pyrrolo[3,2-b]pyridin-1-yl)pyrimidine-5-carboxylate | 603.4 |
| 55 | 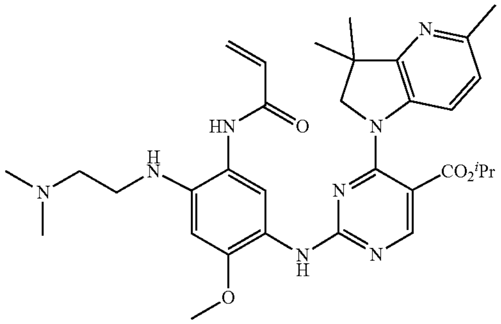 | isopropyl 2-((5-acrylamido-4-((2-(dimethylamino)ethyl)amino)-2-methoxy-phenyl)amino)-4-(3,3,5-trimethyl-2,3-dihydro-1H-pyrrolo[3,2-b]pyridin-1-yl)pyrimidine-5-carboxylate | 603.4 |
| 65 | 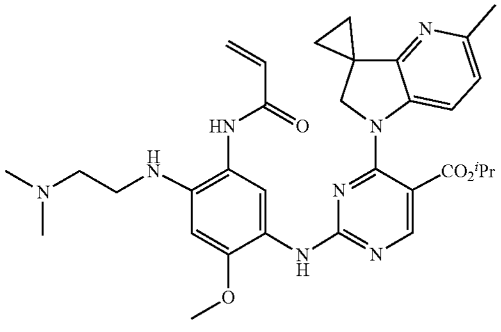 | isopropyl 2-((5-acrylamido-4-((2-(dimethylamino)ethyl)amino)-2-methoxy-phenyl)amino)-4-(5'-methylspiro(cyclo-propane-1,3'-pyrrolo[3,2-b]pyridin)-1'(2'H)-yl)pyrimidine-5-carboxylate | 601.4 |

$^1$H NMR data of the compounds prepared in the above examples are as follows:

| Example No. | $^1$H NMR |
|---|---|
| 25 | ($MeOH-d_4$) δ 9.09-7.77 (m, 3H), 7.52 (s, 1H), 7.03 (s, 1H), 6.83 (d, J = 13.2 Hz, 1H), 6.35 (d, J = 16.9 Hz, 1H), 5.82 (dd, J = 10.3, 1.7 Hz, 1H), 5.20 (p, J = 6.2 Hz, 1H), 4.40 (s, 2H), 4.10-3.98 (m, 1H), 3.94 (s, 3H), 3.48 (dd, J = 6.8, 4.3 Hz, 2H), 3.25 (t, J = 5.4 Hz, 2H), 2.76 (s, 3H), 2.75 (s, 3H), 2.70 (s, 3H), 1.80 (q, J = 5.1 Hz, 2H), 1.61 (q, J = 5.3 Hz, 2H), 1.38 (d. J = 6.3 Hz, 6H). |
| 54 | ($DMSO-d_6$) δ 9.94 (s, 1H), 9.63 (s, 1H), 8.58 (d, J = 49.0 Hz, 3H), 7.28 (s, 1H), 6.82 (d, J = 20.9 Hz, 2H), 6.40 (dd, J = 16.9, 10.1 Hz, 1H), 6.21 (dd, J = 16.8, 2.2 Hz, 1H), 5.73 (dd, J = 10.0, 2.2 Hz, 1H), 3.86 (s, 2H), 2.81 (t, J = 5.9 Hz, 2H), 2.65 (s, 3H), 2.38 (s, 3H), 2.31 (d, J = 5.9 Hz, 2H), 2.19 (s, 6H), 1.26 (s, 6H), 1.13 (d, J = 6.3 Hz, 6H). |
| 55 | ($DMSO-d_6$) δ 9.74 (s, 1H), 9.48 (d, J = 10.5 Hz, 1H), 8.70 (s, 1H), 8.54 (s, 1H), 7.70 (s, 1H), 7.31 (d, J = 18.8 Hz, 1H), 7.09 (dd, J = 51.0, 6.7 Hz, 1H), 6.94 (s, 1H), 6.55 (dd, J = 17.1, 9.9 Hz, 1H), 6.45 (d, J = 7.7 Hz, 1H), 6.22 (d, J = 16.9 Hz, 1H), 5.74 (d, J = 10.1 Hz, 1H), 4.94 (d, J = 6.9 Hz, 1H), 3.82 (s, 5H), 3.29 (d, J = 7.5 Hz, 2H), 2.86 (s, 3H), 2.41 (s, 2H), 1.27 (s, 6H), 1.16 (d, J = 6.6 Hz, 6H). |
| 65 | ($DMSO-d_6$) δ 9.36 (s, 1H), 8.54 (d, J = 14.7 Hz, 2H), 7.37 (s, 1H), 6.69 (d, J = 18.4 Hz, 1H), 6.46 (dd, J = 17.0, 10.2 Hz, 1H), 6.39 (s, 1H), 6.18 (dd, J = 16.8, 2. 1 Hz, 1H), 5.71 (dd, J = 10.2, 2.1 Hz, 1H), 4.98 (p, J = 6.1 Hz, 1H), 4.91 (s, 1H), 3.97 (s, 2H), 3.76 (s, 3H), 3.21 (q, J = 6.2 Hz, 2H), 2.31 (s, 3H), 2.20 (s, 6H), 1.99 (p, J = 7.0, 6.5 Hz, 2H), 1.23 (d, J = 6.1 Hz, 12H), 1.11 (s, 2H), 1.06 (d, J = 3.5 Hz, 2H). |

Biological Test Evaluation

Cell Proliferation Study (I) Reagents and Materials

Fetal bovine serum FBS (GBICO, Cat #10099-141);

CellTiter-Glo® luminescent cell viability assay kit (Promega, Cat #G7572);

Black transparent flat-bottom 96-well plate (Corning®, Cat #3603).

(II) Instruments

SpectraMax multi-label microplate reader MD, 2104-0010A;

Carbon dioxide incubator, Thermo Scientific 3100 series;

Biological safety cabinet, Thermo Scientific, 1300 series model A2;

Inverted microscope, Olympus, CKX41SF;

Siemens refrigerator KK25E76T1.

(III) Cell Lines and Culture Conditions

| No. | Cell lines | Cell culture medium | Cell density |
|---|---|---|---|
| 1 | A431 | DMEM + 15% FBS | 5000 |
| 2 | Ba/F3 EGFR-D770-N771ins_SVD | RPMI1640 + 10% FBS | 3000 |
| 3 | Ba/F3 EGFR-V769_D770insASV | RPMI1640 + 10% FBS | 3000 |

(IV) Experimental Procedures

1. Cell Culture and Inoculation:

(1) Cells in the logarithmic growth phase were harvested and counted using a platelet counter. The cell viability was determined by the trypan blue dye exclusion method to ensure cell viability above 90%.

(2) The cell concentration was adjusted to reach a desired final density; 90 μL of cell suspension was added to a 96-well plate.

(3) The cells were incubated overnight in the 96-well plate at 37° C., 5% $CO_2$ and with 95% humidity.

2. T0 Benchmark Data:

(1) 10 μL of PBS was added to each well of the TO plate containing the cells.

(2) The CTG reagent was thawed and the cell plate was equilibrated to room temperature for 30 min.

(3) An equal volume of CTG solution was added to each well.

(4) The cells were lysed by shaking on an orbital shaker for 5 min.

(5) The cell plate was left to stand at room temperature for 20 min to stabilize the fluorescence signal.

(6) The fluorescence signal values of TO were read.

3. Dilution and Addition of Compounds (1) According to the compound information table, a corresponding volume of DMSO was added to the corresponding compound powder to prepare a 10 mM stock solution.

(2) A 1000-fold, 3.16-fold-diluted compound solution was prepared.

(3) The 1000× diluted compound solution was diluted 100-fold with PBS to prepare a 10-fold compound solution with a maximum concentration of 10 μM, including 9 concentrations, with 3.16-fold dilution, and 10 μL of the medicament solution was added to each well of the 96-well plate to seed the cells. Triplicate wells were set for each compound concentration, with a final concentration of DMSO being 0.1%.

(4) The cells were placed in the 96-well plate containing the medicament at 37° C., 5% $CO_2$ and with 95% humidity, and cultured for 72 hrs before CTG analysis.

4. Fluorescence Signal Reading (1) The CTG reagent was thawed and the cell plate was equilibrated to room temperature for 30 min.

(2) An equal volume of CTG solution was added to each well.

(3) The cells were lysed by shaking on an orbital shaker for 5 min.

(4) The cell plate was left to stand at room temperature for 20 min to stabilize the fluorescence signal.

(5) The fluorescence values were read.

5. Data Processing

Data were analyzed using GraphPad Prism 7.0 software and fitted data were regressed using non-linear S-curves to obtain dose-response curves from which $IC_{50}$ values (in nM) were calculated. The specific experimental results are shown in Table 1:

$$\text{Cell viability (\%)} = (Lum\ \text{test medicament} - Lum\ \text{medium control}) / (Lum\ \text{cell control} - Lum\ \text{medium control}) * 100\%.$$

TABLE 1

Biological Test Results

| Example No. | A431 (EGFR-WT) | Ba/F3 EGFR-D770-N771ins_SVD | Ba/F3 EGFR-V769_D770insASV |
|---|---|---|---|
| 1 | 105.1 | 7.0 | 10.4 |
| 2 | 478.9 | 26.8 | 35.0 |
| 3 | 371.3 | 23.2 | 33.1 |
| 4 | 162.6 | 59.5 | NT |
| 5 | 515.8 | 15.8 | 30.4 |
| 6 | 626.6 | 12.4 | 35.1 |
| 7 | 734.7 | 18.8 | 29.9 |
| 8 | 102.3 | 11.0 | 18.7 |
| 9 | 23.3 | 17.8 | 31.8 |
| 10 | 278 | 36.9 | 39.4 |
| 11 | 827.7 | 30.2 | 37.3 |
| 12 | 599 | 18.5 | 36.9 |
| 13 | NT | 78.3 | NT |
| 14 | NT | 39.0 | NT |
| 15 | 878.6 | 35.0 | 49.2 |
| 16 | NT | 309.4 | NT |
| 17 | NT | 134.7 | NT |
| 18 | NT | 50.8 | NT |
| 19 | NT | 119.1 | NT |
| 20 | 746.1 | 34.3 | 66.6 |
| 21 | 404.5 | 24.6 | 56.8 |
| 22 | 127.3 | 20.6 | 48.8 |
| 23 | NT | 92.2 | NT |
| 24 | NT | 110.9 | NT |
| 25 | 222.3 | 34.2 | 53.8 |
| 26 | 363.1 | 29.7 | 52.8 |
| 27 | 580.2 | 14.1 | NT |
| 28 | NT | 203.6 | NT |
| 29 | 281.7 | 13.3 | 16.0 |
| 30 | 557 | 7.6 | 21.5 |
| 31 | 183.4 | 11.8 | 13.9 |
| 32 | NT | 44.4 | NT |
| 33 | NT | 502.8 | NT |
| 34 | NT | 443.4 | NT |
| 35 | 1070 | 36.0 | NT |
| 36 | 352.9 | 14.8 | 22.8 |
| 37 | NT | 72.9 | NT |
| 38 | NT | 339.0 | NT |
| 39 | NT | 544.6 | NT |
| 40 | 294.8 | 33.9 | 44.2 |
| 41 | 213.4 | 36.3 | NT |
| 42 | 114 | 11.3 | 23.6 |
| 43 | NT | 452.8 | NT |
| 44 | 235.2 | 30.4 | 76.5 |
| 45 | NT | 76.2 | NT |
| 46 | 270 | 20.5 | 33.5 |
| 47 | 56.1 | 13.4 | 22.4 |
| 48 | 4.4 | 11.1 | 37.0 |
| 49 | 1419 | 31.3 | 24.4 |
| 50 | 813.3 | 36.7 | 27.9 |
| 51 | NT | 198.7 | NT |
| 52 | 184.6 | 24.1 | 61.9 |
| 53 | NT | 552.4 | NT |
| 54 | 1145 | 77.0 | 81.9 |
| 55 | 432.3 | 22.8 | 52.0 |
| 56 | 301.2 | 33.5 | 91.1 |
| 57 | 987.7 | 23.3 | 62.4 |
| 58 | 1277 | 28.7 | 38.1 |
| 59 | 150.4 | 18.4 | 18.4 |
| 60 | 761.2 | 31.9 | 37.9 |
| 61 | NT | 255.1 | NT |
| 62 | 120.5 | 12.3 | 16.0 |
| 63 | 110.2 | 10.7 | 18.3 |
| 64 | 39.7 | 8.8 | 12.3 |
| 65 | 282.2 | 39.0 | 34.4 |
| 66 | NT | 16.9 | 27.2 |
| 67 | 515.2 | 23.9 | 37.1 |
| 68 | NT | 30.6 | NT |
| 69 | NT | 26.9 | 35.2 |
| 70 | NT | 501.2 | NT |
| 71 | 65.5 | 14.8 | 30.4 |
| 72 | 119.8 | 24.8 | 35.3 |
| 73 | 90.0 | 12.3 | 34.8 |
| 74 | 99.3 | 15.5 | 43.6 |
| 75 | NT | 2845.1 | NT |
| 76 | 1257 | 30.9 | 93.9 |
| 77 | 97.2 | 11.7 | 32.2 |
| 78 | 72.0 | 12.3 | 36.4 |
| 79 | 252 | 20.2 | 58.2 |
| 80 | NT | 44.9 | NT |
| 81 | 127.5 | 9.0 | 29.3 |
| 82 | 76.0 | 11.2 | 12.9 |
| 83 | 57.0 | 10.9 | 13.6 |
| 84 | 220.4 | 12.0 | 12.6 |
| 85 | 560.8 | 23.6 | 13.8 |
| 86 | 14.1 | 9.8 | 8.0 |
| 87 | 58.1 | 25.8 | 12.5 |
| 88 | 20.9 | 15.4 | 9.2 |
| 89 | 177.5 | 13.1 | 242.2 |
| 90 | NT | 116.1 | NT |
| 91 | 1078 | 37.5 | 32.2 |
| 92 | 962.5 | 33.2 | 27.9 |
| 93 | 777.8 | 34.6 | 28.8 |
| 94 | NT | 60.0 | NT |
| 95 | NT | 254.4 | NT |
| Positive compound | 280.1* | 66.8* | 58.6* |

Notes

1. "NT" is an abbreviation of "Not Tested", and means that an object has not been detected yet.
2. The data marked with "*" indicates the average value of multiple measurements.
3. The positive compound is the compound of Example 4 of patent WO2018210246A1, which has a chemical structure shown as follows:

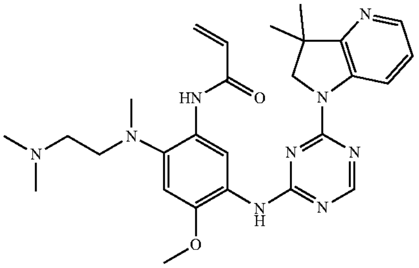 [SMILES: C=CC(=O)Nc1cc(Nc2ncnc(N3CC(C)(C)c4ncccc43)n2)c(OC)cc1N(C)CCN(C)C]

From the biological activity data of the compounds of the specific examples, the series of compounds of the present invention had strong inhibitory effects on an insertion, deletion or other mutation of EGFR Exon 20 at cellular level, and the selectivity for EGFR WT reached more than 10-fold; the compounds of some examples even obtained more than 20-fold selectivity, and compared with the less than 5-fold selectivity of the positive compound, the series of compounds of the present invention obtained higher selectivity, thus having better development prospects.

All documents mentioned in the present invention are incorporated as references, just as each document is individually cited as a reference. In addition, it should be understood that various modifications or changes may be made by those skilled in the art after reading the above disclosure of the present invention, and these equivalent forms also fall within the scope defined by the claims appended hereto.

We claim:

1. A compound of formula (I), or a stereoisomer or pharmaceutically acceptable salt thereof:

(I)

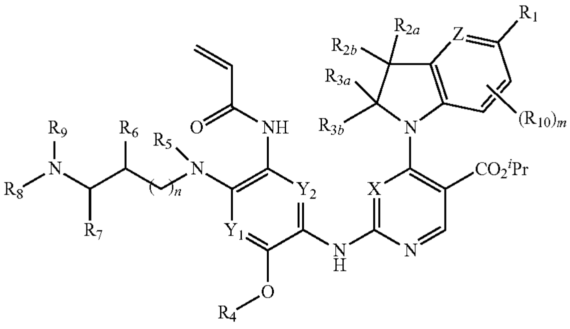

wherein,

X is CH or N;

$Y_1$ and $Y_2$ are each independently CH or N;

Z is $CR_{11}$ or N;

$R_1$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-$C(O)OR_{13}$, —$C_{0-8}$ alkyl-$C(O)R_{14}$, —$C_{0-8}$ alkyl-O—$C(O)R_{14}$, —$C_{0-8}$ alkyl-$NR_{15}R_{16}$, —$C_{0-8}$ alkyl-$C(=NR_{15})R_{14}$, —$C_{0-8}$ alkyl-$N(R_{15})$—$C(=NR_{16})R_{14}$, —$C_{0-8}$ alkyl-$C(O)NR_{15}R_{16}$, and —$C_{0-8}$ alkyl-$N(R_{15})$—$C(O)R_{14}$, or $R_1$ and adjacent $R_{10}$, together with the moiety to which $R_1$ and adjacent $R_{10}$ are directly attached, form a $C_{3-12}$ cycloalkyl or 3-12 membered heterocyclyl, each of the above $R_1$ or $R_1$ and adjacent $R_{10}$ groups optionally further substituted with one or more substituents independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-$C(O)OR_{13}$, —$C_{0-8}$ alkyl-$C(O)R_{14}$, —$C_{0-8}$ alkyl-O—$C(O)R_{14}$, —$C_{0-8}$ alkyl-$NR_{15}R_{16}$, —$C_{0-8}$ alkyl-$C(=NR_{15})R_{14}$, —$C_{0-8}$ alkyl-$N(R_{15})$—$C(=NR_{16})R_{14}$, —$C_{0-8}$ alkyl-$C(O)NR_{15}R_{16}$, and —$C_{0-8}$ alkyl-$N(R_{15})$—$C(O)R_{14}$;

$R_{2a}$ and $R_{2b}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, and 5-10 membered heteroaryl, or $R_{2a}$ and $R_{2b}$, together with the carbon atom to which $R_{2a}$ and $R_{2b}$ are directly attached, form a $C_{3-6}$ cycloalkyl or 3-6 membered heterocyclyl, each of the above $R_{2a}$ and $R_{2b}$ groups optionally further substituted with one or more substituents independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-$C(O)OR_{13}$, —$C_{0-8}$ alkyl-$C(O)R_{14}$, —$C_{0-8}$ alkyl-O—$C(O)R_{14}$, —$C_{0-8}$ alkyl-$NR_{15}R_{16}$, —$C_{0-8}$ alkyl-$C(=NR_{15})R_{14}$, —$C_{0-8}$ alkyl-$N(R_{15})$—$C(=NR_{16})R_{14}$, —$C_{0-8}$ alkyl-$C(O)NR_{15}R_{16}$, and —$C_{0-8}$ alkyl-$N(R_{15})$—$C(O)R_{14}$;

$R_{3a}$ and $R_{3b}$ are each independently selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, and 5-10 membered heteroaryl;

$R_4$ is selected from the group consisting of hydrogen, deuterium, $C_{1-10}$ alkyl, $C_{2-10}$ alkenyl, $C_{3-12}$ cycloalkyl, 3-12 membered heterocyclyl, $C_{6-10}$ aryl, and 5-10 membered heteroaryl, each of the above $R_4$ groups optionally independently further substituted with one or more substituents selected from the group consisting of deuterium, halogen, hydroxy, =O, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$;

$R_5$ is selected from the group consisting of hydrogen, deuterium, hydroxy, $C_{1-10}$ alkyl, $C_{1-10}$ haloalkyl, $C_{1-10}$ deuterioalkyl, $C_{2-4}$ alkenyl, $C_{3-6}$ cycloalkyl, and 3-6 membered heterocyclyl;

$R_6$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-$C(O)OR_{13}$, —$C_{0-8}$ alkyl-$C(O)R_{14}$, —$C_{0-8}$ alkyl-O—$C(O)R_{14}$, —$C_{0-8}$ alkyl-$NR_{15}R_{16}$, —$C_{0-8}$ alkyl-$C(=NR_{15})R_{14}$, —$C_{0-8}$ alkyl-$N(R_{15})$—$C(=NR_{16})R_{14}$, —$C_{0-8}$ alkyl-$C(O)NR_{15}R_{16}$, and —$C_{0-8}$ alkyl-$N(R_{15})$—$C(O)R_{14}$;

$R_7$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-$C(O)OR_{13}$, —$C_{0-8}$ alkyl-$C(O)R_{14}$, —$C_{0-8}$ alkyl-O—$C(O)R_{14}$, —$C_{0-8}$ alkyl-$NR_{15}R_{16}$, —$C_{0-8}$ alkyl-$C(=NR_{15})R_{14}$, —$C_{0-8}$ alkyl-$N(R_{15})$—$C(=NR_{16})R_{14}$, —$C_{0-8}$ alkyl-$C(O)NR_{15}R_{16}$, and —$C_{0-8}$ alkyl-$N(R_{15})$—$C(O)R_{14}$;

$R_8$ and $R_9$ are each independently selected from the group consisting of hydrogen, deuterium, hydroxy, $C_{1-10}$ alkyl, $C_{2-4}$ alkenyl, $C_{3-6}$ cycloalkyl, and 3-6 membered heterocyclyl, or $R_8$ and $R_9$, together with the nitrogen atom to which $R_8$ and $R_9$ are directly attached, form a 3-12 membered heterocyclyl, each of the above $R_8$ and $R_9$ groups optionally further substituted with one or more substituents independently selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$;

or, $R_5$ and one of $R_6$, $R_7$, or $R_8$, together with the moiety to which $R_5$ and one of $R_6$, $R_7$, or $R_9$ are directly attached, form a 4-6 membered heterocyclyl, the other two of $R_6$, $R_7$, and $R_9$ are as previously defined, the 4-6 membered heteorcyclyl is optionally further substituted with one or more substituents independently selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$, and —$C_{0-8}$ alkyl-N($R_{15}$)—C(O)$R_{14}$, or $R_7$ and $R_8$, together with the moiety to which $R_7$ and $R_8$ are directly attached, form a 4-6 membered heterocyclyl, the 4-6 membered heterocyclyl is optionally further substituted with one or more substituents independently selected from the group consisting of deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$, and —$C_{0-8}$ alkyl-N($R_{15}$)—C(O)$R_{14}$, or

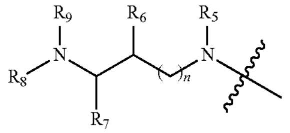

is

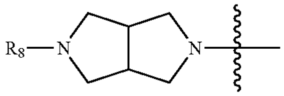

;

each $R_{10}$ is independently selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$, and —$C_{0-8}$ alkyl-N($R_{15}$)—C(O)$R_{14}$, or when m=2, two $R_{10}$, together with the moiety to which the two $R_{10}$ are directly attached, form a $C_{3-12}$ cycloalkyl or 3-12 membered heterocyclyl;

$R_{11}$ is selected from the group consisting of hydrogen, deuterium, halogen, cyano, nitro, azido, $C_{1-10}$ alkyl, $C_{1-10}$ haloalkyl, $C_{1-10}$ deuterioalkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-$S(O)_rR_{12}$, —$C_{0-8}$ alkyl-O—$R_{13}$, —$C_{0-8}$ alkyl-C(O)$OR_{13}$, —$C_{0-8}$ alkyl-C(O)$R_{14}$, —$C_{0-8}$ alkyl-O—C(O)$R_{14}$, —$C_{0-8}$ alkyl-$NR_{15}R_{16}$, —$C_{0-8}$ alkyl-C(=$NR_{15}$)$R_{14}$, —$C_{0-8}$ alkyl-N($R_{15}$)—C(=$NR_{16}$)$R_{14}$, —$C_{0-8}$ alkyl-C(O)$NR_{15}R_{16}$, and —$C_{0-8}$ alkyl-N($R_{15}$)—C(O)$R_{14}$;

each $R_{12}$ is independently selected from the group consisting of hydrogen, deuterium, hydroxy, $C_{1-10}$ alkyl, $C_{2-10}$ alkenyl, $C_{3-12}$ cycloalkyl, 3-12 membered heterocyclyl, $C_{6-10}$ aryl, 5-10 membered heteroaryl, and —$C_{0-8}$ alkyl-$NR_{15}R_{16}$, each of the above $R_{12}$ groups optionally further substituted with one or more substituents independently selected from the group consisting of deuterium, halogen, hydroxy, oxo, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$;

each $R_{13}$ is independently selected from the group consisting of hydrogen, deuterium, $C_{1-10}$ alkyl, $C_{2-10}$ alkenyl, $C_{3-12}$ cycloalkyl, 3-12 membered heterocyclyl, $C_{6-10}$ aryl, and 5-10 membered heteroaryl, each of the above $R_{13}$ groups independently optionally further substituted with one or more substituents independently selected from the group consisting of deuterium, halogen, hydroxy, oxo, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$;

each $R_{14}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$, each of the above $R_{14}$ groups optionally further substituted with one or more substituents independently selected from the group consisting of deuterium, halogen, hydroxy, cyano, $C_{1-10}$ alkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, and —$C_{0-8}$ alkyl-$NR_{15}R_{16}$;

each of $R_{15}$ and $R_{16}$ is independently selected from the group consisting of hydrogen, deuterium, hydroxy, $C_{1-10}$ alkoxy, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-10}$ alkylamino, di$C_{1-10}$alkylamino, and $C_{1-10}$ alkanoyl, each of the above $R_{15}$ and $R_{16}$ groups optionally further substituted with one or more substituents independently selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ dialkylamino, di$C_{1-10}$ alkylamino, and $C_{1-10}$ alkanoyl, or, $R_{15}$ and $R_{16}$, together with the nitrogen atom to which $R_{15}$ and $R_{16}$ are directly attached, form a 5-10 membered heterocyclyl or 5-10 membered heteroaryl, each of the above $R_{15}$ and $R_{16}$ groups optionally further substituted with one or more substituents independently selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino, and $C_{1-10}$ alkanoyl;

m is 0, 1, or 2;

n is 0, 1, or 2; and each r is independently 0, 1, or 2.

2. The compound of formula (I), or the stereoisomer or pharmaceutically acceptable salt thereof, of claim 1, wherein Z is $CR_{11}$ or N;

$R_1$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}R_{16}$, —$C_{0-4}$ alkyl-C═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}R_{16}$, and —$C_{0-4}$ alkyl-N($R_{15}$)—C(O)$R_{14}$, or $R_1$ and adjacent $R_{10}$, together with the moiety to which $R_1$ and adjacent $R_{10}$ are directly attached, form a $C_{3-6}$ cycloalkyl or 3-6 membered heterocyclyl, each of the above $R_1$ or $R_1$ and adjacent $R_{10}$ groups optionally further substituted with one or more substituents independently selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, ═O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}R_{16}$, and —$C_{0-4}$ alkyl-N($R_{15}$)—C(O)$R_{14}$;

$R_{2a}$ and $R_{2b}$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, and 5-8 membered heteroaryl, or $R_{2a}$ and $R_{2b}$, together with the carbon atom to which $R_{2a}$ and $R_{2b}$ are directly attached, form a $C_{3-6}$ cycloalkyl or 3-6 membered heterocyclyl, each of the above $R_{2a}$ and $R_{2b}$ groups optionally further substituted with one or more substituents independently selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, ═O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}R_{16}$, and —$C_{0-4}$ alkyl-N($R_{15}$)—C(O)$R_{14}$;

$R_{3a}$ and $R_{3b}$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, and 5-8 membered heteroaryl;

$R_4$ is selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl, and 5-8 membered heteroaryl, each of the above $R_4$ groups optionally further substituted with one or more substituents independently selected from the group consisting of deuterium, halogen, hydroxy, ═O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and —$C_{0-4}$ alkyl-N$R_{15}R_{16}$;

$R_5$ is selected from the group consisting of hydrogen, deuterium, hydroxy, $C_{1-4}$ alkyl, $C_{1-4}$ haloalkyl, $C_{1-4}$ deuterioalkyl, $C_{2-4}$ alkenyl, $C_{3-6}$ cycloalkyl, and 3-6 membered heterocyclyl;

$R_6$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}R_{16}$, and —$C_{0-4}$ alkyl-N($R_{15}$)—C(O)$R_{14}$;

$R_7$ is selected from the group consisting of hydrogen, deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)O$R_{13}$, —$C_{0-4}$ alkyl-C(O)$R_{14}$, —$C_{0-4}$ alkyl-O—C(O)$R_{14}$, —$C_{0-4}$ alkyl-N$R_{15}R_{16}$, —$C_{0-4}$ alkyl-C(═N$R_{15}$)$R_{14}$, —$C_{0-4}$ alkyl-N($R_{15}$)—C(═N$R_{16}$)$R_{14}$, —$C_{0-4}$ alkyl-C(O)N$R_{15}R_{16}$, and —$C_{0-4}$ alkyl-N($R_{15}$)—C(O)$R_{14}$;

$R_8$ and $R_9$ are each independently selected from the group consisting of hydrogen, deuterium, hydroxy, $C_{1-4}$ alkyl, $C_{2-4}$ alkenyl, $C_{3-6}$ cycloalkyl, and 3-6 membered heterocyclyl, or $R_8$ and $R_9$, together with the nitrogen atom to which $R_8$ and $R_9$ are directly attached, form a 3-6 membered heterocyclyl, each of the above $R_8$ and $R_9$ groups optionally further substituted with one or more substituents independently selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and —$C_{0-4}$ alkyl-N$R_{15}R_{16}$;

or, $R_5$ and one of $R_6$, $R_7$, or $R_9$, together with the moiety to which $R_5$ and one of $R_6$, $R_7$, or $R_9$ are directly attached, form a 4-6 membered heterocyclyl optionally further substituted with one or more substituents independently selected from the group consisting of deuterium, halogen, cyano, nitro, azido, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, ═O, —$C_{0-4}$ alkyl-$SF_5$, —$C_{0-4}$ alkyl-$S(O)_rR_{12}$, —$C_{0-4}$ alkyl-O—$R_{13}$, —$C_{0-4}$ alkyl-C(O)OR$_{13}$, —C$_{0-4}$ alkyl-C(O)R$_{14}$, —C$_{0-4}$ alkyl-O—C(O)R$_{14}$, —C$_{0-4}$ alkyl-NR$_{15}$R$_{16}$, —C$_{0-4}$ alkyl-C(=NR$_{15}$)R$_{14}$, —C$_{0-4}$ alkyl-N(R$_{15}$)—C(=NR$_{16}$)R$_{14}$, —C$_{0-4}$ alkyl-C(O)NR$_{15}$R$_{16}$, and —C$_{0-4}$ alkyl-N(R$_{15}$)—C(O)R$_{14}$, or R$_7$ and R$_8$, together with the moiety to which R$_7$ and R$_8$ are directly attached, form a 4-6 membered heterocyclyl, the 4-6 membered heterocyclyl optionally further substituted with one or more substituents independently selected from the group consisting of deuterium, halogen, cyano, nitro, azido, C$_{1-4}$ alkyl, C$_{1-4}$ haloalkyl, C$_{1-4}$ deuterioalkyl, C$_{2-4}$ alkenyl, C$_{2-4}$ alkynyl, C$_{3-6}$ cycloalkyl, 3-6 membered heterocyclyl, C$_{6-8}$ aryl, 5-8 membered heteroaryl, =O, —C$_{0-4}$ alkyl-SF$_5$, —C$_{0-4}$ alkyl-S(O)$_r$R$_{12}$, —C$_{0-4}$ alkyl-O—R$_{13}$, —C$_{0-4}$ alkyl-C(O)OR$_{13}$, —C$_{0-4}$ alkyl-C(O)R$_{14}$, —C$_{0-4}$ alkyl-O—C(O)R$_{14}$, —C$_{0-4}$ alkyl-NR$_{15}$R$_{16}$, —C$_{0-4}$ alkyl-C(=NR$_{15}$)R$_{14}$, —C$_{0-4}$ alkyl-N(R$_{15}$)—C(=NR$_{16}$)R$_{14}$, —C$_{0-4}$ alkyl-C(O)NR$_{15}$R$_{16}$, and —C$_{0-4}$ alkyl-N(R$_{15}$)—C(O)R$_{14}$, or

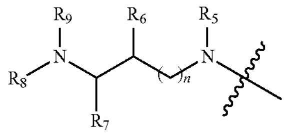

is

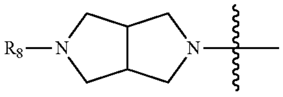
;

each R$_{10}$ is independently selected from the group consisting of hydrogen, deuterium, halogen, cyano, nitro, azido, C$_{1-4}$ alkyl, C$_{1-4}$ haloalkyl, C$_{1-4}$ deuterioalkyl, C$_{2-4}$ alkenyl, C$_{2-4}$ alkynyl, C$_{3-6}$ cycloalkyl, 3-6 membered heterocyclyl, C$_{6-8}$ aryl, 5-8 membered heteroaryl, —C$_{0-4}$ alkyl-SF$_5$, —C$_{0-4}$ alkyl-S(O)$_r$R$_{12}$, —C$_{0-4}$ alkyl-O—R$_{13}$, —C$_{0-4}$ alkyl-C(O)OR$_{13}$, —C$_{0-4}$ alkyl-C(O)R$_{14}$, —C$_{0-4}$ alkyl-O—C(O)R$_{14}$, —C$_{0-4}$ alkyl alkyl-NR$_{15}$R$_{16}$, —C$_{0-4}$ alkyl-C(=NR$_{15}$)R$_{14}$, —C$_{0-4}$ alkyl-N(R$_{15}$)—C(=NR$_{16}$)R$_{14}$, —C$_{0-4}$ alkyl-C(O)NR$_{15}$R$_{16}$, and —C$_{0-4}$ alkyl-N(R$_{15}$)—C(O)R$_{14}$, or when m=2, two R$_{10}$, together with the moiety to which the two R$_{10}$ are directly attached, form a C$_{3-6}$ cycloalkyl or 3-6 membered heterocyclyl; and R$_{11}$ is selected from the group consisting of hydrogen, deuterium, halogen, cyano, nitro, azido, C$_{1-4}$ alkyl, C$_{1-4}$ haloalkyl, C$_{1-4}$ deuterioalkyl, C$_{2-4}$ alkenyl, C$_{2-4}$ alkynyl, C$_{3-6}$ cycloalkyl, 3-6 membered heterocyclyl, C$_{6-8}$ aryl, 5-8 membered heteroaryl, —C$_{0-4}$ alkyl-SF$_5$, —C$_{0-4}$ alkyl-S(O)$_r$R$_{12}$, —C$_{0-4}$ alkyl-O—R$_{13}$, —C$_{0-4}$ alkyl-C(O)OR$_{13}$, —C$_{0-4}$ alkyl-C(O)R$_{14}$, —C$_{0-4}$ alkyl-O—C(O)R$_{14}$, —C$_{0-4}$ alkyl-NR$_{15}$R$_{16}$, —C$_{0-4}$ alkyl-C(=NR$_{15}$)R$_{14}$, —C$_{0-4}$ alkyl-N(R$_{15}$)—C(=NR$_{16}$)R$_{14}$, —C$_{0-4}$ alkyl-C(O)NR$_{15}$R$_{16}$, and —C$_{0-4}$ alkyl-N(R$_{15}$)—C(O)R$_{14}$.

3. The compound of formula (I), or the stereoisomer or pharmaceutically acceptable salt thereof, of claim 1, wherein each R$_{12}$ is independently selected from the group consisting of hydrogen, deuterium, hydroxy, C$_{1-4}$ alkyl, C$_{2-4}$ alkenyl, C$_{3-6}$ cycloalkyl, 3-6 membered heterocyclyl, C$_{6-8}$ aryl, 5-8 membered heteroaryl, and —C$_{0-4}$ alkyl-NR$_{15}$R$_{16}$, each of the above R$_{12}$ groups optionally further substituted with one or more substituents independently selected from the group consisting of deuterium, halogen, hydroxy, oxo, C$_{1-4}$ alkyl, C$_{1-4}$ alkoxy, C$_{3-6}$ cycloalkyl, C$_{3-6}$ cycloalkyloxy, 3-6 membered heterocyclyl, 3-6 membered heterocyclyloxy, C$_{6-8}$ aryl, C$_{6-8}$ aryloxy, 5-8 membered heteroaryl, 5-8 membered heteroaryloxy, and —C$_{0-4}$ alkyl-NR$_{15}$R$_{16}$;

each R$_{14}$ is independently selected from the group consisting of hydrogen, deuterium, hydroxy, C$_{1-4}$ alkyl, C$_{1-4}$ alkoxy, C$_{2-4}$ alkenyl, C$_{2-4}$ alkynyl, C$_{3-6}$ cycloalkyl, C$_{3-6}$ cycloalkyloxy, 3-6 membered heterocyclyl, 3-6 membered heterocyclyloxy, C$_{6-8}$ aryl, C$_{6-8}$ aryloxy, 5-8 membered heteroaryl, 5-8 membered heteroaryloxy, and —C$_{0-4}$ alkyl-NR$_{15}$R$_{16}$, each of the above R$_{14}$ groups optionally further substituted with one or more substituents independently selected from the group consisting of deuterium, halogen, hydroxy, cyano, C$_{1-4}$ alkyl, C$_{1-4}$ alkoxy, C$_{3-6}$ cycloalkyl, C$_{3-6}$ cycloalkyloxy, 3-6 membered heterocyclyl, 3-6 membered heterocyclyloxy, C$_{6-8}$ aryl, C$_{6-8}$ aryloxy, 5-8 membered heteroaryl, 5-8 membered heteroaryloxy, and —C$_{0-4}$ alkyl-NR$_{15}$R$_{16}$, each of the above R$_{14}$ groups optionally further substituted with one or more substituents independently selected from the group consisting of deuterium, halogen, hydroxy, cyano, C$_{1-4}$ alkyl, C$_{1-4}$ alkoxy, C$_{3-6}$ cycloalkyl, C$_{3-6}$ cycloalkyloxy, 3-6 membered heterocyclyl, 3-6 membered heterocyclyloxy, C$_{6-8}$ aryl, C$_{6-8}$ aryloxy, 5-8 membered heteroaryl, 5-8 membered heteroaryloxy, and —C$_{0-4}$ alkyl-NR$_{15}$R$_{16}$; and each of R$_{15}$ and R$_{16}$ is independently selected from the group consisting of hydrogen, deuterium, hydroxy, C$_{1-4}$ alkoxy, C$_{1-4}$ alkyl, C$_{2-4}$ alkenyl, C$_{2-4}$ alkynyl, C$_{3-6}$ cycloalkyl, 3-6 membered heterocyclyl, C$_{6-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoC$_{1-4}$ alkylamino, diC$_{1-4}$ alkylamino, and C$_{1-4}$ alkanoyl, each of the above R$_{15}$ and R$_{16}$ groups optionally further substituted with one or more substituents independently selected from the group consisting of deuterium, halogen, hydroxy, C$_{1-4}$ alkyl, C$_{2-4}$ alkenyl, C$_{2-4}$ alkynyl, C$_{1-4}$ haloalkyl, C$_{1-4}$ deuterioalkyl, C$_{1-4}$ alkoxy, C$_{3-6}$ cycloalkyl, C$_{3-6}$ cycloalkoxy, 3-6 membered heterocyclyl, 3-6 membered heterocyclyloxy, C$_{6-8}$ aryloxy, 5-8 membered heteroaryl, 5-8 membered heteroaryloxy, amino, monoC$_{1-4}$ alkylamino, diC$_{1-4}$ alkylamino, and C$_{1-4}$ alkanoyl, or, R$_{15}$ and R$_{16}$, together with the nitrogen atom to which R$_{15}$ and R$_{16}$ are directly attached, form a 5-8 membered heterocyclyl or 5-8 membered heteroaryl, each of the above R$_{15}$ and R$_{16}$ groups optionally further substituted with one or more substituents independently selected from the group consisting of deuterium, halogen, hydroxy, C$_{1-4}$ alkyl, C$_{2-4}$ alkenyl, C$_{2-4}$ alkynyl, C$_{1-4}$ haloalkyl, C$_{1-4}$ deuterioalkyl, C$_{1-4}$ alkoxy, C$_{3-6}$ cycloalkyl, C$_{3-6}$ cycloalkyloxy, 3-6 membered heterocyclyl, 3-6 membered heterocyclyloxy, C$_{6-8}$ aryl, C$_{6-8}$ aryloxy, 5-8 membered heteroaryl, 5-8 membered heteroaryloxy, amino, monoC$_{1-4}$ alkylamino, diC$_{1-4}$ alkylamino, and C$_{1-4}$ alkanoyl.

4. The compound of formula (I), or the stereoisomer or pharmaceutically acceptable salt thereof, of claim 1, wherein the compound of formula (I) is a compound of formula (II):

(II)

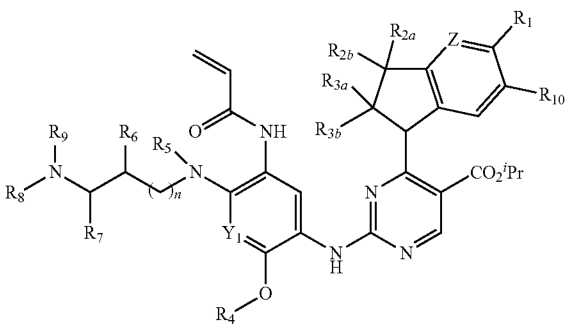

wherein,

Y is CH or N;

Z is CH or N;

$R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$, or $R_1$ and $R_{10}$, together with the moiety to which $R_1$ and $R_{10}$ are directly attached, form a $C_{3-6}$ cycloalkyl or 3-6 membered heterocyclyl, each of the above $R_1$ or $R_1$ and adjacent $R_{10}$ groups optionally further substituted with one or more substituents independently selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$;

$R_{2a}$ and $R_{2b}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, and 3-6 membered heterocyclyl, or $R_{2a}$ and $R_{2b}$, together with the carbon atom to which $R_{2a}$ and $R_{2b}$ are directly attached, form a $C_{3-6}$ cycloalkyl or 3-6 membered heterocyclyl, each of the above $R_{2a}$ and $R_{2b}$ groups optionally further substituted with one or more substituents independently selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$;

$R_{3a}$ and $R_{3b}$ are each independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, and 3-6 membered heterocyclyl;

$R_4$ is selected from hydrogen, deuterium, $C_{1-4}$ alkyl, $C_{2-4}$ alkenyl, $C_{3-6}$ cycloalkyl, and 3-6 membered heterocyclyl, each of the above $R_4$ groups optionally further substituted with one or more substituents independently selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and —$NR_{15}R_{16}$;

$R_5$ is selected from the group consisting of hydrogen, deuterium, hydroxy, $C_{1-4}$ alkyl, $C_{1-4}$ haloalkyl, $C_{1-4}$ deuterioalkyl, and $C_{3-6}$ cycloalkyl;

$R_6$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$;

$R_7$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$;

$R_8$ and $R_9$ are each independently selected from the group consisting of hydrogen, deuterium, hydroxy, $C_{1-4}$ alkyl, $C_{2-4}$ alkenyl, $C_{3-6}$ cycloalkyl, and 3-6 membered heterocyclyl, or $R_8$ and $R_9$, together with the nitrogen atom to which $R_8$ and $R_9$ are directly attached, form a 3-6 membered heterocyclyl, each of the above $R_8$ and $R_9$ groups optionally further substituted with one or more substituents independently selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and —$C_{0-4}$ alkyl-$NR_{15}R_{16}$;

or, $R_5$ and one of $R_6$, $R_7$, or $R_9$, together with the moiety to which $R_5$ and one of $R_6$, $R_7$, or $R_9$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —$C(=NR_{15})R_{14}$, —$N(R_{15})$—$C(=NR_{16})R_{14}$, —$C(O)NR_{15}R_{16}$, and —$N(R_{15})$—$C(O)R_{14}$, or, $R_7$ and $R_8$, together with the moiety to which $R_7$ and $R_8$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —$C(O)OR_{13}$, —$C(O)R_{14}$, —O—$C(O)R_{14}$, —$NR_{15}R_{16}$, —C(=$NR_{15}$)$R_{14}$, —N($R_{15}$)—C(=$NR_{16}$)$R_{14}$, —C(O)$NR_{15}R_{16}$, and —N($R_{15}$)—C(O)$R_{14}$, or

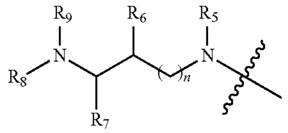

is

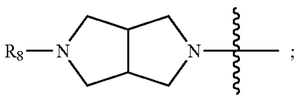

and $R_{10}$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —$S(O)_rR_{12}$, —O—$R_{13}$, —C(O)O$R_{13}$, —C(O)$R_{14}$, —O—C(O)$R_{14}$, —$NR_{15}R_{16}$, —C(=$NR_{15}$)$R_{14}$, —N($R_{15}$)—C(=$NR_{16}$)$R_{14}$, —C(O)$NR_{15}R_{16}$, and —N($R_{15}$)—C(O)$R_{14}$.

5. The compound of formula (I), or the stereoisomer or pharmaceutically acceptable salt thereof, of claim 4, wherein $R_1$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$SF_5$, —O—$R_{13}$, —O—C(O)$R_{14}$, and —$NR_{15}R_{16}$, or $R_1$ and $R_{10}$, together with the moiety to which $R_1$ and $R_{10}$ are directly attached, form a $C_{4-6}$ cycloalkyl or 4-6 membered heterocyclyl, each of the above $R_1$ or $R_1$ and adjacent $R_{10}$ groups optionally further substituted with one or more substituents independently selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-6}$ cycloalkyl, 3-6 membered heterocyclyl, $C_{6-8}$ aryl, 5-8 membered heteroaryl, =O, —$SF_5$, —$S(O)_rR_{12}$, —O—$R_{13}$, —C(O)O$R_{13}$, —C(O)$R_{14}$, —O—C(O)$R_{14}$, —$NR_{15}R_{16}$, —C(=$NR_{15}$)$R_{14}$, —N($R_{15}$)—C(=$NR_{16}$)$R_{14}$, —C(O)$NR_{15}R_{16}$, and —N($R_{15}$)—C(O)$R_{14}$;

$R_{2a}$ and $R_{2b}$ are each independently hydrogen, deuterium, $C_{1-4}$ alkyl, or $C_{3-6}$ cycloalkyl, or $R_{2a}$ and $R_{2b}$, together with the carbon atom to which $R_{2a}$ and $R_{2b}$ are directly attached, form a $C_{3-6}$ cycloalkyl or 3-6 membered heterocyclyl, each of the above $R_{2a}$ and $R_{2b}$ groups optionally further substituted with one or more substituents independently selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, and $C_{3-6}$ cycloalkyl;

$R_{3a}$ and $R_{3b}$ are each independently selected from the group consisting of hydrogen, deuterium, halogen, $C_{1-4}$ alkyl, and $C_{3-6}$ cycloalkyl;

$R_4$ is hydrogen, deuterium, $C_{1-4}$ alkyl, or $C_{3-6}$ cycloalkyl, each of the above $R_4$ groups optionally further substituted with one or more substituents independently selected from the group consisting of deuterium, halogen, hydroxy, =O, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and —$NR_{15}R_{16}$;

$R_5$ is selected from the group consisting of hydrogen, deuterium, hydroxy, $C_{1-4}$ alkyl, $C_{1-4}$ haloalkyl, $C_{1-4}$ deuterioalkyl, and $C_{3-6}$ cycloalkyl;

$R_6$ is selected from the group consisting of hydrogen, deuterium, halogen, cyano, $C_{1-4}$ alkyl, $C_{1-4}$ haloalkyl, $C_{1-4}$ deuterioalkyl, and $C_{3-6}$ cycloalkyl;

$R_7$ is selected from the group consisting of hydrogen, deuterium, halogen, cyano, $C_{1-4}$ alkyl, $C_{1-4}$ haloalkyl, $C_{1-4}$ deuterioalkyl, and $C_{3-6}$ cycloalkyl; and $R_8$ and $R_9$ are each independently selected from the group consisting of hydrogen, deuterium, hydroxy, $C_{1-4}$ alkyl, and $C_{3-6}$ cycloalkyl, or $R_8$ and $R_9$, together with the nitrogen atom to which $R_8$ and $R_9$ are directly attached, form a 3-6 membered heterocyclyl, each of the above $R_8$ and $R_9$ groups optionally further substituted with one or more substituents independently selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, and —$NR_{15}R_{16}$;

or, $R_5$ and one of $R_6$, $R_7$, or $R_9$, together with the moiety to which $R_5$ and one of $R_6$, $R_7$, or $R_9$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, and $C_{3-6}$ cycloalkyl, or, $R_7$ and $R_8$, together with the moiety to which $R_7$ and $R_8$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, and $C_{3-6}$ cycloalkyl, or

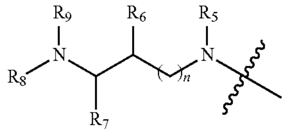

is

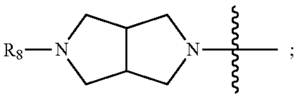

$R_{10}$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkenyl, $C_{2-4}$ alkynyl, and $C_{3-6}$ cycloalkyl.

6. The compound of formula (I), or the stereoisomer or pharmaceutically acceptable salt thereof, of claim 4, wherein each $R_1$ is independently selected from the group consisting of hydrogen, deuterium, fluoro, chloro, bromo, cyano, methyl, ethyl, isopropyl, vinyl, ethynyl, cyclopropyl, cyclobutyl, oxacyclobutyl, azacyclobutyl, pyrazolyl, imidazolyl, oxazolyl, triazolyl, methoxy, amino, dimethylamino, and methylamino, or $R_1$ and $R_{10}$, together with the moiety to which $R_1$ and $R_{10}$ are directly attached, form a cyclopentyl, each of the above $R_1$ or $R_1$ and adjacent $R_{10}$ groups optionally further substituted with one or more substituents independently selected from the group consisting of deuterium, fluoro, chloro, bromo, cyano, methyl, ethyl, isopropyl, vinyl, ethynyl, trifluoromethyl, difluoromethyl, trideuteriomethyl, dideuteriomethyl, cyclopropyl, and cyclobutyl; and $R_{10}$ is selected from the group consisting of hydrogen, deuterium, fluoro, chloro, bromo, cyano, methyl, ethyl, isopropyl, trifluoromethyl, difluoromethyl, trideuteriomethyl, dideuteriomethyl, vinyl, ethynyl, cyclopropyl, and cyclobutyl.

7. The compound of formula (I), or the stereoisomer or pharmaceutically acceptable salt thereof, of claim 4, wherein $R_4$ is selected from the group consisting of hydrogen, deuterium, methyl, ethyl, isopropyl, cyclopropyl, and cyclobutyl, each of the above $R_4$ groups optionally further substituted with one or more substituents independently selected from deuterium, fluoro, $C_{1-4}$ alkyl, and $C_{3-6}$ cycloalkyl.

8. The compound of formula (I), or the stereoisomer or pharmaceutically acceptable salt thereof, of claim 4, wherein $R_{2a}$ and $R_{2b}$ are each independently selected from the group consisting of hydrogen, deuterium, methyl, ethyl, isopropyl, cyclopropyl, and cyclobutyl, or $R_{2a}$ and $R_{2b}$, together with the carbon atom to which $R_{2a}$ and $R_{2b}$ are directly attached, form a cyclopropyl, cyclobutyl, or cyclopentyl, each of the above $R_{2a}$ and $R_{2b}$ groups optionally further substituted with one or more substituents independently selected from the group consisting of deuterium, fluoro, chloro, bromo, cyano, methyl, ethyl, isopropyl, trifluoromethyl, difluoromethyl, trideuteriomethyl, dideuteriomethyl, cyclopropyl, and cyclobutyl.

9. The compound of formula (I), or the stereoisomer or pharmaceutically acceptable salt thereof, of claim 4, wherein $R_{3a}$ and $R_{3b}$ are each independently selected from the group consisting of hydrogen, deuterium, methyl, ethyl, isopropyl, cyclopropyl, and cyclobutyl.

10. The compound of formula (I), or the stereoisomer or pharmaceutically acceptable salt thereof, of claim 4, wherein $R_5$ is selected from the group consisting of hydrogen, deuterium, methyl, ethyl, isopropyl, trifluoromethyl, difluoromethyl, trideuteriomethyl, dideuteriomethyl, cyclopropyl, and cyclobutyl;

$R_6$ is selected from the group consisting of hydrogen, deuterium, methyl, ethyl, isopropyl, trifluoromethyl, difluoromethyl, trideuteriomethyl, dideuteriomethyl, cyclopropyl, and cyclobutyl;

$R_7$ is selected from the group consisting of hydrogen, deuterium, methyl, ethyl, isopropyl, trifluoromethyl, difluoromethyl, trideuteriomethyl, dideuteriomethyl, cyclopropyl, and cyclobutyl; and $R_8$ and $R_9$ are each independently selected from the group consisting of hydrogen, deuterium, methyl, ethyl, isopropyl, trifluoromethyl, difluoromethyl, trideuteriomethyl, dideuteriomethyl, cyclopropyl, and cyclobutyl, or $R_8$ and $R_9$, together with the nitrogen atom to which $R_8$ and $R_9$ are directly attached, form a 4-6 membered heterocyclyl;

or, $R_5$ and one of $R_6$, $R_7$, or $R_9$, together with the moiety to which $R_5$ and one of $R_6$, $R_7$, or $R_9$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, and $C_{3-6}$ cycloalkyl, or, $R_7$ and $R_8$, together with the moiety to which $R_7$ and $R_8$ are directly attached, form a 4-6 membered heterocyclyl, the 4-6 membered heterocyclyl optionally further substituted with one or more substituents independently selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, and $C_{3-6}$ cycloalkyl, or

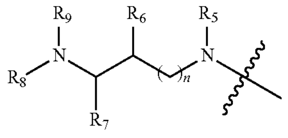

is

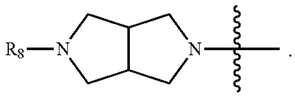

11. The compound of formula (I), or the stereoisomer or pharmaceutically acceptable salt thereof of claim 4, wherein

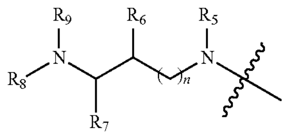

is selected from the group consisting of:

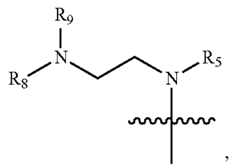
,
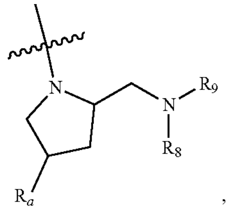
,
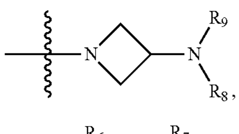

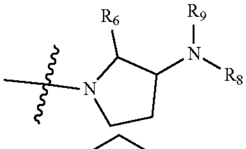
,
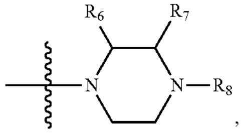
,
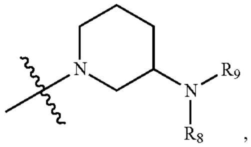
,
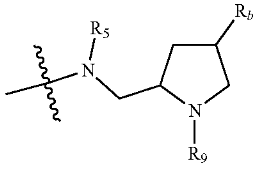
, and

-continued

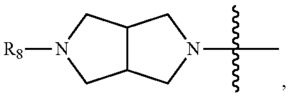

, wherein, each $R_5$ is independently selected from the group consisting of hydrogen, deuterium, methyl, ethyl, trideuteriomethyl, and dideuteriomethyl;

each $R_6$ is independently selected from the group consisting of hydrogen, deuterium, methyl, ethyl, isopropyl, trifluoromethyl, difluoromethyl, trideuteriomethyl, dideuteriomethyl, cyclopropyl, and cyclobutyl;

$R_7$ is selected from the group consisting of hydrogen, deuterium, halogen, cyano, $C_{1-4}$ alkyl, $C_{1-4}$ haloalkyl, $C_{1-4}$ deuterioalkyl, and $C_{3-6}$ cycloalkyl, each of $R_8$ and $R_9$ is independently selected from the group consisting of hydrogen, deuterium, methyl, ethyl, isopropyl, trifluoromethyl, difluoromethyl, trideuteriomethyl, dideuteriomethyl, cyclopropyl, and cyclobutyl, or $R_8$ and $R_9$, together with the nitrogen atom to which $R_8$ and $R_9$ are directly attached, form a 4-6 membered heterocyclyl;

$R_a$ is selected from the group consisting of hydrogen, deuterium, halogen, cyano, $C_{1-4}$ alkyl, $C_{1-4}$ haloalkyl, $C_{1-4}$ deuterioalkyl, and $C_{3-6}$ cycloalkyl; and $R_b$ is selected from the group consisting of hydrogen, deuterium, halogen, cyano, $C_{1-4}$ alkyl, $C_{1-4}$ haloalkyl, $C_{1-4}$ deuterioalkyl, and $C_{3-6}$ cycloalkyl.

12. The compound of formula (I), or the stereoisomer or pharmaceutically acceptable salt thereof, of claim 1, wherein the compound is selected from the group consisting of:

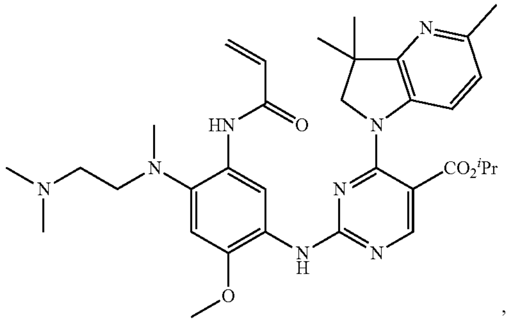

,

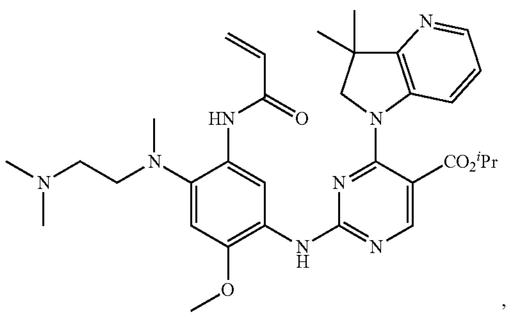

,

-continued

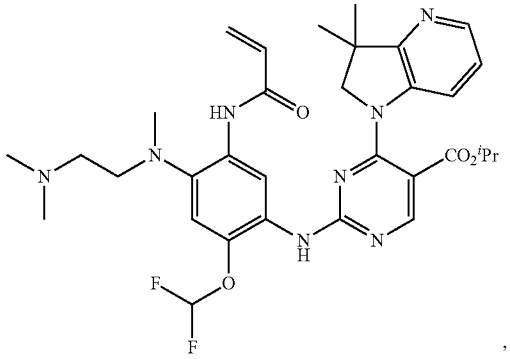

,

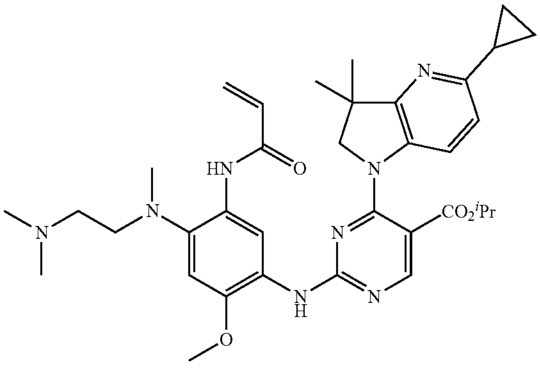

,

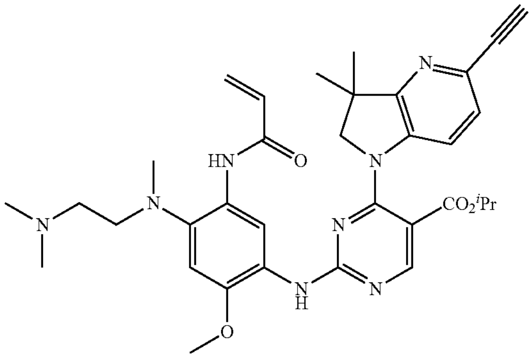

,

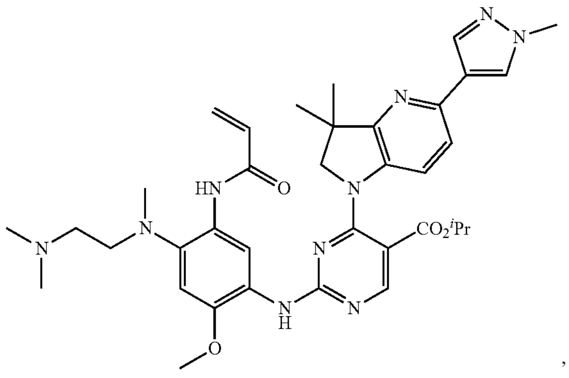

,

-continued
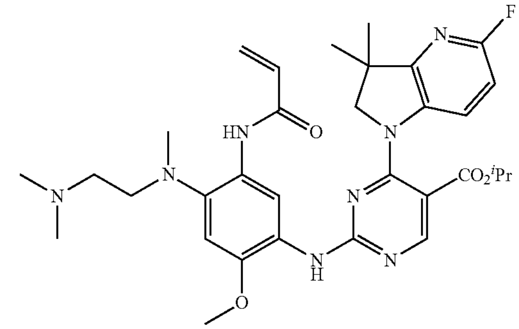
,
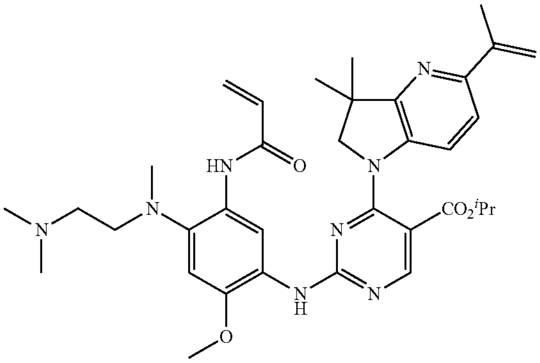
,
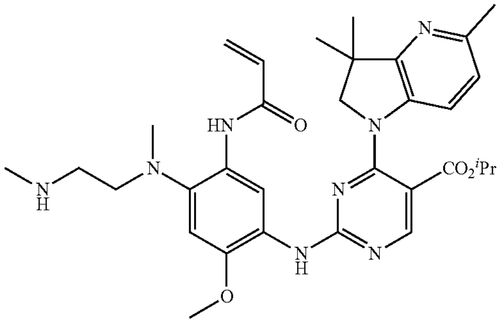
,
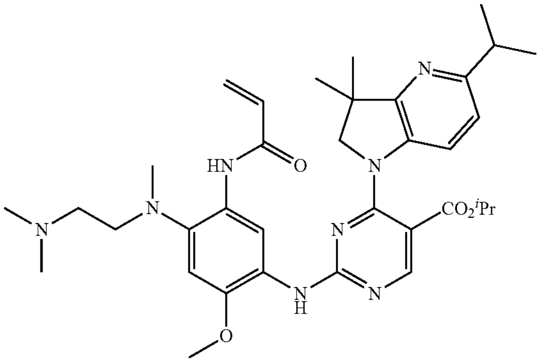
,
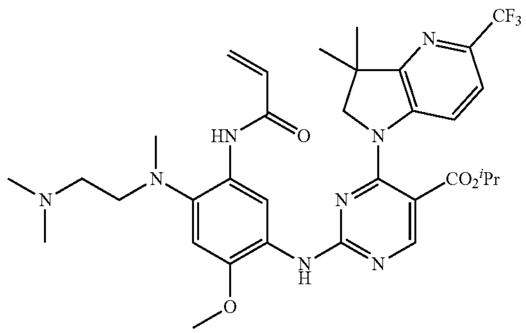
,
-continued
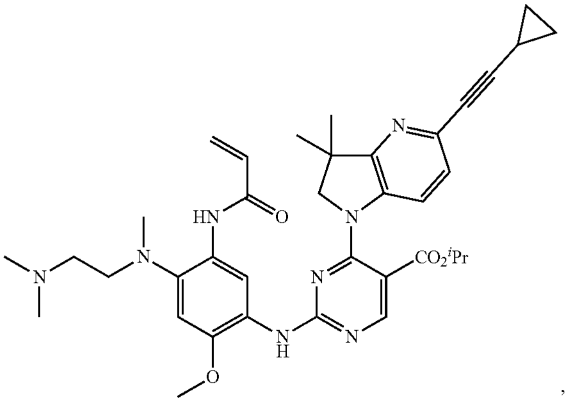
,
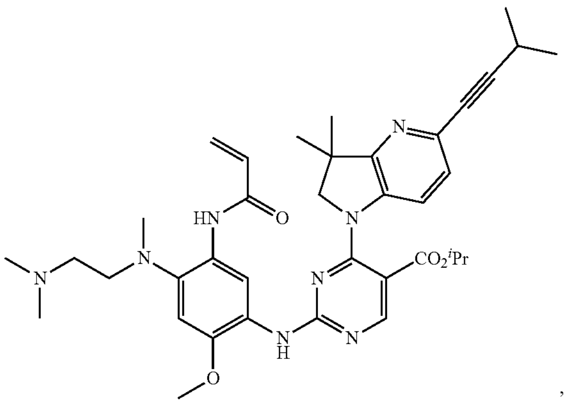
,
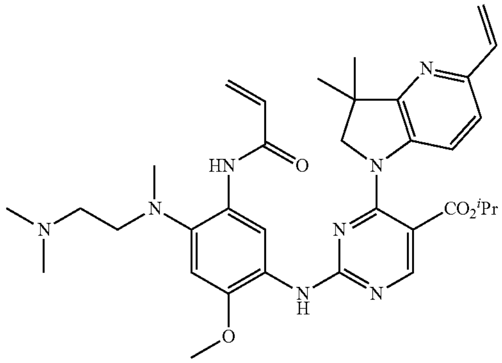
,
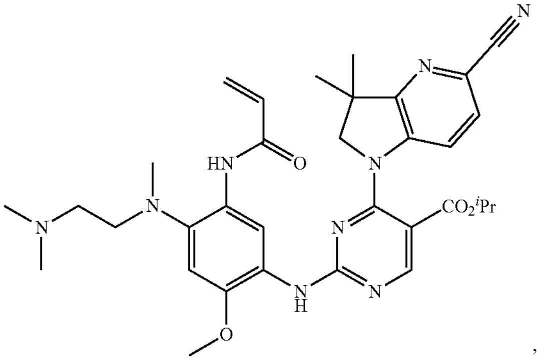
, -continued
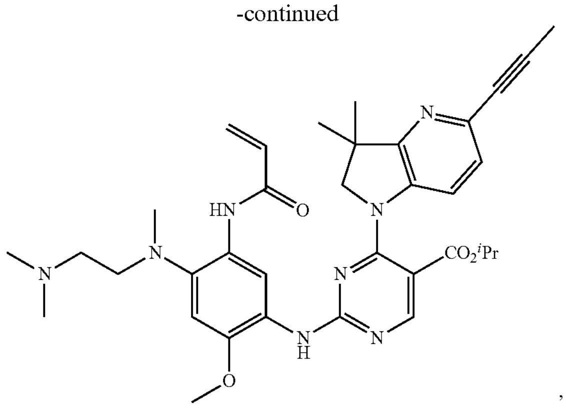
,
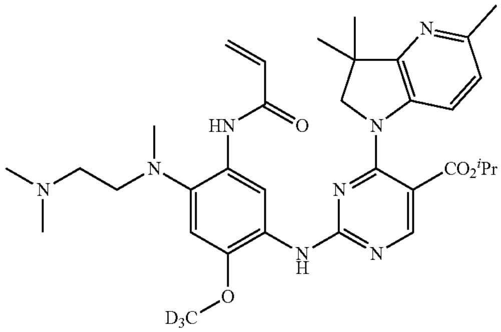
,
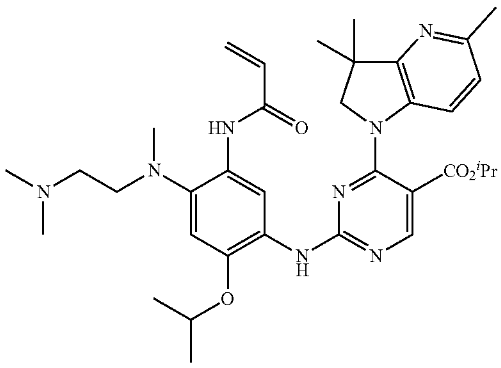
,
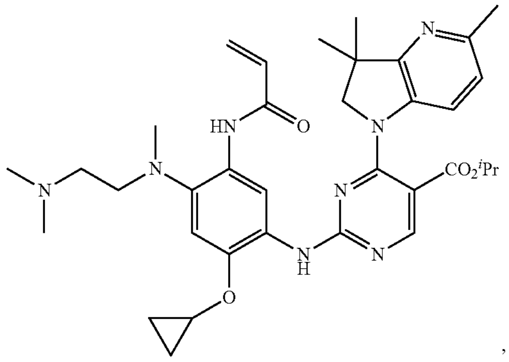
,
-continued
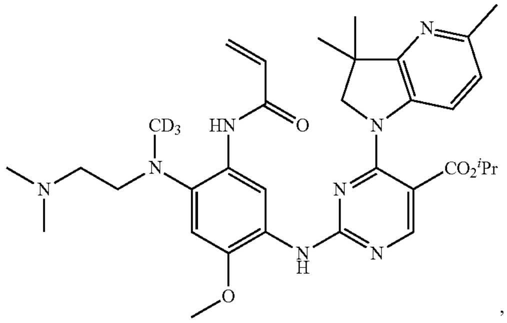
,
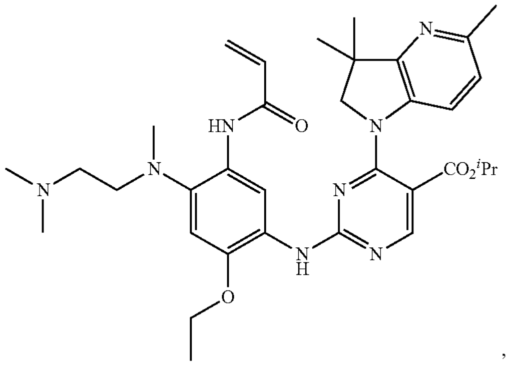
,
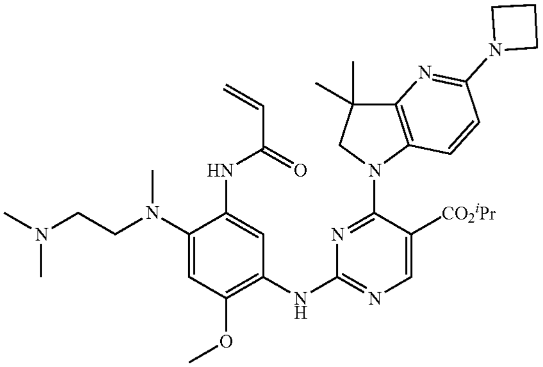
,
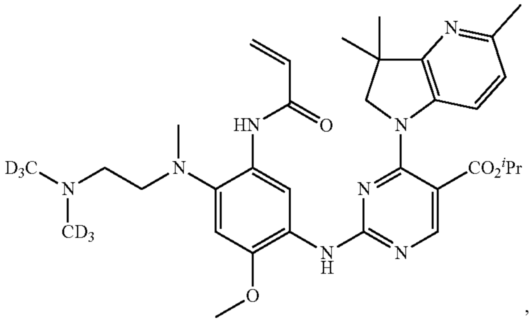
,
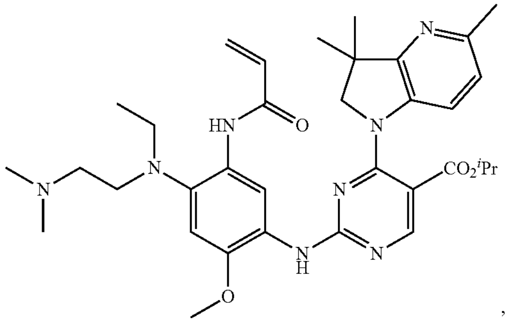
, -continued
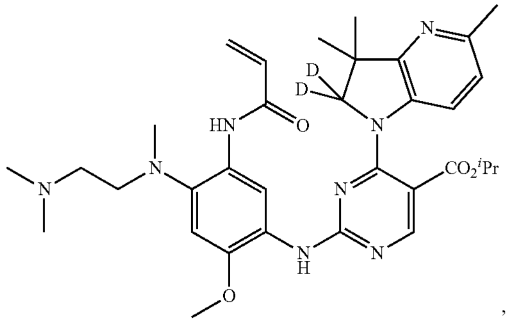
,
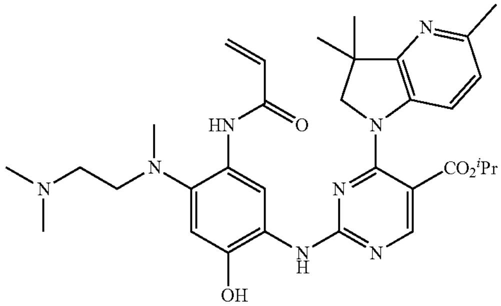
,
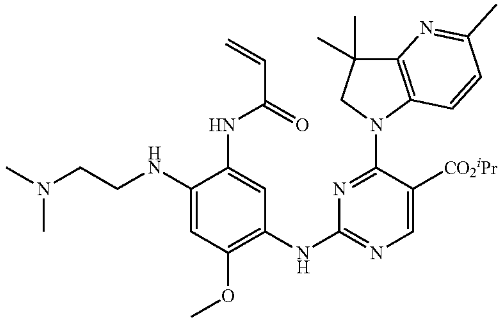
,
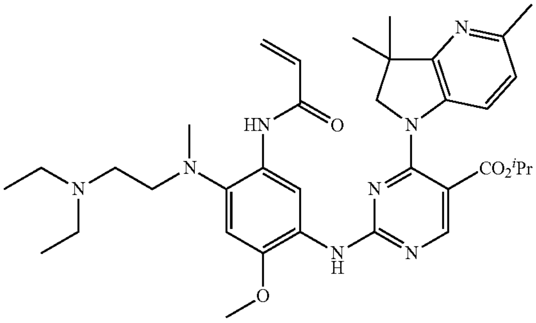
,
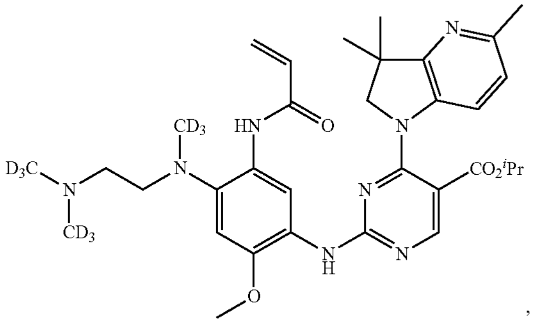
,
-continued
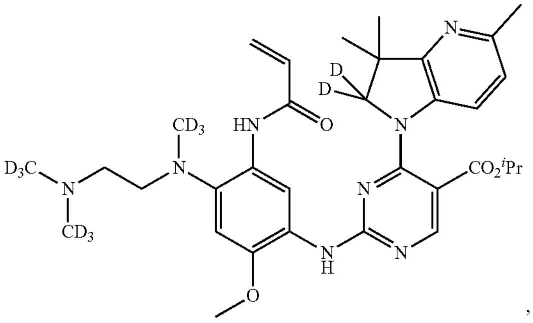
,
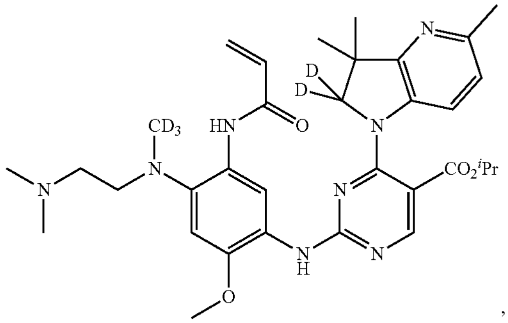
,
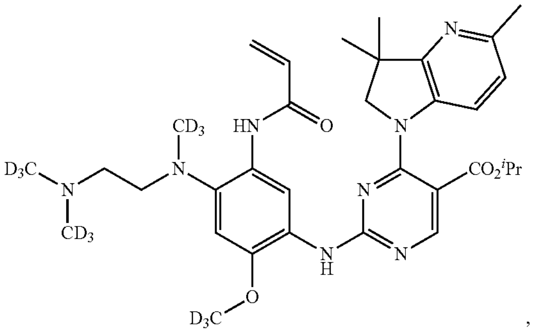
,
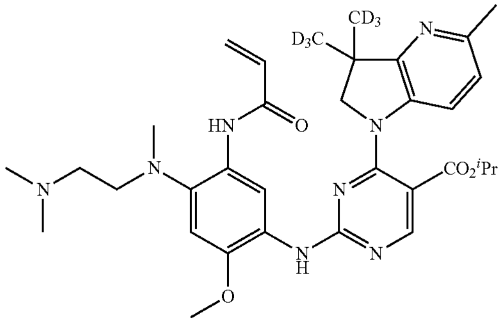
,
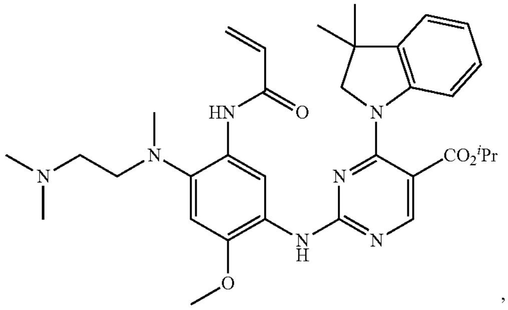
, -continued
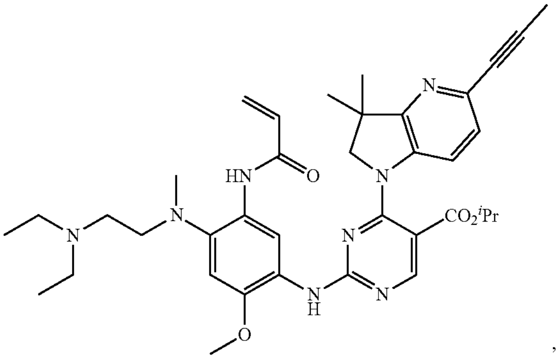
,
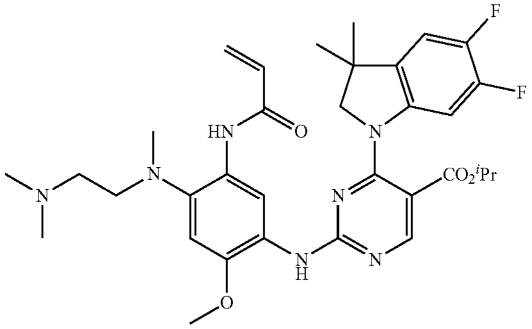
,
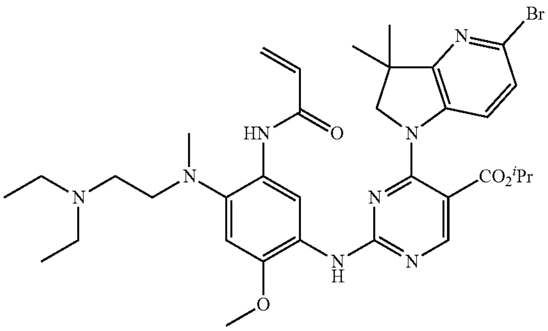
,
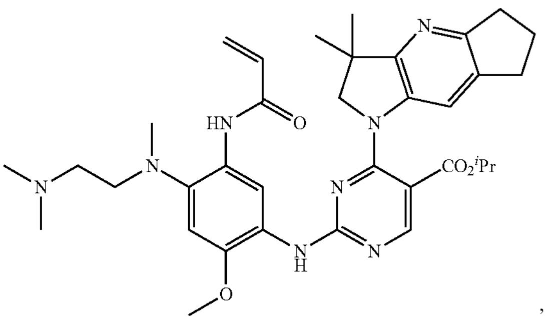
,
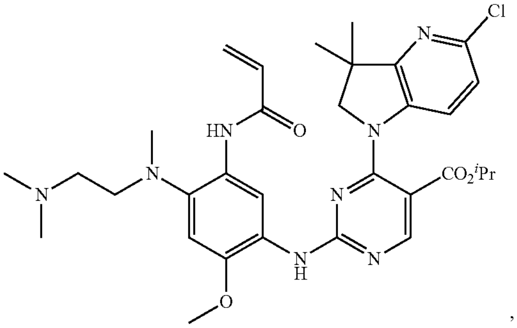
,
-continued
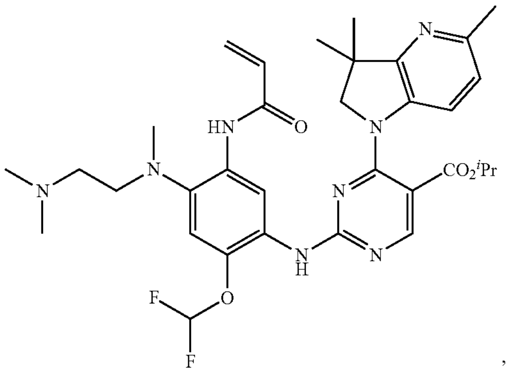
,
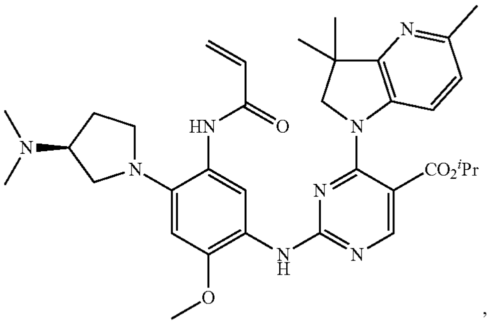
,
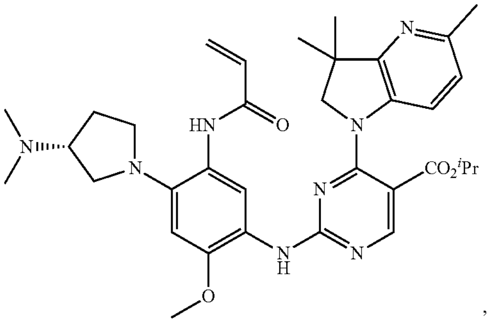
,
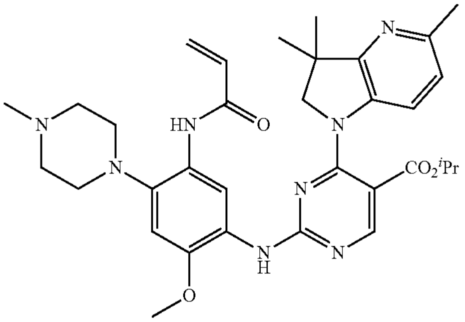
,
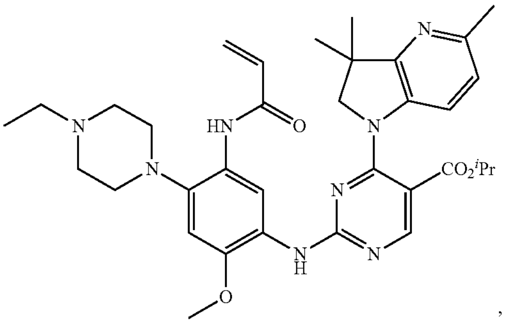
, -continued
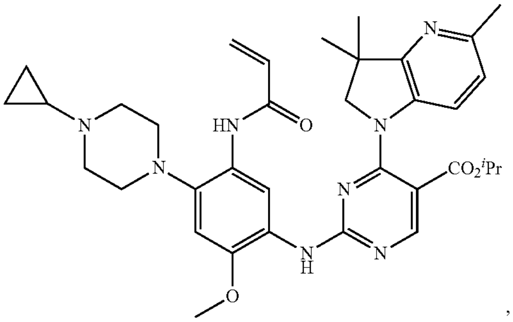
,
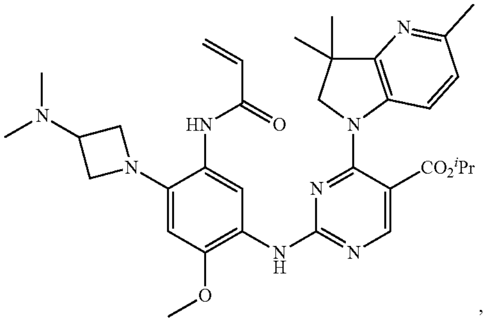
,
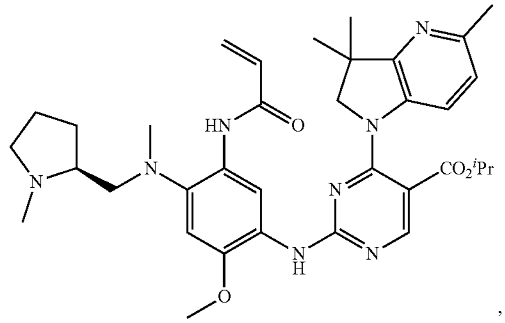
,
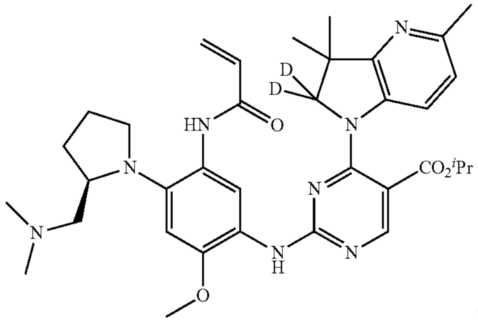
,
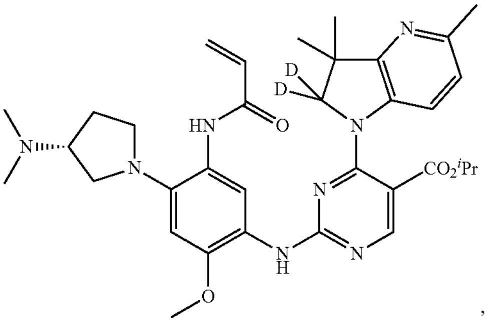
,
-continued
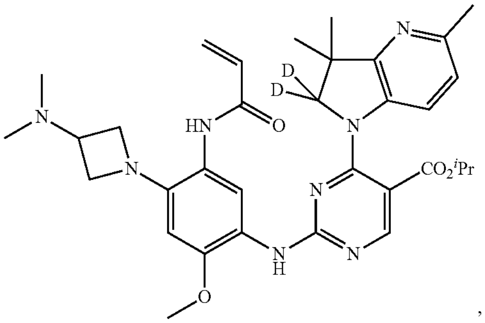
,
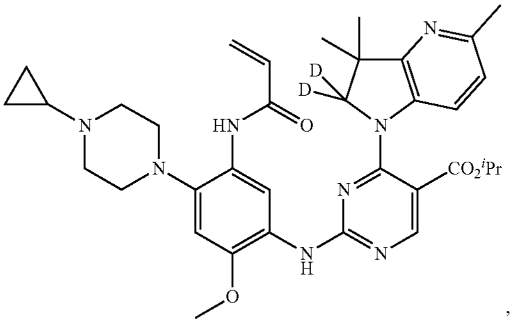
,
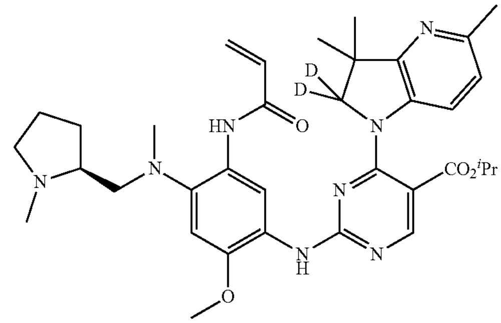
,
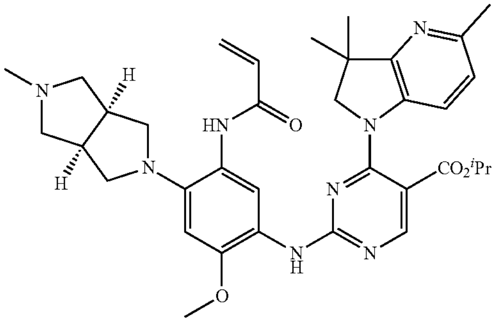
,
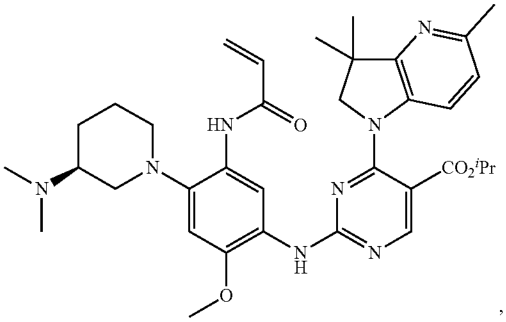
, -continued
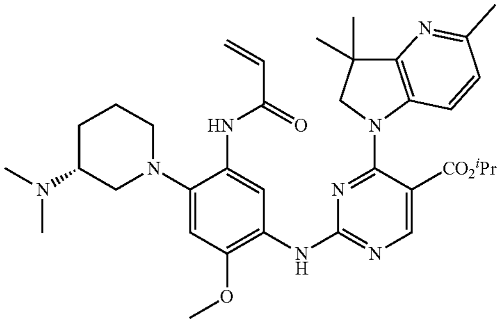
,
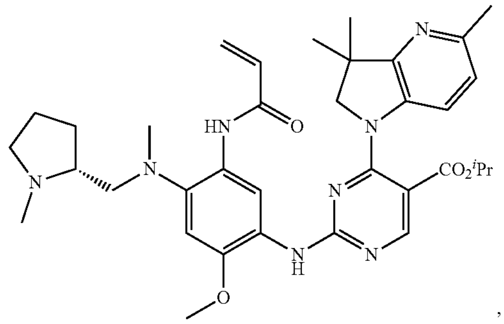
,
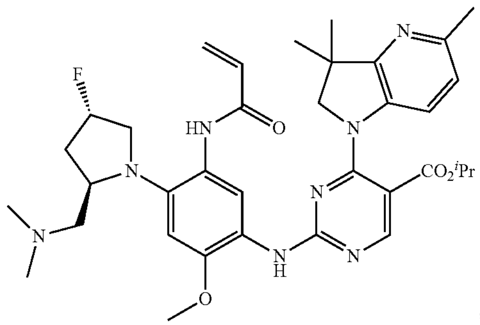
,
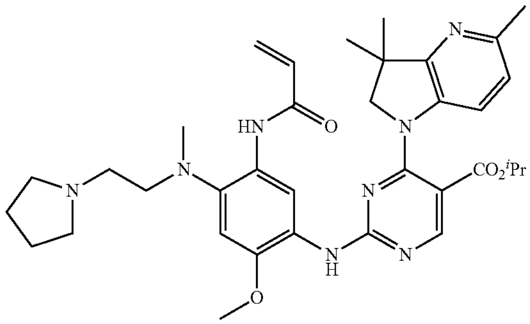
,
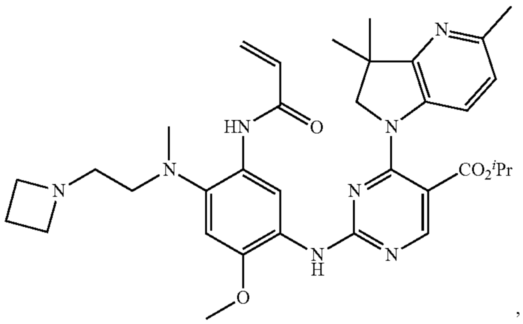
,
-continued
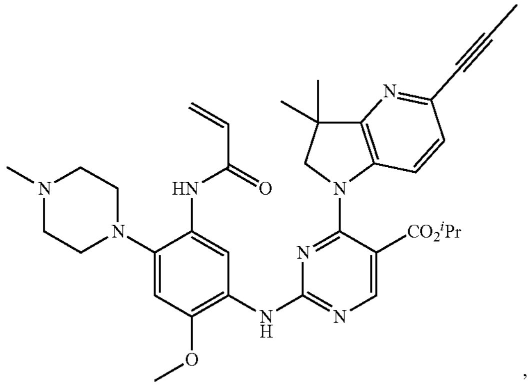
,
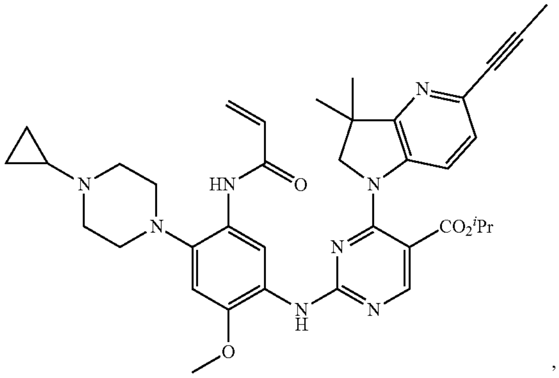
,
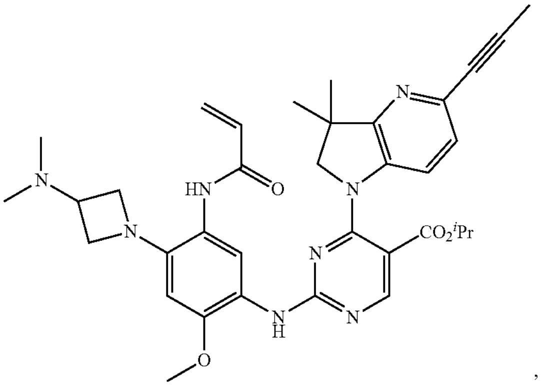
,
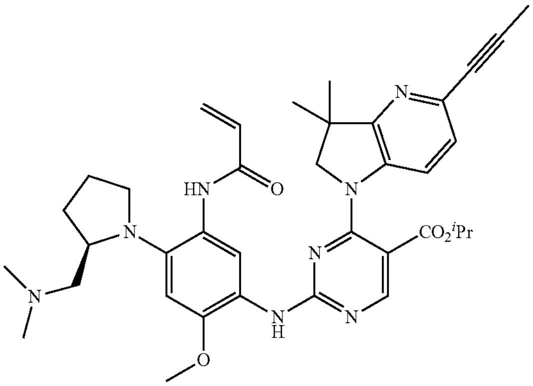
, -continued
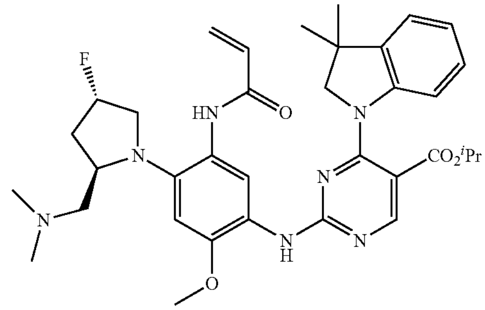
,
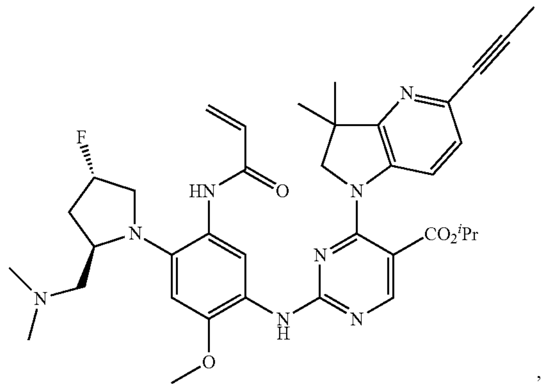
,
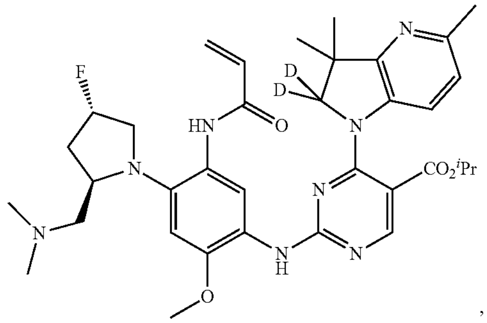
,
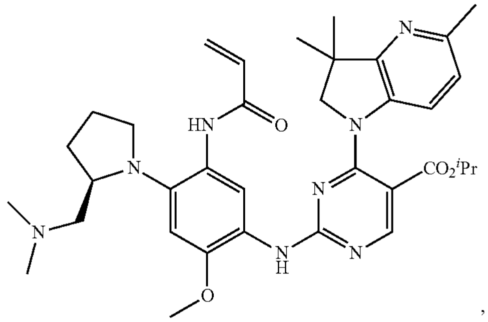
,
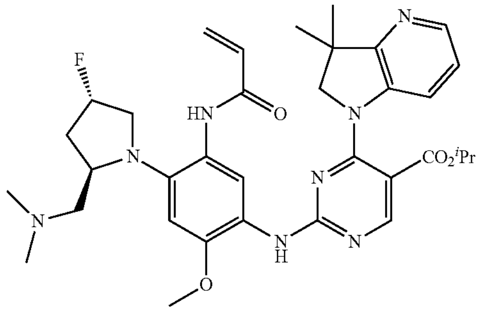
,
-continued
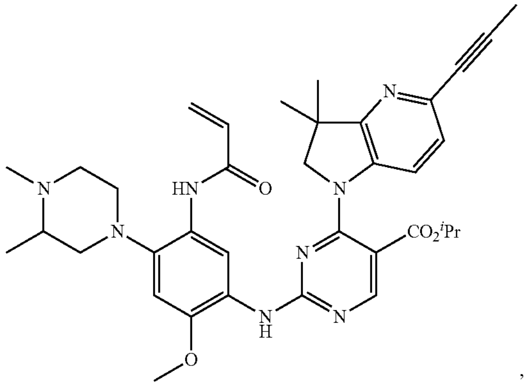
,
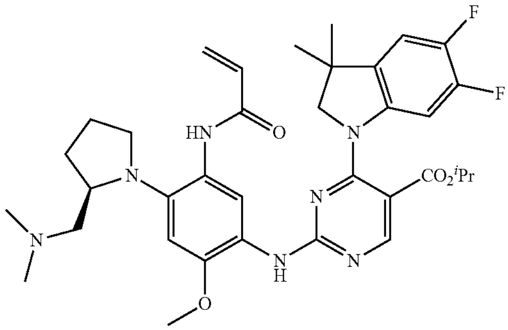
,
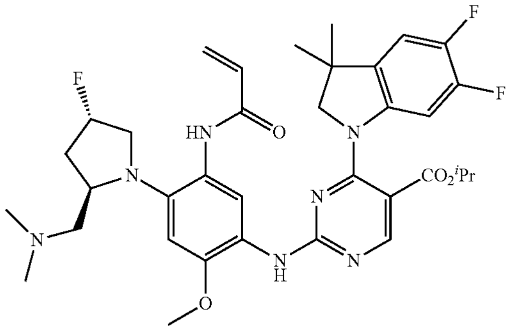
,
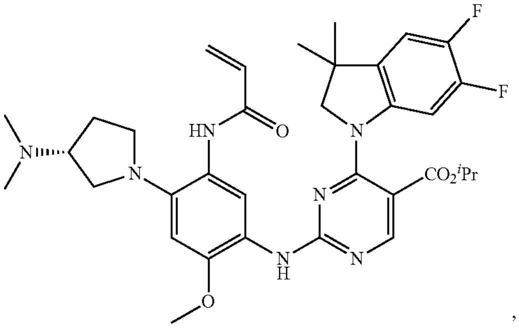
, -continued
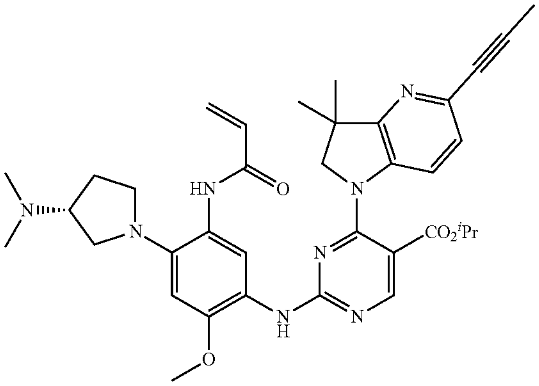
,
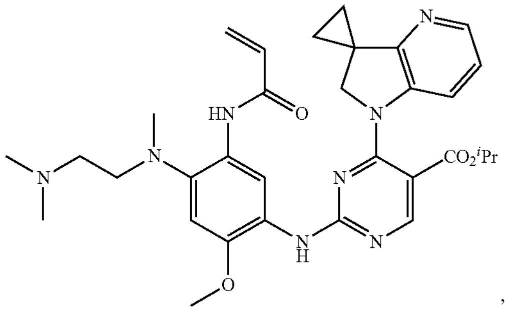
,
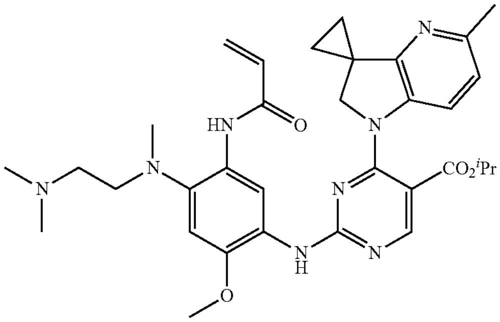
,
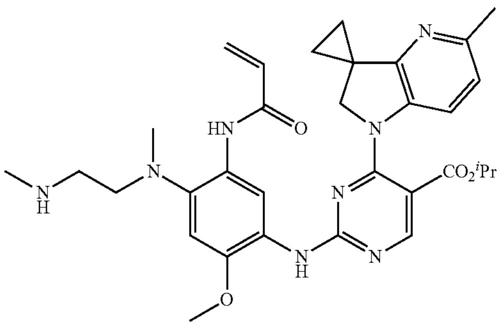
,
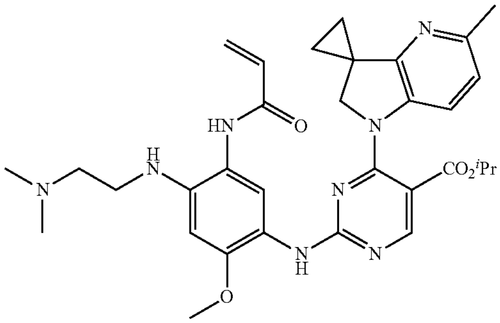
,
-continued
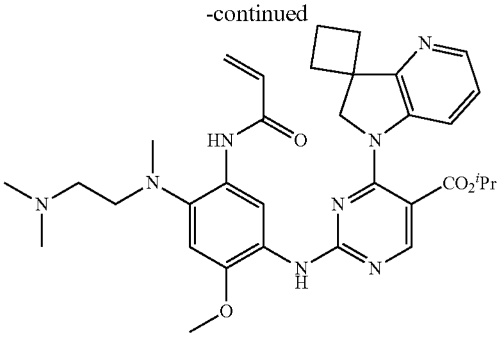
,
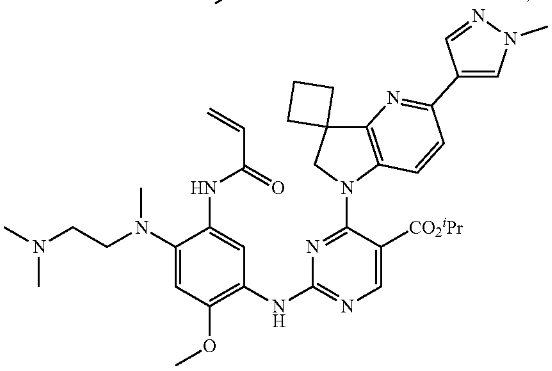
,
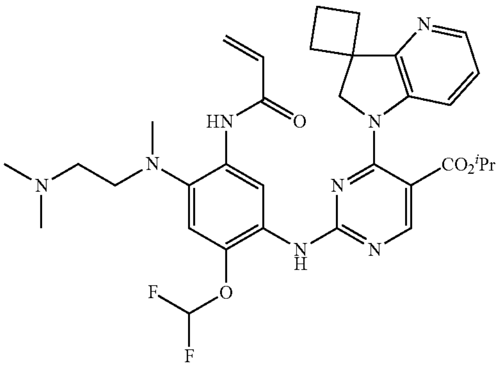
,
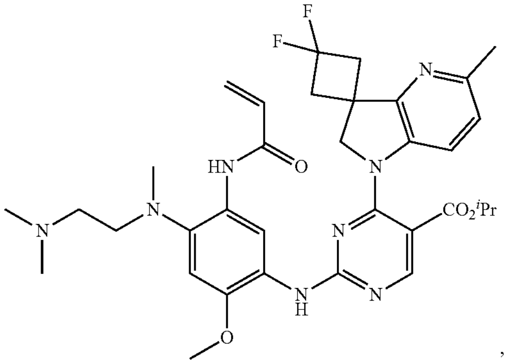
,
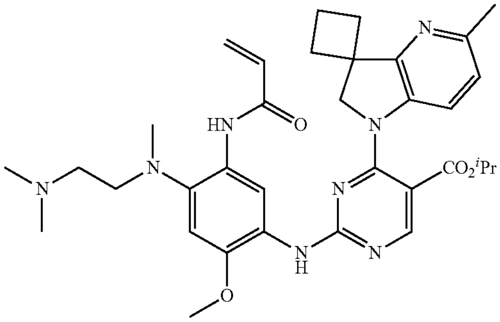
, -continued
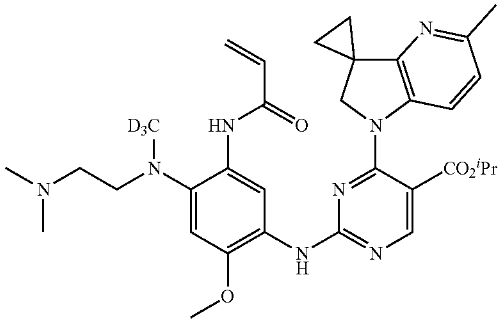
,
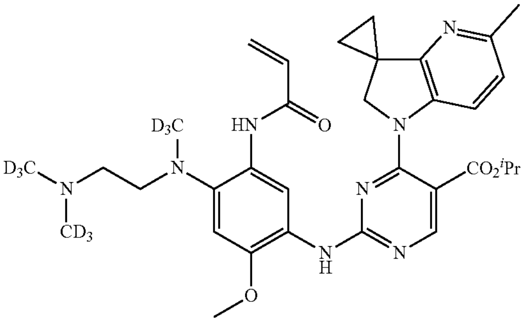
,
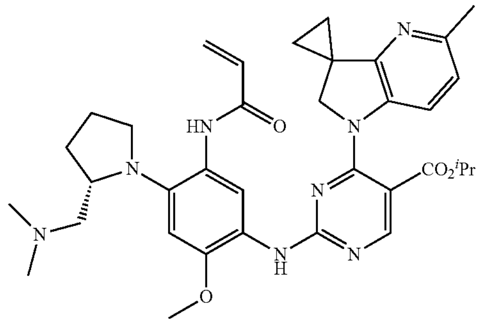
,
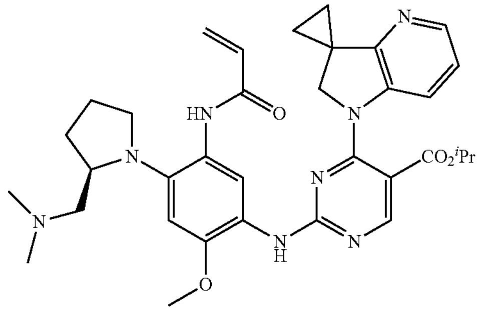
,
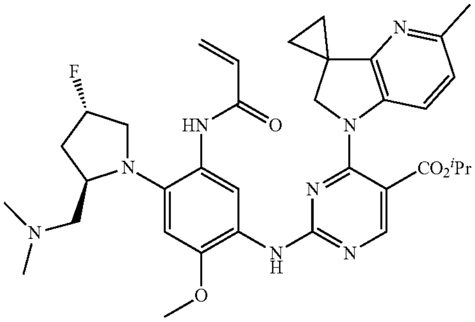
,
-continued
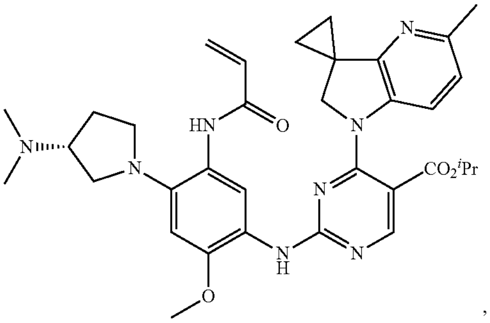
,
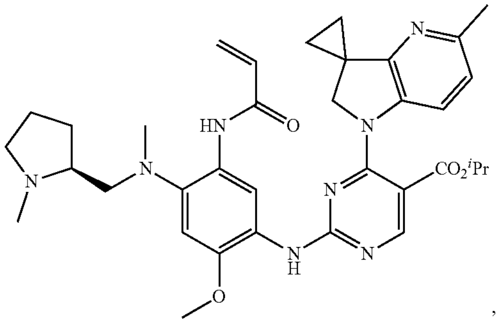
,
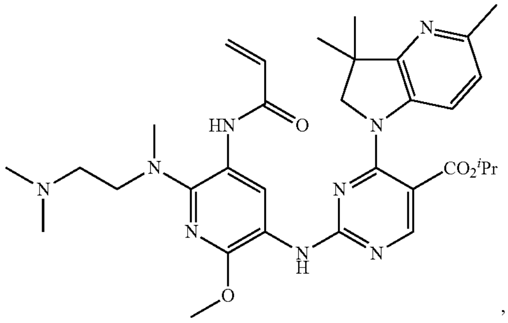
,
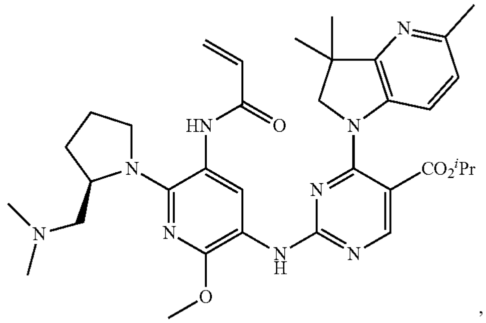
,
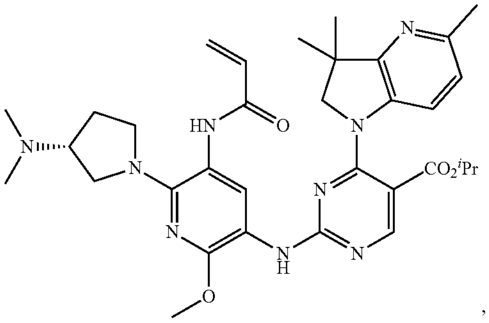
, -continued
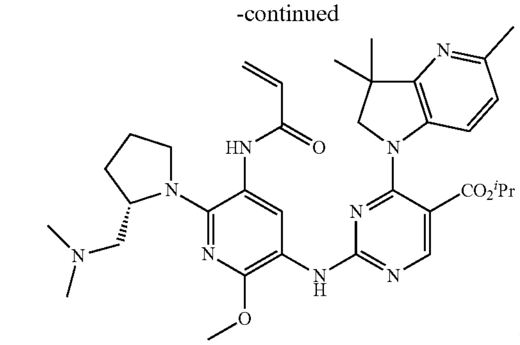
,
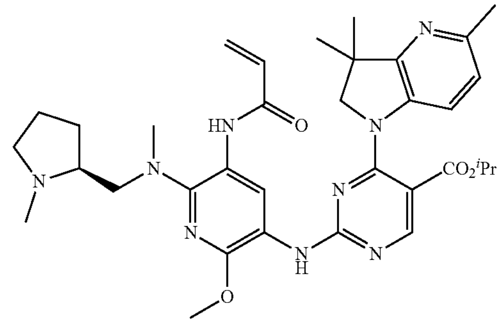
, and
-continued
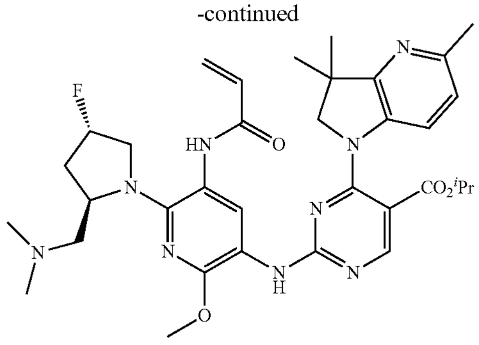
.
13. A pharmaceutical composition, comprising the compound of formula (I), or the stereoisomer or pharmaceutically acceptable salt thereof, of claim 1, and a pharmaceutically acceptable carrier.
* * * * *